US012619145B2

(12) United States Patent
Shimada et al.

(10) Patent No.: US 12,619,145 B2
(45) **Date of Patent: *May 5, 2026**

(54) CARBOXYLATE, CARBOXYLIC ACID GENERATOR, RESIN, RESIST COMPOSITION AND METHOD FOR PRODUCING RESIST PATTERN

(71) Applicant: SUMITOMO CHEMICAL COMPANY, LIMITED, Tokyo (JP)

(72) Inventors: Masahiko Shimada, Osaka (JP); Koji Ichikawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/051,050

(22) Filed: Oct. 31, 2022

(65) Prior Publication Data

US 2023/0152693 A1 May 18, 2023

(30) Foreign Application Priority Data

Nov. 10, 2021 (JP) ................................ 2021-183586
Mar. 11, 2022 (JP) ................................ 2022-038540

(51) Int. Cl.

| | |
|---|---|
| ***G03F 7/028*** | (2006.01) |
| ***C07C 43/205*** | (2006.01) |
| ***C07C 43/225*** | (2006.01) |
| ***G03F 7/004*** | (2006.01) |

(52) U.S. Cl.

CPC ............ *G03F 7/028* (2013.01); *C07C 43/205* (2013.01); *C07C 43/225* (2013.01); *G03F 7/0045* (2013.01)

(58) Field of Classification Search

CPC ...... G03F 7/0045; C08F 18/02; C07C 43/205; C07C 43/225

See application file for complete search history.

(56) References Cited

U.S. PATENT DOCUMENTS

| | | | | |
|---|---|---|---|---|
| 3,759,989 A * | 9/1973 | Jezic | C07C 53/16 562/605 |
| 6,558,871 B1 * | 5/2003 | Takahashi | C08G 59/68 570/101 |
| 11,505,524 B2 * | 11/2022 | Komuro | C07C 309/17 |
| 11,840,503 B2 * | 12/2023 | Komuro | C07C 309/12 |
| 2005/0053861 A1 * | 3/2005 | Yoneda | C07C 317/14 430/270.1 |
| 2011/0014566 A1 * | 1/2011 | Ichikawa | C08F 20/38 562/598 |
| 2012/0065291 A1 * | 3/2012 | Matsumura | G03F 7/0397 526/248 |
| 2012/0141939 A1 * | 6/2012 | Thackeray | G03F 7/0046 430/311 |
| 2020/0048191 A1 * | 2/2020 | Suga | C07C 43/315 |
| 2022/0127225 A1 * | 4/2022 | Fujiwara | C07C 65/10 |
| 2023/0028443 A1 * | 1/2023 | Komuro | G03F 7/0397 |
| 2023/0152693 A1 * | 5/2023 | Shimada | C07C 43/205 430/270.1 |

FOREIGN PATENT DOCUMENTS

| | | | |
|---|---|---|---|
| JP | 2011037834 A | | 2/2011 |
| JP | 2018193305 A | * | 12/2018 |
| TW | 201042385 A | | 12/2010 |
| TW | 201231445 A | | 8/2012 |

OTHER PUBLICATIONS

English translation of JP2018193305. (Year: 2018).*

* cited by examiner

*Primary Examiner* — Mark F. Huff
*Assistant Examiner* — Anna Malloy
(74) *Attorney, Agent, or Firm* — Panitch Schwarze Belisario & Nadel LLP

(57) ABSTRACT

A carboxylate represented by formula (I), a resin comprising a structural unit derived from the carboxylate represented by formula (I), a resit composition comprising the carboxylate represented by formula (I) or a resin comprising a structural unit derived from the carboxylate represented by formula (I).

(I)

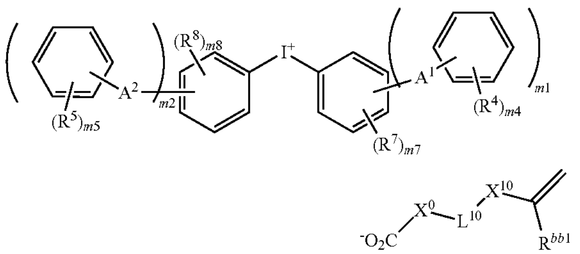

23 Claims, No Drawings

CARBOXYLATE, CARBOXYLIC ACID GENERATOR, RESIN, RESIST COMPOSITION AND METHOD FOR PRODUCING RESIST PATTERN

CROSS-REFERENCE TO RELATED APPLICATIONS

This application claims priority under 35 U.S.C 119 to Japanese Patent Application No. 2021-183586 filed on Nov. 10, 2021 and Japanese Patent Application No. 2022-038540 filed on Mar. 11, 2022. Each of the above applications is hereby expressly incorporated by reference, in its entirety, into the present application.

FIELD

The present disclosure relates to a carboxylate, a carboxylic acid generator, a resin, a resist composition and a method for producing a resist pattern.

BACKGROUND ART

JP 2011-037834 A mentions a resist composition comprising a resin including a structural unit derived from a carboxylate represented by the following formula.

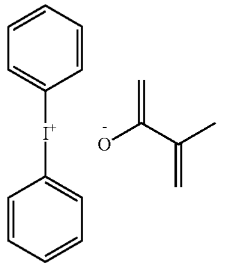

The present disclosure provides a carboxylate forming a resist pattern with mask error factor (MEF) which is better than that of the above resist composition comprising a resin including a structural unit derived from a carboxylate.

SUMMARY

The present disclosure includes the following some embodiments.

Some embodiments are a salt represented by formula (I) and a resin comprising a structural unit represented by formula (IP):

(I)

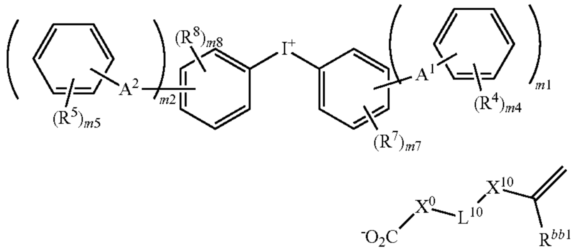

-continued (IP)

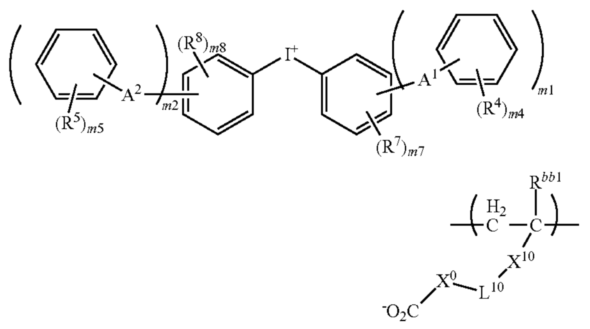

wherein, in formula (I) and formula (IP), $R^4$, $R^5$, $R^7$ and $R^8$ each independently represent a halogen atom, a hydroxy group, a haloalkyl group having 1 to 12 carbon atoms or a hydrocarbon group having 1 to 18 carbon atoms, each of the hydrocarbon group may have a substituent, and a —$CH_2$— included in each of the haloalkyl group and the hydrocarbon group may be replaced by —O—, —CO—, —S— or —$SO_2$—, $A^1$ and $A^2$ each independently represent a hydrocarbon group having 1 to 20 carbon atoms, each of the hydrocarbon group may have a substituent, and —$CH_2$— included in each of the hydrocarbon group may be replaced by —O—, —CO—, —S— or —$SO_2$—, m1 represents an integer of 1 to 5, and when m1 is 2 or more, a plurality of groups in parentheses may be the same or different from each other, m2 represents an integer of 0 to 5, and when m2 is 2 or more, a plurality of groups in parentheses may be the same or different from each other, m4 represents an integer of 0 to 5, and when m4 is 2 or more, a plurality of $R^4$ may be the same or different from each other, m5 represents an integer of 0 to 5, and when m5 is 2 or more, a plurality of $R^5$ may be the same or different from each other, m7 represents an integer of 0 to 4, and when m7 is 2 or more, a plurality of $R^7$ may be the same or different from each other, m8 represents an integer of 0 to 5, and when m8 is 2 or more, a plurality of $R^8$ may be the same or different from each other, in which $1 \leq m1+m7 \leq 5$, $0 \leq m2+m8 \leq 5$, $X^0$ represents a single bond or a hydrocarbon group having 1 to 72 carbon atoms which may have a substituent, and —$CH_2$— included in the hydrocarbon group may be replaced by —O—, —S—, —CO— or —$SO_2$—, $R^{bb1}$ represents a hydrogen atom, a halogen atom, or an alkyl group having 1 to 6 carbon atoms which may have a halogen atom, $X^{10}$ represents a single bond, *—O—**, *—CO—O—**, *—O—CO—O—** or *-Ax-Ph-Ay-**, Ph represents a phenylene group which may have a substituent, Ax represents a single bond, an ether bond, an ester bond or a carbonic acid ester bond, Ay represents a single bond, an ether bond, an ester bond or a carbonic acid ester bond,

* represents a bonding site to carbon atoms to which $R^{bb1}$ is bonded,

** represents a bonding site to $L^{10}$, and $L^{10}$ represents a single bond or a hydrocarbon group having 1 to 36 carbon atoms which may have a substituent, and a —$CH_2$— included in each of the hydrocarbon group may be replaced by —O—, —S—, —$SO_2$— or —CO—.

Some embodiments are resist compositions comprising a salt represented by above formula (I).

Some embodiments are resist compositions comprising a resin including a structural unit represented by above formula (IP).

Some embodiments are methods for producing a resist pattern, which comprises:

(1) a step of applying the resist compositions comprising the salt represented by formula (I) and/or the resin including a structural unit represented by above formula (IP).

It is possible to produce a resist pattern with satisfactory mask error factor (MEF) by using a resist composition which uses a carboxylate of the present disclosure.

DETAILED DESCRIPTION

In the present specification, "(meth)acrylic monomer" means "at least one of acrylic monomer and methacrylic monomer". Notations such as "(meth)acrylate" and "(meth) acrylic acid" have the same meaning. In groups mentioned in the present specification, regarding groups capable of having both a linear structure and a branched structure, they may have either the linear or branched structure. When —$CH_2$— included in the hydrocarbon group or the like is replaced by —O—, —S—, —CO— or —$SO_2$—, the same examples shall apply for each group. "Combined group" means a group in which two or more exemplified groups are bonded, and valences of those groups may be appropriately varied by bonding forms. "Derived" means that a polymerizable C═C bond included in the molecule becomes a —C—C— group by polymerization. When stereoisomers exist, all stereoisomers are included.

In the present specification, "solid component of the resist composition" means the total amount of components in which the below-mentioned solvent (E) is removed from the total amount of the resist composition.

[Carboxylate Represented by Formula (I)]

The present disclosure relates to a carboxylate represented by formula (I) (hereinafter sometimes referred to as "salt (I)").

Of the salt (I), the side having negative charge is sometimes referred to as "anion (I)", and the side having positive charge is sometimes referred to as "cation (I)".

[Cation (I)]

The cation (I) of the salt represented by formula (I) is a cation represented by formula (I-C).

(I-C)

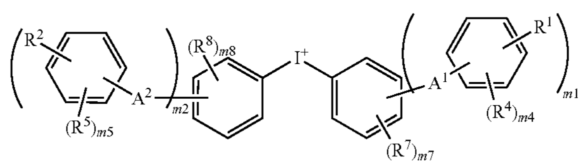

wherein, in formula (I-C), all symbols are the same as defined in formula (I).

Examples of the halogen atom as for $R^4$, $R^5$, $R^7$ and $R^8$ include a fluorine atom, a chlorine atom, a bromine atom and an iodine atom.

The haloalkyl group having 1 to 12 carbon atoms in $R^4$, $R^5$, $R^7$ and $R^8$ represents an alkyl group having 1 to 12 carbon atoms which has a halogen atom, and examples thereof include an alkyl fluoride group having 1 to 12 carbon atoms, an alkyl chloride group having 1 to 12 carbon atoms, an alkyl bromide group having 1 to 12 carbon atoms, an alkyl iodide group having 1 to 12 carbon atoms and the like. Examples of the haloalkyl group include a perfluoroalkyl group having 1 to 12 carbon atoms (a trifluoromethyl group, a pentafluoroethyl group, a heptafluoropropyl group, a nonafluorobutyl group, etc.), a 2,2,2-trifluoroethyl group, a 3,3,3-trifluoropropyl group, a 4,4,4-trifluorobutyl group, a 3,3,4,4,4-pentafluorobutyl group, a chloromethyl group, a bromomethyl group, a fluoromethyl group, a difluoromethyl group, a trifluoromethyl group, a perfluorobutyl group and the like. In some embodiments, the number of carbon atoms of the haloalkyl group is preferably 1 to 9, more preferably 1 to 6, still more preferably 1 to 4, and yet more preferably 1 to 3.

Examples of the hydrocarbon group having 1 to 18 carbon atoms as for $R^4$, $R^5$, $R^7$ and $R^8$ include a chain hydrocarbon group such as an alkyl group and alkanediyl group, an alicyclic hydrocarbon group, an aromatic hydrocarbon group, and groups formed by combining these groups.

Examples of the alkyl group include linear or branched alkyl groups, for example, alkyl groups such as a methyl group, an ethyl group, a propyl group, an isopropyl group, a butyl group, an isobutyl group, a tert-butyl group, a pentyl group, a hexyl group, an octyl group and a nonyl group.

Example of the alkanediyl group included a linear or branched alkanediyl group, liner alkanediyl group includes a methylene group, an ethylene group, a propane-1,3-diyl group, a butane-1,4-diyl group, a pentane-1,5-diyl group and a hexane-1,6-diyl, a branched alkanediyl group includes ethane-1,1-diyl group, propane-1,1-diyl group, propane-1,2-diyl group, propane-2,2-diyl group, pentane-2,4-diyl group, 2-methylpropane-1,3-diyl group, 2-methylpropane-1,2-diyl group, pentane-1,4-diyl group, 2-methylbutane-1,4-diyl group.

In some embodiments, the number of carbon atoms of the chain hydrocarbon group is preferably 1 to 12, more preferably 1 to 9, still more preferably 1 to 6, yet more preferably 1 to 4, and further preferably 1 to 3. The alicyclic hydrocarbon group may be either monocyclic or polycyclic, and examples of the alicyclic hydrocarbon group include groups shown below. The bonding site can be any position in groups shown below.

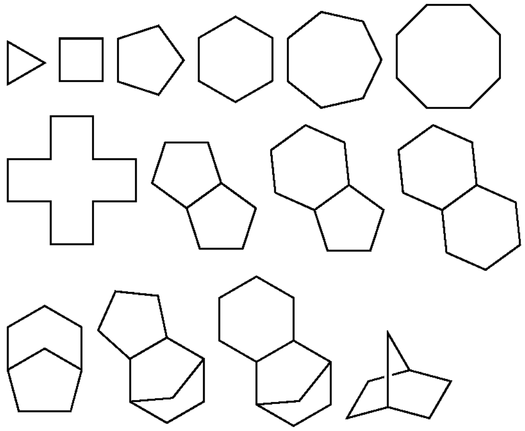

-continued

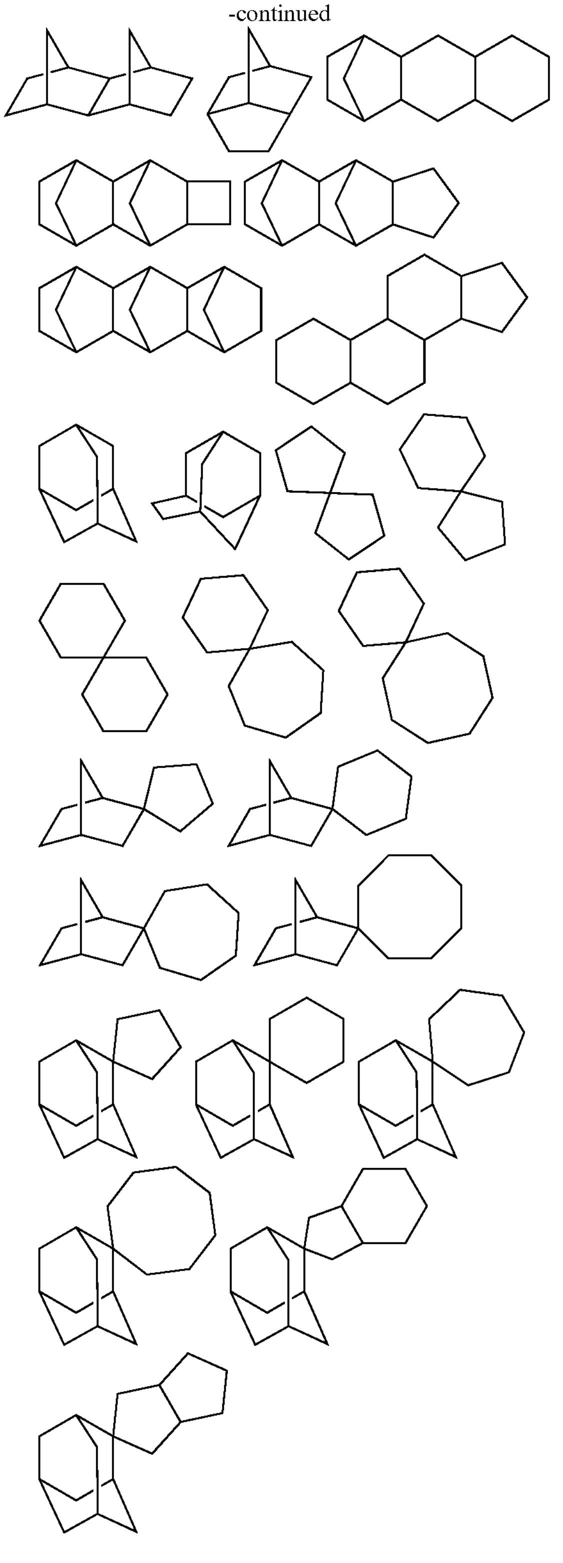

In some embodiments, examples of the monocyclic alicyclic hydrocarbon group include cycloalkyl groups such as a cyclopropyl group, a cyclobutyl group, a cyclopentyl group, a cyclohexyl group, a cycloheptyl group, a cyclooctyl group and a cyclodecyl group. Examples of the polycyclic alicyclic hydrocarbon group include a decahydronaphthyl group, an adamantyl group, a norbornyl group and the like. In some embodiments, the number of carbon atoms of the alicyclic hydrocarbon group is preferably 3 to 18, more preferably 3 to 16, and still more preferably 3 to 12.

Examples of the aromatic hydrocarbon group include a phenyl group, a naphthyl group, a biphenyl group, an anthryl group, a phenanthryl group, a binaphthyl group and the like. In some embodiments, the number of carbon atoms of the aromatic hydrocarbon group is preferably 6 to 18, more preferably 6 to 14, and still more preferably 6 to 10.

Examples of the group formed by combining two or more groups selected from chain hydrocarbon groups, alicyclic hydrocarbon groups, and aromatic hydrocarbon groups include groups formed by combining an aromatic hydrocarbon group with a chain hydrocarbon group (e.g., the aromatic hydrocarbon group-alkanediyl group-*, the alkyl group-aromatic hydrocarbon group-*, and the alkyl group-aromatic hydrocarbon group-alkanediyl group-*, wherein a $—CH_2—$ included in the alkanediyl group and the alkyl group may be replaced by —O—, —CO—, —S— or $—SO_2—$), groups formed by combining an alicyclic hydrocarbon group with a chain hydrocarbon group (e.g., the alicyclic hydrocarbon group-alkanediyl group-*, the alkyl group-alicyclic hydrocarbon group-*, and the alkyl group-alicyclic hydrocarbon group-alkanediyl group-*, wherein a $—CH_2—$ included in the alkanediyl group and the alkyl group may be replaced by —O—, —CO—, —S— or $—SO_2—$) and groups formed by combining an aromatic hydrocarbon group with an alicyclic hydrocarbon group (e.g., an aromatic hydrocarbon group-alicyclic hydrocarbon group-*, an alicyclic hydrocarbon group-aromatic hydrocarbon group-*). * represents a bonding site.

Examples of the aromatic hydrocarbon group-alkanediyl group-* include aralkyl groups such as a benzyl group and a phenethyl group.

Examples of the alkyl group-aromatic hydrocarbon group-* include a tolyl group, a xylyl group, a cumenyl group and the like.

Examples of the alicyclic hydrocarbon group-alkanediyl group-* include cycloalkylalkyl groups such as a cyclohexylmethyl group, a cyclohexylethyl group, a 1-(adamantan-1-yl)methyl group and 1-(adamantan-1-yl)-1-methylethyl group.

Examples of the alkyl group-alicyclic hydrocarbon group-* include cycloalkyl groups having an alkyl group, such as a methylcyclohexyl group, a dimethylcyclohexyl group and a 2-alkyladamantan-2-yl group.

Examples of the aromatic hydrocarbon group-alicyclic hydrocarbon group-* include a phenylcyclohexyl group and the like.

Examples of the alicyclic hydrocarbon group-aromatic hydrocarbon group-* include a cyclohexylphenyl group and the like.

In the group formed by combining two or more groups selected from chain hydrocarbon groups, alicyclic hydrocarbon groups, and aromatic hydrocarbon groups, two or more of alicyclic hydrocarbon groups, aromatic hydrocarbon groups and chain hydrocarbon groups may be respectively combined. Any group of the combined groups may be bonded to the benzene ring.

When a $—CH_2—$ included in the haloalkyl group or hydrocarbon group represented by $R^4$, $R^5$, $R^7$ and $R^8$ is replaced by —O—, —CO—, —S— or $—SO_2—$, the number of carbon atoms before replacement is taken as the total number of the haloalkyl group or hydrocarbon group. The number may be either 1, or 2 or more.

Examples of the group in which a $—CH_2—$ included in the haloalkyl group and the hydrocarbon group is replaced by —O—, —CO—, —S— or —$SO_2$— include a hydroxy group (a group in which a —$CH_2$— included in the methyl group is replaced by —O—), a carboxy group (a group in which a —$CH_2$—$CH_2$— included in the ethyl group is replaced by —O—CO—), thiol group (a group in which a —$CH_2$— included in the methyl group is replaced by —S—), an alkoxy group (a group in which a —$CH_2$— at any position included in the alkyl group is replaced by —O—), an alkylthio group (a group in which a —$CH_2$— at any position included in the alkyl group is replaced by —S—), an alkylsulfonyl group (a group in which a —$CH_2$— at any position included in alkyl group is replaced by —$SO_2$—), an alkoxycarbonyl group (a group in which a —$CH_2$—$CH_2$— at any position included in the alkyl group is replaced by —O—CO—), an alkylcarbonyl group (a group in which a —$CH_2$— at any position included in the alkyl group is replaced by —CO—), an alkylcarbonyloxy group (a group in which a —$CH_2$—$CH_2$— at any position included in the alkyl group is replaced by —CO—O—), an oxy group (a group in which a —$CH_2$— included in the methylene group is replaced by —O—), a carbonyl group (a group in which a —$CH_2$— included in the methylene group is replaced by —CO—), a thio group (a group in which a —$CH_2$— at any position included in the methylene group is replaced by —S—), a sulfonyl group (a group in which a —$CH_2$— included in the methylene group is replaced by —$SO_2$—), an alkanediyloxy group (a group in which a —$CH_2$— at any position included in the alkanediyl group is replaced by —O—), an alkanediyloxycarbonyl group (a group in which a —$CH_2$—$CH_2$— at any position included in the alkanediyl group is replaced by —O—CO—), an alkanediylcarbonyl group (a group in which a —$CH_2$— at any position included in the alkanediyl group is replaced by —CO—), an alkanediylcarbonyloxy group (a group in which a —$CH_2$—$CH_2$— at any position included in the alkanediyl group is replaced by —CO—O—), an alkanediylthio group (a group in which a —$CH_2$— at any position included in the alkanediyl group is replaced by —S—), an alkanediylsulfonyl group (a group in which a —$CH_2$— at any position included in the alkanediyl group is replaced by —$SO_2$—), a cycloalkoxy group, a cycloalkylalkoxy group, an alkoxycarbonyloxy group, an aromatic hydrocarbon group-carbonyloxy group, an aromatic hydrocarbon group-carbonyl group, an aromatic hydrocarbon group-oxy group, a haloalkoxy group (a group in which a —$CH_2$— at any position included in the haloalkyl group is replaced by —O—), a haloalkoxycarbonyl group (a group in which a —$CH_2$—$CH_2$— at any position included in the haloalkyl group is replaced by —O—CO—), a haloalkylcarbonyl group (a group in which a —$CH_2$— at any position included in the haloalkyl group is replaced by —CO—), a haloalkylcarbonyloxy group (a group in which a —$CH_2$—$CH_2$— at any position included in the haloalkyl group is replaced by —CO—O—), and a group obtained by combining two or more of these groups.

Examples of the alkoxy group include alkoxy group having 1 to 17 carbon atoms, for example, a methoxy group, an ethoxy group, a propoxy group, a butoxy group, a pentyloxy group, a hexyloxy group, an octyloxy group, a 2-ethylhexyloxy group, a nonyloxy group, a decyloxy group, an undecyloxy group and the like. In some embodiments, the number of carbon atoms of the alkoxy group is preferably 1 to 11, more preferably 1 to 6, still more preferably 1 to 4, and yet more preferably 1 to 3.

Examples of the alkylthio group include alkylthio groups having 1 to 17 carbon atoms, for example, a methylthio group, an ethylthio group, a propylthio group, a butylthio group, a pentylthio group, a hexylthio group, an octylthio group, a 2-ethylhexylthio group, a nonylthio group, a decylthio group and an undecylthio group. In some embodiments, the number of carbon atoms of the alkylthio group is preferably 1 to 11, more preferably 1 to 6, still more preferably 1 to 4, and yet more preferably 1 to 3.

Examples of the alkylsulfonyl group include alkylsulfonyl groups having 1 to 12 carbon atoms, for example, a methylsulfonyl group, an ethylsulfonyl group, a propylsulfonyl group, a butylsulfonyl group, a pentylsulfonyl group, a hexylsulfonyl group, an octylsulfonyl group, a 2-ethylhexylsulfonyl group, a nonylsulfonyl group, a decylsulfonyl group, an undecylsulfonyl group and the like. In some embodiments, the number of carbon atoms of the alkylsulfonyl group is preferably 1 to 11, more preferably 1 to 6, and still more preferably 1 to 4, and yet more preferably 1 to 3.

The alkoxycarbonyl group, the alkylcarbonyl group and the alkylcarbonyloxy group represent a group in which a carbonyl group or a carbonyloxy group is bonded to the above-mentioned alkyl group or alkoxy group.

Examples of the alkoxycarbonyl group include alkoxycarbonyl groups having 2 to 17 carbon atoms, for example, a methoxycarbonyl group, an ethoxycarbonyl group, a butoxycarbonyl group and the like, examples of the alkylcarbonyl group include alkylcarbonyl groups having 2 to 18 carbon atoms, for example, an acetyl group, a propionyl group and a butyryl group, examples of the alkylcarbonyloxy group include alkylcarbonyloxy groups having 2 to 17 carbon atoms, for example, an acetyloxy group, a propionyloxy group, a butyryloxy group and the like. In some embodiments, the number of carbon atoms of the alkoxycarbonyl group is preferably 2 to 11, more preferably 2 to 6, still more preferably 2 to 4, and yet more preferably 2 or 3. In some embodiments, the number of carbon atoms of the alkylcarbonyl group is preferably 2 to 12, more preferably 2 to 6, still more preferably 2 to 4, and yet more preferably 2 or 3. In some embodiments, the number of carbon atoms of the alkylcarbonyloxy group is preferably 2 to 11, more preferably 2 to 6, still more preferably 2 to 4, and yet more preferably 2 or 3.

Examples of the alkanediyloxy group include alkanediyloxy groups having 1 to 17 carbon atoms, for example, a methyleneoxy group, an ethyleneoxy group, a propanediyloxy group, a butanediyloxy group, a pentanediyloxy group and the like. In some embodiments, the number of carbon atoms of the alkanediyloxy group is preferably 1 to 11, more preferably 1 to 6, still more preferably 1 to 4, and yet more preferably 1 to 3.

Examples of the alkanediyloxycarbonyl group include alkanediyloxycarbonyl groups having 2 to 17 carbon atoms, for example, a methyleneoxycarbonyl group, an ethyleneoxycarbonyl group, a propanediyloxycarbonyl group, a butanediyloxycarbonyl group and the like. Examples of the alkanediylcarbonyl group include alkanediylcarbonyl groups having 2 to 17 carbon atoms, for example, a methylenecarbonyl group, an ethylenecarbonyl group, a propanediylcarbonyl group, a butanediylcarbonyl group, a pentanediylcarbonyl group and the like. Examples of the alkanediylcarbonyloxy group include alkanediylcarbonyloxy groups having 2 to 17 carbon atoms, for example, a methylenecarbonyloxy group, an ethylenecarbonyloxy group, a propanediylcarbonyloxy group, a butanediylcarbonyloxy group and the like. In some embodiments, the number of carbon atoms of the alkanediyloxycarbonyl group is preferably 2 to 11, more preferably 2 to 6, still more preferably 2 to 4, and yet more preferably 2 or 3. In some embodiments, the number of carbon atoms of the alkanediylcarbonyl group is preferably 2 to 12, more preferably 2 to 6, still more preferably 2 to 4, and yet more preferably 2 or 3. In some embodiments, the number of carbon atoms of the alkanediylcarbonyloxy group is preferably 2 to 11, more preferably 2 to 6, still more preferably 2 to 4, and yet more preferably 2 or 3.

Examples of the alkanediylthio group include alkanediylthio groups having 1 to 17 carbon atoms, for example, a methylenethio group, an ethylenethio group, a propylenethio group and the like. In some embodiments, the number of carbon atoms of the alkanediylthio group is preferably 1 to 11, more preferably 1 to 6, still more preferably 1 to 4, and yet more preferably 1 to 3.

Examples of the alkanediylsulfonyl group include alkanediylsulfonyl groups having 1 to 18 carbon atoms, for example, a methylenesulfonyl group, an ethylenesulfonyl group, a propylenesulfonyl group and the like. In some embodiments, the number of carbon atoms of the alkanediylsulfonyl group is preferably 1 to 11, more preferably 1 to 6, still more preferably 1 to 4, and yet more preferably 1 to 3.

Examples of the cycloalkoxy group include cycloalkoxy groups having 3 to 17 carbon atoms, for example, a cyclohexyloxy group and the like. Examples of the cycloalkylalkoxy group include cycloalkylalkoxy groups having 4 to 18 carbon atoms, for example, a cyclohexylmethoxy group and the like. Examples of the alkoxycarbonyloxy group include alkoxycarbonyloxy group having 2 to 16 carbon atoms, for example, a butoxycarbonyloxy group and the like. Examples of the aromatic hydrocarbon group-carbonyloxy group include aromatic hydrocarbon group-carbonyloxy group having 7 to 18 carbon atoms, for example, a benzoyloxy group and the like. Examples of the aromatic hydrocarbon group-carbonyl group include aromatic hydrocarbon group-carbonyl groups having 7 to 18 carbon atoms, for example, a benzoyl group and the like. Examples of the aromatic hydrocarbon group-oxy group include aromatic hydrocarbon group-oxy groups having 6 to 16 carbon atoms, for example, a phenyloxy group and the like.

Examples of the haloalkoxy group, the haloalkoxycarbonyl group, the haloalkylcarbonyl group and the haloalkylcarbonyloxy group include haloalkoxy groups having 1 to 12 carbon atoms, haloalkoxycarbonyl groups having 2 to 12 carbon atoms, haloalkylcarbonyl groups having 2 to 12 carbon atoms and haloalkylcarbonyloxy groups having 2 to 12 carbon atoms, for example, groups in which one or more hydrogen atoms of the above-mentioned groups are substituted with a halogen atom.

Examples of the group in which a —$CH_2$— included in the alicyclic hydrocarbon group is replaced by O—, —CO—, —S— or —$SO_2$— include groups shown below. The bonding site can be any position in groups shown below.

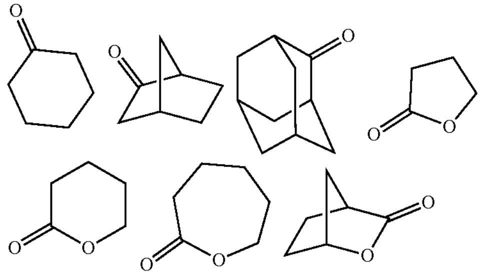

-continued

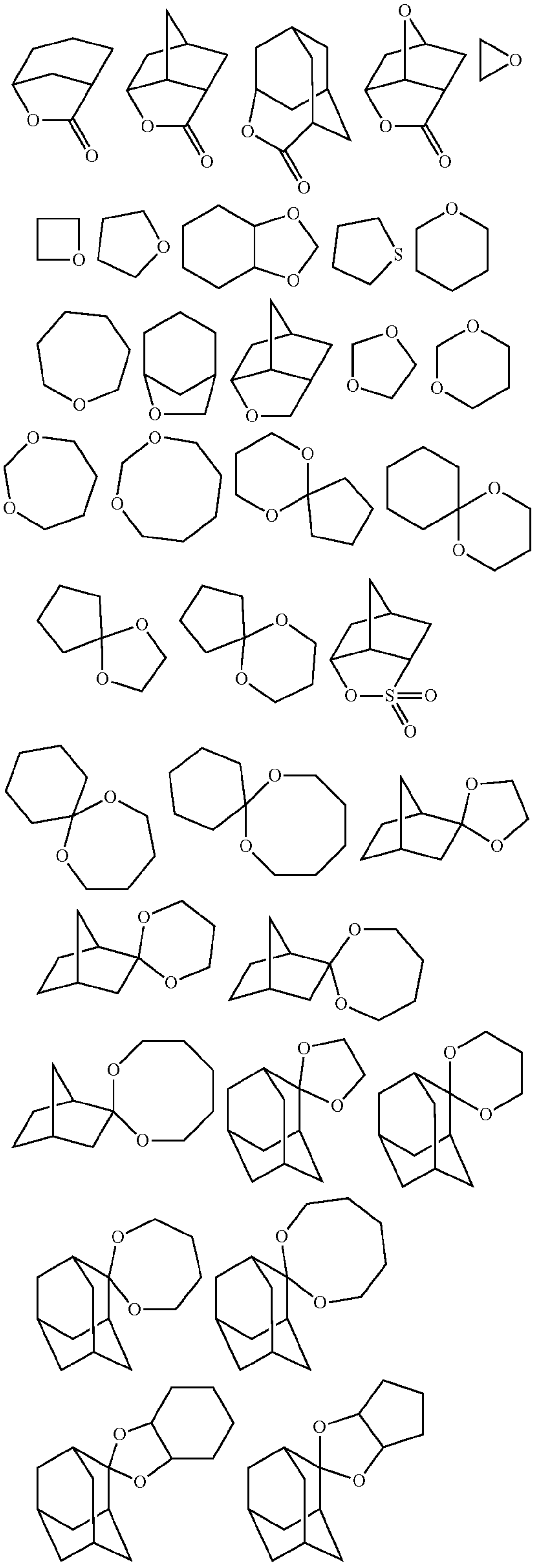

Examples of the substituent which may be possessed by the hydrocarbon group as for $R^4$, $R^5$, $R^7$ and $R^8$ include a halogen atom and a cyano group.

Examples of the halogen atom include the same groups as mentioned above.

The hydrocarbon group may have one substituent or a plurality of substituents.

Examples of the hydrocarbon group as for $A^1$ and $A^2$ include linear or branched chain hydrocarbon groups (e.g., an alkanediyl group, etc.), monocyclic or polycyclic alicyclic hydrocarbon groups, aromatic hydrocarbon groups and the like, and the hydrocarbon group may be groups formed by combining two or more of these groups.

Examples of the chain hydrocarbon group include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group; and branched alkanediyl groups such as an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group and a 2-methylbutane-1,4-diyl group.

In some embodiments, the number of carbon atoms of the chain hydrocarbon group is preferably 1 to 18, more preferably 1 to 12, still more preferably 1 to 9, yet more preferably 1 to 6, further preferably 1 to 4, and still further preferably 1 to 3.

The alicyclic hydrocarbon group may be either monocyclic or polycyclic, and examples thereof include groups show below. The bonding site can be any position in groups shown below.

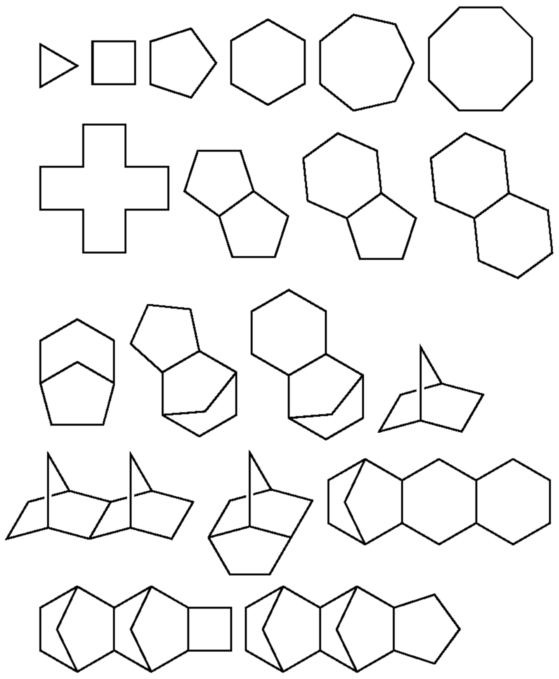

-continued

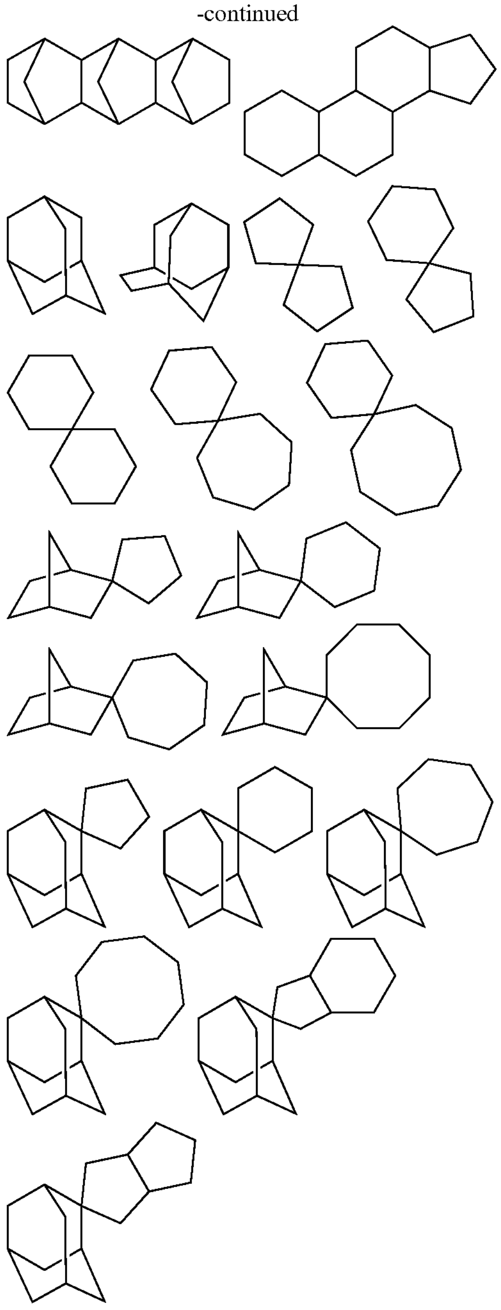

In some embodiments, monoclylic alicyclic hydrocarbon groups includes cycloalkanediyl groups such as a cyclobutane-1,3-diyl group, a cyclopentane-1,3-diyl group, a cyclohexane-1,4-diyl group and a cyclooctane-1,5-diyl group; and polycyclic alicyclic hydrocarbon groups includes a norbornane-1,4-diyl group, a norbornane-2,5-diyl group, an adamantane-1,5-diyl group, an adamantane-2,6-diyl group, and spiro rings having a cycloalkyl group, a norbornyl group or an adamantyl group, and a cycloalkyl group spiro-bonded to each of them, such as spirocyclohexane-1,2'cyclopentane and spiroadamantane-2,3'-cyclopentane groups.

In some embodiments, the number of carbon atoms of the alicyclic hydrocarbon group is preferably 3 to 18, more preferably 3 to 16, still more preferably 3 to 12, and yet more preferably 3 to 10.

Examples of the aromatic hydrocarbon group include aromatic hydrocarbon groups, for example, arylene groups such as a phenylene group, a naphthylene group, an anthrylene group, a biphenylene group and a phenanthrylene group. In some embodiments, the number of carbon atoms of the aromatic hydrocarbon group is preferably 6 to 18, more preferably 6 to 14, and still more preferably 6 to 10.

Examples of the group formed by combining two or more groups selected from chain hydrocarbon groups, alicyclic hydrocarbon groups, and aromatic hydrocarbon groups include groups formed by combining an alicyclic hydrocarbon group with an alkanediyl group, groups formed by combining an aromatic hydrocarbon group with an alkanediyl, and groups formed by combining an alicyclic hydrocarbon group with an aromatic hydrocarbon group. In combination, two or more of chain hydrocarbon groups, alicyclic hydrocarbon groups and aromatic hydrocarbon groups may be respectively combined. Any group may be bonded to the benzene ring.

Examples of the group formed by combining an alicyclic hydrocarbon group with an alkanediyl group include a -divalent alicyclic hydrocarbon group-alkanediyl group-, an -alkanediyl group-divalent alicyclic hydrocarbon group-alkanediyl group-, an -alkanediyl group-divalent alicyclic hydrocarbon group- and the like.

Examples of the group formed by combining an aromatic hydrocarbon group with an alkanediyl group include a -divalent aromatic hydrocarbon group-alkanediyl group-, an -alkanediyl group-divalent aromatic hydrocarbon group-alkanediyl group-, an -alkanediyl group-divalent aromatic hydrocarbon group- and the like.

Examples of the group formed by combining an alicyclic hydrocarbon group with an aromatic hydrocarbon group include an -aromatic hydrocarbon group-alicyclic hydrocarbon group-, an -alicyclic hydrocarbon group-aromatic hydrocarbon group-, an -alicyclic hydrocarbon group-aromatic hydrocarbon group-an alicyclic hydrocarbon group- and the like.

In $A^1$ and $A^2$, when $—CH_2—$ included in the hydrocarbon group is replaced by —O—, —CO—, —S— or $—SO_2—$, the number of carbon atoms before replacement is taken as the total number of the hydrocarbon group. The number may be either 1, or 2 or more, and is preferably 1 to 3.

Examples of the group in which a $—CH_2—$ included in the hydrocarbon group is replaced by —O—, —CO—, —S— or $—SO_2—$ include a hydroxy group (a group in which a $—CH_2—$ included in the methyl group is replaced by —O—), a carboxy group (a group in which $—CH_2—CH_2—$ included in the ethyl group is replaced by —O—CO—), a thiol group (a group in which a $—CH_2—$ included in the methyl group is replaced by —S—), an alkoxy group (a group in which a $—CH_2—$ at any position included in the alkyl group is replaced by —O—), an alkoxycarbonyl group (a group in which a $—CH_2—CH_2—$ at any position included in the alkyl group is replaced by —O—CO—), an alkylcarbonyl group (a group in which a $—CH_2—$ at any position included in the alkyl group is replaced by —CO—), an alkylcarbonyloxy group (a group in which a $—CH_2—CH_2—$ at any position included in the alkyl group is replaced by —CO—O—), an alkylthio group (a group in which a $—CH_2—$ at any position included in the alkyl group is replaced by —S—), alkylsulfonyl group (a group in which a $—CH_2—$ at any position included in the alkyl group is replaced by $—SO_2—$), an oxy group (a group in which a $—CH_2—$ included in the methylene group is replaced by —O—), a carbonyl group (a group in which a $—CH_2—$ included in the methylene group is replaced by —CO—), a thio group (a group in which a $—CH_2—$ included in the methylene group is replaced by —S—), a sulfonyl group (a group in which a $—CH_2—$ included in the methylene group is replaced by $—SO_2—$), an alkanediyloxy group (a group in which a $—CH_2—$ at any position included in the alkanediyl group is replaced by —O—), an alkanediyloxycarbonyl group (a group in which a $—CH_2—CH_2—$ at any position included in the alkanediyl group is replaced by —O—CO—), an alkanediylcarbonyl group (a group in which a $—CH_2—$ at any position included in the alkanediyl group is replaced by —CO—), an alkanediylcarbonyloxy group (a group in which a $—CH_2—CH_2—$ at any position included in the alkanediyl group is replaced by —CO—O—), an alkanediylsulfonyl group (a group in which $—CH_2—$ at any position included in the alkanediyl group is replaced by $—SO_2—$), an alkanediylthio group (a group in which $—CH_2—$ at any position included in the alkanediyl group is replaced by —S—), a cycloalkoxy group, a cycloalkylalkoxy group, an alkoxycarbonyloxy group, an aromatic hydrocarbon group-carbonyloxy group, a group obtained by combining two or more groups of these groups, and the like.

Examples of the alkoxy group include alkoxy groups having 1 to 20 carbon atoms, for example, a methoxy group, an ethoxy group, a propoxy group, a butoxy group, a pentyloxy group, a hexyloxy group, an octyloxy group, a 2-ethylhexyloxy group, a nonyloxy group, a decyloxy group, an undecyloxy group and the like. The number of carbon atoms of the alkoxy group is preferably 1 to 11, more preferably 1 to 6, still more preferably 1 to 4, and yet more preferably 1 to 3.

The alkoxycarbonyl group, the alkylcarbonyl group and the alkylcarbonyloxy group represent a group in which a carbonyl group or a carbonyloxy group is bonded to the above-mentioned alkyl group or alkoxy group.

Examples of the alkoxycarbonyl group include alkoxycarbonyl groups having 2 to 20 carbon atoms, for example, a methoxycarbonyl group, an ethoxycarbonyl group, a butoxycarbonyl group and the like. Examples of the alkylcarbonyl group include alkylcarbonyl groups having 2 to 20 carbon atoms, for example, an acetyl group, a propionyl group and a butyryl group. Examples of the alkylcarbonyloxy group include alkylcarbonyloxy groups having 2 to 20 carbon atoms, for example, an acetyloxy group, a propionyloxy group, a butyryloxy group and the like. The number of carbon atoms of the alkoxycarbonyl group is preferably 2 to 11, more preferably 2 to 6, still more preferably 2 to 4, and yet more preferably 2 or 3. In some embodiments, the number of carbon atoms of the alkylcarbonyl group is preferably 2 to 12, more preferably 2 to 6, still more preferably 2 to 4, and yet more preferably 2 or 3. The number of carbon atoms of the alkylcarbonyloxy group is preferably 2 to 11, more preferably 2 to 6, still more preferably 2 to 4, and yet more preferably 2 or 3.

Examples of the alkylthio group include alkylthio groups having 1 to 20 carbon atoms, for example, a methylthio group, an ethylthio group, a propylthio group, a butylthio group and the like. In some embodiments, the number of carbon atoms of the alkylthio group is preferably 1 to 11, more preferably 1 to 6, still more preferably 1 to 4, and yet more preferably 1 to 3.

Examples of the alkylsulfonyl group include alkylsulfonyl groups having 1 to 20 carbon atoms, for example, a methylsulfonyl group, an ethylsulfonyl group, a propylsulfonyl group and the like. In some embodiments, the number of carbon atoms of the alkylsulfonyl group is preferably 1 to 11, more preferably 1 to 6, still more preferably 1 to 4, and yet more preferably 1 to 3.

Examples of the alkanediyloxy group include alkanediyloxy group having 1 to 20 carbon atoms, for example, a methyleneoxy group, an ethyleneoxy group, a propanediyloxy group, a butanediyloxy group, a pentanediyloxy group and the like. In some embodiments, the number of carbon atoms of the alkanediyloxy group is preferably 1 to 11, more preferably 1 to 6, still more preferably 1 to 4, and yet more preferably 1 to 3.

Examples of the alkanediyloxycarbonyl group include alkanediyloxycarbonyl groups having 2 to 20 carbon atoms, for example, a methyleneoxycarbonyl group, an ethyleneoxycarbonyl group, a propanediyloxycarbonyl group, a butanediyloxycarbonyl group and the like. Examples of the alkanediylcarbonyl group include alkanediylcarbonyl groups having 2 to 20 carbon atoms, for example, a methylenecarbonyl group, an ethylenecarbonyl group, a propanediylcarbonyl group, a butanediylcarbonyl group, a pentanediylcarbonyl group and the like. Examples of the alkanediylcarbonyloxy group include alkanediylcarbonyloxy groups having 2 to 20 carbon atoms, for example, a methylenecarbonyloxy group, an ethylenecarbonyloxy group, a propanediylcarbonyloxy group, a butanediylcarbonyloxy group and the like. The number of carbon atoms of the alkanediyloxycarbonyl group is preferably 2 to 11, more preferably 2 to 6, still more preferably 2 to 4, and yet more preferably 2 or 3. In some embodiments, the number of carbon atoms of the alkanediylcarbonyl group is preferably 2 to 12, more preferably 2 to 6, still more preferably 2 to 4, and yet more preferably 2 or 3. In some embodiments, the number of carbon atoms of the alkanediylcarbonyloxy group is preferably 2 to 11, more preferably 2 to 6, still more preferably 2 to 4, and yet more preferably 2 or 3.

Examples of the alkanediylsulfonyl group include alkanediylsulfonyl groups having 1 to 20 carbon atoms, for example, a methylenesulfonyl group, an ethylenesulfonyl group, a propylenesulfonyl group and the like. In some embodiments, the number of carbon atoms of the alkanediylsulfonyl group is preferably 1 to 11, more preferably 1 to 6, still more preferably 1 to 4, and yet more preferably 1 to 3.

Examples of the alkanediylthio group include alkanediylthio groups having 1 to 20 carbon atoms, for example, a methylenethio group, an ethylenethio group, a propylenethio group and the like. In some embodiments, the number of carbon atoms of the alkanediylthio group is preferably 1 to 11, more preferably 1 to 6, still more preferably 1 to 4, and yet more preferably 1 to 3.

Examples of the cycloalkoxy group include cycloalkoxy group having 3 to 20 carbon atoms, for example, a cyclohexyloxy group and the like. Examples of the cycloalkylalkoxy group include cycloalkylalkoxy groups having 4 to 17 carbon atoms, for example, a cyclohexylmethoxy group and the like. Examples of the alkoxycarbonyloxy group include alkoxycarbonyloxy groups having 2 to 16 carbon atoms, for example, a butoxycarbonyloxy group and the like.

Examples of the aromatic hydrocarbon group-carbonyloxy group include aromatic hydrocarbon group-carbonyloxy groups having 7 to 20 carbon atoms, for example, a benzoyloxy group and the like.

Examples of the group in which a —$CH_2$— included in the alicyclic hydrocarbon group is replaced by —O—, —CO—, —S— or —$SO_2$— include groups shown below. Examples of the group also include groups in which —O— is replaced by —S— and —CO— is replaced by —$SO_2$—, respectively, among the groups shown below. The bonding site can be any position in groups shown below.

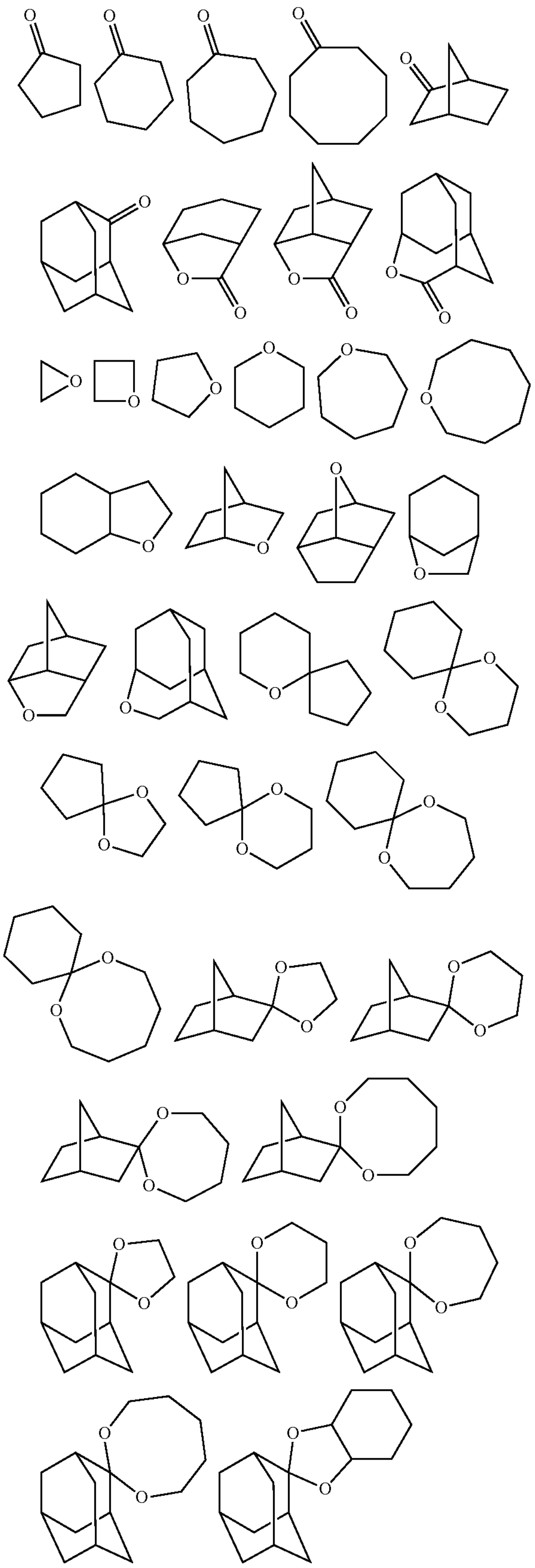

-continued

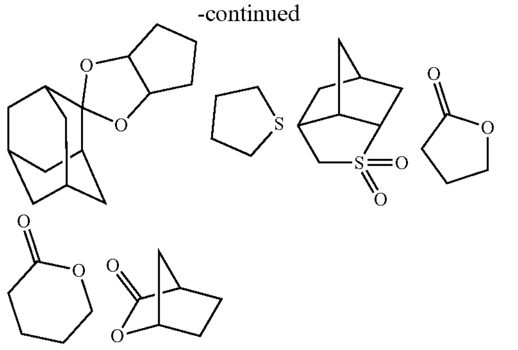

Examples of the substituent which may be possessed by the hydrocarbon group as for $A^1$, $A^2$ and $A^3$ include the same groups as mentioned for the substituent which may be possessed by the hydrocarbon group as for $R^4$ and $R^5$.

In some embodiments, it is preferable that $A^1$ and $A^2$ are each independently a hydrocarbon group having 1 to 20 carbon atoms (the hydrocarbon group may have a substituent, and at least one of a —$CH_2$— included in the hydrocarbon group may be replaced by —O—, —CO—, —S— or —$SO_2$—). In some embodiments, it is preferable that $A^1$ is *-$L^{011}$-$X^{01}$-$L^{012}$- and $A^2$ is *-$L^{021}$-$X^{02}$-$L^{022}$- ($X^{01}$ and $X^{02}$ each independently represent —O—, —CO—, —S— or —$SO_2$—, $L^{011}$, $L^{012}$, $L^{021}$ and $L^{022}$ each independently represent a single bond or a hydrocarbon group having 1 to 18 carbon atoms, in which the total number of carbon atoms of $L^{011}$ and $L^{012}$ is 0 to 18, the total number of carbon atoms of $L^{021}$ and $L^{022}$ is 0 to 18, and * represents a bonding site to the benzene ring to which $I^+$ is bonded), and it is still more preferable that $A^1$ is *—$X^{01}$-$L^{01}$- or *-$L^{01}$-$X^{01}$— and $A^2$ is *—$X^{02}$-$L^{02}$- or *-$L^{02}$-$X^{02}$—($X^{01}$ and $X^{02}$ each independently represent —O—, —CO—, —S— or —$SO_2$—, $L^{01}$ and $L^{02}$ each independently represent a single bond or a hydrocarbon group having 1 to 18 carbon atoms, and * represents a bonding site to the benzene ring to which $I^+$ is bondable). In some embodiments, $A^1$ and $A^2$ are preferably those having no substituent, except for replacement by —O—, —CO—, —S— or —$SO_2$—.

Examples of the hydrocarbon group having 1 to 18 carbon atoms as for $L^{011}$, $L^{02}$, $L^{021}$, $L^{022}$, $L^{01}$ and $L^{02}$ (the hydrocarbon group may have a substituent, and a —$CH_2$— included in the hydrocarbon group may be replaced by —O—, —CO—, —S— or —$SO_2$—) include the same groups as mentioned for $A^1$ and $A^2$ in the range of the number of carbon atoms of 1 to 18.

In some embodiments, $X^{01}$ and $X^{02}$ are each independently —O— or —S—, and more preferably —O—.

In some embodiments, $L^{011}$, $L^{012}$, $L^{021}$, $L^{022}$, $L^{01}$ and $L^{02}$ are each independently a single bond, a hydrocarbon group having 1 to 12 carbon atoms (a —$CH_2$— included in the hydrocarbon group may be replaced by —O—, —CO—, —S— or —$SO_2$—), preferably a single bond, a chain hydrocarbon group having 1 to 9 carbon atoms (a —$CH_2$— included in the chain hydrocarbon group may be replaced by —O—, —CO—, —S— or —$SO_2$—), more preferably a single bond, an alkanediyl group having 1 to 6 carbon atoms (a —$CH_2$— included in the alkanediyl group may be replaced by —O— or —CO—), yet more preferably a single bond, an alkanediyl group having 1 to 4 carbon atoms (a —$CH_2$— included in the alkanediyl group may be replaced by —O— or —CO—), and further preferably a single bond, an alkanediyl group having 1 to 3 carbon atoms (a —$CH_2$— included in the alkanediyl group may be replaced by —O— or —CO—). Of these, a single bond, a methylene group, an ethane-1,1-diyl group, a propane-1,1-diyl group, a propane-2,2-diyl group, a carbonyl group, a carbonyloxy group, a carbonyloxymethylene group, an ethyleneoxy group, a methylenecarbonyloxymethylene group or an ethyleneoxycarbonyl group is preferable, and a single bond, a methylene group or a carbonyl group is more preferable.

In some embodiments, the bonding site of $A^1$ and $A^2$ to the benzene ring to which $I^+$ is bonded may be the o-position, the m-position or the p-position, with respect to the site at which $I^+$ is bonded. Particularly, it is bonded preferably at the p-position or the m-position, and more preferably at the p-position, with respect to the bonding site of $I^+$.

In some embodiments, m1 is preferably 1 or 2.

In some embodiments, m2 is preferably 0, 1 or 2.

In some embodiments, m4 is preferably 0, 1, 2, 4 or 5.

In some embodiments, m5 is preferably 0 or 1.

In some embodiments, m7 is preferably 0, 1 or 2, and more preferably 0 or 1.

In some embodiments, m8 is preferably 1 or 2.

In some embodiments, $R^4$ and $R^5$ are each independently preferably an iodine atom, a fluorine atom, a hydroxy group, a haloalkyl group having 1 to 6 carbon atoms or an alkyl group having 1 to 6 carbon atoms (a —$CH_2$— included in the haloalkyl group and the alkyl group may be replaced by —O— or —CO—), more preferably an iodine atom, a fluorine atom, a hydroxy group, an alkyl group having 1 to 4 carbon atoms, a haloalkyl group having 1 to 4 carbon atoms or an alkoxy group having 1 to 3 carbon atoms, still more preferably an iodine atom, a fluorine atom, a hydroxy group or an alkoxy group having 1 to 3 carbon atoms, and yet more preferably an iodine atom, a fluorine atom or a hydroxy group.

In some embodiments, the bonding site of $R^4$ and $R^5$ to the benzene ring may be each independently the o-position, the m-position or the p-position with respect to the bonding site of $A^1$ and $A^2$. Particularly, when m4 and m5 are 1, $R^4$ and $R^5$ are each independently bonded preferably at the p-position or the m-position, and more preferably at the p-position, with respect to the bonding site of $A^1$ and $A^2$. When m4 and m5 are 2, it is preferable that one of $R^4$ and $R^5$ is each independently bonded at the o-position or the m-position and one of them is each independently bonded at the p-position or the m-position, with respect to the bonding site of $A^1$ and $A^2$, and it is more preferable that two of $R^4$ and $R^5$ are each independently bonded at the m-position, with respect to the bonding site of $A^1$ and $A^2$. When m4 and m5 are 3, it is preferable that two of $R^4$ and $R^5$ are each independently bonded at the o-position or the m-position and one of them is each independently bonded at the p-position or the m-position, with respect to the bonding site of $A^1$ and $A^2$, and it is more preferable that two of $R^4$ and $R^5$ are each independently bonded at the m-position and one of them is each independently bonded at the p-position, with respect to the bonding site of $A^1$ and $A^2$. When m4 and m5 are 4, it is preferable that two of $R^4$ and $R^5$ are each independently bonded at the o-position or the m-position and two of them are each independently bonded at the p-position or the m-position, with respect to the bonding site of $A^1$ and $A^2$, and it is more preferable that two of $R^4$ and $R^5$ are each independently bonded at the m-position, one of them is each independently bonded at the o-position and one of them is each independently bonded at the p-position, with respect to the bonding site of $A^1$ and $A^2$.

In some embodiments, $R^7$ and $R^8$ are each independently preferably an iodine atom, a fluorine atom, a hydroxy group, a haloalkyl group having 1 to 6 carbon atoms or an alkyl group having 1 to 6 carbon atoms (a —$CH_2$— included in the haloalkyl group and the alkyl group may be replaced by —O— or —CO—), more preferably an iodine atom, a fluorine atom, a hydroxy group, an alkyl group having 1 to 4 carbon atoms, a haloalkyl group having 1 to 4 carbon atoms or an alkoxy group having 1 to 3 carbon atoms, and still more preferably an iodine atom, a fluorine atom, a trifluoromethyl group, an alkyl group having 1 to 4 carbon atoms or an alkoxy group having 1 to 3 carbon atoms.

In some embodiments, the bonding site of $R^7$ and $R^8$ to the benzene ring may be each independently the o-position, the m-position or the p-position with respect to the bonding site of $I^+$. Particularly, when m7 and m8 are 1, $R^7$ and $R^8$ are each independently bonded preferably at the p-position or the m-position, and more preferably at the p-position, with respect to the bonding site of $I^+$. When m7 and m8 are 2, it is preferable that one of $R^7$ and $R^8$ is each independently bonded at the o-position or the m-position and one of them is each independently bonded at the p-position or the m-position, with respect to the bonding site of $I^+$, and it is more preferable that one of $R^7$ and $R^8$ is each independently bonded at the m-position and one of them is each independently bonded at the p-position, with respect to the bonding site of $I^+$. When m7 and m8 are 3, it is preferable that two of $R^7$ and $R^8$ are each independently bonded at the o-position or the m-position and one of them is each independently bonded at the p-position or the m-position, with respect to the bonding site of $I^+$, and it is more preferable that two of $R^7$ and $R^8$ are each independently bonded at the m-position and one of them is each independently bonded at the p-position, with respect to the bonding site of $I^+$. When m7 and m8 are 4, it is preferable that two of $R^7$ and $R^8$ are each independently bonded at the o-position or the m-position and two of them are each independently bonded at the p-position or the m-position, with respect to the bonding site of $I^+$, and it is more preferable that two of $R^7$ and $R^8$ are each independently bonded at the m-position, one of them is each independently bonded at the o-position and one of them is each independently bonded at the p-position, with respect to the bonding site of $I^+$.

In some embodiments, it is preferable that m1 and m2 are 1, or m1 and m2 are 2, respectively.

In some embodiments in which m2=0, it is preferable that m8 is 1 and $R^8$ is a branched alkyl group having 3 or 4 carbon atoms.

In some embodiments in which m4 is 2, it is preferable that one of two $R^4$ (s) is an iodine atom or a fluorine atom and other one is a hydroxy group, and it is more preferable that the hydroxy group is bonded at the p-position, with respect to the bonding site of $I^+$.

In some embodiments, examples of the cation (I) represented by formula (I-C) include a cation represented by formula (I-C-1) (hereinafter sometimes referred to as "cation (I-C-1)"):

(I-C-1)

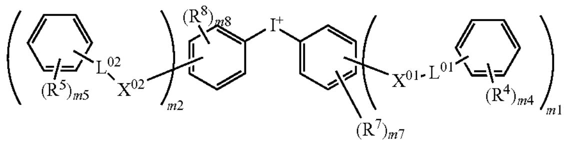

wherein, in formula (I-C-1), symbols $R^1$, $R^2$, $R^4$, $R^5$, $R^7$, $R^8$, m1, m2, m4, m5, m7 and m8 are the same as defined in formula (I), and $L^{01}$, $L^{02}$, $X^{01}$ and $X^{02}$ are the same as defined above.

$X^{01}$ and $X^{12}$ are preferably —O—.

The bonding site of $X^{01}$ and $X^{02}$ to the benzene ring is respectively the same bonding site of $A^1$ and $A^2$ to the benzene ring.

Examples of the cation (I) include the following cations.

(I-c-1)

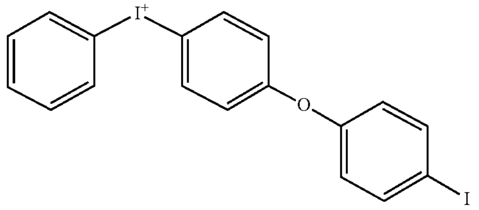

(I-c-2)

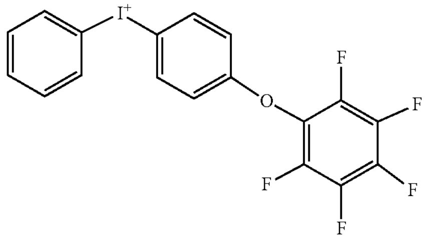

(I-c-3)

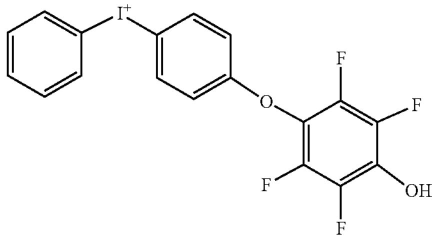

(I-c-4)

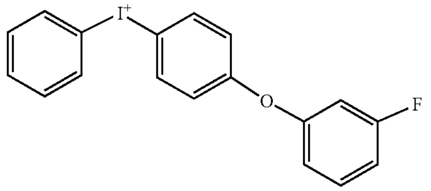

(I-c-5)

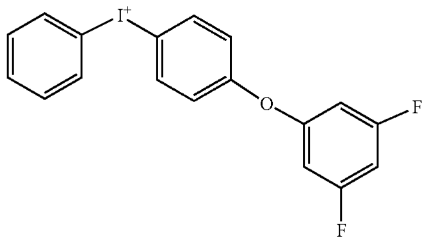

(I-c-6)

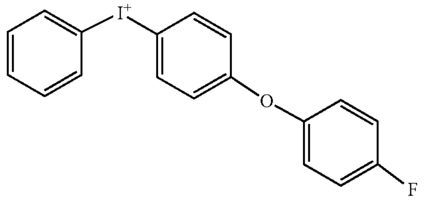

-continued
(I-c-7)
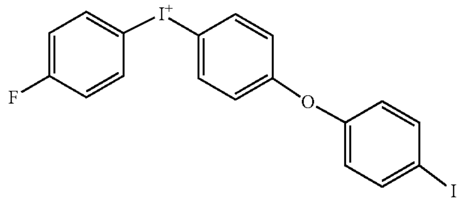
(I-c-8)
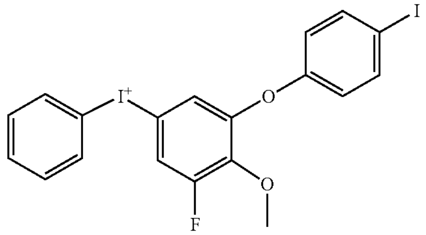
(I-c-9)
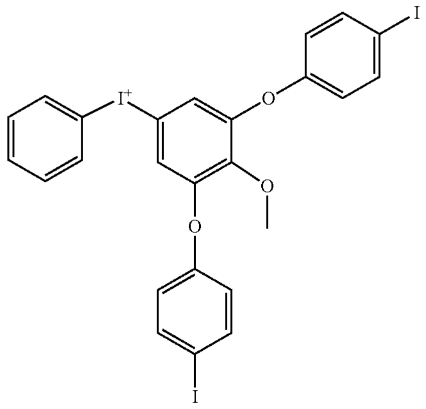
(I-c-10)
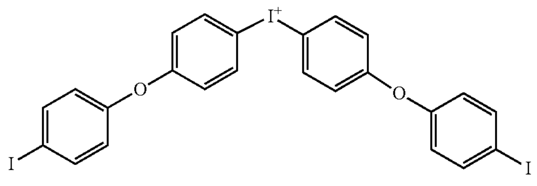
(I-c-11)
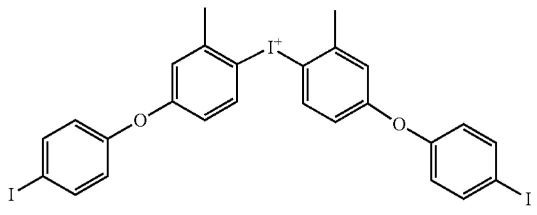
-continued
(I-c-12)
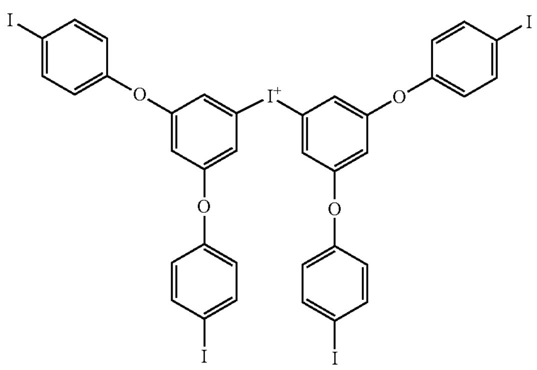
(I-c-13)
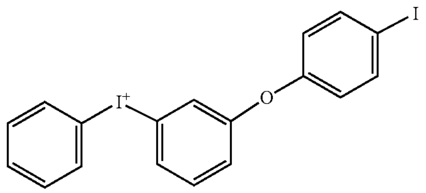
(I-c-14)
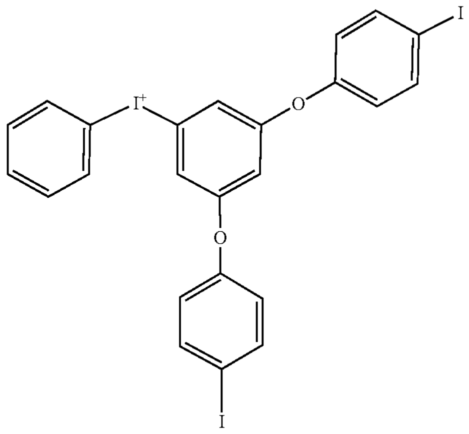
(I-c-15)
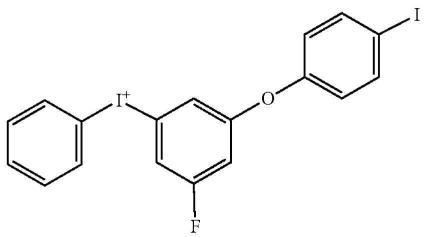
(I-c-16)
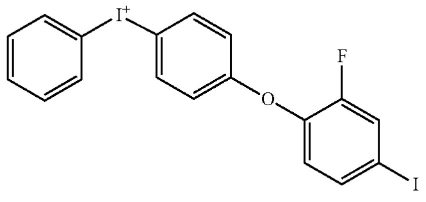

-continued
(I-c-17)
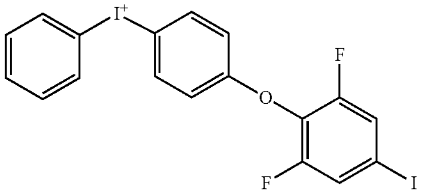
(I-c-18)
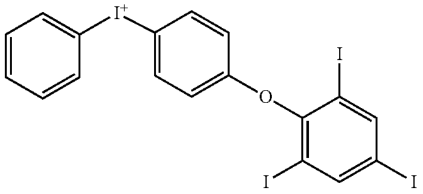
(I-c-19)
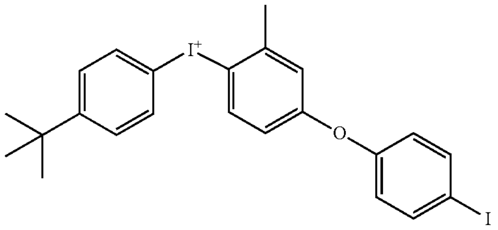
(I-c-20)
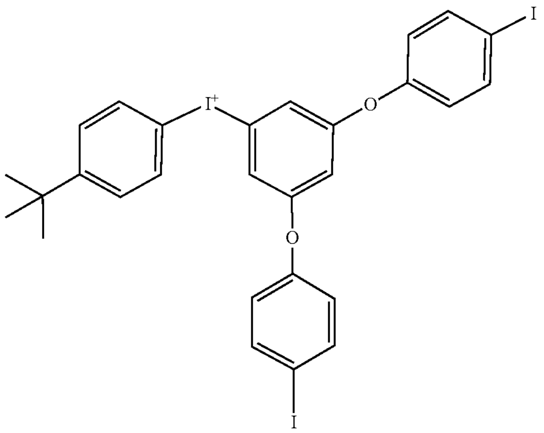
(I-c-21)
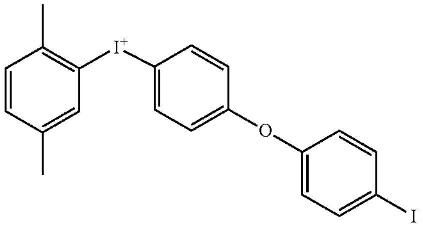
(I-c-22)
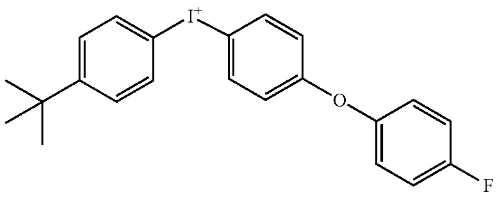
-continued
(I-c-23)
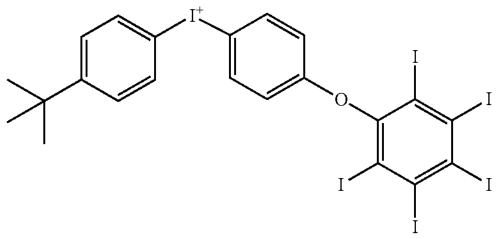
(I-c-24)
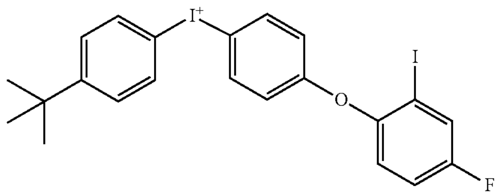
(I-c-25)
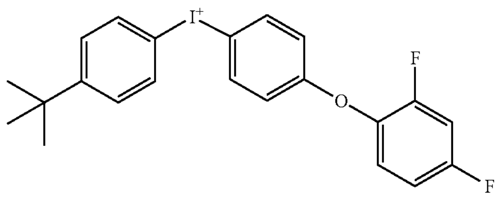
(I-c-26)
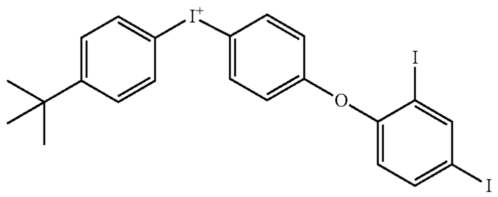
(I-c-27)
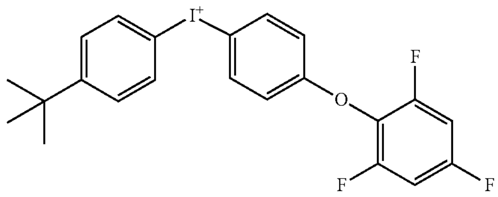
(I-c-28)
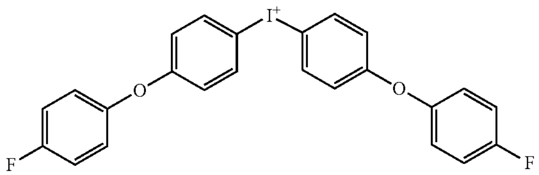
(I-c-29)
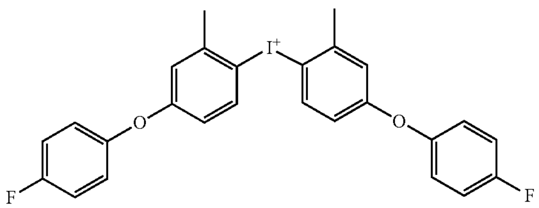

-continued
(I-c-30)
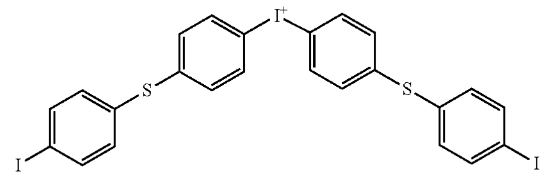
(I-c-31)
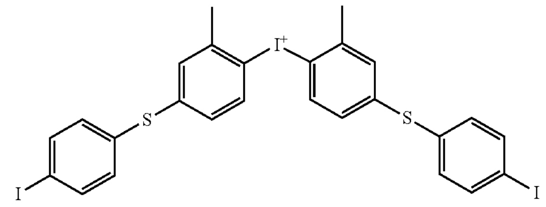
(I-c-32)
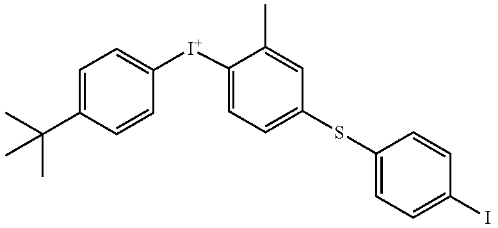
(I-c-33)
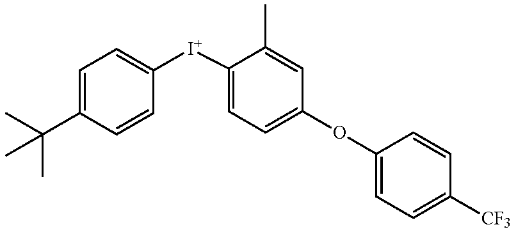
(I-c-34)
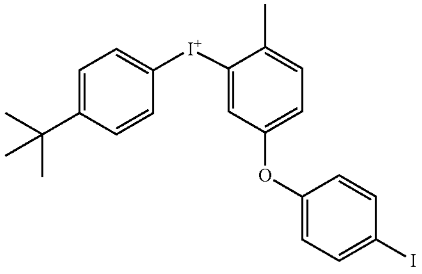
(I-c-35)
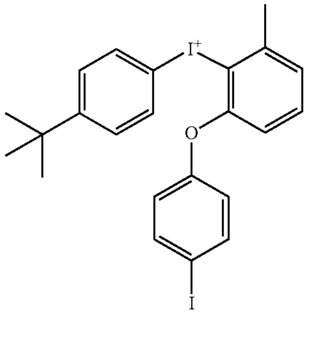
-continued
(I-c-36)
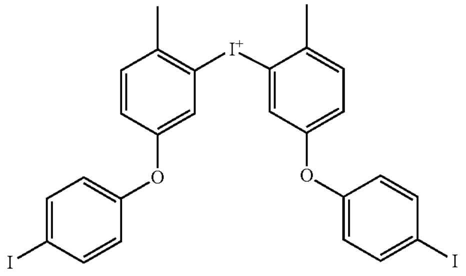
(I-c-37)
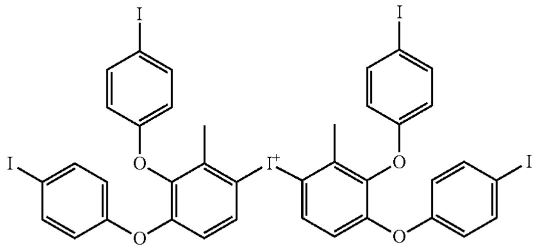
(I-c-38)
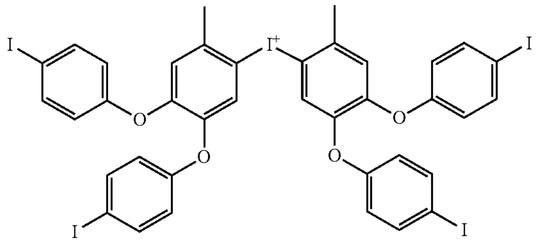
(I-c-39)
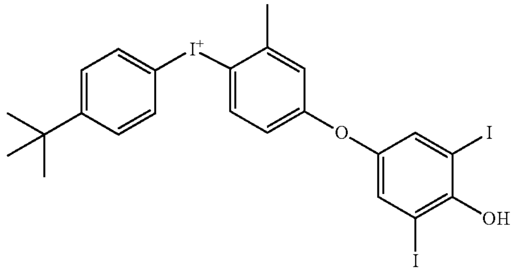
(I-c-40)
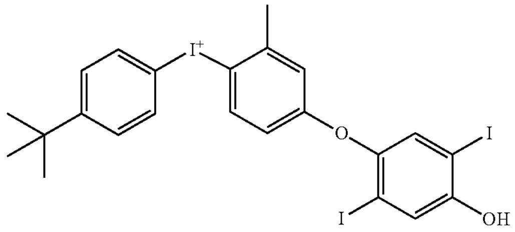

-continued
(I-c-41)
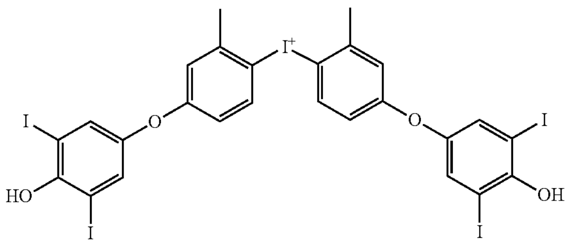
(I-c-42)
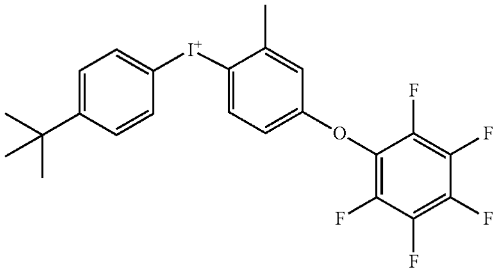
(I-c-43)
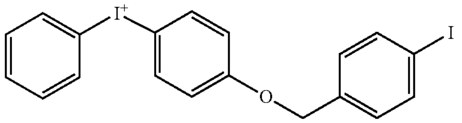
(I-c-44)
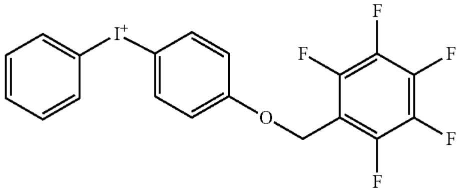
(I-c-45)
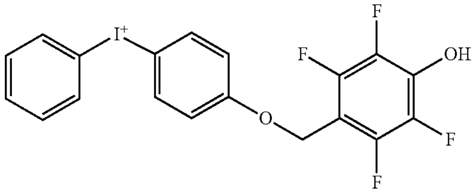
(I-c-46)
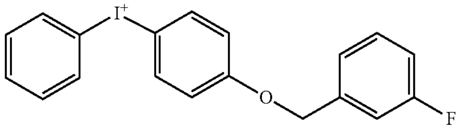
(I-c-47)
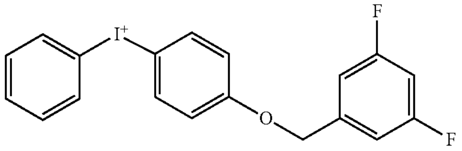
-continued
(I-c-48)
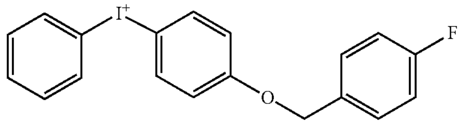
(I-c-49)
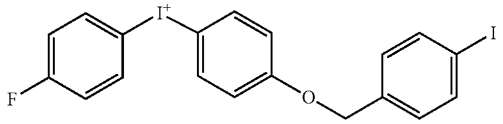
(I-c-50)
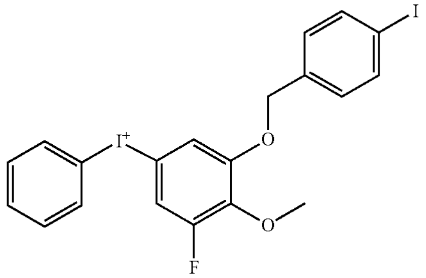
(I-c-51)
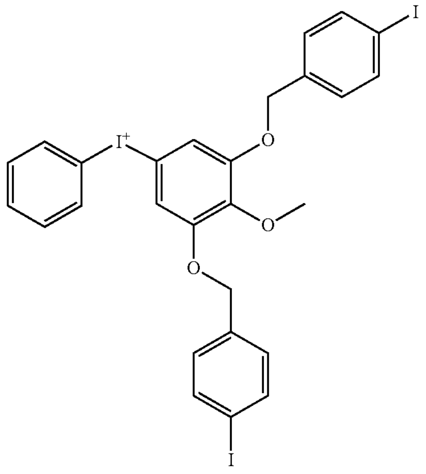
(I-c-52)
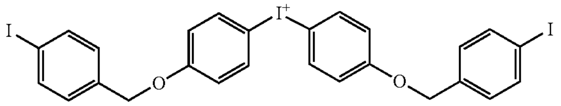
(I-c-53)
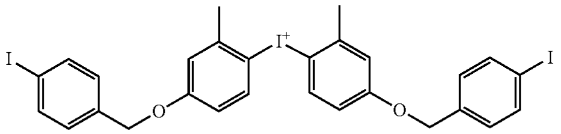

-continued
(I-c-54)
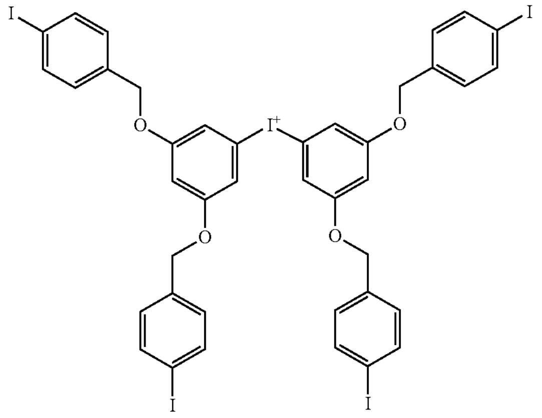
(I-c-55)
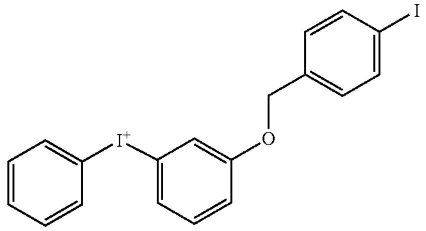
(I-c-56)
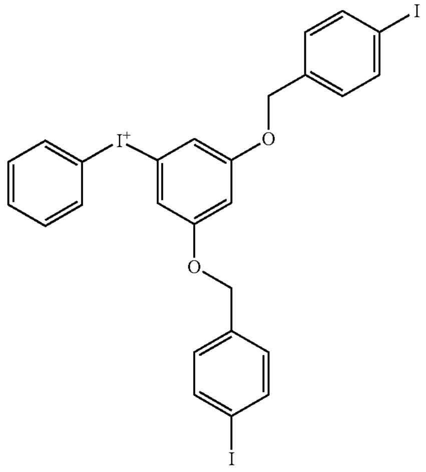
(I-c-57)
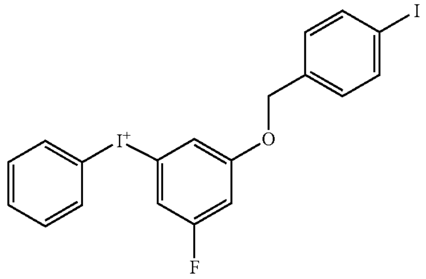
(I-c-58)
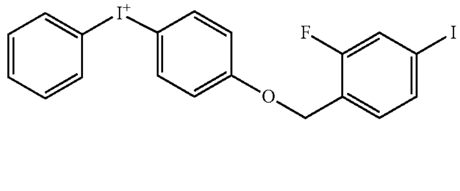
-continued
(I-c-59)
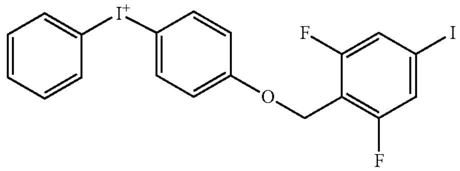
(I-c-60)
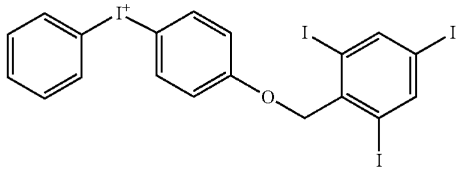
(I-c-61)
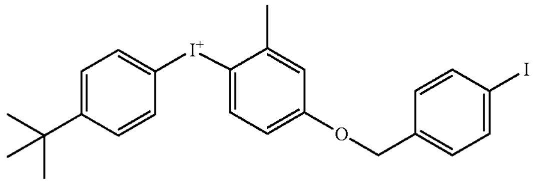
(I-c-62)
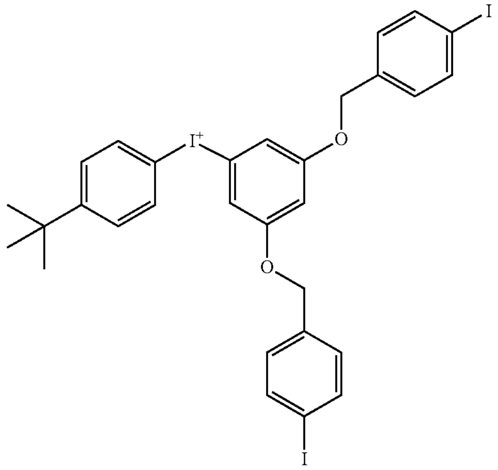
(I-c-63)
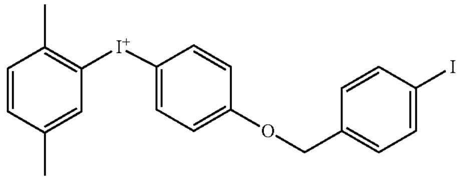
(I-c-64)
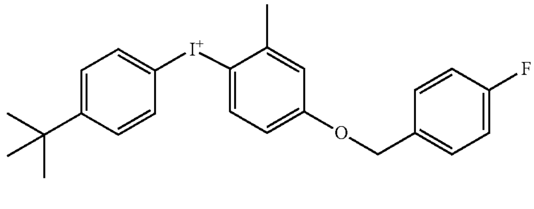

-continued
(I-c-65)
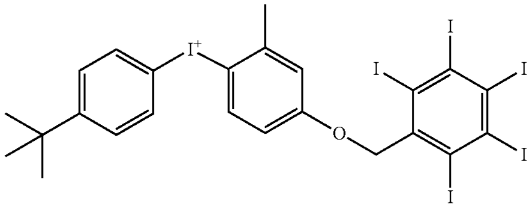
(I-c-66)
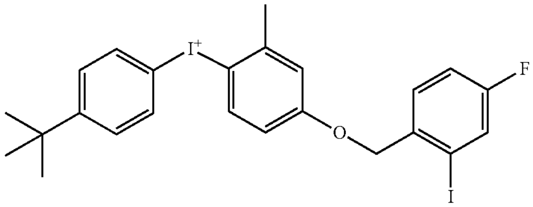
(I-c-67)
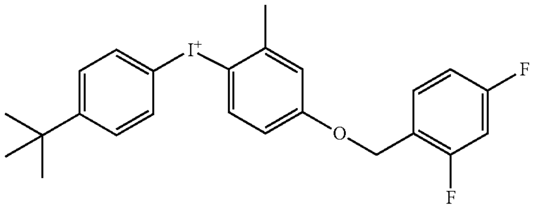
(I-c-68)
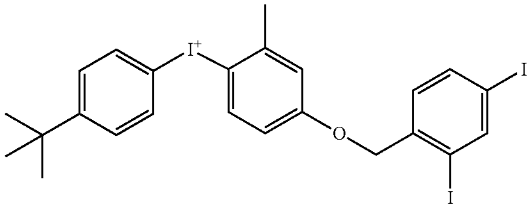
(I-c-69)
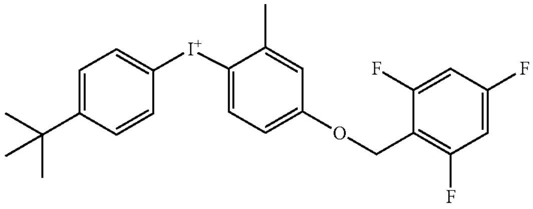
(I-c-70)
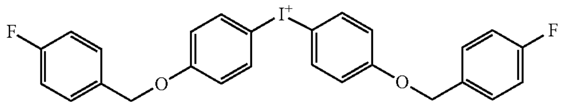
(I-c-71)
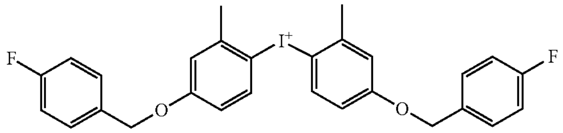
(I-c-72)
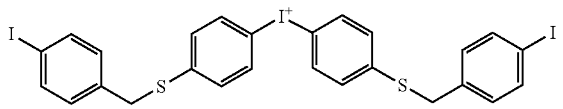
-continued
(I-c-73)
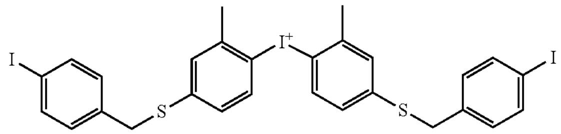
(I-c-74)
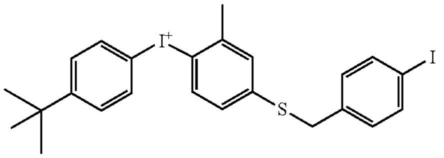
(I-c-75)
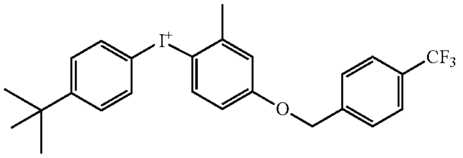
(I-c-76)
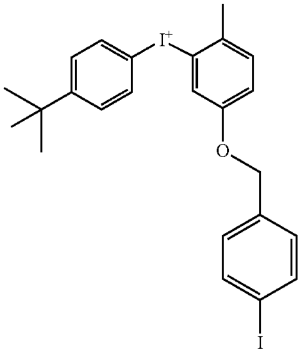
(I-c-77)
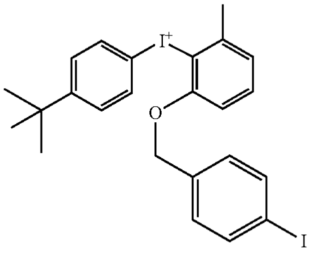
(I-c-78)
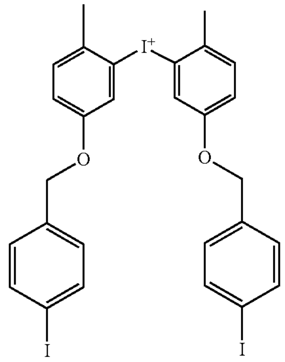

-continued (I-c-79)

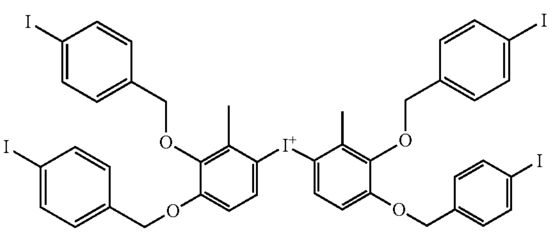

(I-c-80)

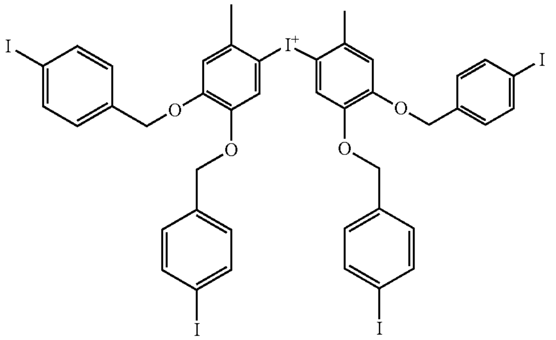

(I-c-81)

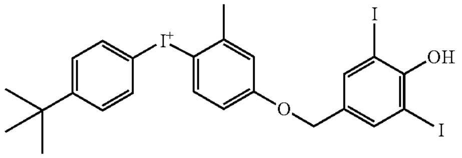

(I-c-82)

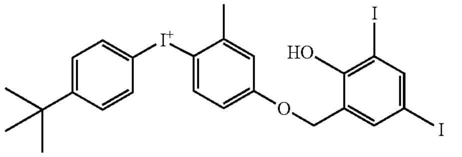

(I-c-83)

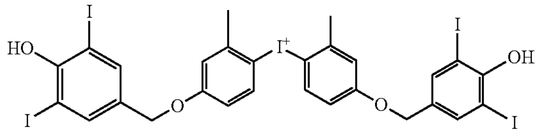

[Anion (I)]

The anion (I) of a salt represented by formula (I) is an anion represented by formula (I-A):

(I-A)

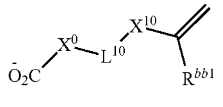

wherein, in formula (I-A), all symbols are the same as defined in formula (I).

Examples of the hydrocarbon group represented by $X^0$ in formula (I) include aliphatic hydrocarbon groups (chain hydrocarbon groups and alicyclic hydrocarbon groups, such as an alkanediyl group, an alkenediyl group and an alkynediyl group), aromatic hydrocarbon groups, and a group obtained by combining these groups. a —$CH_2$— included in the aliphatic hydrocarbon group may be replaced by —O—, —S—, —CO— or —$SO_2$—.

Examples of the alkanediyl group include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group and a dodecane-1,12-diyl group; and branched alkanediyl groups such as an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group and a 2-methylbutane-1,4-diyl group.

Examples of the alkenediyl group include an ethenediyl group, a propenediyl group, an isopropenediyl group, a butenediyl group, an isobutenediyl group, a tert-butenediyl group, a pentenediyl group, a hexenediyl group, a heptenediyl group, an octanediyl group, an isooctanediyl group and a nonenediyl group.

Examples of the alkynedyl group include an ethynediyl group, a propynediyl group, an isopropynediyl group, a butynediyl group, an isobutynediyl group, a tert-butynediyl group, a pentynediyl group, a hexynediyl group, an octynediyl group, a nonynediyl group and the like.

Examples of the group in which a —$CH_2$— included in the chain hydrocarbon group is replaced by —O—, —S—, —CO— or —$SO_2$— include a hydroxy group (a group in which a —$CH_2$— included in the methyl group is replaced by —O—), a carboxy group (a group in which a —$CH_2$—$CH_2$— included in the ethyl group is replaced by —O—CO—), a thiol group (a group in which a —$CH_2$— included in the methyl group is replaced by —S—), an alkoxy group (a group in which a —$CH_2$— at any position included in the alkyl group is replaced by —O—), an alkoxycarbonyl group (a group in which a —$CH_2$—$CH_2$— at any position included in the alkyl group is replaced by —O—CO—), an alkylcarbonyl group (a group in which a —$CH_2$— at any position included in the alkyl group is replaced by —CO—), an alkylcarbonyloxy group (a group in which a —$CH_2$—$CH_2$— at any position included in the alkyl group is replaced by —CO—O—), an alkylthio group (a group in which a —$CH_2$— at any position included in the alkyl group is replaced by —S—) and the like.

Examples of the alkoxy group, the alkoxycarbonyl group, the sulfide group, the alkylcarbonyl group, the alkylcarbonyloxy group and the alkylthio group include the same groups as mentioned above.

Replacement in the alkenediyl group and the alkynediyl group may be those including a carbon-carbon double bond or a carbon-carbon triple bond at any position in exemplification of the replacement in the above-mentioned alkyl group.

The alicyclic hydrocarbon group may be monocyclic, polycyclic or spiro ring. Examples of the divalent alicyclic hydrocarbon group include groups shown below. The bonding site can be any position in groups shown below.

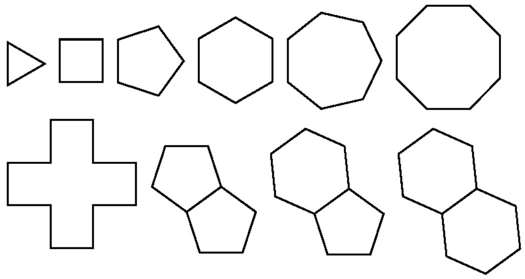

-continued

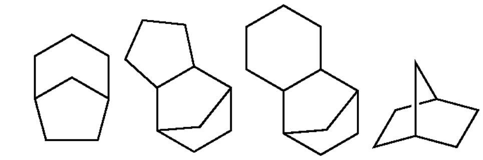
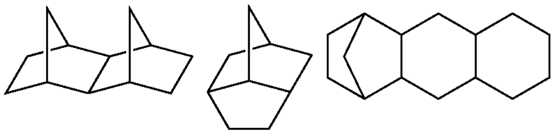
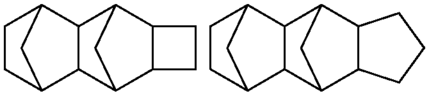
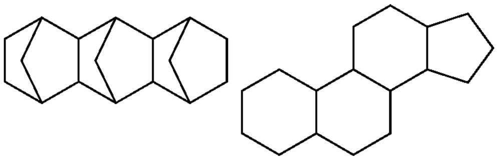
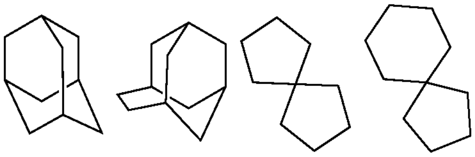
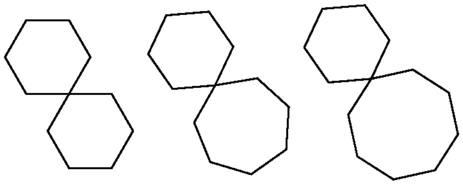
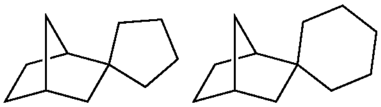
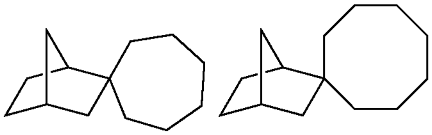
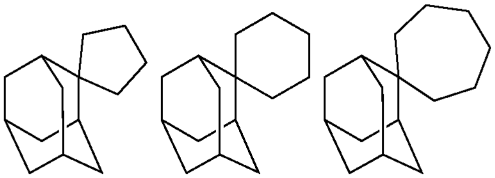
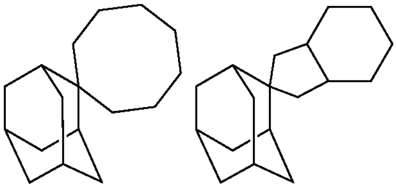
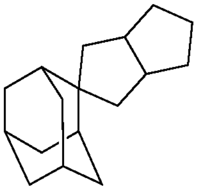

Specifically, examples of the monocyclic divalent alicyclic hydrocarbon group include monocyclic cycloalkanediyl groups such as a cyclobutane-1,3-diyl group, a cyclopentane-1,3-diyl group, a cyclohexane-1,4-diyl group, a cyclohexene-3,6-diyl group and a cyclooctane-1,5-diyl group, and examples of the polycyclic divalent alicyclic hydrocarbon group include polycyclic cycloalkanediyl groups such as a norbornane-1,4-diyl group, a norbornane-2,5-diyl group, a 5-norbornene-2,3-diyl group, an adamantane-1,5-diyl group and an adamantane-2,6-diyl group.

In some embodiments, the number of carbon atoms of the divalent alicyclic hydrocarbon group is preferably 3 to 18, more preferably 3 to 16, and still more preferably 3 to 12.

Specifically, examples of the group in which a $—CH_2—$ included in the alicyclic hydrocarbon group or the alicyclic hydrocarbon group is replaced by —O—, —S—, —CO— or $—SO_2—$ include the following groups. The bonding site can be any position in groups shown below.

(y12)

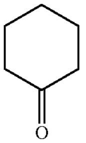

(y13)

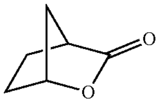

(y14)

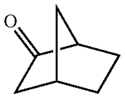

(y15)

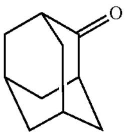

(y16)

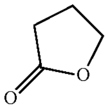

(y17)

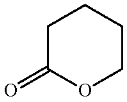

(y18)

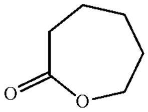

(y19)

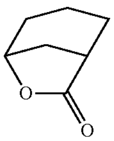

-continued
(y20)
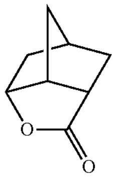
(y21)
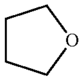
(y22)
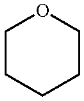
(y23)
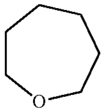
(y24)
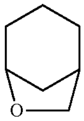
(y25)
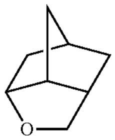
(y26)
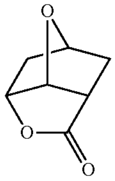
(y27)
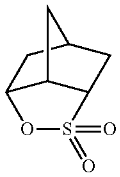
(y28)
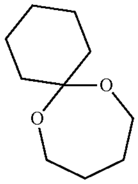
(y29)
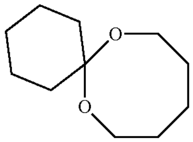
-continued
(y30)
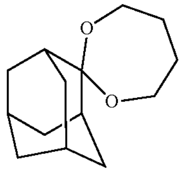
(y31)
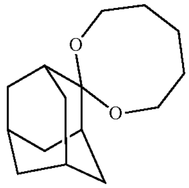
(y32)
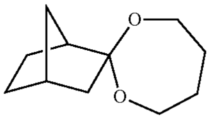
(y33)
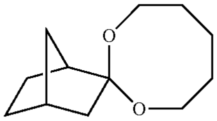
(y34)
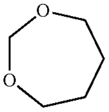
(y35)
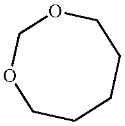
(y39)
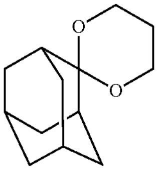
(y40)
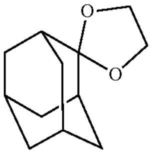
(y41)
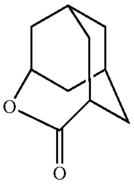

-continued
(y42)
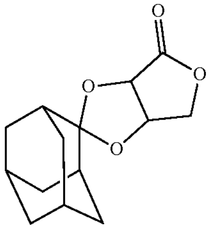
(y43)
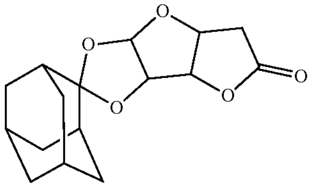
(y49)
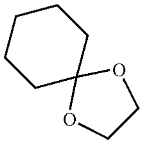
(y50)
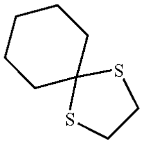
(y51)
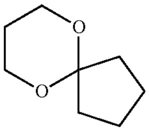
(y52)
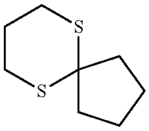
(y53)
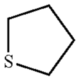
(y54)
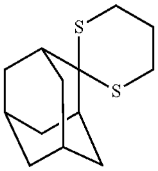
(y55)
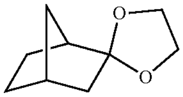
(y56)
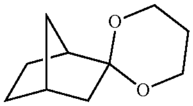
-continued
(y57)
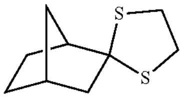
(y58)
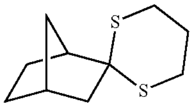
(y62)
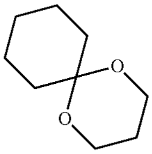
(y63)
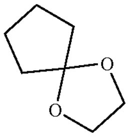
(y64)
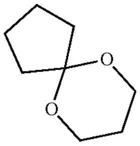
(y65)
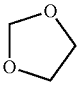
(y66)
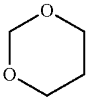
(y67)
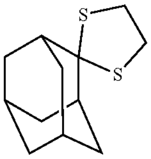
(y68)
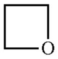
(y69)
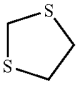
(y70)
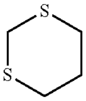
(y71)
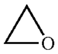

-continued (y88)

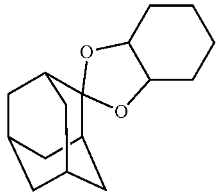

(y89)

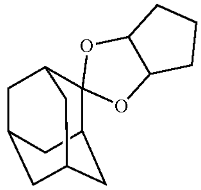

The group in which a —$CH_2$— included in the alicyclic hydrocarbon group or the alicyclic hydrocarbon group is replaced by —O—, —S—, —CO— or —$SO_2$— is preferably groups represented by formulas (y1) to (y71), more preferably a group represented by any one of formula (y1) to formula (y20), formula (y26), formula (y27), formula (y30), formula (y31) and formula (y39) to formula (y71), and still more preferably groups represented by formula (y3), formula (y4), formula (y9), formula (y11), formula (y14), formula (y15), formula (y16), formula (y20), formula (y26), formula (y27), formula (y30), formula (y31), formula (y39), formula (y40), formula (y42), formula (y43), formula (y49) to formula (y58) and formula (y62) to formula (y71). In some embodiments, the number of carbon atoms of the alicyclic hydrocarbon group is preferably 3 to 36, more preferably 3 to 24, still more preferably 3 to 18, yet more preferably 3 to 16, and further preferably 3 to 12.

Examples of the aromatic hydrocarbon group include a phenylene group, a naphthylene group, an anthrylene group, a biphenylene group, a phenanthrylene group and the like. In some embodiments, the number of carbon atoms of the aromatic hydrocarbon group is preferably 6 to 18, more preferably 6 to 14, and still more preferably 6 to 10.

Examples of the hydrocarbon group obtained by combining two or more groups include groups obtained by combining an alkanediyl group, an alicyclic hydrocarbon group and/or an aromatic hydrocarbon groups, such as an -alicyclic hydrocarbon group-alkanediyl group-, an -alkanediyl group-alicyclic hydrocarbon group-, an -alkanediyl group-alicyclic hydrocarbon group-alkanediyl group-, an -alkanediyl group-aromatic hydrocarbon group-, an -aromatic hydrocarbon group-alkanediyl group- and the like.

When a —$CH_2$— included in the hydrocarbon group represented by $X^0$ is replaced by —O—, —S—, —CO— or —$SO_2$—, the number of carbon atoms before replacement is taken as the total number of carbon atoms of the hydrocarbon group. When the substituent is bonded to the hydrocarbon group represented by $X^0$, the number of carbon atoms before replacement is taken as the total number of carbon atoms of the hydrocarbon group.

The hydrocarbon group represented by $X^0$ may have one or a plurality of substituents.

Examples of the substituent include a hydroxy group, a halogen atom, a cyano group, an alkyl group having 1 to 12 carbon atoms, an alkoxy group having 1 to 12 carbon atoms, an alkoxycarbonyl group having 2 to 13 carbon atoms, an alkylcarbonyl group having 2 to 13 carbon atoms, an alkylcarbonyloxy group having 2 to 13 carbon atoms, an alicyclic hydrocarbon group having 3 to 12 carbon atoms, an aromatic hydrocarbon group having 6 to 10 carbon atoms, or a group obtained by combining these groups.

Examples of the halogen atom include a fluorine atom, a chlorine atom, a bromine atom and an iodine atom.

Examples of the alkyl group having 1 to 12 carbon atoms include a methyl group, an ethyl group, a propyl group, an isopropyl group, a butyl group, an isobutyl group, a tert-butyl group, a pentyl group, a hexyl group, an octyl group, a nonyl group and the like.

Examples of the alkoxy group having 1 to 12 carbon atoms include a methoxy group, an ethoxy group, a propoxy group, a butoxy group, a pentyloxy group, a hexyloxy group, an octyloxy group, a 2-ethylhexyloxy group, a nonyloxy group, a decyloxy group, an undecyloxy group, a dodecyloxy group and the like.

The alkoxycarbonyl group having 2 to 13 carbon atoms, the alkylcarbonyl group having 2 to 13 carbon atoms and the alkylcarbonyloxy group having 2 to 13 carbon atoms represent groups in which a carbonyl group or a carbonyloxy group is bonded to the above-mentioned alkyl group or alkoxy group.

Examples of the alkoxycarbonyl group having 2 to 13 carbon atoms include a methoxycarbonyl group, an ethoxycarbonyl group, a butoxycarbonyl group and the like, examples of the alkylcarbonyl group having 2 to 13 carbon atoms include an acetyl group, a propionyl group and a butyryl group, and examples of the alkylcarbonyloxy group having 2 to 13 carbon atoms include an acetyloxy group, a propionyloxy group, a butyryloxy group and the like.

Examples of the alicyclic hydrocarbon group having 3 to 12 carbon atoms include groups shown below. ** represents a bonding site to $X^0$.

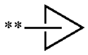

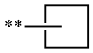

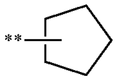

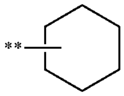

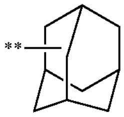

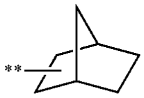

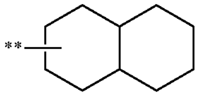

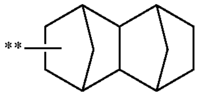

Examples of the aromatic hydrocarbon group having 6 to 10 carbon atoms include aryl groups such as a phenyl group and a naphthyl group.

Examples of the combined group include a group obtained by combining a hydroxy group with an alkyl group having 1 to 12 carbon atoms, a group obtained by combining an alkyl group having 1 to 12 carbon atoms with an aromatic hydrocarbon group having 6 to 10 carbon atoms, a group obtained by combining an alicyclic hydrocarbon group having 3 to 12 carbon atoms with an aromatic hydrocarbon group having 6 to 10 carbon atoms and the like.

Examples of the group obtained by combining a hydroxy group with an alkyl group having 1 to 12 carbon atoms include hydroxyalkyl groups having 1 to 12 carbon atoms, such as a hydroxymethyl group and a hydroxyethyl group.

Examples of the group obtained by combining an alkyl group having 1 to 12 carbon atoms with an aromatic hydrocarbon group having 6 to 10 carbon atoms include aralkyl groups having 7 to 22 carbon atoms such as a benzyl group, and alkylaryl groups having 7 to 22 carbon atoms such as a tolyl group and a xylyl group.

Examples of the group obtained by combining an alicyclic hydrocarbon group having 3 to 12 carbon atoms with an aromatic hydrocarbon group having 6 to 10 carbon atoms include cyclohexylphenyl groups and the like.

The hydrocarbon group represented by $X^0$ is preferably an aliphatic hydrocarbon group having 1 to 72 carbon atoms which may have a substituent (a $—CH_2—$ included in the aliphatic hydrocarbon group may be replaced by —O—, —S—, —CO— or $—SO_2—$), or an aromatic hydrocarbon group having 6 to 36 carbon atoms which may have a substituent, more preferably an alicyclic hydrocarbon group having 3 to 36 carbon atoms which may have a substituent (in which a $—CH_2—$ included in the alicyclic hydrocarbon group may be replaced by —O—, —S—, —CO— or $—SO_2$), a group obtained by combining an alicyclic hydrocarbon group having 3 to 36 carbon atoms which may have a substituent with a chain hydrocarbon group having 1 to 18 carbon atoms which may have a substituent (a $—CH_2—$ included in the alicyclic hydrocarbon group may be replaced by —O—, —S—, —CO— or $—SO_2—$, a $—CH_2—$ included in the chain hydrocarbon group may be replaced by —O— or —CO—, and the alicyclic hydrocarbon group and the chain hydrocarbon group may have a substituent), or an aromatic hydrocarbon group having 6 to 36 carbon atoms which may have a substituent or an aromatic hydrocarbon group having 6 to 36 carbon atoms which may have a substituent and a chain hydrocarbon group having 1 to 18 carbon atoms which may have a substituent, still more preferably an *-alicyclic hydrocarbon group (a $—CH_2—$ included in the alicyclic hydrocarbon group may be replaced by —O—, —S—, —CO— or $—SO_2—$, the alicyclic hydrocarbon group may have a hydroxy group or a fluorine atom, and * represents a bonding site to carbon atoms of $—CO^-$), an *-alicyclic hydrocarbon group-chain hydrocarbon group (a $—CH_2—$ included in the alicyclic hydrocarbon group may be replaced by —O—, —S—, —CO— or $—SO_2—$, a $—CH_2—$ included in the chain hydrocarbon group may be replaced by —O— or —CO—, the alicyclic hydrocarbon group and the chain hydrocarbon group may have a fluorine atom or a hydroxy group, and * represents a bonding site to carbon atoms of $—CO^-$), a *-chain hydrocarbon group-alicyclic hydrocarbon group (a $—CH_2—$ included in the chain hydrocarbon group may be replaced by —O— or —CO—, a $—CH_2—$ included in the alicyclic hydrocarbon group may be replaced by —O—, —S—, —CO— or $—SO_2—$, the chain hydrocarbon group and the alicyclic hydrocarbon group may have a fluorine atom or a hydroxy group, and * represents a bonding site to carbon atoms of $—COO^-$), an *-aromatic hydrocarbon group (the aromatic hydrocarbon group may have a fluorine atom or a hydroxy group, and * represents a bonding site to carbon atoms of $—COO^-$), or a *-chain hydrocarbon group-aromatic hydrocarbon group (a $—CH_2—$ included in the chain hydrocarbon group may be replaced by —O— or —CO—, the chain hydrocarbon group and the aromatic hydrocarbon group may have a fluorine atom or a hydroxy group, and * represents a bonding site to carbon atoms of $—CO^-$), and yet more preferably a *-monocyclic alicyclic hydrocarbon group (a $—CH_2—$ included in the alicyclic hydrocarbon group may be replaced by —O—, —S—, —CO— or $—SO_2—$), a *-polycyclic alicyclic hydrocarbon group (a $—CH_2—$ included in the polycyclic alicyclic hydrocarbon group may be replaced by —O—, —S—, —CO— or $—SO_2—$, the polycyclic alicyclic hydrocarbon group may be spiro ring, the polycyclic alicyclic hydrocarbon group may have a hydroxy group or a fluorine atom, and * represents a bonding site to carbon atoms of $—CO^-$), a *-polycyclic alicyclic hydrocarbon group-chain hydrocarbon group (a $—CH_2—$ included in the polycyclic alicyclic hydrocarbon group may be replaced by —O—, —S—, —CO— or $—SO_2—$, a $—CH_2—$ included in the chain hydrocarbon group may be replaced by —O— or —CO—, the polycyclic alicyclic hydrocarbon group and the chain hydrocarbon group may have a fluorine atom or a hydroxy group, and * represents a bonding site to carbon atoms of $—COO^-$), a *-chain hydrocarbon group-polycyclic alicyclic hydrocarbon group (a $—CH_2—$ included in the chain hydrocarbon group may be replaced by —O— or —CO—, a $—CH_2—$ included in the polycyclic alicyclic hydrocarbon group may be replaced by —O—, —S—, —CO— or $—SO_2—$, the chain hydrocarbon group and the polycyclic alicyclic hydrocarbon group may have a fluorine atom or a hydroxy group, and * represents a bonding site to carbon atoms of $—COO^-$), or an aromatic hydrocarbon group which may have a fluorine atom or a hydroxy group.

In the above groups, the number of carbon atoms of the alicyclic hydrocarbon group is preferably 3 to 36, more preferably 3 to 24, still more preferably 3 to 18, yet more preferably 3 to 16, and further preferably 3 to 12. In some embodiments, the number of carbon atoms of the chain hydrocarbon group is preferably 1 to 18, more preferably 1 to 12, still more preferably 1 to 9, yet more preferably 1 to 6, and further preferably 1 to 4. In some embodiments, the number of carbon atoms of the aromatic hydrocarbon group is preferably 6 to 36, more preferably 6 to 24, still more preferably 6 to 18, yet more preferably 6 to 14, and further preferably 6 to 10.

In the above groups, the number of carbon atoms of the chain hydrocarbon group is preferably 1 to 6.

The above monocyclic alicyclic hydrocarbon group is a cycloalkanediyl group having 5 or 6 carbon atoms (a $—CH_2—$ included in the cycloalkanediyl group may be replaced by —O— or —CO—, and the cycloalkanediyl group may be an acetal ring), the above polycyclic alicyclic hydrocarbon group is an adamandiyl group, a norbornanediyl group, or a polycyclic alicyclic hydrocarbon group in which a cycloalkanediyl group having 5 or 6 carbon atoms and an adamantanediyl group are spiro-bonded, (a $—CH_2—$ included in the adamantanediyl group, the norbornanediyl group and the cycloalkanediyl group may be replaced by —O— or —CO—, a —$CH_2$—$CH_2$— included in the adamantanediyl group and norbornanediyl group may be replaced by —O—CO—, and the cycloalkanediyl group may be an acetal ring), and the above aromatic hydrocarbon group is a phenylene group.

In the above groups, the chain hydrocarbon group preferably has a fluorine atom.

$X^0$ is an alkanediyl group having 1 to 6 carbon atoms, a cycloalkanediyl group having 5 or 6 carbon atoms, an adamantanediyl group, a norbornanediyl group, a phenylene group, a group obtained by combining an alkanediyl group having 1 to 6 carbon atoms bonded to $COO^-$ with the cycloalkanediyl group having 5 or 6 carbon atoms bonded to the alkanediyl group, the adamantanediyl group, the norbornanediyl group, the phenylene group, or a polycyclic alicyclic hydrocarbon group in which a cycloalkanediyl group having 5 or 6 carbon atoms and an adamantanediyl group are spiro-bonded, a —$CH_2$— included in the alkanediyl group, the cycloalkanediyl group, the adamantanediyl group and the norbornanediyl group may be replaced by —O— or —CO—, a —$CH_2$—$CH_2$— included in the alkanediyl group, the adamantanediyl group and the norbornanediyl group may be replaced by —O—CO— or —CO—O—, and one or more hydrogen atoms included in the alkanediyl group, the cycloalkanediyl group, the adamantanediyl group, the norbornanediyl group and phenyl group may be substituted with a fluorine atom, a perfluoroalkyl group having 1 to 4 carbon atoms, a hydroxy group or a methylhydroxy group.

$X^0$ is particularly preferably an adamantanediyl group, a hydroxyadamantanediyl group, a group obtained by combining an alkanediyl group having 1 to 6 carbon atoms bonded to $COO^-$ with an adamantanediyl group (a —$CH_2$— included in the alkanediyl group may be replaced by —O— or —CO—), a phenylene group, or a phenylene group having a hydroxy group.

Examples of the halogen atom as for $R^{bb1}$ include the same halogen atoms as mentioned for $R^4$ to $R^9$. Examples of the alkyl group which may have a halogen atom as for $R^{bb1}$ include the same alkyl groups and haloalkyl groups as mentioned for $R^4$ to $R^9$ as long as the upper limit of the number of carbon atoms permits.

$R^{bb1}$ is preferably a hydrogen atom or a methyl group, and more preferably a methyl group.

$X^{10}$ is preferably a group represented by *-Ax-Ph-Ay-**.

(X10)

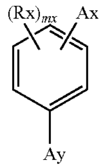

In formula (X10), Ax represents bond species bonded to carbon atoms to which $R^{10}$ is bonded, and represents one bond species selected from the group consisting of a single bond, an ether bond, an ester bond and a carbonic acid ester bond.

Ay represents bond species bonded to $L^{10}$, and represents one bond species selected from the group consisting of a single bond, an ether bond, an ester bond and a carbonic acid ester bond.

When either Ax or Ay is a single bond, the other is preferably one selected from the group consisting of an ether bond, an ester bond and a carbonic acid ester bond.

Rx represents a halogen atom, a hydroxy group, an alkyl fluoride group having 1 to 6 carbon atoms, an alkyl group having 1 to 18 carbon atoms or an alkoxy group having 1 to 6 carbon atoms. Of these, a fluorine atom, an iodine atom, a trifluoromethyl group, a methyl group or an ethyl group is preferable.

mx represents an integer of 0 to 4, and preferably 0, 1 or 2. When mx is an integer of 2 or more, a plurality of Rx may be the same or different from each other.

The bonding site of Ay in the phenylene group is preferably the m-position or the p-position, and more preferably the p-position, with respect to Ax.

In some embodiments, examples of $X^{10}$ include groups represented by the following formula ($X^1$-1), formula ($X^1$-2') to formula ($X^1$-7') and formula ($X^1$-8). * represents a bonding site to carbon atoms to which —$R^{10}$ is bonded. ** represents a bonding site to $L^{10}$.

($X^1$-1)

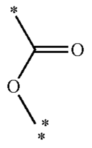

($X^1$-2')

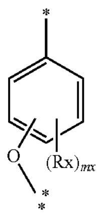

($X^1$-3)'

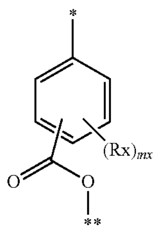

($X^1$-4')

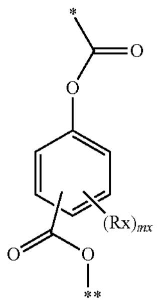

-continued
(X[1]-7')
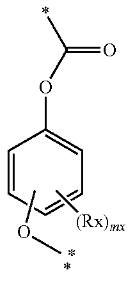
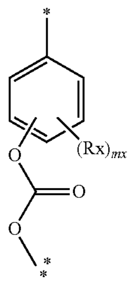
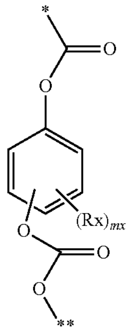
(X[1]-8)
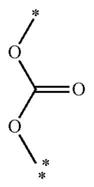
In some embodiments, examples of the group represented by formula (X[1]-2') to formula (X[1]-7') include the following groups.
(X[1]-2)
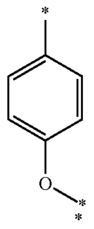
-continued
(X[1]-3)
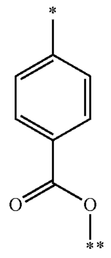
(X[1]-4)
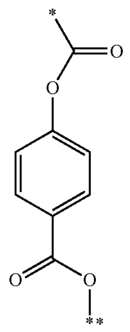
(X[1]-5)
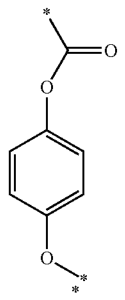
(X[1]-6)
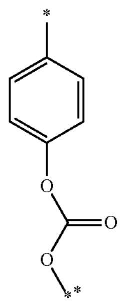
(X[1]-7)
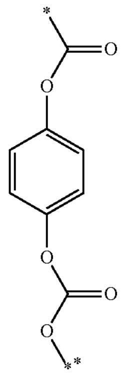

-continued (X$^1$-9)

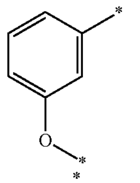

(X$^1$-10)

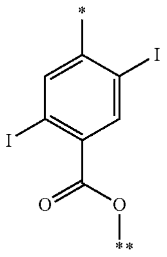

(X$^1$-11)

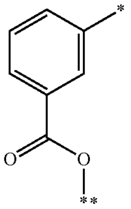

(X$^1$-12)

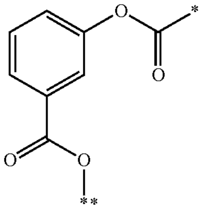

(X$^1$-13)

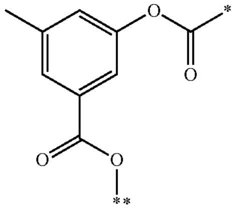

(X$^1$-14)

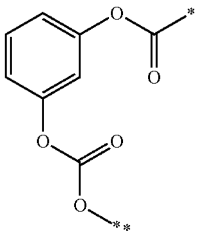

Particularly, X$^1$ is preferably groups represented by formula (X$^1$-1) to formula (X$^1$-7), more preferably a group represented by formula (X$^1$-1), formula (X$^1$-3), formula (X$^1$-4) or formula (X$^1$-5), and still more preferably a group represented by formula (X$^1$-1), a group represented by formula (X$^1$-4) or a group represented by formula (X$^1$-5).

The divalent hydrocarbon group having 1 to 36 carbon atoms as for L$^{10}$ includes divalent aliphatic hydrocarbon groups (divalent chain hydrocarbon groups and divalent alicyclic hydrocarbon groups, such as an alkanediyl group, an alkenediyl group and an alkynedyl group), divalent aromatic hydrocarbon groups and the like, and may be divalent hydrocarbon groups obtained by combining two or more of these groups.

Examples of the alkanediyl group include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group and a dodecane-1,12-diyl group; and branched alkanediyl groups such as an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group and a 2-methylbutane-1,4-diyl group.

Examples of the alkenediyl group include an ethenediyl group, a propenediyl group, an isopropenediyl group, a butenediyl group, an isobutenediyl group, a tert-butenediyl group, a pentenediyl group, a hexenediyl group, a heptenediyl group, an octanediyl group, an isooctanediyl group and a nonenediyl group.

Examples of the alkynedyl group include an ethynediyl group, a propynediyl group, an isopropynediyl group, a butynediyl group, an isobutynediyl group, a tert-butynediyl group, a pentynediyl group, a hexynediyl group, an octynediyl group, a nonynediyl group and the like.

In some embodiments, the number of carbon atoms of the chain hydrocarbon group is preferably 1 to 12, more preferably 1 to 9, still more preferably 1 to 6, yet more preferably 1 to 4, and further preferably 1 to 3.

The divalent alicyclic hydrocarbon group may be monocyclic, polycyclic or spiro ring. Examples of the divalent alicyclic hydrocarbon group include groups shown below. The bonding site can be any position in groups shown below.

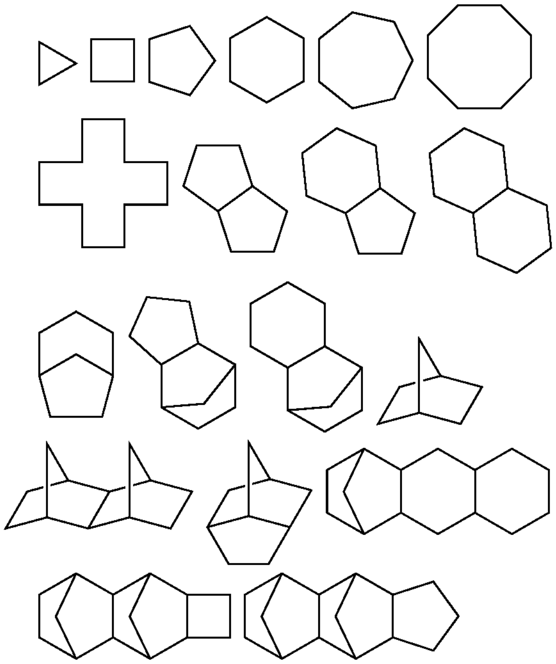

-continued

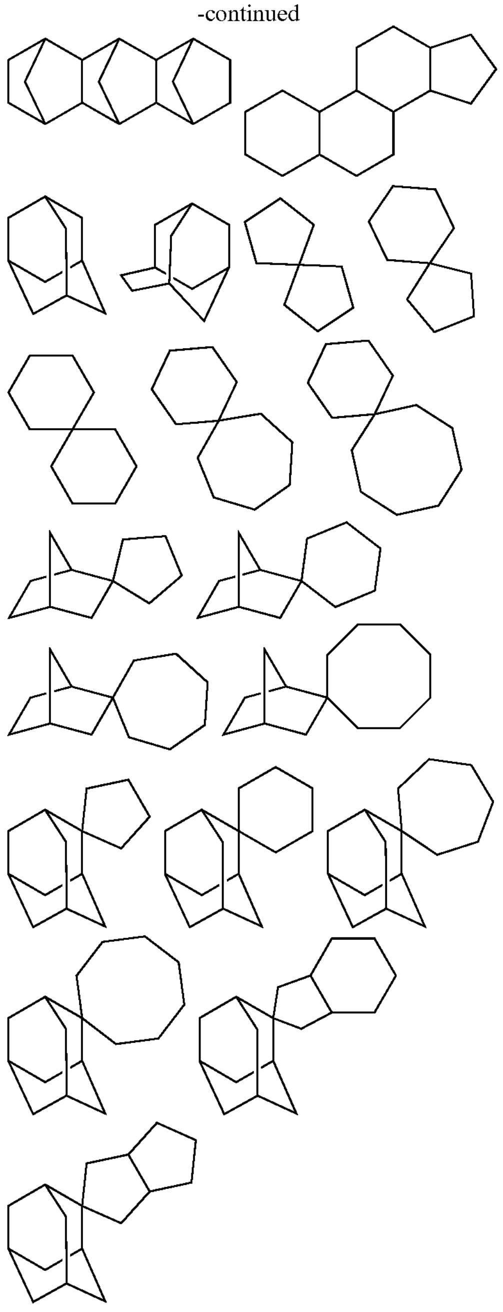

In some embodiments, examples of the monocyclic divalent alicyclic hydrocarbon group include monocyclic cycloalkanediyl groups such as a cyclobutane-1,3-diyl group, a cyclopentane-1,3-diyl group, a cyclohexane-1,4-diyl group, a cyclohexene-3,6-diyl group and a cyclooctane-1,5-diyl group; and examples of the polycyclic divalent alicyclic hydrocarbon group include polycyclic cycloalkanediyl groups such as a norbornane-1,4-diyl group, a norbornane-2,5-diyl group, a 5-norbornene-2,3-diyl group, an adamantane-1,5-diyl group and an adamantane-2,6-diyl group.

In some embodiments, the number of carbon atoms of the divalent alicyclic hydrocarbon group is preferably 3 to 18, more preferably 3 to 16, and still more preferably 3 to 12.

Examples of the divalent aromatic hydrocarbon group include a phenylene group, a naphthylene group, an anthrylene group, a biphenylene group, a phenanthrylene group and the like. In some embodiments, the number of carbon atoms of the aromatic hydrocarbon group is preferably 6 to 18, more preferably 6 to 14, and still more preferably 6 to 10.

Examples of the hydrocarbon group obtained by combining two or more groups include groups obtained by combining an alkanediyl group, an alicyclic hydrocarbon group and/or an aromatic hydrocarbon group, and examples thereof include an -alicyclic hydrocarbon group-alkanediyl group-, an -alkanediyl group-alicyclic hydrocarbon group-, an -alkanediyl group-alicyclic hydrocarbon group-alkanediyl group-, an -alkanediyl group-aromatic hydrocarbon group-, an -aromatic hydrocarbon group-alkanediyl group- and the like.

A $—CH_2—$ included in the hydrocarbon group having 1 to 36 carbon atoms as for $L^{10}$ may be replaced by —O—, —S—, —CO— or $—SO_2—$.

When the hydrocarbon group having 1 to 36 carbon atoms as for $L^{10}$ has a substituent, or when a $—CH_2—$ included in the hydrocarbon group is replaced by —O—, —S—, —CO— or $—SO_2—$, the number of carbon atoms before replacement is taken as the number of carbon atoms of the hydrocarbon group.

Examples of the group in which a $—CH_2—$ included in the hydrocarbon group is replaced by —O—, —S—, $—SO_2—$ or —CO— include a hydroxy group (a group in which a $—CH_2—$ included in the methyl group is replaced by —O—), a carboxy group (a group in which a $—CH_2—CH_2—$ included in the ethyl group is replaced by —O—CO—), a thiol group (a group in which a $—CH_2—$ included in the methyl group is replaced by —S—), an alkoxy group (a group in which a $—CH_2—$ at any position included in the alkyl group is replaced by —O—), an alkoxycarbonyl group (a group in which a $—CH_2—CH_2—$ at any position included in the alkyl group is replaced by —O—CO—), an alkylcarbonyl group (a group in which a $—CH_2—$ at any position included in the alkyl group is replaced by —CO—), an alkylcarbonyloxy group (a group in which a $—CH_2—CH_2—$ at any position included in the alkyl group is replaced by —CO—O—), an alkanediyloxy group (a group in which a $—CH_2—$ at any position included in the alkanediyl group is replaced by —O—), an alkanediyloxycarbonyl group (a group in which a $—CH_2—CH_2—$ at any position included in the alkanediyl group is replaced by —O—CO—), an alkanediylcarbonyl group (a group in which a $—CH_2—$ at any position included in the alkanediyl group is replaced by —CO—), an alkanediylcarbonyloxy group (a group in which a $—CH_2—CH_2—$ at any position included in the alkanediyl group is replaced by —CO—O—), an alkylthio group (a group in which a $—CH_2—$ at any position included in the alkyl group is replaced by —S—), an alkylsulfonyl group (a group in which a $—CH_2—$ at any position included in the alkyl group is replaced by $—SO_2—$), a cycloalkoxy group, a cycloalkylalkoxy group, an alkoxycarbonyloxy group, an aromatic hydrocarbon group-carbonyloxy group, a group obtained by combining two or more of these groups and the like.

Examples of the alkoxy group include alkoxy groups having 1 to 17 carbon atoms, for example, a methoxy group, an ethoxy group, a propoxy group, a butoxy group, a pentyloxy group, a hexyloxy group, an octyloxy group, a 2-ethylhexyloxy group, a nonyloxy group, a decyloxy group, an undecyloxy group and the like. In some embodiments, the number of carbon atoms of the alkoxy group is preferably 1 to 11, more preferably 1 to 6, still more preferably 1 to 4, and yet more preferably 1 to 3.

The alkoxycarbonyl group, the alkylcarbonyl group and the alkylcarbonyloxy group represent a group in which a carbonyl group or a carbonyloxy group is bonded to the above-mentioned alkyl group or alkoxy group.

Examples of the alkoxycarbonyl group include alkoxycarbonyl groups having 2 to 17 carbon atoms, for example, a methoxycarbonyl group, an ethoxycarbonyl group, a butoxycarbonyl group and the like. Examples of the alkylcarbonyl group include alkylcarbonyl groups having 2 to 18 carbon atoms, for example, an acetyl group, a propionyl group and a butyryl group. Examples of the alkylcarbonyloxy group include alkylcarbonyloxy groups having 2 to 17 carbon atoms, for example, an acetyloxy group, a propionyloxy group, a butyryloxy group and the like. In some embodiments, the number of carbon atoms of the alkoxycarbonyl group, the alkylcarbonyl group and the alkylcarbonyloxy group is preferably 2 to 11, more preferably 2 to 6, still more preferably 2 to 4, and yet more preferably 2 to 3. Examples of the alkanediyloxy group include alkanediyloxy groups having 1 to 17 carbon atoms, for example, a methyleneoxy group, an ethyleneoxy group, a propanediyloxy group, a butanediyloxy group, a pentanediyloxy group and the like. In some embodiments, the number of carbon atoms of the alkanediyloxy group is preferably 1 to 11, more preferably 1 to 6, and still more preferably 1 to 4 or 1 to 3.

Examples of the alkanediyloxycarbonyl group include alkanediyloxycarbonyl groups having 2 to 17 carbon atoms, for example, a methyleneoxycarbonyl group, an ethyleneoxycarbonyl group, a propanediyloxycarbonyl group, a butanediyloxycarbonyl group and the like. Examples of the alkanediylcarbonyl group include alkanediylcarbonyl groups having 2 to 18 carbon atoms, for example, a methylenecarbonyl group, an ethylenecarbonyl group, a propanediylcarbonyl group, a butanediylcarbonyl group, a pentanediylcarbonyl group and the like. Examples of the alkanediylcarbonyloxy group include alkanediylcarbonyloxy groups having 2 to 17 carbon atoms, for example, a methylenecarbonyloxy group, an ethylenecarbonyloxy group, a propanediylcarbonyloxy group, a butanediylcarbonyloxy group and the like. In some embodiments, the number of carbon atoms of the alkanediyloxycarbonyl group, the alkanediylcarbonyl group and the alkanediylcarbonyloxy group is preferably 2 to 11, more preferably 2 to 6, and still more preferably 2 to 4 or 2 to 3.

Examples of the alkylthio group include alkylthio groups having 1 to 17 carbon atoms, for example, a methylthio group, an ethylthio group, a propylthio group and the like. In some embodiments, the number of carbon atoms of the alkylthio group is preferably 1 to 11, more preferably 1 to 6, and still more preferably 1 to 4 or 1 to 3.

Examples of the alkylsulfonyl group include alkylsulfonyl groups having 1 to 17 carbon atoms, for example, a methylsulfonyl group, an ethylsulfonyl group, a propylsulfonyl group and the like. In some embodiments, the number of carbon atoms of the alkylsulfonyl group is preferably 1 to 11, more preferably 1 to 6, and still more preferably 1 to 4 or 1 to 3.

Examples of the cycloalkoxy group include cycloalkoxy groups having 3 to 17 carbon atoms, for example, a cyclohexyloxy group and the like. Examples of the cycloalkylalkoxy group include cycloalkylalkoxy groups having 4 to 17 carbon atoms, for example, a cyclohexylmethoxy group and the like. Examples of the alkoxycarbonyloxy group include alkoxycarbonyloxy group having 2 to 35 carbon atoms, for example, a butoxycarbonyloxy group and the like. In some embodiments, the number of carbon atoms of the cycloalkoxy group and the cycloalkylalkoxy group is preferably 3 to 11, and more preferably 3 to 6. In some embodiments, the number of carbon atoms of the alkoxycarbonyloxy group is preferably 2 to 11, more preferably 2 to 6, still more preferably 2 to 4, and yet more preferably 2 to 3. Examples of the aromatic hydrocarbon group-carbonyloxy group include aromatic hydrocarbon group-carbonyloxy groups having 7 to 35 carbon atoms, for example, a benzoyloxy group and the like. Examples of the group in which a $-CH_2-$ included in the alicyclic hydrocarbon group is replaced by $-O-$, $-S-$, $-CO-$ or $-SO_2-$ include the following groups shown below. The position of $-O-$ or $-CO-$ of the groups shown below may be respectively replaced by $-S-$ or $-SO_2-$. The bonding site can be any position in groups shown below.

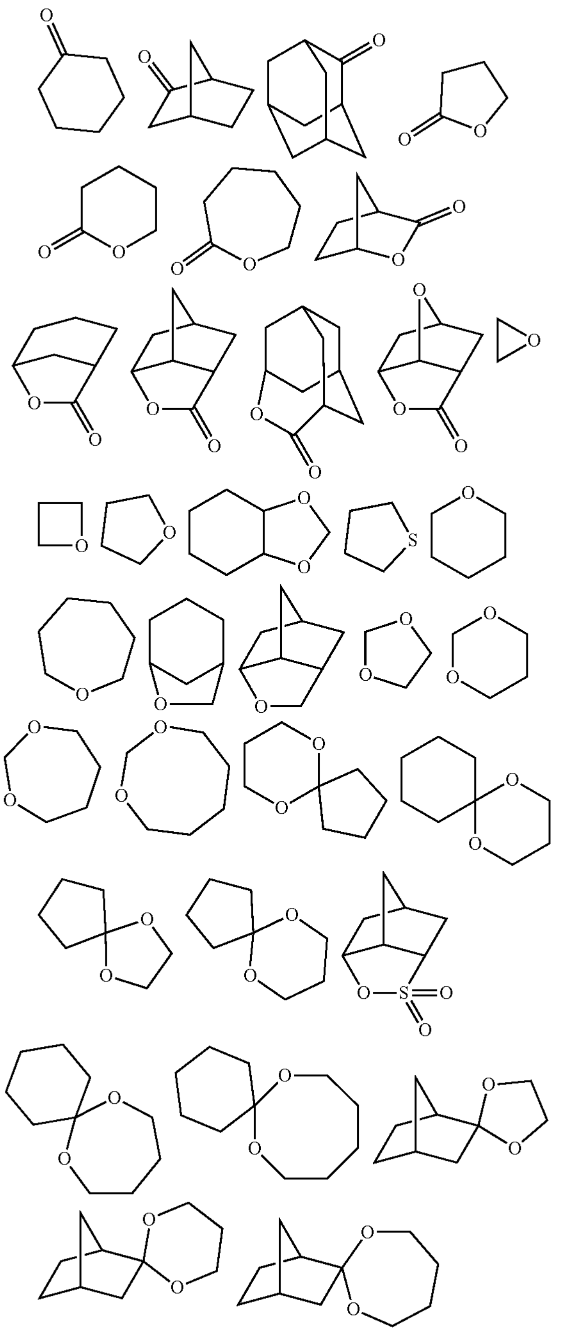

-continued

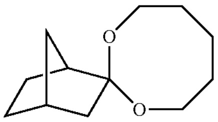

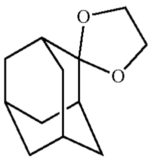

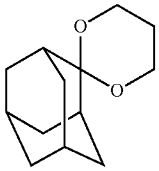

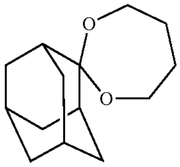

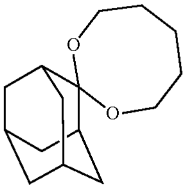

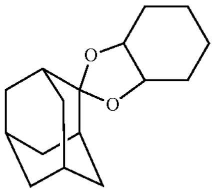

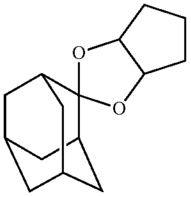

Examples of the substituent which may be possessed by the hydrocarbon group as for $L^{10}$ include a halogen atom, a cyano group and the like.

By the group in which a —$CH_2$— included in the hydrocarbon group as for $L^{10}$ is replaced by —O— or —CO—, $L^{10}$ can substantially have a substituent of a hydroxy group, a carboxy group, an alkoxy group, an alkoxycarbonyl group, an alkylcarbonyl group or an alkylcarbonyloxy group.

Examples of the halogen atom include a fluorine atom, a chlorine atom, a bromine atom and an iodine atom.

The divalent hydrocarbon group having 1 to 36 carbon atoms as for $L^{10}$ may have one substituent or a plurality of substituents.

$L^{10}$ is preferably a single bond, an alkanediyl group having 1 to 4 carbon atoms (in which a —$CH_2$— included in the alkanediyl group may be replaced by —O— or —CO—), an alicyclic hydrocarbon group having 3 to 18 carbon atoms (in which a —$CH_2$— included in the alicyclic hydrocarbon group may be replaced by —O—, —S—, —$SO_2$— or —CO—), a group obtained by combining an aromatic hydrocarbon group having 6 to 18 carbon atoms which may have a substituent, an alkanediyl group having 1 to 4 carbon atoms and an alicyclic hydrocarbon group having 3 to 18 carbon atoms (in which a —$CH_2$— included in the alkanediyl group may be replaced by —O— or —CO—, and a —$CH_2$— included in the alicyclic hydrocarbon group may be replaced by —O—, —S—, —$SO_2$— or —CO—) or a group obtained by combining an alkanediyl group having 1 to 4 carbon atoms with an aromatic hydrocarbon group having 6 to 18 carbon atoms which may have a substituent (a —$CH_2$— included in the alkanediyl group may be replaced by —O— or —CO—), more preferably a single bond, an alkanediyl group having 1 to 4 carbon atoms (in which a —$CH_2$— included in the alkanediyl group may be replaced by —O— or —CO—), an alicyclic hydrocarbon group having 3 to 18 carbon atoms (in which a —$CH_2$— included in the alicyclic hydrocarbon group may be replaced by —O— or —CO—), a group obtained by combining a phenylene group which may have a substituent, an alkanediyl group having 1 to 4 carbon atoms and an alicyclic hydrocarbon group having 3 to 18 carbon atoms (in which a —$CH_2$— included in the alkanediyl group may be replaced by —O— or —CO—, and a —$CH_2$— included in the alicyclic hydrocarbon group may be replaced by —O— or —CO—) or a group obtained by combining an alkanediyl group having 1 to 4 carbon atoms with a phenylene group which may have a substituent (in which a —$CH_2$— included in the alkanediyl group may be replaced by —O— or —CO—), and still more preferably a single bond or alkanediyl group having 1 to 4 carbon atoms (in which a —$CH_2$— included in the alkanediyl group may be replaced by —O— or —CO—).

Examples of the anion (I) include the following anions.

(I-a-1)

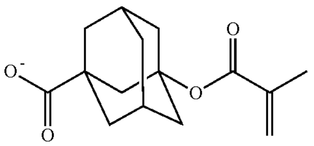

(I-a-2)

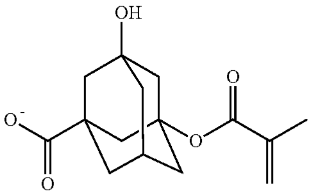

(I-a-3)

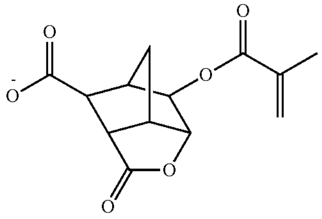

(I-a-4)

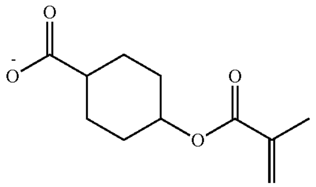

(I-a-5)

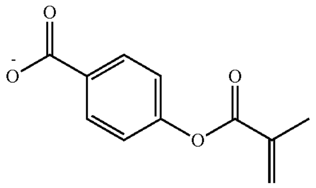

(I-a-6)

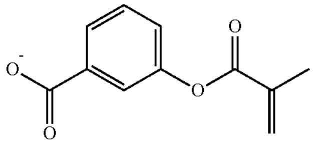

(I-a-7)

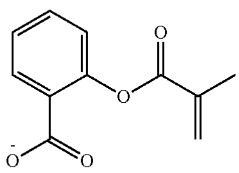

-continued
(I-a-8)
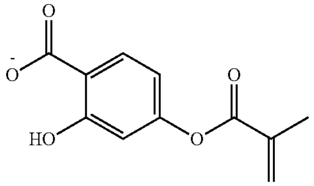
(I-a-9)
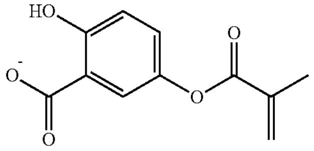
(I-a-10)
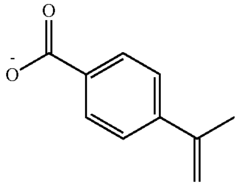
(I-a-11)
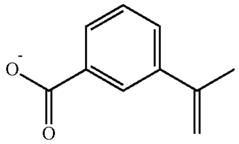
(I-a-12)
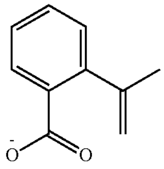
(I-a-13)
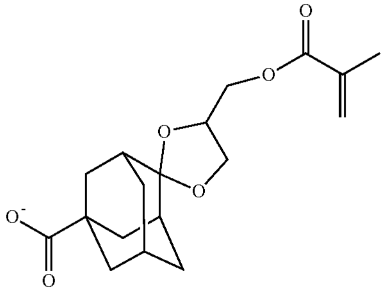
(I-a-14)
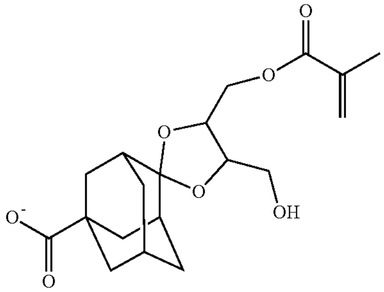
-continued
(I-a-15)
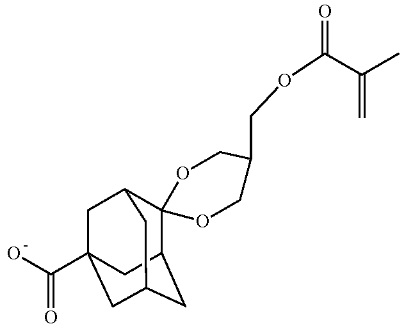
(I-a-16)
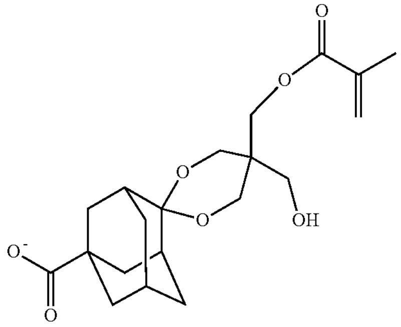
(I-a-17)
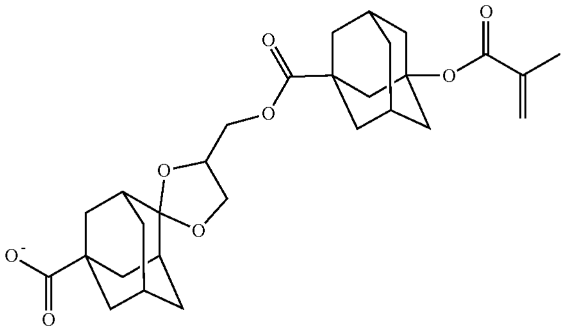
(I-a-18)
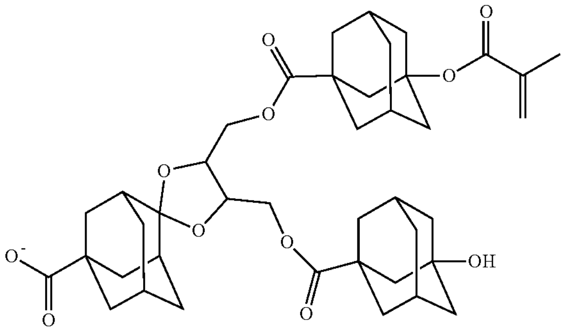

-continued (I-a-19)

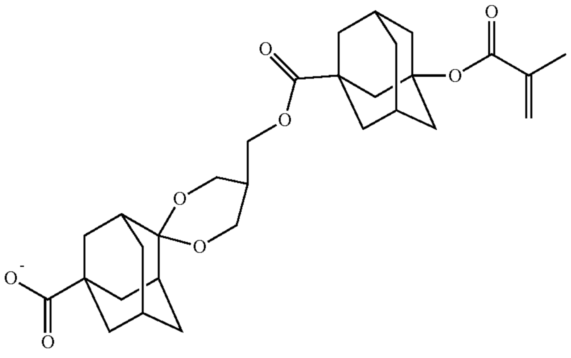

(I-a-20)

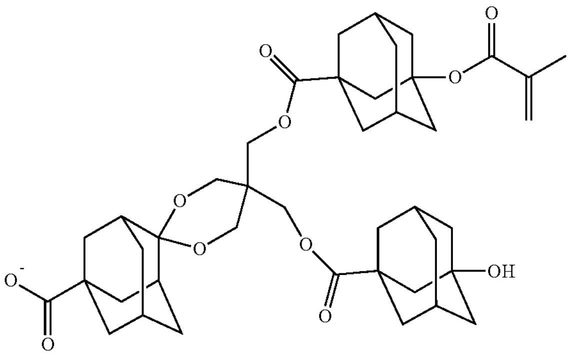

(I-a-22)

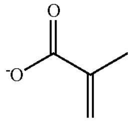

(I-a-22)

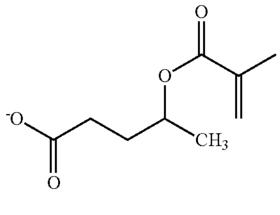

(I-a-23)

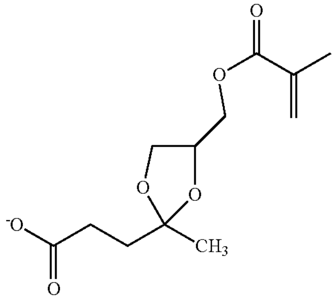

-continued (I-a-24)

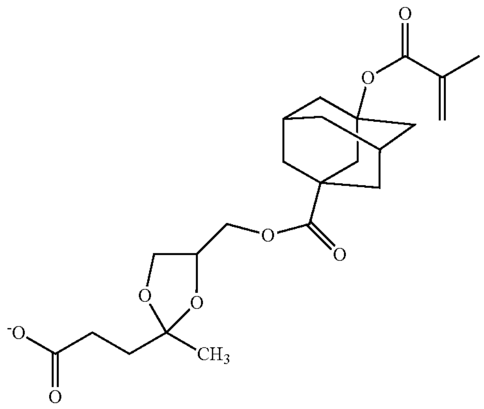

(I-a-25)

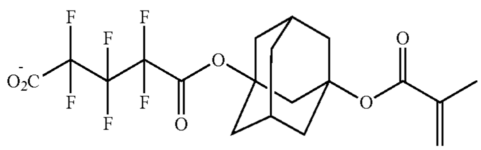

(I-a-26)

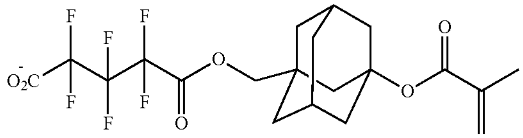

(I-a-27)

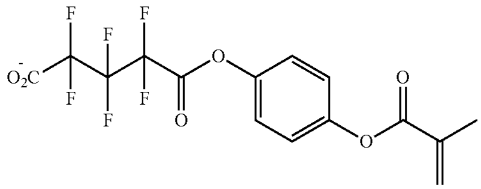

In some embodiments, examples of the carboxylate (I) include salts obtained by optionally combining the above-mentioned cations and anions. In some embodiments, examples of the salt (I) are shown in the following table.

In the following table, the respective symbols represent symbols imparted to structures showing the above-mentioned anions and cations, and "to" indicates that the salt (I) and the anion (I) correspond to each other. For example, the carboxylate (I-1) indicates a salt composed of an anion represented by formula (I-a-1) and a cation represented by formula (I-c-1), the salt (I-2) indicates a salt composed of an anion represented by formula (I-a-2) and a cation represented by formula (I-c-1), and the salt (I-28) indicates a salt composed of an anion represented by formula (I-a-1) and a cation represented by formula (I-c-2).

(I-1)

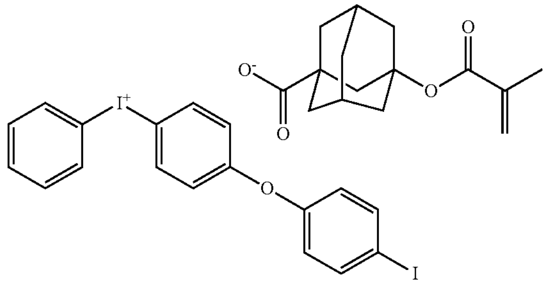

TABLE 1

| Carboxylate (I) | Anion (I) | Cation (I) |
|---|---|---|
| (I-1) to (I-27) | (I-a-1) to (I-a-27) | (I-c-1) |
| (I-28) to (I-54) | (I-a-1) to (I-a-27) | (I-c-2) |
| (I-55) to (I-81) | (I-a-1) to (I-a-27) | (I-c-3) |
| (I-82) to (I-108) | (I-a-1) to (I-a-27) | (I-c-4) |
| (I-109) to (I-135) | (I-a-1) to (I-a-27) | (I-c-5) |
| (I-136) to (I-162) | (I-a-1) to (I-a-27) | (I-c-6) |
| (I-163) to (I-189) | (I-a-1) to (I-a-27) | (I-c-7) |
| (I-190) to (I-216) | (I-a-1) to (I-a-27) | (I-c-8) |
| (I-217) to (I-243) | (I-a-1) to (I-a-27) | (I-c-9) |
| (I-244) to (I-270) | (I-a-1) to (I-a-27) | (I-c-10) |
| (I-271) to (I-297) | (I-a-1) to (I-a-27) | (I-c-11) |
| (I-298) to (I-324) | (I-a-1) to (I-a-27) | (I-c-12) |
| (I-325) to (I-351) | (I-a-1) to (I-a-27) | (I-c-13) |
| (I-352) to (I-378) | (I-a-1) to (I-a-27) | (I-c-14) |
| (I-379) to (I-405) | (I-a-1) to (I-a-27) | (I-c-15) |
| (I-406) to (I-432) | (I-a-1) to (I-a-27) | (I-c-16) |
| (I-433) to (I-459) | (I-a-1) to (I-a-27) | (I-c-17) |
| (I-460) to (I-486) | (I-a-1) to (I-a-27) | (I-c-18) |
| (I-487) to (I-513) | (I-a-1) to (I-a-27) | (I-c-19) |
| (I-514) to (I-540) | (I-a-1) to (I-a-27) | (I-c-20) |
| (I-541) to (I-567) | (I-a-1) to (I-a-27) | (I-c-21) |
| (I-568) to (I-594) | (I-a-1) to (I-a-27) | (I-c-22) |
| (I-595) to (I-621) | (I-a-1) to (I-a-27) | (I-c-23) |
| (I-622) to (I-648) | (I-a-1) to (I-a-27) | (I-c-24) |
| (I-649) to (I-675) | (I-a-1) to (I-a-27) | (I-c-25) |
| (I-676) to (I-702) | (I-a-1) to (I-a-27) | (I-c-26) |
| (I-703) to (I-729) | (I-a-1) to (I-a-27) | (I-c-27) |
| (I-730) to (I-756) | (I-a-1) to (I-a-27) | (I-c-28) |
| (I-757) to (I-783) | (I-a-1) to (I-a-27) | (I-c-29) |
| (I-784) to (I-810) | (I-a-1) to (I-a-27) | (I-c-30) |
| (I-811) to (I-837) | (I-a-1) to (I-a-27) | (I-c-31) |
| (I-838) to (I-864) | (I-a-1) to (I-a-27) | (I-c-32) |
| (I-865) to (I-891) | (I-a-1) to (I-a-27) | (I-c-33) |
| (I-892) to (I-918) | (I-a-1) to (I-a-27) | (I-c-34) |
| (I-919) to (I-945) | (I-a-1) to (I-a-27) | (I-c-35) |
| (I-946) to (I-972) | (I-a-1) to (I-a-27) | (I-c-36) |
| (I-973) to (I-999) | (I-a-1) to (I-a-27) | (I-c-37) |
| (I-1000) to (I-1026) | (I-a-1) to (I-a-27) | (I-c-38) |
| (I-1027) to (I-1053) | (I-a-1) to (I-a-27) | (I-c-39) |
| (I-1054) to (I-1080) | (I-a-1) to (I-a-27) | (I-c-40) |
| (I-1081) to (I-1107) | (I-a-1) to (I-a-27) | (I-c-41) |
| (I-1108) to (I-1134) | (I-a-1) to (I-a-27) | (I-c-42) |
| (I-1135) to (I-1161) | (I-a-1) to (I-a-27) | (I-c-43) |
| (I-1162) to (I-1188) | (I-a-1) to (I-a-27) | (I-c-44) |
| (I-1189) to (I-1215) | (I-a-1) to (I-a-27) | (I-c-45) |
| (I-1216) to (I-1242) | (I-a-1) to (I-a-27) | (I-c-46) |
| (I-1243) to (I-1269) | (I-a-1) to (I-a-27) | (I-c-47) |
| (I-1270) to (I-1296) | (I-a-1) to (I-a-27) | (I-c-48) |
| (I-1297) to (I-1323) | (I-a-1) to (I-a-27) | (I-c-49) |
| (I-1324) to (I-1350) | (I-a-1) to (I-a-27) | (I-c-50) |
| (I-1351) to (I-1377) | (I-a-1) to (I-a-27) | (I-c-51) |
| (I-1378) to (I-1404) | (I-a-1) to (I-a-27) | (I-c-52) |
| (I-1405) to (I-1431) | (I-a-1) to (I-a-27) | (I-c-53) |
| (I-1432) to (I-1458) | (I-a-1) to (I-a-27) | (I-c-54) |
| (I-1459) to (I-1485) | (I-a-1) to (I-a-27) | (I-c-55) |
| (I-1486) to (I-1512) | (I-a-1) to (I-a-27) | (I-c-56) |
| (I-1513) to (I-1539) | (I-a-1) to (I-a-27) | (I-c-57) |
| (I-1540) to (I-1566) | (I-a-1) to (I-a-27) | (I-c-58) |

TABLE 1-continued

| Carboxylate (I) | Anion (I) | Cation (I) |
|---|---|---|
| (I-1567) to (I-1593) | (I-a-1) to (I-a-27) | (I-c-59) |
| (I-1594) to (I-1620) | (I-a-1) to (I-a-27) | (I-c-60) |
| (I-1621) to (I-1647) | (I-a-1) to (I-a-27) | (I-c-61) |
| (I-1648) to (I-1674) | (I-a-1) to (I-a-27) | (I-c-62) |
| (I-1675) to (I-1701) | (I-a-1) to (I-a-27) | (I-c-63) |
| (I-1702) to (I-1728) | (I-a-1) to (I-a-27) | (I-c-64) |
| (I-1729) to (I-1755) | (I-a-1) to (I-a-27) | (I-c-65) |
| (I-1756) to (I-1782) | (I-a-1) to (I-a-27) | (I-c-66) |
| (I-1783) to (I-1809) | (I-a-1) to (I-a-27) | (I-c-67) |
| (I-1810) to (I-1836) | (I-a-1) to (I-a-27) | (I-c-68) |
| (I-1837) to (I-1863) | (I-a-1) to (I-a-27) | (I-c-69) |
| (I-1864) to (I-1890) | (I-a-1) to (I-a-27) | (I-c-70) |
| (I-1891) to (I-1917) | (I-a-1) to (I-a-27) | (I-c-71) |
| (I-1918) to (I-1944) | (I-a-1) to (I-a-27) | (I-c-72) |
| (I-1945) to (I-1971) | (I-a-1) to (I-a-27) | (I-c-73) |
| (I-1972) to (I-1998) | (I-a-1) to (I-a-27) | (I-c-74) |
| (I-1999) to (I-2025) | (I-a-1) to (I-a-27) | (I-c-75) |
| (I-2026) to (I-2052) | (I-a-1) to (I-a-27) | (I-c-76) |
| (I-2053) to (I-2079) | (I-a-1) to (I-a-27) | (I-c-77) |
| (I-2080) to (I-2106) | (I-a-1) to (I-a-27) | (I-c-78) |
| (I-2107) to (I-2133) | (I-a-1) to (I-a-27) | (I-c-79) |
| (I-2134) to (I-2160) | (I-a-1) to (I-a-27) | (I-c-80) |
| (I-2161) to (I-2187) | (I-a-1) to (I-a-27) | (I-c-81) |
| (I-2188) to (I-2214) | (I-a-1) to (I-a-27) | (I-c-82) |
| (I-2215) to (I-2241) | (I-a-1) to (I-a-27) | (I-c-83) |

Of these, the carboxylate (I) is preferably carboxylate (I-1) to carboxylate (I-12), carboxylate (I-28) to carboxylate (I-39), carboxylate (I-55) to carboxylate (I-66), carboxylate (I-82) to carboxylate (I-93), carboxylate (I-109) to carboxylate (I-120), carboxylate (I-136) to carboxylate (I-147), carboxylate (I-163) to carboxylate (I-174), carboxylate (I-190) to carboxylate (I-201), carboxylate (I-217) to carboxylate (I-228), carboxylate (I-244) to carboxylate (I-255), carboxylate (I-271) to carboxylate (I-282), carboxylate (I-298) to carboxylate (I-309), carboxylate (I-325) to carboxylate (I-336), carboxylate (I-352) to carboxylate (I-363), carboxylate (I-379) to carboxylate (I-390), carboxylate (I-406) to carboxylate (I-417), carboxylate (I-433) to carboxylate (I-444), carboxylate (I-460) to carboxylate (I-471), carboxylate (I-487) to carboxylate (I-498), carboxylate (I-514) to carboxylate (I-525), carboxylate (I-541) to carboxylate (I-552), carboxylate (I-568) to carboxylate (I-579), carboxylate (I-595) to carboxylate (I-606), carboxylate (I-622) to carboxylate (I-633), carboxylate (I-649) to carboxylate (I-660), carboxylate (I-676) to carboxylate (I-687), carboxylate (I-703) to carboxylate (I-714), carboxylate (I-730) to carboxylate (I-741), carboxylate (I-757) to carboxylate (I-768), carboxylate (I-784) to carboxylate (I-795), carboxylate (I-811) to carboxylate (I-822), carboxylate (I-838) to carboxylate (I-849), carboxylate (I-865) to carboxylate (I-876), carboxylate (I-892) to carboxylate (I-903), carboxylate (I-919) to carboxylate (I-930), carboxylate (I-946) to carboxylate (I-957), carboxylate (I-973) to carboxylate (I-984), carboxylate (I-1000) to carboxylate (I-1011), carboxylate (I-1027) to carboxylate (I-1038), carboxylate (I-1054) to carboxylate (I-1065), carboxylate (I-1081) to carboxylate (I-1092), carboxylate (I-1108) to carboxylate (I-1119), carboxylate (I-1135) to carboxylate (I-1146), carboxylate (I-1162) to carboxylate (I-1173), carboxylate (I-1189) to carboxylate (I-1200), carboxylate (I-1216) to carboxylate (I-1227), carboxylate (I-1243) to carboxylate (I-1254), carboxylate (I-1270) to carboxylate (I-1281), carboxylate (I-1297) to carboxylate (I-1308), carboxylate (I-1324) to carboxylate (I-1335), carboxylate (I-1351) to carboxylate (I-1362), carboxylate (I-1378) to carboxylate (I-1389), carboxylate (I-1405) to carboxylate (I-1416), carboxylate (I-1432) to carboxylate (I-1443), carboxylate (I-1459) to carboxylate (I-1470), carboxylate (I-1486) to carboxylate (I-1497), carboxylate (I-1513) to carboxylate (I-1524), carboxylate (I-1540) to carboxylate (I-1551), carboxylate (I-1567) to carboxylate (I-1578), carboxylate (I-1594) to carboxylate (I-1605), carboxylate (I-1621) to carboxylate (I-1632), carboxylate (I-1648) to carboxylate (I-1659), carboxylate (I-1675) to carboxylate (I-1686), carboxylate (I-1702) to carboxylate (I-1713), carboxylate (I-1729) to carboxylate (I-1740), carboxylate (I-1756) to carboxylate (I-1767), carboxylate (I-1783) to carboxylate (I-1794), carboxylate (I-1810) to carboxylate (I-1821), carboxylate (I-1837) to carboxylate (I-1848), carboxylate (I-1864) to carboxylate (I-1875), carboxylate (I-1891) to carboxylate (I-1902), carboxylate (I-1918) to carboxylate (I-1929), carboxylate (I-1945) to carboxylate (I-1956), carboxylate (I-1972) to carboxylate (I-1983), carboxylate (I-1999) to carboxylate (I-2010), carboxylate (I-2026) to carboxylate (I-2037), carboxylate (I-2053) to carboxylate (I-2064), carboxylate (I-2080) to carboxylate (I-2091), carboxylate (I-2107) to carboxylate (I-2118), carboxylate (I-2134) to carboxylate (I-2145), carboxylate (I-2161) to carboxylate (I-2172), carboxylate (I-2188) to carboxylate (I-2199), carboxylate (I-2215) to carboxylate (I-2226).

<Method for Producing Carboxylate (I)>

The carboxylate (I) can be produced by reacting a salt represented by formula (I-a) with a salt represented by formula (I-b) in a solvent:

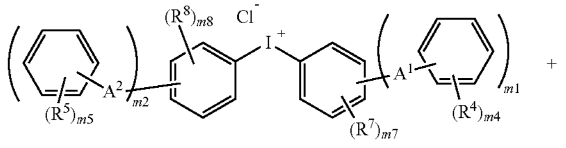

(I-a)

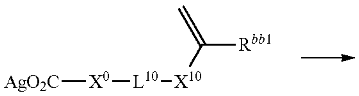

(I-b)

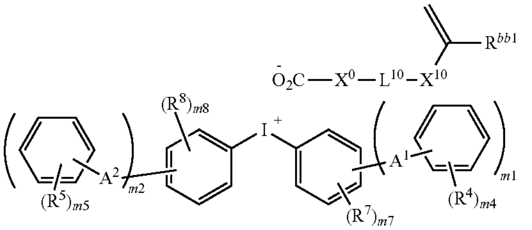

(I)

wherein symbols $R^4$, $R^5$, $R^7$, $R^8$, $R^{bb1}$, m1, m2, m4, m5, m7, m8, $A^1$, $A^2$, $X^0$, $X^{10}$ and $L^{10}$ are the same as defined above.

Examples of the solvent in this reaction include chloroform, acetonitrile, ion-exchanged water and the like.

The reaction temperature is usually 15° C. to 80° C., and the reaction time is usually 0.5 to 24 hours.

Examples of the salt represented by formula (I-a) include salts represented by the following formulas. These salts can be easily produced by the method mentioned in JP 2020-15713 A, or a known production method.

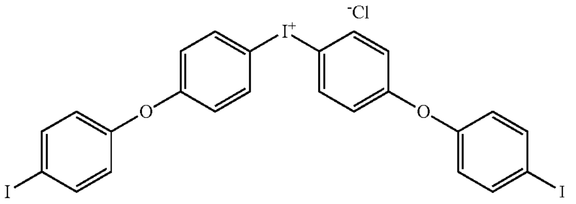

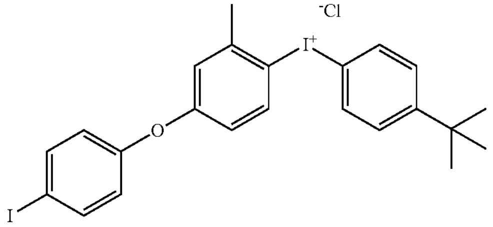

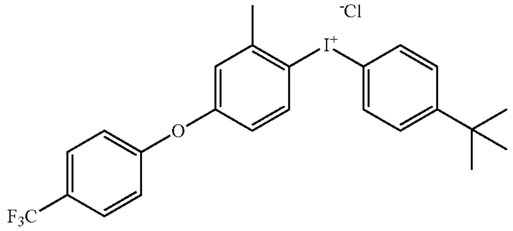

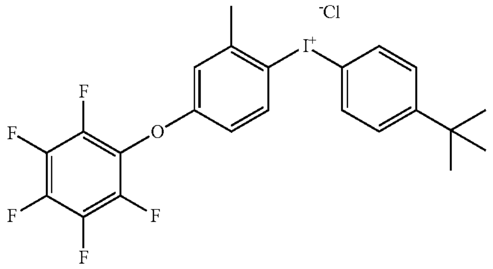

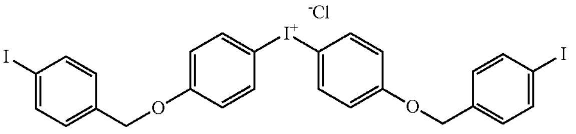

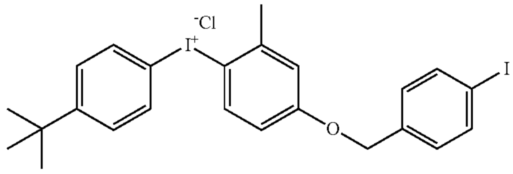

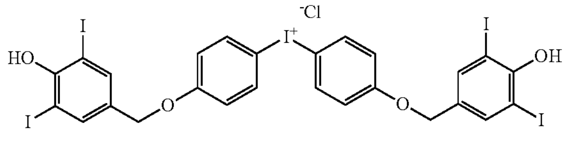

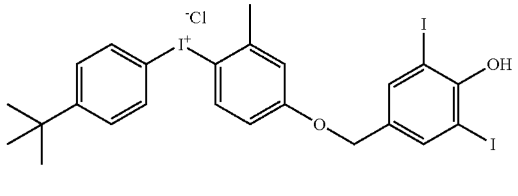

The salt represented by formula (I-b) can be produced by reacting a compound represented by formula (I-c) with silver oxide in a solvent.

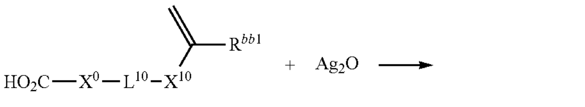

(I-c)

(I-b)

wherein all symbols are the same as defined above.

Examples of the solvent in this reaction include chloroform, acetonitrile and the like.

The reaction temperature is usually 15° C. to 80° C., and the reaction time is usually 0.5 to 24 hours.

Examples of the compound represented by formula (I-c) include compounds represented by the following formulas and the like. These compound are easily available on the market, or can be easily produced by a known production method.

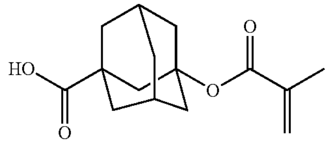

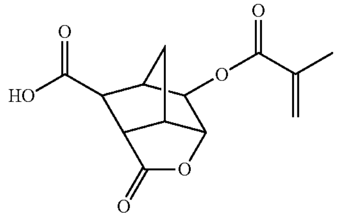

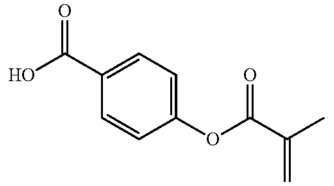

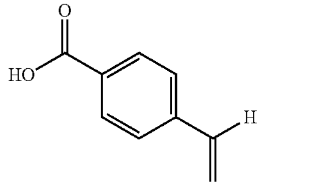

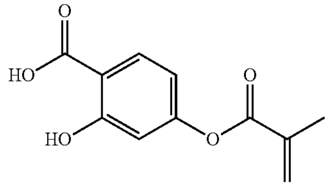

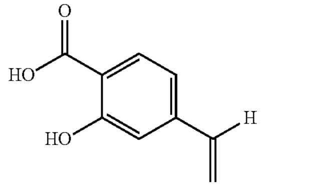

-continued

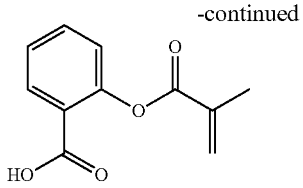

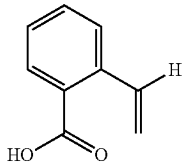

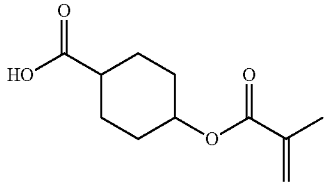

[Carboxylic Acid Generator]

The carboxylic acid generator of the present disclosure is an acid generator including a carboxylate (I). The carboxylate (I) of the present disclosure can act as an acid generator in the resist composition. When using the carboxylate (I) as the acid generator in the resist composition, the acid generator may include the carboxylate (I) alone, or two or more thereof.

As mentioned later, the carboxylic acid generator of the present disclosure may further include an acid generator known in the resist field other than the carboxylate (I) (hereinafter sometimes referred to as "acid generator (B)") and/or a carboxylic acid generator known in the resist field other than the carboxylate (I). The acid generator (B) may be used alone, or in combination of two or more thereof.

When the carboxylic acid generator of the present disclosure includes the acid generator (B), a ratio of the content of the carboxylate (I) to that of the acid generator (B) (mass ratio; carboxylate (I):acid generator (B)) is usually 1:99 to 100:0, preferably 1:99 to 99:1, more preferably 2:98 to 98:2, still more preferably 5:95 to 95:5, and yet more preferably 10:90 to 90:10 or 15:85 to 85:15.

[Structural Unit Derived from Salt Represented by Formula (I)]

The structural unit derived from a salt represented by formula (I) is a structural unit represented by formula (IP) (hereinafter sometimes referred to as "structural unit (IP)").

Such structural unit (IP) also functions as the acid generator similarly to the salt (I), and also functions as the structural unit constituting the compound or the resin.

[Structural Unit Derived from Carboxylate Represented by Formula (I)]

The resin of the present disclosure is a resin including structural unit (IP) derived from a carboxylate represented by formula (I) (hereinafter sometimes referred to as "resin (Ap)")

(IP)

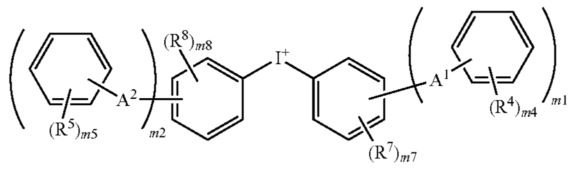

-continued

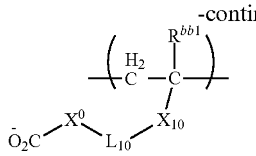

wherein symbols $R^4$, $R^5$, $R^7$, $R^8$, $R^{bb1}$, m1, m2, m4, m5, m7, m8, $A^1$, $A^2$, $X^0$, $X^{10}$ and $L^{10}$ are respectively the same as defined above.

The structural unit (IP) indicates a state where a double bond $CH_2{=}C{-}R^{bb1}$ included in the salt (I) is cleaved.

The resin (Ap) may be either a homopolymer including the structural unit (IP) alone, or a copolymer including two or more structural units (IP).

The resin (Ap) may include a structural unit other than the structural unit (IP). As mentioned later, examples of the structural unit other than the structural unit (IP) include a structural unit having an acid-labile group (hereinafter sometimes referred to as "structural unit (a1)"), a structural unit having no acid-labile group (hereinafter sometimes referred to as "structural unit (s)"), other structural unit (hereinafter sometimes referred to as "structural unit (t)") and a structural unit known in the relevant field. Here, the "acid-labile group" means a group having a leaving group which is eliminated by contact with an acid, thus converting a constitutional unit into a constitutional unit having a hydrophilic group (e.g. a hydroxy group or a carboxy group).

The content of the structural unit (IP) is usually 0.1 to 100 mol %, preferably 0.5 to 50 mol %, more preferably 0.8 to 30 mol %, and still more preferably 1 to 10 mol %, based on the total amount of the resin (Ap).

As mentioned later, when the resin (Ap) is used for a resist composition, it may preferably include, in addition to the structural unit (IP), a structural unit (a1).

As mentioned later, when the resin (Ap) is used for a resist composition, regardless of whether or not the structural unit (a1) is included, it may be used in combination with a resin including a structural unit (a1) (hereinafter sometimes referred to as "resin (A)") and/or a resin other than the resin (A). Hereinafter, the resin (Ap) and/or the resin (A) is/are sometimes referred to as "resin (A) and/or the like".

It is preferable that the resin (Ap) and the resin (A) further include a structural unit other than the structural unit (a1).

Examples of the structural unit other than the structural unit (a1) include a structural unit having no acid-labile group (hereinafter sometimes referred to as "structural unit (s)"), other structural unit (hereinafter sometimes referred to as "structural unit (t)") and a structural unit known in the relevant field.

<Structural Unit (a1)>

The structural unit (a1) is derived from a monomer having an acid-labile group (hereinafter sometimes referred to as "monomer (a1)").

The acid-labile group contained in the resin (A) is preferably a group represented by formula (1) (hereinafter also referred to as group (1)) and/or a group represented by formula (2) (hereinafter also referred to as group (2)):

(1)

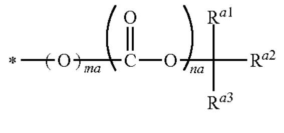

wherein, in formula (1), $R^{a1}$, $R^{a2}$ and $R^{a3}$ each independently represent an alkyl group having 1 to 8 carbon atoms, an alkenyl group having 2 to 8 carbon atoms, an alicyclic hydrocarbon group having 3 to 20 carbon atoms, an aromatic hydrocarbon group having 6 to 18 carbon atoms, or a group obtained by combining these groups, and $R^{a1}$ and $R^{a2}$ are bonded to each other to form a nonaromatic hydrocarbon ring having 3 to 20 carbon atoms together with carbon atoms to which $R^{a1}$ and $R^{a2}$ are bonded, ma and na each independently represent 0 or 1, and at least one of ma and na represents 1, and

* represents a bonding site:

(2)

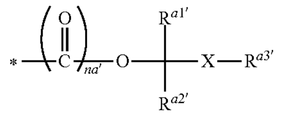

wherein, in formula (2), $R^{a1'}$ and $R^{a2'}$ each independently represent a hydrogen atom or a hydrocarbon group having 1 to 12 carbon atoms, $R^{a3'}$ represents a hydrocarbon group having 1 to 20 carbon atoms, or $R^{a2'}$ and $R^{a3'}$ are bonded to each other to form a heterocyclic ring having 3 to 20 carbon atoms together with carbon atoms and X to which $R^{a2'}$ and $R^{a3'}$ are bonded, and $-CH_2-$ included in the hydrocarbon group and the heterocyclic ring may be replaced by $-O-$ or $-S-$, X represents an oxygen atom or a sulfur atom, na' represents 0 or 1, and

* represents a bonding site.

Examples of the alkyl group in $R^{a1}$, $R^{a2}$ and $R^{a3}$ include a methyl group, an ethyl group, a propyl group, a butyl group, a pentyl group, a hexyl group, a heptyl group, an octyl group and the like.

Examples of the alkenyl group in $R^{a1}$, $R^{a2}$ and $R^{a3}$ include an ethenyl group, a propenyl group, an isopropenyl group, a butenyl group, an isobutenyl group, a tert-butenyl group, a pentenyl group, a hexenyl group, a heptenyl group, an octenyl group, an isooctenyl group and a nonenyl group.

The alicyclic hydrocarbon group in $R^{a1}$, $R^{a2}$ and $R^{a3}$ may be either monocyclic or polycyclic. Examples of the monocyclic alicyclic hydrocarbon group include cycloalkyl groups such as a cyclopentyl group, a cyclohexyl group, a cycloheptyl group and a cyclooctyl group. Examples of the polycyclic alicyclic hydrocarbon group include a decahydronaphthyl group, an adamantyl group, a norbornyl group and the following groups (* represents a bonding site). In some embodiments, the number of carbon atoms of the alicyclic hydrocarbon group of $R^{a1}$, $R^{a2}$ and $R^{a3}$ is preferably 3 to 16.

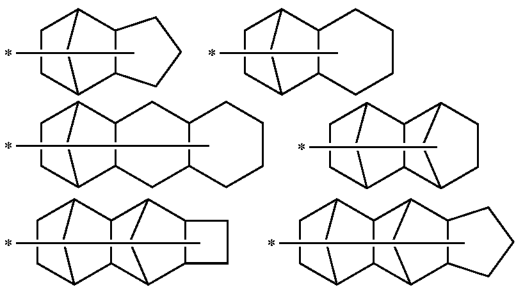

-continued

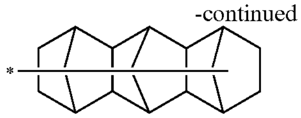

Examples of the aromatic hydrocarbon group in $R^{a1}$, $R^{a2}$ and $R^{a3}$ include aryl groups such as a phenyl group, a naphthyl group, an anthryl group, a biphenyl group and a phenanthryl group.

Examples of the combined group include groups obtained by combining the above-mentioned alkyl group and alicyclic hydrocarbon group (e.g., alkylcycloalkyl groups or cycloalkylalkyl groups, such as a methylcyclohexyl group, a dimethylcyclohexyl group, a methylnorbornyl group, a cyclohexylmethyl group, an adamantylmethyl group, an adamantyldimethyl group and a norbornylethyl group), aralkyl groups such as a benzyl group, aromatic hydrocarbon groups having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), aromatic hydrocarbon groups having an alicyclic hydrocarbon group (a p-cyclohexylphenyl group, a p-adamantylphenyl group, etc.), aryl-cycloalkyl groups such as a phenylcyclohexyl group, and the like.

Preferably, ma is 0 and na is 1.

When $R^{a1}$ and $R^{a2}$ are bonded to each other to form a nonaromatic hydrocarbon ring, examples of —C($R^{a1}$) ($R^{a2}$) ($R^{a3}$) include the following rings. The nonaromatic hydrocarbon ring preferably has 3 to 12 carbon atoms. * represents a bonding site to —O—.

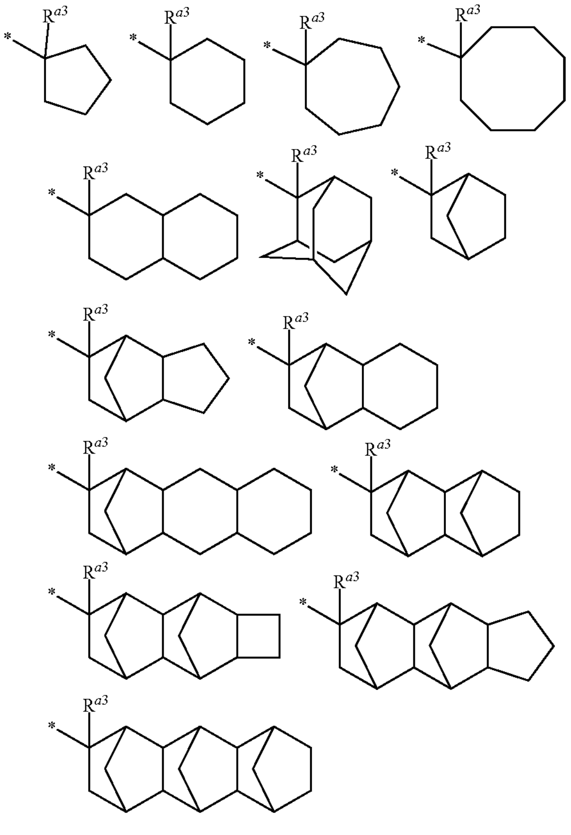

Examples of the hydrocarbon group in $R^{a1'}$, $R^{a2'}$ and $R^{a3'}$ include an alkyl group, an alicyclic hydrocarbon group, an aromatic hydrocarbon group, and groups formed by combining these groups.

Examples of the alkyl group and the alicyclic hydrocarbon group include those which are the same as mentioned in $R^{a1}$, $R^{a2}$ and $R^{a3}$.

Examples of the aromatic hydrocarbon group include aryl groups such as a phenyl group, a naphthyl group, an anthryl group, a biphenyl group and a phenanthryl group.

Examples of the combined group include groups obtained by combining the above-mentioned alkyl group and alicyclic hydrocarbon group (e.g., alkylcycloalkyl groups or cycloalkylalkyl groups, such as a methylcyclohexyl group, a dimethylcyclohexyl group, a methylnorbornyl group, a cyclohexylmethyl group, an adamantylmethyl group, an adamantyldimethyl group and a norbornylethyl group), aralkyl groups such as a benzyl group, aromatic hydrocarbon groups having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), aromatic hydrocarbon groups having an alicyclic hydrocarbon group (a p-cyclohexylphenyl group, a p-adamantylphenyl group, etc.), aryl-cycloalkyl groups such as a phenylcyclohexyl group and the like.

When $R^{a2'}$ and $R^{a3'}$ are bonded to each other to form a heterocyclic ring together with carbon atoms and X to which $R^{a2'}$ and $R^{a3'}$ are bonded, examples of —C($R^{a1'}$)($R^{a2'}$)—X—$R^{a3'}$ include the following rings. * represents a bonding site.

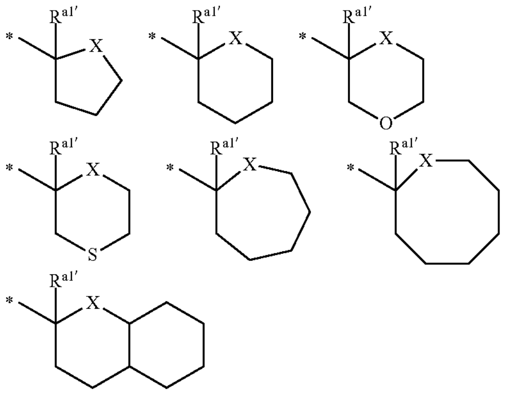

At least one of $R^{a1'}$ and $R^{a2'}$ is preferably a hydrogen atom.

na' is preferably 0.

Examples of the group (1) include the following groups.

A group wherein, in formula (1), $R^{a1}$, $R^{a2}$ and $R^{a3}$ are alkyl groups, ma=0 and na=1. The group is preferably a tert-butoxycarbonyl group.

A group wherein, in formula (1), $R^{a1}$ and $R^{a2}$ are bonded to each other to form an adamantyl group together with carbon atoms to which $R^{a1}$ and $R^{a2}$ are bonded, $R^{a3}$ is an alkyl group, ma=0 and na=1.

A group wherein, in formula (1), $R^{a1}$ and $R^{a2}$ are each independently an alkyl group, $R^{a3}$ is an adamantyl group, ma=0 and na=1.

Specific examples of the group (1) include the following groups. * represents a bonding site.

-continued
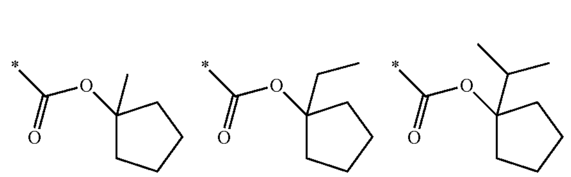
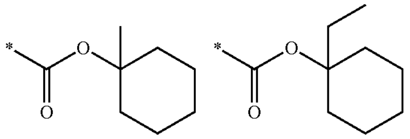
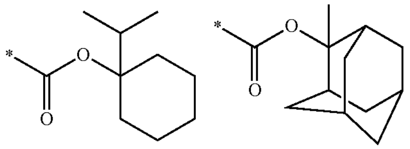
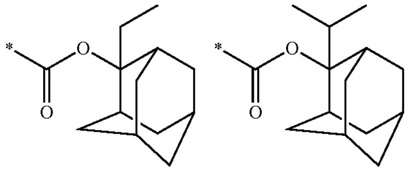
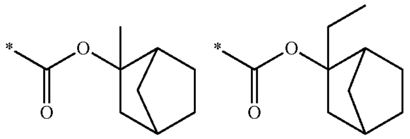
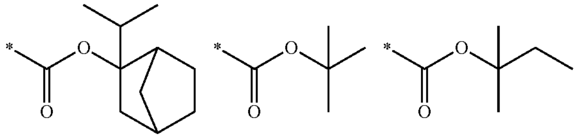
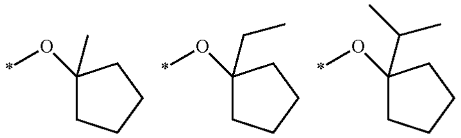
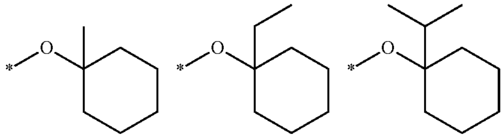
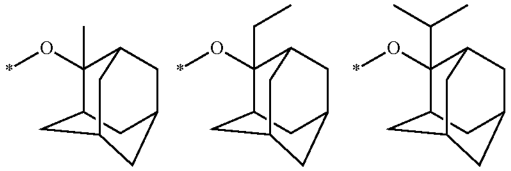
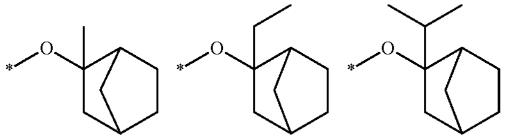
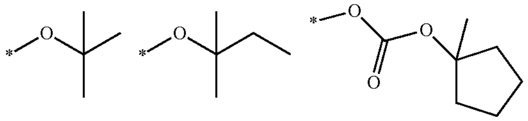
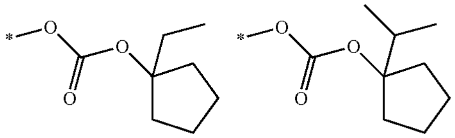
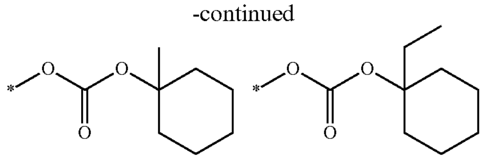
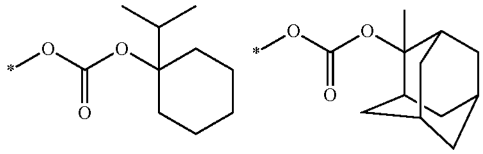
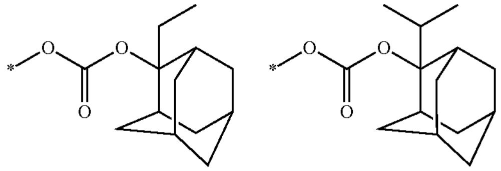
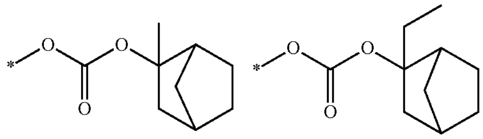
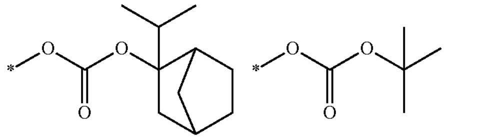
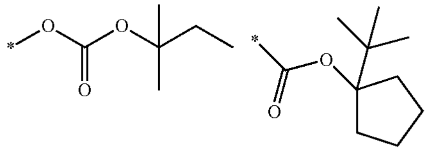
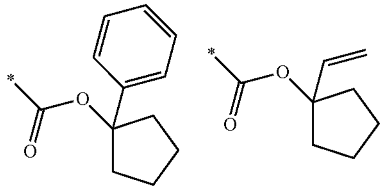
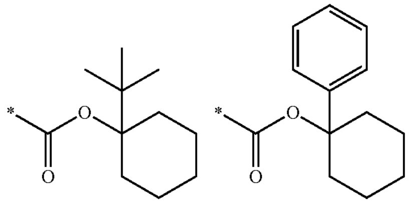
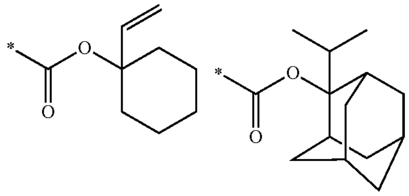
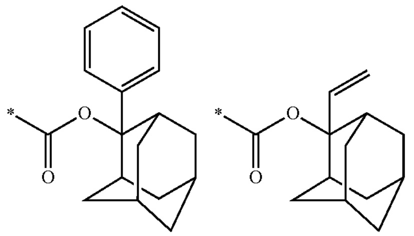

-continued
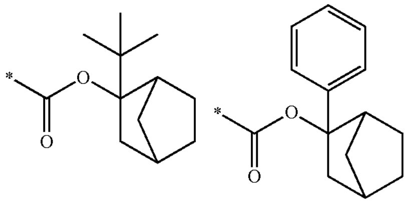
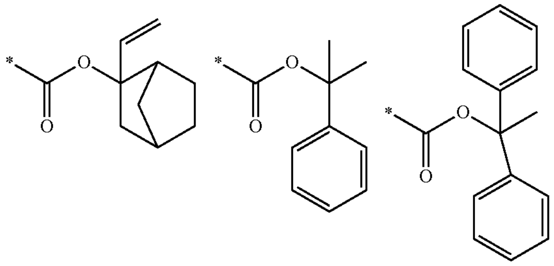
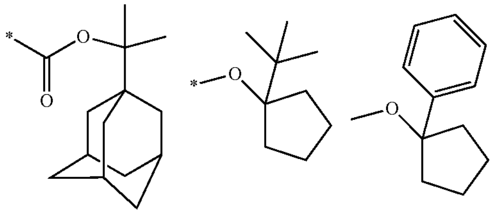
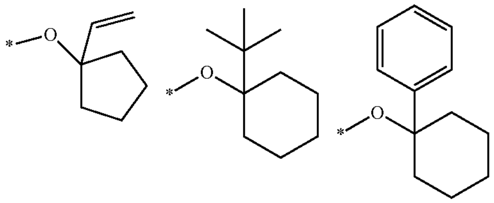
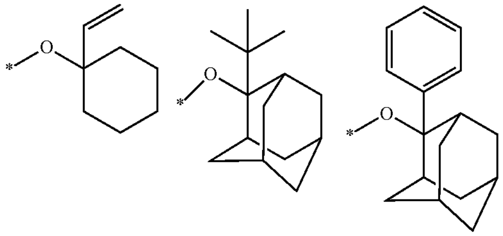
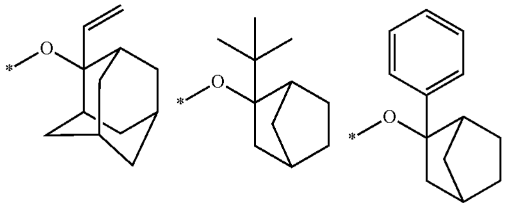
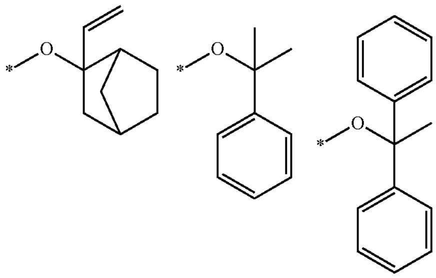
-continued
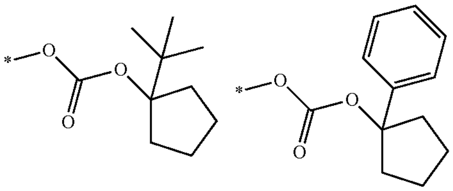
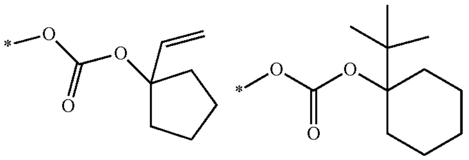
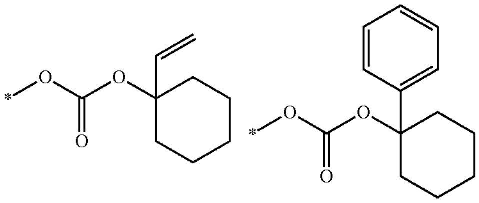
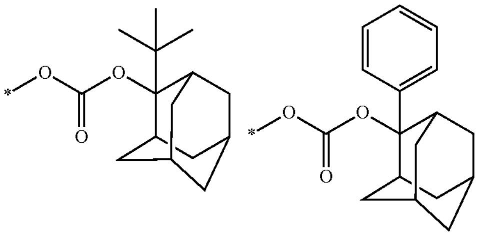
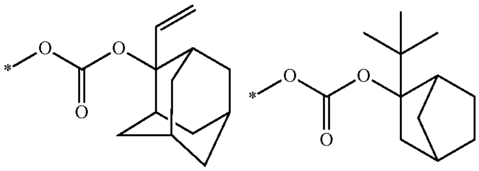
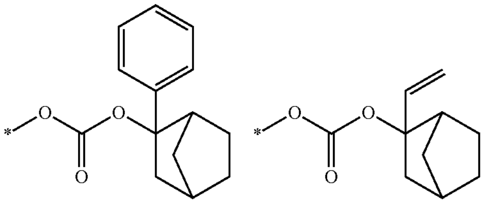
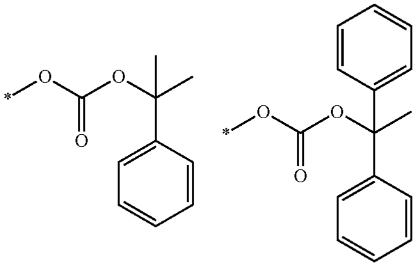
Specific examples of the group (2) include the following groups. * represents a bonding site.
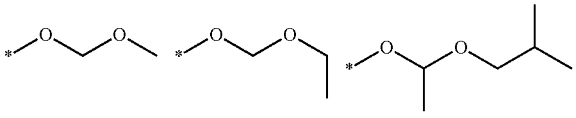

-continued

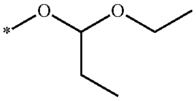

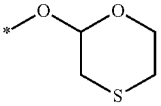

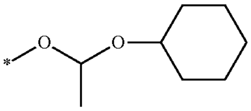

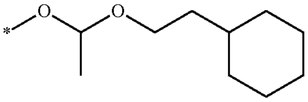

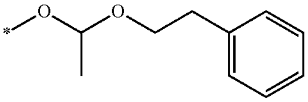

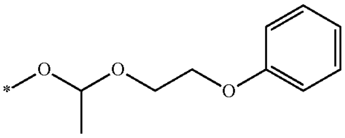

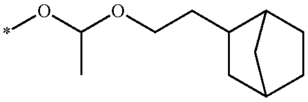

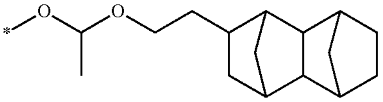

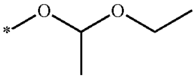

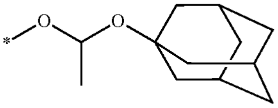

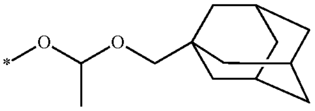

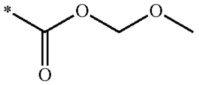

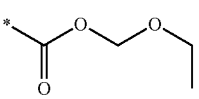

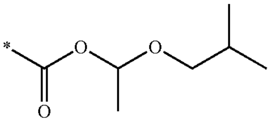

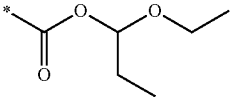

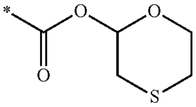

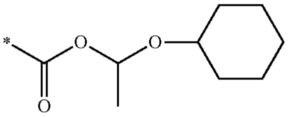

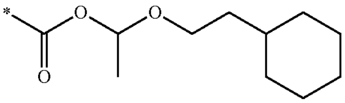

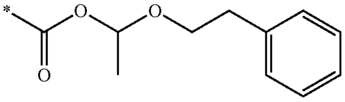

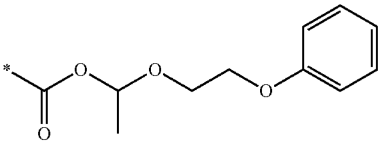

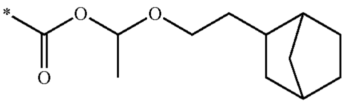

-continued

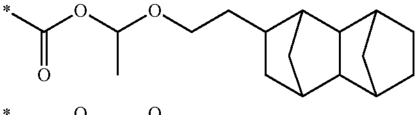

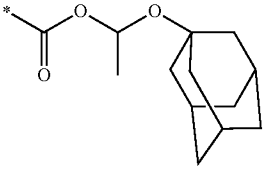

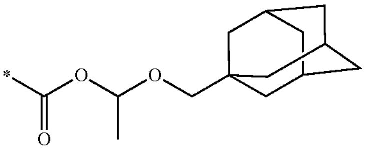

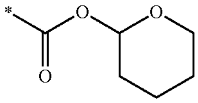

The monomer (a1) is preferably a monomer having an acid-labile group and an ethylenic unsaturated bond, and more preferably a (meth)acrylic monomer having an acid-labile group.

Of the (meth)acrylic monomers having an acid-labile group, those having an alicyclic hydrocarbon group having 5 to 20 carbon atoms are preferably exemplified. When a resin (A) including a structural unit derived from a monomer (a1) having a bulky structure such as an alicyclic hydrocarbon group is used in a resist composition, it is possible to improve the resolution of a resist pattern.

The structural unit derived from a (meth)acrylic monomer having a group (1) includes a structural unit represented by formula (a1-0) (hereinafter sometimes referred to as structural unit (a1-0)), a structural unit represented by formula (a1-1) (hereinafter sometimes referred to as structural unit (a1-1)) or a structural unit represented by formula (a1-2) (hereinafter sometimes referred to as structural unit (a1-2)). Preferably, the structural unit is at least one structural unit selected from the group consisting of structural unit (a1-0), structural unit (a1-1) and structural unit (a1-2), and more preferably at least one structural unit selected from the group consisting of structural unit (a1-1) and structural unit (a1-2). These structural units may be used alone, or two or more structural units may be used in combination.

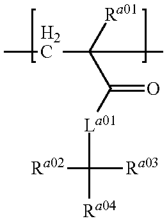

(a1-0)

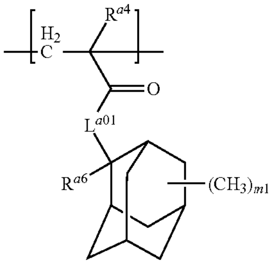

(a1-1)

-continued (a1-2)

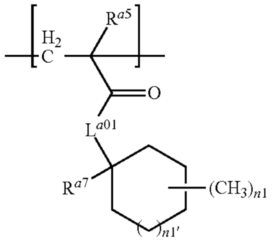

In formula (a1-0), formula (a1-1) and formula (a1-2), $L^{a01}$, $L^{a1}$ and $L^{a2}$ each independently represent —O— or *—O—$(CH_2)_{k1}$—CO—O—, k1 represents an integer of 1 to 7, and * represents a bonding site to —CO—, $R^{a01}$, $R^{a4}$ and $R^{a5}$ each independently represent a hydrogen atom, a halogen atom or an alkyl group having 1 to 6 carbon atoms which may have a halogen atom, $R^{a02}$, $R^{a03}$ and $R^{a04}$ each independently represent an alkyl group having 1 to 8 carbon atoms, an alicyclic hydrocarbon group having 3 to 18 carbon atoms, an aromatic hydrocarbon group having 6 to 18 carbon atoms, or a group obtained by combining these groups, $R^{a6}$ and $R^{a7}$ each independently represent an alkyl group having 1 to 8 carbon atoms, an alkenyl group having 2 to 8 carbon atoms, an alicyclic hydrocarbon group having 3 to 18 carbon atoms, an aromatic hydrocarbon group having 6 to 18 carbon atoms, or a group obtained by combining these groups, m1 represents an integer of 0 to 14, n1 represents an integer of 0 to 10, and n1' represents an integer of 0 to 3.

$R^{a01}$, $R^{a4}$ and $R^{a5}$ are preferably a hydrogen atom or a methyl group, and more preferably a methyl group.

$L^{a01}$, $L^{a1}$ and $L^{a2}$ are preferably an oxygen atom or *—O—$(CH_2)_{k01}$—CO—O— (in which k01 is preferably an integer of 1 to 4, and more preferably 1), and more preferably an oxygen atom.

Examples of the alkyl group, the alicyclic hydrocarbon group, the aromatic hydrocarbon group, and groups obtained by combining these groups in $R^{a02}$, $R^{a03}$ and $R^{a04}$ include the same groups as mentioned as for $R^{a1}$, $R^{a2}$ and $R^{a3}$ of the group (1).

Examples of the alkyl group, the alkenyl group, the alicyclic hydrocarbon group, the aromatic hydrocarbon group, and groups obtained by combining these groups in $R^{a6}$ and $R^{a7}$ include the same groups as mentioned as for $R^{a1}$, $R^{a2}$ and $R^{a3}$ of formula (1).

The alkyl group in $R^{a02}$, $R^{a03}$ and $R^{a04}$ is preferably an alkyl group having 1 to 6 carbon atoms, more preferably a methyl group or an ethyl group, and still more preferably a methyl group.

The alkyl group in $R^{a6}$ and $R^{a7}$ is preferably an alkyl group having 1 to 6 carbon atoms, more preferably a methyl group, an ethyl group, an isopropyl group or a t-butyl group, and still more preferably an ethyl group, an isopropyl group or a t-butyl group.

The alkenyl group in $R^{a6}$ and $R^{a7}$ is preferably an alkenyl group having 2 to 6 carbon atoms, and more preferably an ethenyl group, a propenyl group, an isopropenyl group or a butenyl group.

In some embodiments, the number of carbon atoms of the alicyclic hydrocarbon group as for $R^{a02}$, $R^{a03}$, $R^{a04}$, $R^{a6}$ and $R^{a7}$ is preferably 5 to 12, and more preferably 5 to 10.

In some embodiments, the number of carbon atoms of the aromatic hydrocarbon group of $R^{a02}$, $R^{a03}$, $R^{a04}$, Ra and $R^{a7}$ is preferably 6 to 12, and more preferably 6 to 10.

The total number of carbon atoms of the group obtained by combining the alkyl group with the alicyclic hydrocarbon group is preferably 18 or less.

The total number of carbon atoms of the group obtained by combining the alkyl group with the aromatic hydrocarbon group is preferably 18 or less.

$R^{a02}$ and $R^{a03}$ are preferably an alkyl group having 1 to 6 carbon atoms or an aromatic hydrocarbon group having 6 to 12 carbon atoms, and more preferably a methyl group, an ethyl group, a phenyl group or a naphthyl group.

$R^{a04}$ is preferably an alkyl group having 1 to 6 carbon atoms or an alicyclic hydrocarbon group having 5 to 12 carbon atoms, and more preferably a methyl group, an ethyl group, a cyclohexyl group or an adamantyl group.

Preferably, $R^{a6}$ and $R^{a7}$ are each independently an alkyl group having 1 to 6 carbon atoms, an alkenyl group having 2 to 6 carbon atoms or an aromatic hydrocarbon group having 6 to 12 carbon atoms, more preferably a methyl group, an ethyl group, an isopropyl group, a t-butyl group, an ethenyl group, a phenyl group or a naphthyl group, and still more preferably an ethyl group, an isopropyl group, a t-butyl group, an ethenyl group or a phenyl group.

m1 is preferably an integer of 0 to 3, and more preferably 0 or 1.

n1 is preferably an integer of 0 to 3, and more preferably 0 or 1.

n1' is preferably 0 or 1.

The structural unit (a1-0) includes, for example, a structural unit represented by any one of formula (a1-0-1) to formula (a1-0-18) and a structural unit in which a methyl group corresponding to $R^{a01}$ in the structural unit (a1-0) is substituted with a hydrogen atom, a halogen atom, a haloalkyl group or other alkyl groups, and is preferably a structural unit represented by any one of formula (a1-0-1) to formula (a1-0-10), formula (a1-0-13) and formula (a1-0-14).

(a1-0-1)

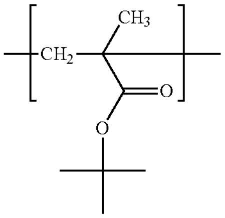

(a1-0-2)

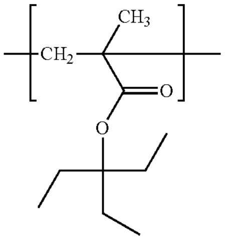

-continued
(a1-0-3)
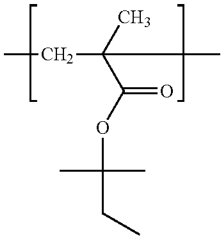
(a1-0-4)
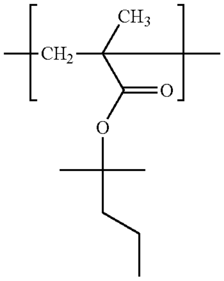
(a1-0-5)
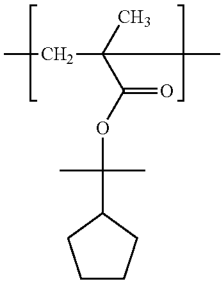
(a1-0-6)
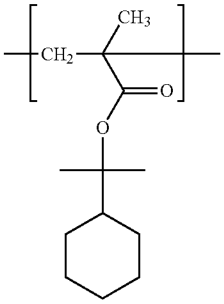
(a1-0-7)
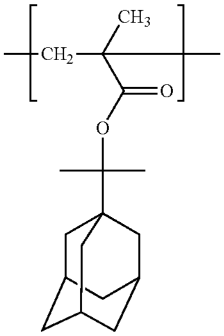
-continued
(a1-0-8)
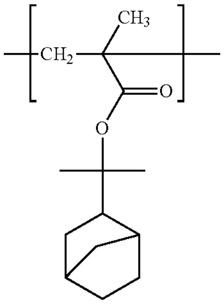
(a1-0-9)
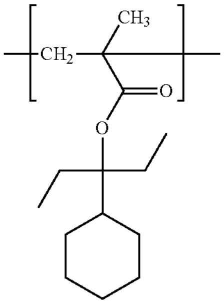
(a1-0-10)
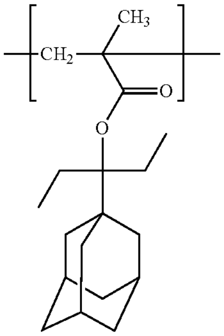
(a1-0-11)
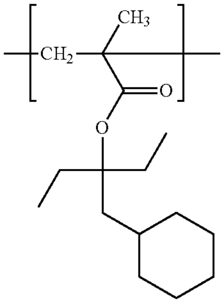
(a1-0-12)
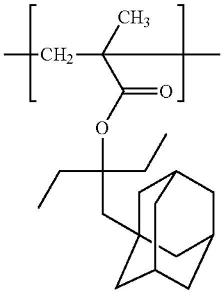

-continued (a1-0-13)

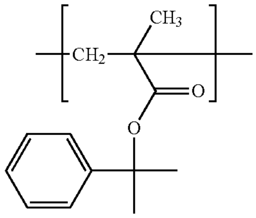

(a1-0-14)

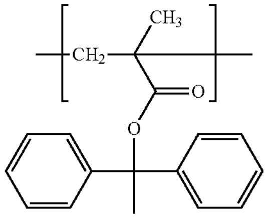

(a1-0-15)

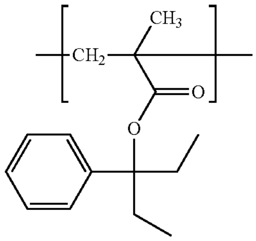

(a1-0-16)

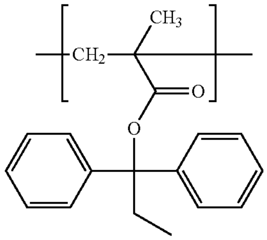

(a1-0-17)

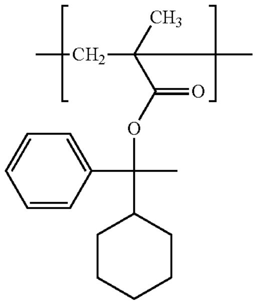

(a1-0-18)

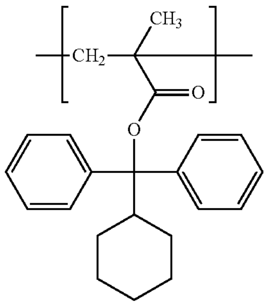

The structural unit (a1-1) includes, for example, structural units derived from the monomers mentioned in JP 2010-204646 A. Of these structural units, a structural unit represented by any one of formula (a1-1-1) to formula (a1-1-7) and a structural unit in which a methyl group corresponding to $R^{a4}$ in the structural unit (a1-1) is substituted with a hydrogen atom, a halogen atom, a haloalkyl group or other alkyl groups are preferable, and a structural unit represented by any one of formula (a1-1-1) to formula (a1-1-4) is more preferable.

(a1-1-1)

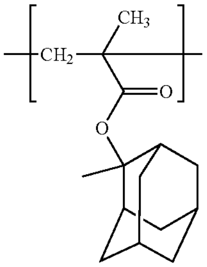

(a1-1-2)

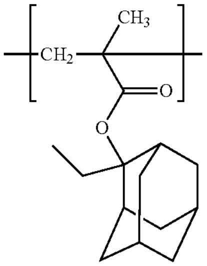

(a1-1-3)

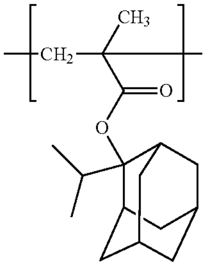

(a1-1-4)

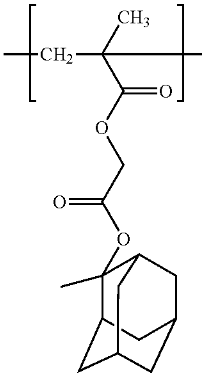

-continued (a1-1-5)

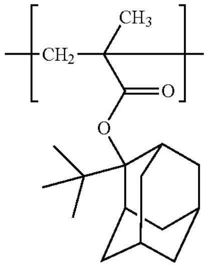

(a1-1-6)

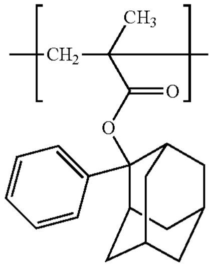

(a1-1-7)

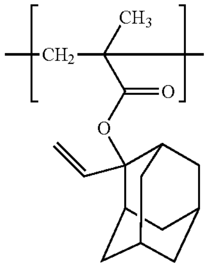

Examples of the structural unit (a1-2) include a structural unit represented by any one of formula (a1-2-1) to formula (a1-2-14), and a structural unit in which a methyl group corresponding to $R^{a5}$ in the structural unit (a1-2) is substituted with a hydrogen atom, a halogen atom, a haloalkyl group or other alkyl groups, and a structure unit represented by any one of formula (a1-2-2), formula (a1-2-5), formula (a1-2-6) and formula (a1-2-10) to formula (a1-2-14) is preferable.

(a1-2-1)

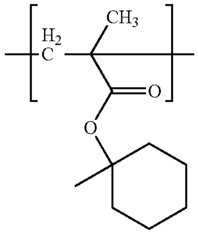

(a1-2-2)

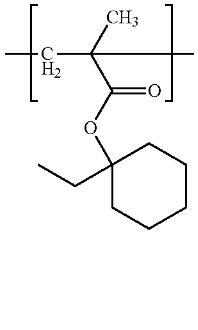

-continued (a1-2-3)

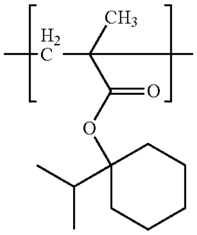

(a1-2-4)

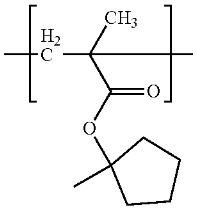

(a1-2-5)

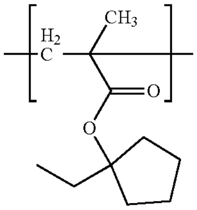

(a1-2-6)

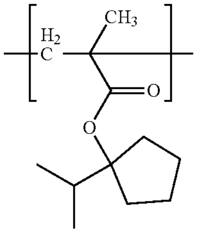

(a1-2-7)

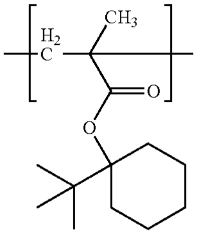

(a1-2-8)

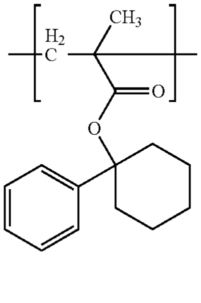

-continued (a1-2-9)

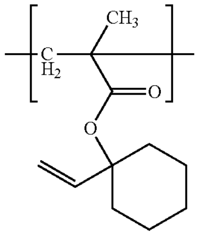

(a1-2-10)

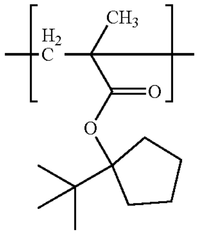

(a1-2-11)

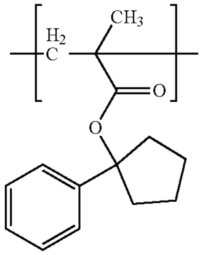

(a1-2-12)

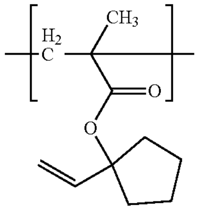

(a1-2-13)

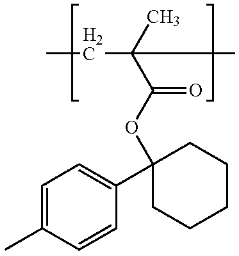

(a1-2-14)

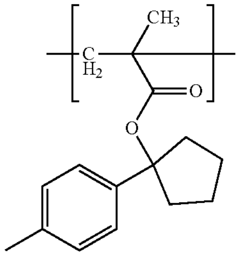

When the resin (A) or the like contains the structural unit (a1-0) and/or the structural unit (a1-1) and/or the structural unit (a1-2), the total content of these is the resin (A) or the like. 10 mol % or more, preferably 15 mol % or more, more preferably 20 mol % or more, still more preferably 25 mol % or more, still more preferably 30 mol %, based on the total structural units % or more. Further, it is 95 mol % or less, preferably 90 mol % or less, more preferably 85 mol % or less, still more preferably 70 mol % or less. Specifically, it is 10 to 95 mol %, preferably 15 to 90 mol %, more preferably 20 to 85 mol %, still more preferably 25 to 70 mol %, still more preferably 30 to 70 mol %.

When the resin (A) or the like contains the structural unit (a1-0), the content thereof may be 5 mol % or more, preferably 10 mol % or more, based on the total structural units of the resin (A). be. Also, it is 80 mol % or less, preferably 75 mol % or less, and more preferably 70 mol % or less. Specifically, it is usually 5 to 80 mol %, preferably 5 to 75 mol %, more preferably 10 to 70 mol %.

When the resin (A) or the like contains the structural unit (a1-1) and/or the structural unit (a1-2), the total content of these is usually 10 mol with respect to the total structural units of the resin (A) or the like. % or more, preferably 15 mol % or more, more preferably 20 mol % or more. Also, it is 90 mol % or less, preferably 85 mol % or less, more preferably 80 mol % or less, still more preferably 75 mol % or less, and even more preferably 70 mol % or less. Specifically, it is 10 to 90 mol %, preferably 15 to 85 mol %, more preferably 20 to 80 mol %, still more preferably 20 to 75 mol %, still more preferably 20~70 mol %.

In the structural unit (a1), examples of the structural unit having a group (2) include a structural unit represented by formula (a1-4) (hereinafter sometimes referred to as "structural unit (a1-4)"):

(a1-4)

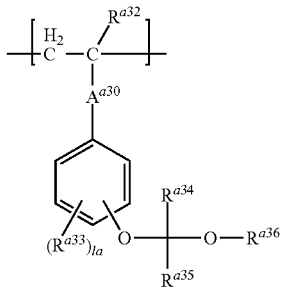

wherein, in formula (a1-4), $R^{a32}$ represents a hydrogen atom, a halogen atom, or an alkyl group having 1 to 6 carbon atoms which may have a halogen atom, $R^{a33}$ represents a halogen atom, a hydroxy group, an alkyl group having 1 to 6 carbon atoms, an alkoxy group having 1 to 6 carbon atoms, an alkoxyalkyl group having 2 to 12 carbon atoms, an alkoxyalkoxy group having 2 to 12 carbon atoms, an alkylcarbonyl group having 2 to 4 carbon atoms, an alkylcarbonyloxy group having 2 to 4 carbon atoms, an acryloyloxy group or a methacryloyloxy group, $A^{a30}$ represents a single bond or *—$X^{a31}$-($A^{a32}$-$X^{a32}$) and * represents a bonding site to carbon atoms to which —$R^{a32}$ is bonded, $A^{a32}$ represents an alkanediyl group having 1 to 6 carbon atoms, $X^{a31}$ and $X^{a32}$ each independently represent —O—, —CO—O— or —O—CO—, nc represents 0 or 1, la represents an integer of 0 to 4, and when la is an integer of 2 or more, a plurality of $R^{a33}$ may be the same or different from each other, and $R^{a34}$ and $R^{a35}$ each independently represent a hydrogen atom or a hydrocarbon group having 1 to 12 carbon atoms, $R^{a36}$ represents a hydrocarbon group having 1 to 20 carbon atoms, or $R^{a35}$ and $R^{a36}$ are bonded to each other to form a divalent hydrocarbon group having 2 to 20 carbon atoms together with —C—O— to which $R^{a35}$ and $R^{a36}$ are bonded, and $—CH_2—$ included in the hydrocarbon group and the divalent hydrocarbon group may be replaced by —O— or —S—.

Examples of the halogen atom in $R^{a32}$ and $R^{a33}$ include a fluorine atom, a chlorine atom and a bromine atom.

Examples of the alkyl group having 1 to 6 carbon atoms which may have a halogen atom in $R^{a32}$ include a trifluoromethyl group, a difluoromethyl group, a methyl group, a perfluoroethyl group, a 2,2,2-trifluoroethyl group, a 1,1,2,2-tetrafluoroethyl group, an ethyl group, a perfluoropropyl group, a 2,2,3,3,3-pentafluoropropyl group, a propyl group, a perfluorobutyl group, a 1,1,2,2,3,3,4,4-octafluorobutyl group, a butyl group, a perfluoropentyl group, a 2,2,3,3,4,4,5,5,5-nonafluoropentyl group, a pentyl group, a hexyl group and a perfluorohexyl group.

$R^{a32}$ is preferably a hydrogen atom or an alkyl group having 1 to 4 carbon atoms, more preferably a hydrogen atom, a methyl group or an ethyl group, and still more preferably a hydrogen atom or a methyl group.

Examples of the alkyl group in $R^{a33}$ include a methyl group, an ethyl group, a propyl group, an isopropyl group, a butyl group, a sec-butyl group, a tert-butyl group, a pentyl group and a hexyl group. The alkyl group is preferably an alkyl group having 1 to 4 carbon atoms, more preferably a methyl group or an ethyl group, and still more preferably a methyl group.

Examples of the alkoxy group in $R^{a33}$ include a methoxy group, an ethoxy group, a propoxy group, an isopropoxy group, a butoxy group, a sec-butoxy group, a tert-butoxy group, a pentyloxy group and a hexyloxy group. The alkoxy group is preferably an alkoxy group having 1 to 4 carbon atoms, more preferably a methoxy group or an ethoxy group, and still more preferably a methoxy group.

Examples of the alkoxyalkyl group in $R^{a33}$ include a methoxymethyl group, an ethoxyethyl group, a propoxymethyl group, an isopropoxymethyl group, a butoxymethyl group, a sec-butoxymethyl group and a tert-butoxymethyl group. The alkoxyalkyl group is preferably an alkoxyalkyl group having 2 to 8 carbon atoms, more preferably a methoxymethyl group or an ethoxyethyl group, and still more preferably a methoxymethyl group.

Examples of the alkoxyalkoxy group in $R^{a33}$ include a methoxymethoxy group, a methoxyethoxy group, an ethoxymethoxy group, an ethoxyethoxy group, a propoxymethoxy group, an isopropoxymethoxy group, a butoxymethoxy group, a sec-butoxymethoxy group and a tert-butoxymethoxy group. The alkoxyalkoxy group is preferably an alkoxyalkoxy group having 2 to 8 carbon atoms, and more preferably a methoxyethoxy group or an ethoxyethoxy group.

Examples of the alkylcarbonyl group in $R^{a33}$ include an acetyl group, a propionyl group and a butyryl group. The alkylcarbonyl group is preferably an alkylcarbonyl group having 2 to 3 carbon atoms, and more preferably an acetyl group.

Examples of the alkylcarbonyloxy group in $R^{a33}$ include an acetyloxy group, a propionyloxy group and a butyryloxy group. The alkylcarbonyloxy group is preferably an alkylcarbonyloxy group having 2 to 3 carbon atoms, and more preferably an acetyloxy group.

$R^{a33}$ is preferably a halogen atom, a hydroxy group, an alkyl group having 1 to 4 carbon atoms, an alkoxy group having 1 to 4 carbon atoms or an alkoxyalkoxy group having 2 to 8 carbon atoms, more preferably a fluorine atom, an iodine atom, a hydroxy group, a methyl group, a methoxy group, an ethoxy group, an ethoxyethoxy group or an ethoxymethoxy group, and still more preferably a fluorine atom, an iodine atom, a hydroxy group, a methyl group, a methoxy group or an ethoxyethoxy group.

Examples of the $*—X^{a31}\text{-}(A^{a32}\text{-}X^{a32})_{nc}—$ include *—O—, *—CO—O—, *—O—CO—, $*—CO—O\text{-}A^{a32}\text{-}CO—O—$, $*—O—CO\text{-}A^{a32}\text{-}O—$, $*—O\text{-}A^{a32}—CO—O—$, $*—CO—O\text{-}A^{a32}\text{-}O—CO—$ and $*—O—CO\text{-}A^{a32}\text{-}O—CO$. Of these, *—CO—O—, $*—CO—O\text{-}A^{a32}\text{-}CO—O—$ or $*—O\text{-}A^{a32}\text{-}CO—O—$ is preferable.

Examples of the alkanediyl group include a methylene group, an ethylene group, a propane-1,3-diyl group, a propane-1,2-diyl group, a butane-1,4-diyl group, a pentane-1,5-diyl group, a hexane-1,6-diyl group, a butane-1,3-diyl group, a 2-methylpropane-1,3-diyl group, a 2-methylpropane-1,2-diyl group, a pentane-1,4-diyl group and a 2-methylbutane-1,4-diyl group.

$A^{a32}$ is preferably a methylene group or an ethylene group.

$A^{a30}$ is preferably a single bond, *—CO—O— or $*—CO—O\text{-}A^{a32}\text{-}CO—O—$, more preferably a single bond, *—CO—O— or $*—CO—O—CH_2—CO—O—$, and still more preferably a single bond or *—CO—O—.

la is preferably 0, 1 or 2, more preferably 0 or 1, and still more preferably 0.

Examples of the hydrocarbon group in $R^{a34}$, $R^{a35}$ and $R^{a36}$ include an alkyl group, an alicyclic hydrocarbon group, an aromatic hydrocarbon group, and groups obtained by combining these groups.

Examples of the alkyl group include a methyl group, an ethyl group, a propyl group, a butyl group, a pentyl group, a hexyl group, a heptyl group, an octyl group and the like.

The alicyclic hydrocarbon group may be either monocyclic or polycyclic. Examples of the monocyclic alicyclic hydrocarbon group include cycloalkyl groups such as a cyclopentyl group, a cyclohexyl group, a cycloheptyl group and a cyclooctyl group. Examples of the polycyclic alicyclic hydrocarbon group include a decahydronaphthyl group, an adamantyl group, a norbornyl group, and the following groups (* represents a bonding site).

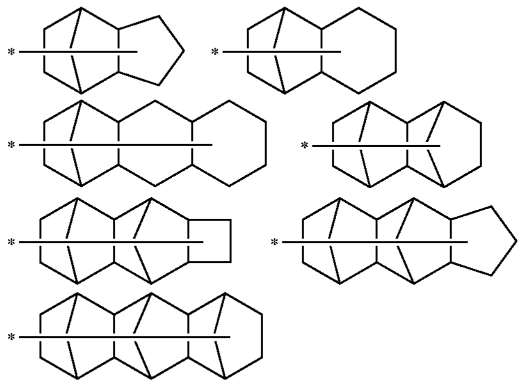

Examples of the aromatic hydrocarbon group include aryl groups such as a phenyl group, a naphthyl group, an anthryl group, a biphenyl group and a phenanthryl group.

Examples of the combined group include groups obtained by combining the above-mentioned alkyl group and alicyclic hydrocarbon group (e.g., alkylcycloalkyl groups or cycloalkylalkyl groups, such as a methylcyclohexyl group, a dimethylcyclohexyl group, a methylnorbornyl group, a cyclohexylmethyl group, an adamantylmethyl group, an adamantyldimethyl group and a norbornylethyl group), aralkyl groups such as a benzyl group, aromatic hydrocarbon groups having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), aromatic hydrocarbon groups having an alicyclic hydrocarbon group (a p-cyclohexylphenyl group, a p-adamantylphenyl group, etc.), aryl-cycloalkyl groups such as a phenylcyclohexyl group and the like. Particularly, examples of $R^{a36}$ include an alkyl group having 1 to 18 carbon atoms, an alicyclic hydrocarbon group having 3 to 18 carbon atoms, an aromatic hydrocarbon group having 6 to 18 carbon atoms, or a group formed by combining these groups.

$R^{a34}$ is preferably a hydrogen atom.

$R^{a35}$ is preferably a hydrogen atom, an alkyl group having 1 to 12 carbon atoms or an alicyclic hydrocarbon group having 3 to 12 carbon atoms, and more preferably a methyl group or an ethyl group.

The hydrocarbon group of $R^{a36}$ is preferably an alkyl group having 1 to 18 carbon atoms, an alicyclic hydrocarbon group having 3 to 18 carbon atoms, an aromatic hydrocarbon group having 6 to 18 carbon atoms, or a group formed by combining these groups, and more preferably an alkyl group having 1 to 18 carbon atoms, an alicyclic hydrocarbon group having 3 to 18 carbon atoms or an aralkyl group having 7 to 18 carbon atoms. The alkyl group and the alicyclic hydrocarbon group in $R^{a36}$ are preferably unsubstituted. The aromatic hydrocarbon group in $R^{a36}$ is preferably an aromatic ring having an aryloxy group having 6 to 10 carbon atoms.

$—OC(R^{a34})(R^{a35})—O—R^{a36}$ in the structural unit (a1-4) is eliminated by contacting with an acid (e.g., p-toluenesulfonic acid) to form a hydroxy group.

$—OC(R^{a34})(R^{a35})—O—R^{a36}$ is preferably bonded at the o-position or the p-position of the benzene ring.

The structural unit (a1-4) includes, for example, structural units derived from the monomers mentioned in JP 2010-204646 A. The structural unit preferably includes structural units represented by formula (a1-4-1) to formula (a1-4-24) and a structural unit in which a hydrogen atom corresponding to $R^{a32}$ in the structural unit (a1-4) is substituted with a halogen atom, a haloalkyl group or an alkyl group, and more preferably structural units represented by formula (a1-4-1) to formula (a1-4-5), formula (a1-4-10), formula (a1-4-13), formula (a1-4-14), formula (a1-4-19) and formula (a1-4-20).

(a-1-4-1)

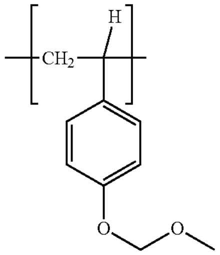

-continued (a1-4-2)

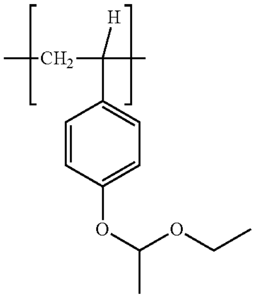

(a1-4-3)

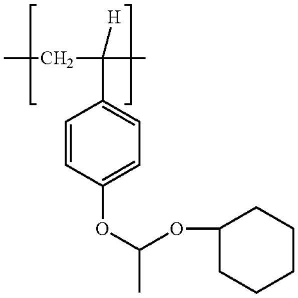

(a1-4-4)

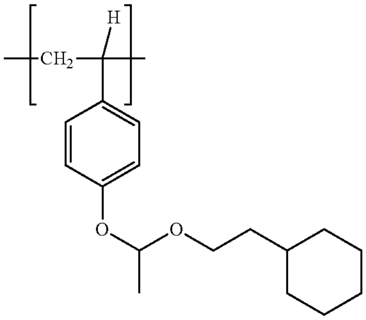

(a1-4-5)

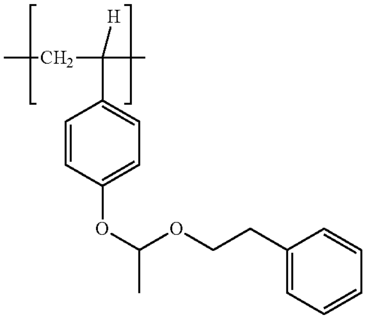

(a1-4-6)

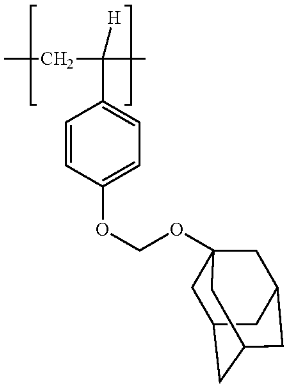

-continued
(a1-4-7)
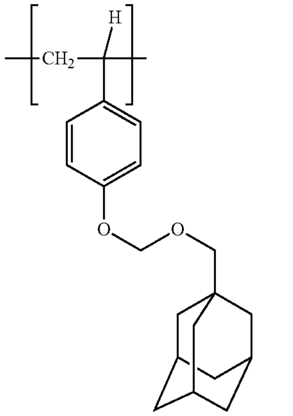
(a1-4-8)
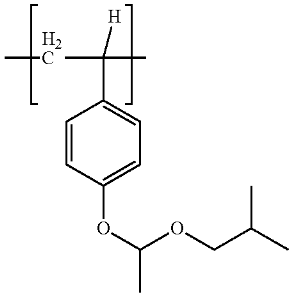
(a1-4-9)
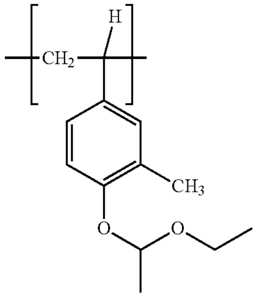
(a1-4-10)
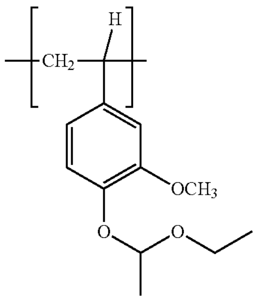
-continued
(a1-4-11)
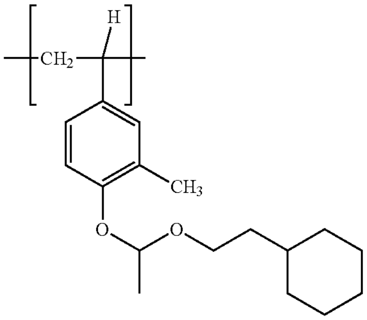
(a1-4-12)
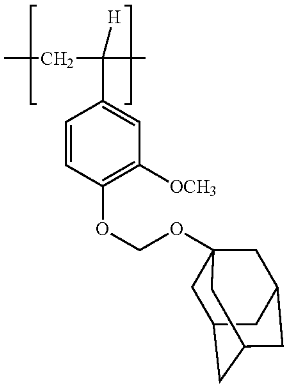
(a1-4-13)
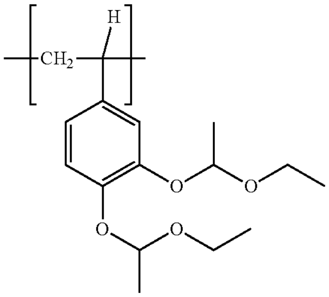
(a1-4-14)
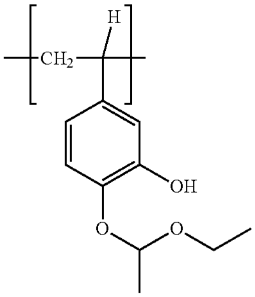
(a1-4-15)
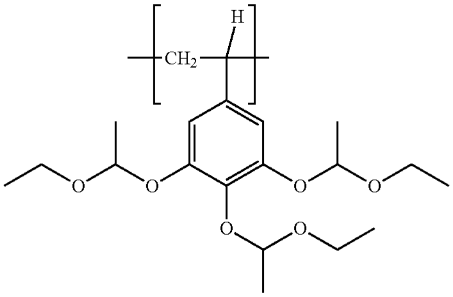

-continued (a1-4-16)

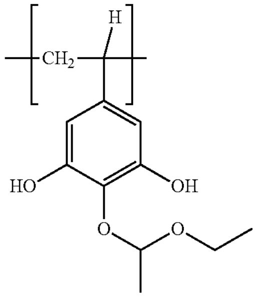

(a1-4-17)

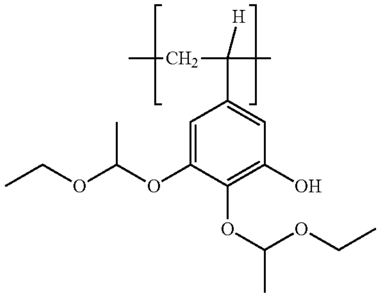

(a1-4-18)

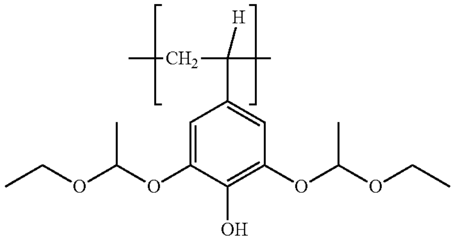

(a1-4-19)

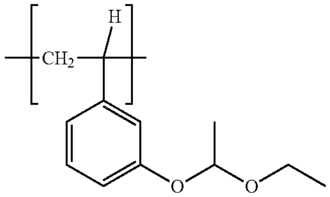

(a1-4-20)

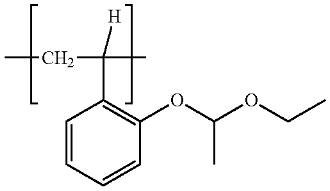

(a1-4-21)

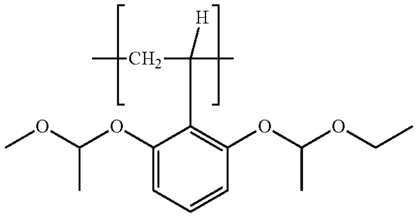

-continued (a1-4-22)

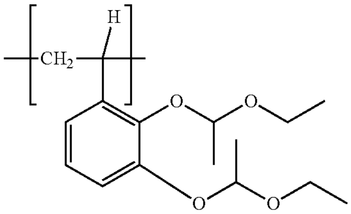

(a1-4-23)

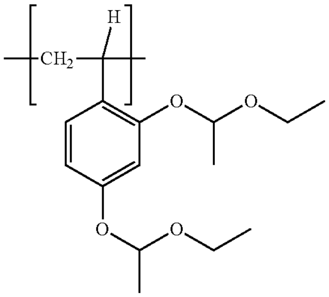

(a1-4-24)

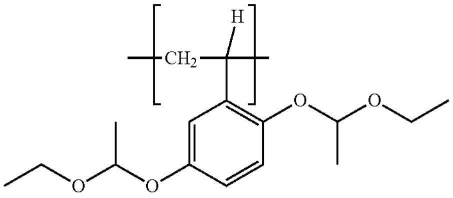

When the resin (A) includes the structural unit (a1-4), the content is preferably 3 to 80 mol %, more preferably 5 to 75 mol %, still more preferably 7 to 70 mol %, yet more preferably 7 to 65 mol %, and particularly preferably 10 to 60 mol %, based on the total of all structural units of the resin (A).

The structural unit derived from a (meth)acrylic monomer having a group (2) also includes a structural unit represented by formula (a1-5) (hereinafter sometimes referred to as "structural unit (a1-5)").

(a1-5)

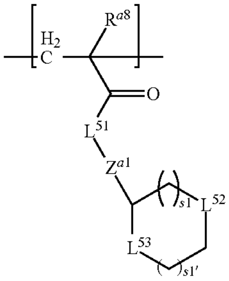

In formula (a1-5), $R^{a8}$ represents an alkyl group having 1 to 6 carbon atoms which may have a halogen atom, a hydrogen atom or a halogen atom, $Z^{a1}$ represents a single bond or $*-(CH_2)_{h3}-CO-L^{54}-$, h3 represents an integer of 1 to 4, and * represents a bonding site to $L^{51}$, $L^{51}$, $L^{52}$, $L^{53}$ and $L^{54}$ each independently represent —O— or —S—, s1 represents an integer of 1 to 3, and s1' represents an integer of 0 to 3.

The halogen atom includes a fluorine atom and a chlorine atom and is preferably a fluorine atom.

Examples of the alkyl group having 1 to 6 carbon atoms which may have a halogen atom include a methyl group, an ethyl group, a propyl group, a butyl group, a pentyl group, a hexyl group, a heptyl group, an octyl group, a fluoromethyl group and a trifluoromethyl group.

In formula (a1-5), $R^{a8}$ is preferably a hydrogen atom, a methyl group or a trifluoromethyl group, $L^{51}$ is preferably an oxygen atom, one of $L^{52}$ and $L^{53}$ is preferably —O— and the other one is preferably —S—, s1 is preferably 1, s1' is preferably an integer of 0 to 2, and $Z^{a1}$ is preferably a single bond or *—$CH_2$—CO—O—.

The structural unit (a1-5) includes, for example, structural units derived from the monomers mentioned in JP 2010-61117 A. Of these structural units, structural units represented by formula (a1-5-1) to formula (a1-5-4) are preferable, and structural units represented by formula (a1-5-1) or formula (a1-5-2) are more preferable.

(a1-5-1)

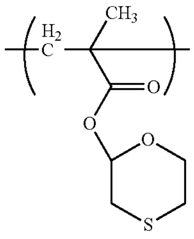

(a1-5-2)

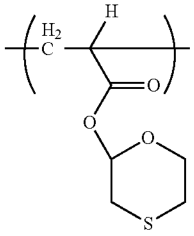

(a1-5-3)

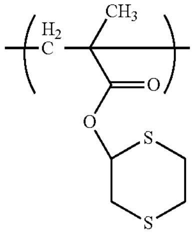

(a1-5-4)

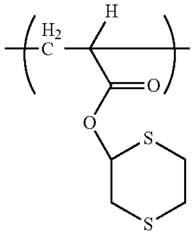

When the resin (A) includes the structural unit (a1-5), the content is preferably 1 to 50 mol %, more preferably 3 to 45 mol %, still more preferably 5 to 40 mol %, and yet more preferably 5 to 30 mol %, based on all structural units of the resin (A).

The structural unit (a1) also includes the following structural units.

(a1-3-1)

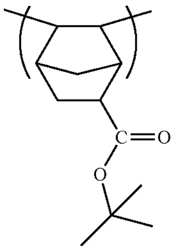

(a1-3-2)

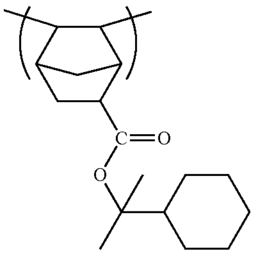

(a1-3-3)

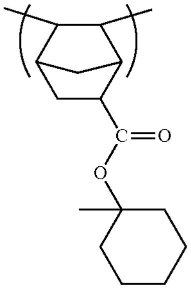

(a1-3-4)

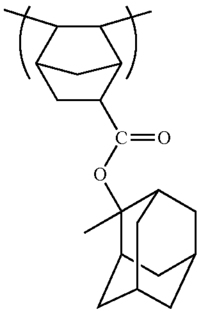

(a-1-3-5)

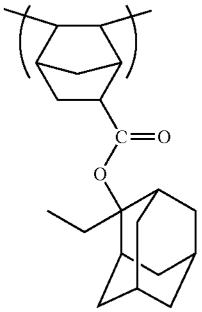

-continued (a-1-3-6)

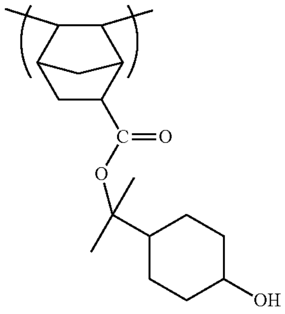

(a-1-3-7)

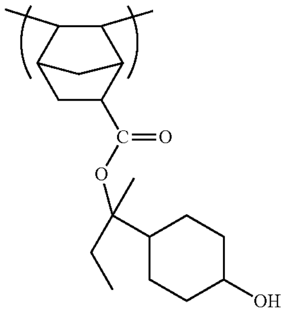

When the resin (A) includes the above-mentioned structural units such as (a1-3-1) to (a1-3-7), the content is preferably 10 to 95 mol %, more preferably 15 to 90 mol %, still more preferably 20 to 85 mol %, yet more preferably 20 to 70 mol %, and particularly preferably 20 to 60 mol %, based on all structural units of the resin (A).

The structural unit (a1) also includes the following structural units.

(a1-6-1)

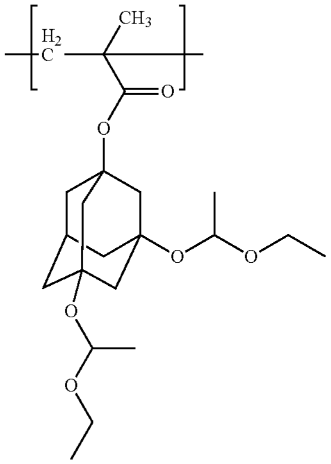

-continued (a1-6-2)

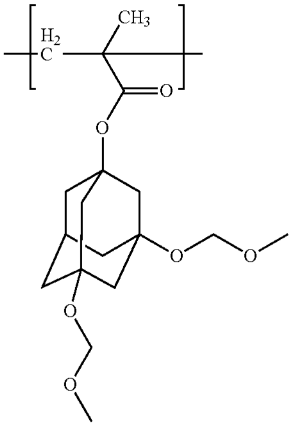

(a1-6-3)

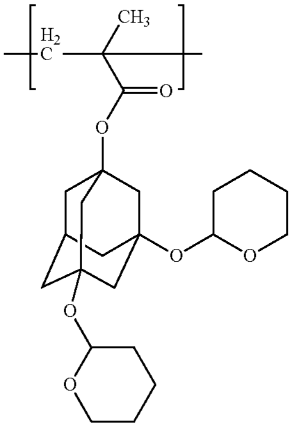

When the resin (A) includes the above-mentioned structural units such as (a1-6-1) to (a1-6-3), the content is preferably 10 to 60 mol %, more preferably 15 to 55 mol %, still more preferably 20 to 50 mol %, yet more preferably 20 to 45 mol %, and particularly preferably 20 to 40 mol %, based on all structural units of the resin (A).

<Structural Unit (s)>

The structural unit (s) is derived from a monomer having no acid-labile group (hereinafter sometimes referred to as "monomer (s)"). It is possible to use, as the monomer from which the structural unit (s) is derived, a monomer having no acid-labile group known in the resist field.

The structural unit (s) preferably has a hydroxy group or a lactone ring. When a resin including a structural unit having a hydroxy group and having no acid-labile group (hereinafter sometimes referred to as "structural unit (a2)") and/or a structural unit having a lactone ring and having no acid-labile group (hereinafter sometimes referred to as "structural unit (a3)") is used in the resist composition of the present disclosure, it is possible to improve the resolution of a resist pattern and the adhesion to a substrate.

<Structural Unit (a2)>

The hydroxy group possessed by the structural unit (a2) may be either an alcoholic hydroxy group or a phenolic hydroxy group.

When a resist pattern is produced from the resist composition of the present disclosure, in the case of using, as an exposure source, high energy rays such as KrF excimer laser (248 nm), electron beam or extreme ultraviolet light (EUV), a structural unit (a2) having a phenolic hydroxy group is preferably used as the structural unit (a2), and the below-mentioned structural unit (a2-A) is more preferably used. When using ArF excimer laser (193 nm) or the like, a structural unit (a2) having an alcoholic hydroxy group is preferably used as the structural unit (a2), and more preferably a structural unit (a2-1) mentioned later. The structural unit (a2) may be included alone, or two or more structural units may be included.

In the structural unit (a2), examples of the structural unit having a phenolic hydroxy group include a structural unit represented by formula (a2-A) (hereinafter sometimes referred to as "structural unit (a2-A)"):

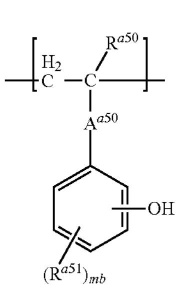

(a2-A)

wherein, in formula (a2-A), $R^{a50}$ represents a hydrogen atom, a halogen atom, or an alkyl group having 1 to 6 carbon atoms which may have a halogen atom, $R^{a51}$ represents a halogen atom, a hydroxy group, an alkyl group having 1 to 6 carbon atoms, an alkoxy group having 1 to 6 carbon atoms, an alkoxyalkyl group having 2 to 12 carbon atoms, an alkoxyalkoxy group having 2 to 12 carbon atoms, an alkylcarbonyl group having 2 to 4 carbon atoms, an alkylcarbonyloxy group having 2 to 4 carbon atoms, an acryloyloxy group or a methacryloyloxy group, $A^{a50}$ represents a single bond or $*—X^{a51}-(A^{a52}-X^{a52})_{nb}—$, and * represents a bonding site to carbon atoms to which $—R^{a50}$ is bonded, $A^{a52}$ represents an alkanediyl group having 1 to 6 carbon atoms, $X^{a51}$ and $X^{a52}$ each independently represent —O—, —CO—O— or —O—CO—, nb represents 0 or 1, and mb represents an integer of 0 to 4, and when mb is an integer of 2 or more, a plurality of $R^{a51}$ may be the same or different from each other.

Examples of the halogen atom in $R^{a50}$ and $R^{a51}$ include a fluorine atom, a chlorine atom and a bromine atom.

Examples of the alkyl group having 1 to 6 carbon atoms which may have a halogen atom in $R^{a50}$ include a trifluoromethyl group, a difluoromethyl group, a methyl group, a perfluoroethyl group, a 2,2,2-trifluoroethyl group, a 1,1,2,2-tetrafluoroethyl group, an ethyl group, a perfluoropropyl group, a 2,2,3,3,3-pentafluoropropyl group, a propyl group, a perfluorobutyl group, a 1,1,2,2,3,3,4,4-octafluorobutyl group, a butyl group, a perfluoropentyl group, a 2,2,3,3,4,4,5,5,5-nonafluoropentyl group, a pentyl group, a hexyl group and a perfluorohexyl group.

$R^{a50}$ is preferably a hydrogen atom or an alkyl group having 1 to 4 carbon atoms, more preferably a hydrogen atom, a methyl group or an ethyl group, and still more preferably a hydrogen atom or a methyl group.

Examples of the alkyl group in $R^{a51}$ include a methyl group, an ethyl group, a propyl group, an isopropyl group, a butyl group, a sec-butyl group, a tert-butyl group, a pentyl group and a hexyl group. The alkyl group is preferably an alkyl group having 1 to 4 carbon atoms, more preferably a methyl group or an ethyl group, and still more preferably a methyl group.

Examples of the alkoxy group in $R^{a51}$ include a methoxy group, an ethoxy group, a propoxy group, an isopropoxy group, a butoxy group, a sec-butoxy group and a tert-butoxy group. The alkoxy group is preferably an alkoxy group having 1 to 4 carbon atoms, more preferably a methoxy group or an ethoxy group, and still more preferably a methoxy group.

Examples of the alkoxyalkyl group in $R^{a51}$ include a methoxymethyl group, an ethoxyethyl group, a propoxymethyl group, an isopropoxymethyl group, a butoxymethyl group, a sec-butoxymethyl group and a tert-butoxymethyl group. The alkoxyalkyl group is preferably an alkoxyalkyl group having 2 to 8 carbon atoms, more preferably a methoxymethyl group or an ethoxyethyl group, and still more preferably a methoxymethyl group.

Examples of the alkoxyalkoxy group in $R^{a51}$ include a methoxymethoxy group, a methoxyethoxy group, an ethoxymethoxy group, an ethoxyethoxy group, a propoxymethoxy group, an isopropoxymethoxy group, a butoxymethoxy group, a sec-butoxymethoxy group and a tert-butoxymethoxy group. The alkoxyalkoxy group is preferably an alkoxyalkoxy group having 2 to 8 carbon atoms, and more preferably a methoxyethoxy group or an ethoxyethoxy group.

Examples of the alkylcarbonyl group in $R^{a51}$ include an acetyl group, a propionyl group and a butyryl group. The alkylcarbonyl group is preferably an alkylcarbonyl group having 2 to 3 carbon atoms, and more preferably an acetyl group.

Examples of the alkylcarbonyloxy group in $R^{a51}$ include an acetyloxy group, a propionyloxy group and a butyryloxy group. The alkylcarbonyloxy group is preferably an alkylcarbonyloxy group having 2 to 3 carbon atoms, and more preferably an acetyloxy group.

$R^{a51}$ is preferably a halogen atom, a hydroxy group, an alkyl group having 1 to 4 carbon atoms, an alkoxy group having 1 to 4 carbon atoms or an alkoxyalkoxy group having 2 to 8 carbon atoms, more preferably a fluorine atom, an iodine atom, a hydroxy group, a methyl group, a methoxy group, an ethoxy group, an ethoxyethoxy group or an ethoxymethoxy group, and still more preferably a fluorine atom, an iodine atom, a hydroxy group, a methyl group, a methoxy group or an ethoxyethoxy group.

Examples of $*—X^{a51}-(A^{a52}-X^{a52})_{nb}—$ include *—O—, *—CO—O—, *—O—CO—, $*—CO—O-A^{a52}-CO—O—$, $*—O—CO-A^{a52}-O—$, $*—O-A^{a52}-CO—O—$, $*—CO—O-A^{a52}-O—CO—$ and $*—O—CO-A^{a52}-O—CO—$. Of these, *—CO—O—, $*—CO—O-A^{a52}-CO—O—$ or $*—O-A^{a52}-CO—O—$ is preferable.

Examples of the alkanediyl group include a methylene group, an ethylene group, a propane-1,3-diyl group, a propane-1,2-diyl group, a butane-1,4-diyl group, a pentane-1,5-diyl group, a hexane-1,6-diyl group, a butane-1,3-diyl group, a 2-methylpropane-1,3-diyl group, a 2-methylpropane-1,2-diyl group, a pentane-1,4-diyl group and a 2-methylbutane-1,4-diyl group.

$A^{a52}$ is preferably a methylene group or an ethylene group.

$A^{a50}$ is preferably a single bond, *—CO—O— or $*—CO—O-A^{a52}-CO—O—$, more preferably a single bond, *—CO—O— or $*—CO—O—CH_2—CO—O—$, and still more preferably a single bond or *—CO—O—.

mb is preferably 0, 1 or 2, more preferably 0 or 1, and still more preferably 0.

The hydroxy group is preferably bonded at the m-position or the o-position of the benzene ring. When having two or more hydroxy groups, two hydroxy groups are preferably bonded at the m-position and the p-position, respectively.

Examples of the structural unit (a2-A) include structural units derived from the monomers mentioned in JP 2010-204634 A and JP 2012-12577 A.

Examples of the structural unit (a2-A) include structural units represented by formula (a2-2-1) to formula (a2-2-24), and a structural unit in which a methyl group corresponding to $R^{a50}$ in the structural unit (a2-A) is substituted with a hydrogen atom, a halogen atom, a haloalkyl group or other alkyl groups in structural units represented by formula (a2-2-1) to formula (a2-2-24). The structural unit (a2-A) is preferably a structural unit represented by formula (a2-2-1) to a structural unit represented by formula (a2-2-4), a structural unit represented by formula (a2-2-6), a structural unit represented by formula (a2-2-8), structural units represented by formula (a2-2-12) to formula (a2-2-18), and a structural unit in which a methyl group corresponding to $R^{a50}$ in the structural unit (a2-A) is substituted with a hydrogen atom in structural units represented by formula (a2-2-1) to formula (a2-2-4), a structural unit represented by formula (a2-2-6), a structural unit represented by formula (a2-2-8) and structural units represented by formula (a2-2-12) to formula (a2-2-18), more preferably a structural unit represented by formula (a2-2-3), a structural unit represented by formula (a2-2-4), a structural unit represented by formula (a2-2-8), structural units represented by formula (a2-2-12) to formula (a2-2-14), a structural unit represented by formula (a2-2-18), and a structural unit in which a methyl group corresponding to $R^{a50}$ in the structural unit (a2-A) is substituted with a hydrogen atom in a structural unit represented by formula (a2-2-3), a structural unit represented by formula (a2-2-4), a structural unit represented by formula (a2-2-8), structural units represented by formula (a2-2-12) to formula (a2-2-14) and a structural unit represented by formula (a2-2-18), and still more preferably a structural unit represented by formula (a2-2-3), a structural unit represented by formula (a2-2-4), a structural unit represented by formula (a2-2-8), and a structural unit in which a methyl group corresponding to $R^{a50}$ in the structural unit (a2-A) is substituted with a hydrogen atom in a structural unit represented by formula (a2-2-3), a structural unit represented by formula (a2-2-4) and a structural unit represented by formula (a2-2-8).

(a2-2-1)

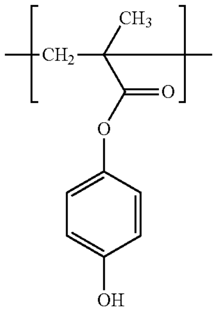

-continued (a2-2-2)

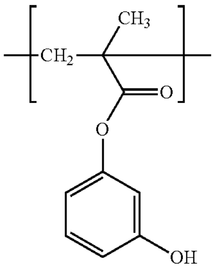

(a2-2-3)

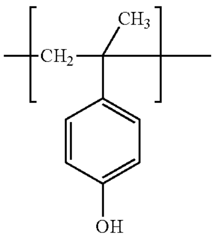

(a2-2-4)

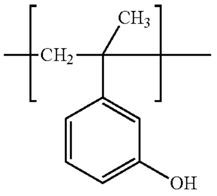

(a2-2-5)

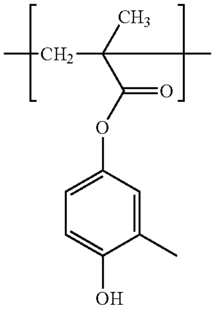

(a2-2-6)

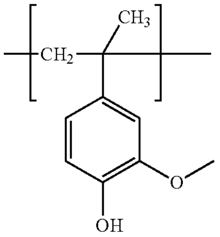

(a2-2-7)

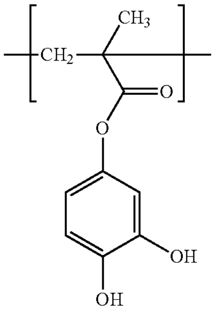

-continued
(a2-2-8)
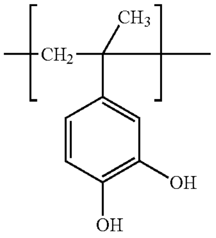
(a2-2-9)
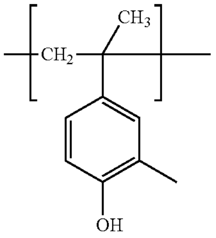
(a2-2-10)
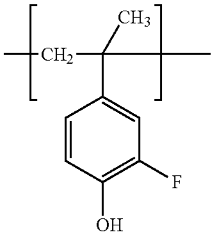
(a2-2-11)
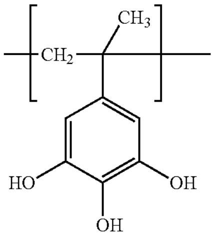
(a2-2-12)
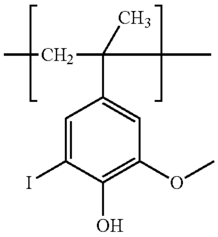
(a2-2-13)
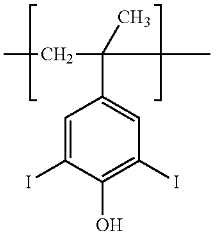
-continued
(a2-2-14)
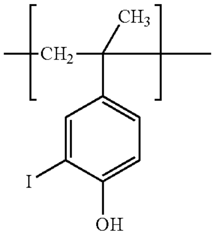
(a2-2-15)
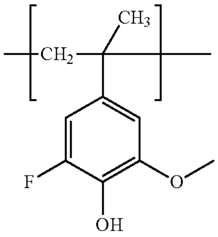
(a2-2-16)
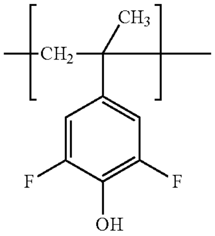
(a2-2-17)
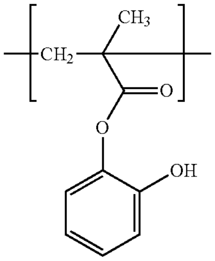
(a2-2-18)
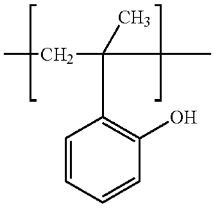
(a2-2-19)
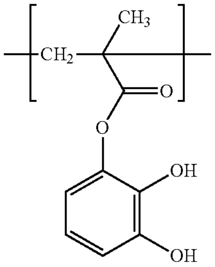

-continued (a2-2-20)

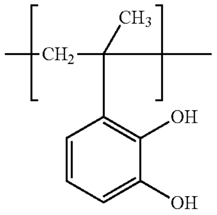

(a2-2-21)

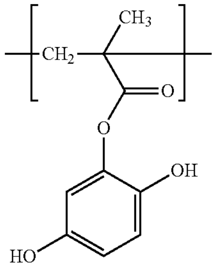

(a2-2-22)

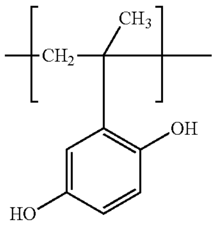

(a2-2-23)

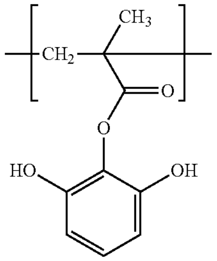

(a2-2-24)

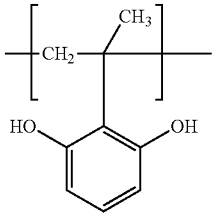

When the structural unit (a2-A) is contained in the resin (A) or the like, the content of the structural unit (a2-A) is preferably 5 mol % or more, more preferably It is 10 mol % or more, more preferably 15 mol % or more, and still more preferably 20 mol % or more. Also, it is preferably 80 mol % or less, more preferably 70 mol % or less, and still more preferably 65 mol % or less. Specifically, it is preferably 5 to 80 mol %, more preferably 10 to 70 mol %, even more preferably 15 to 65 mol %, still more preferably 20 to 65 mol %.

The structural unit (a2-A) can be included in the resin (A) by polymerizing, for example, with a structural unit (a1-4) and treating with an acid such as p-toluenesulfonic acid. The structural unit (a2-A) can also be included in the resin (A) by polymerizing with acetoxystyrene and treating with an alkali such as tetramethylammonium hydroxide.

Examples of the structural unit having an alcoholic hydroxy group in the structural unit (a2) include a structural unit represented by formula (a2-1) (hereinafter sometimes referred to as "structural unit (a2-1)").

(a2-1)

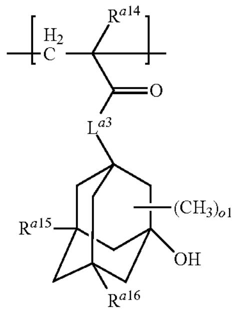

In formula (a2-1), $L^{a3}$ represents —O— or *—O—$(CH_2)_{k2}$—CO—O—, k2 represents an integer of 1 to 7, and * represents a bonding site to —CO—, $R^{a14}$ represents a hydrogen atom or a methyl group, $R^{a15}$ and $R^{a16}$ each independently represent a hydrogen atom, a methyl group or a hydroxy group, and o1 represents an integer of 0 to 10.

In formula (a2-1), $L^{a3}$ is preferably —O— or —O—$(CH_2)_{f1}$—CO—O— (f1 represents an integer of 1 to 4), and more preferably —O—, $R^{a14}$ is preferably a methyl group, $R^{a15}$ is preferably a hydrogen atom, $R^{a16}$ is preferably a hydrogen atom or a hydroxy group, and o1 is preferably an integer of 0 to 3, and more preferably 0 or 1.

The structural unit (a2-1) includes, for example, structural units derived from the monomers mentioned in JP 2010-204646 A. A structural unit represented by any one of formula (a2-1-1) to formula (a2-1-6) is preferable, a structural unit represented by any one of formula (a2-1-1) to formula (a2-1-4) is more preferable, and a structural unit represented by formula (a2-1-1) or formula (a2-1-3) is still more preferable.

(a2-1-1)

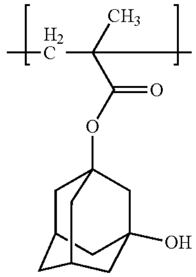

-continued (a2-1-2)

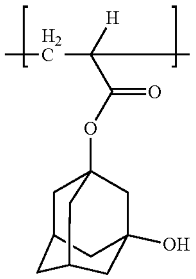

(a2-1-3)

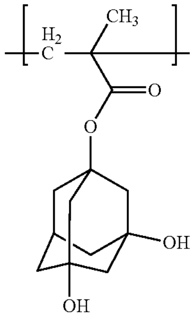

(a2-1-4)

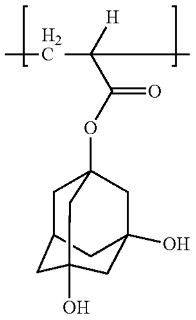

(a2-1-5)

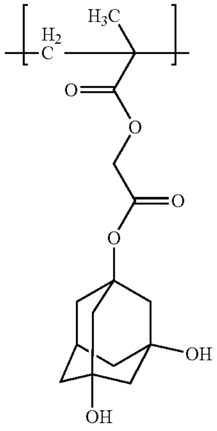

-continued (a2-1-6)

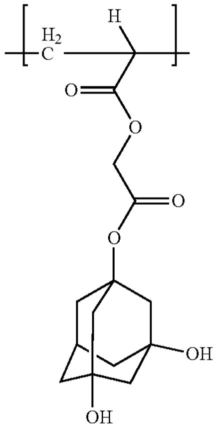

When the resin (A) or the like contains the structural unit (a2-1), the content is usually 1 mol % or more, preferably 2 mol % or more, based on the total structural units of the resin (A) or the like. . Also, it is 45 mol % or less, preferably 40 mol % or less, more preferably 35 mol % or less, still more preferably 20 mol % or less, and even more preferably 10 mol % or less. Specifically, it is 1 to 45 mol %, preferably 1 to 40 mol %, more preferably 1 to 35 mol %, still more preferably 1 to 20 mol %, still more preferably 1~10 mol %.

<Structural Unit (a3)>

The lactone ring possessed by the structural unit (a3) may be a monocyclic ring such as a β-propiolactone ring, a γ-butyrolactone ring or a δ-valerolactone ring, or a fused ring of a monocyclic lactone ring and the other ring. Preferably, a γ-butyrolactone ring, an adamantanelactone ring or a bridged ring including a γ-butyrolactone ring structure (e.g. a structural unit represented by the following formula (a3-2)) is exemplified.

The structural unit (a3) is preferably a structural unit represented by formula (a3-1), formula (a3-2), formula (a3-3) or formula (a3-4). These structural units may be included alone, or two or more structural units may be included:

(a3-1)

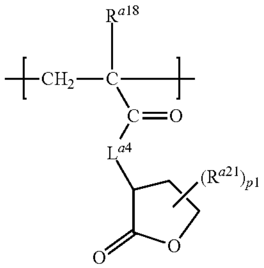

-continued (a3-2)

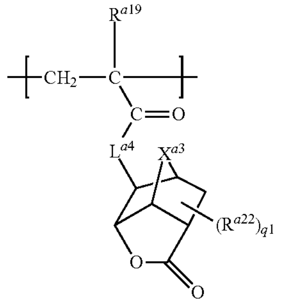

(a3-3)

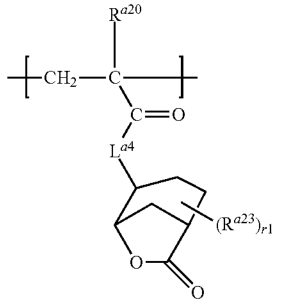

(a3-4)

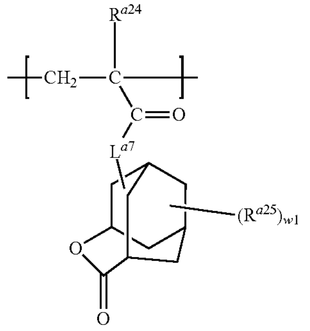

wherein, in formula (a3-1), formula (a3-2), formula (a3-3) and formula (a3-4), $L^{a4}$, $L^{a5}$ and $L^{a6}$ each independently represent —O— or a group represented by *—O—$(CH_2)_{k3}$—CO—O— (k3 represents an integer of 1 to 7), $L^{a7}$ represents —O—, *—O-$L^{a8}$-O—, *—O-$L^{a8}$-CO—O—, *—O-$L^{a8}$-CO—O-$L^{a9}$-CO—O— or *—O-$L^{a8}$-O—CO-$L^{a9}$-O—, $L^{a8}$ and $L^{a9}$ each independently represent an alkanediyl group having 1 to 6 carbon atoms,

* represents a bonding site to a carbonyl group, $R^{a18}$, $R^{a19}$ and $R^{a20}$ each independently represent a hydrogen atom or a methyl group, $R^{a24}$ represents an alkyl group having 1 to 6 carbon atoms which may have a halogen atom, a hydrogen atom or a halogen atom, $X^{a3}$ represents —$CH_2$— or an oxygen atom, $R^{a21}$ represents an aliphatic hydrocarbon group having 1 to 4 carbon atoms, $R^{a22}$, $R^{a23}$ and $R^{a25}$ each independently represent a carboxy group, a cyano group or an aliphatic hydrocarbon group having 1 to 4 carbon atoms, p1 represents an integer of 0 to 5, q1 represents an integer of 0 to 3, r1 represents an integer of 0 to 3, w1 represents an integer of 0 to 8, and when p1, q1, r1 and/or w1 is/are 2 or more, a plurality of $R^{a21}$, $R^{a22}$, $R^{a23}$ and/or $R^{a25}$ may be the same or different from each other.

Examples of the aliphatic hydrocarbon group in $R^{a21}$, $R^{a22}$, $R^{a23}$ and $R^{a25}$ include alkyl groups such as a methyl group, an ethyl group, a propyl group, an isopropyl group, a butyl group, a sec-butyl group and a tert-butyl group.

Examples of the halogen atom in $R^{a24}$ include a fluorine atom, a chlorine atom, a bromine atom and an iodine atom.

Examples of the alkyl group in $R^{a24}$ include a methyl group, an ethyl group, a propyl group, an isopropyl group, a butyl group, a sec-butyl group, a tert-butyl group, a pentyl group and a hexyl group, and the alkyl group is preferably an alkyl group having 1 to 4 carbon atoms, and more preferably a methyl group or an ethyl group.

Examples of the alkyl group having a halogen atom in $R^{a24}$ include a trifluoromethyl group, a perfluoroethyl group, a perfluoropropyl group, a perfluoroisopropyl group, a perfluorobutyl group, a perfluorosec-butyl group, a perfluoro-tert-butyl group, a perfluoropentyl group, a perfluorohexyl group, a trichloromethyl group, a tribromomethyl group, a triiodomethyl group and the like.

Examples of the alkanediyl group in $L^{a8}$ and $L^{a9}$ include a methylene group, an ethylene group, a propane-1,3-diyl group, a propane-1,2-diyl group, a butane-1,4-diyl group, a pentane-1,5-diyl group, a hexane-1,6-diyl group, a butane-1,3-diyl group, a 2-methylpropane-1,3-diyl group, a 2-methylpropane-1,2-diyl group, a pentane-1,4-diyl group and a 2-methylbutane-1,4-diyl group.

In formula (a3-1) to formula (a3-3), preferably, $L^{a4}$ to $L^{a6}$ are each independently —O— or a group in which k3 is an integer of 1 to 4 in *—O—$(CH_2)_{k3}$—CO—O—, more preferably —O— and *—O—$CH_2$—CO—O—, and still more preferably an oxygen atom, $R^{a18}$ to $R^{a21}$ are preferably a methyl group, preferably, $R^{a22}$ and $R^{a23}$ are each independently a carboxy group, a cyano group or a methyl group, and preferably, p1, q1 and r1 are each independently an integer of 0 to 2, and more preferably 0 or 1.

In formula (a3-4), $R^{a24}$ is preferably a hydrogen atom or an alkyl group having 1 to 4 carbon atoms, more preferably a hydrogen atom, a methyl group or an ethyl group, and still more preferably a hydrogen atom or a methyl group, $R^{a25}$ is preferably a carboxy group, a cyano group or a methyl group, $L^{a7}$ is preferably —O— or *—O-$L^{a8}$-CO—O—, and more preferably —O—, —O—$CH_2$—CO—O— or —O—$C_2H_4$—CO—O—, and w1 is preferably an integer of 0 to 2, and more preferably 0 or 1.

Particularly, formula (a3-4) is preferably formula (a3-4)':

(a3-4)'

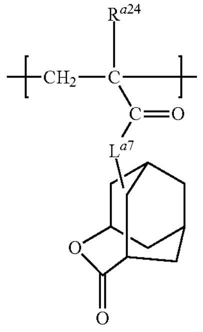

wherein $R^{a24}$ and $L^{a7}$ are the same as defined above.

Examples of the structural unit (a3) include structural units derived from the monomers mentioned in JP 2010-204646 A, the monomers mentioned in JP 2000-122294 A and the monomers mentioned in JP 2012-41274 A. The structural unit (a3) is preferably a structural unit represented by any one of formula (a3-1-1), formula (a3-1-2), formula (a3-2-1), formula (a3-2-2), formula (a3-3-1), formula (a3-3-2) and formula (a3-4-1) to formula (a3-4-12), and structural units in which methyl groups corresponding to $R^{a18}$, $R^{a19}$, $R^{a20}$ and $R^{a24}$ in formula (a3-1) to formula (a3-4) are substituted with hydrogen atoms in the above structural units.

(a3-1-1)

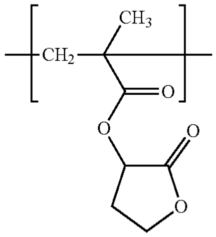

(a3-1-2)

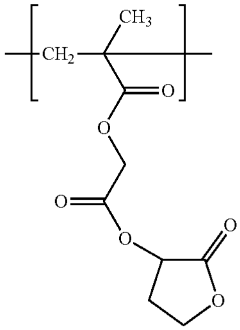

(a3-2-1)

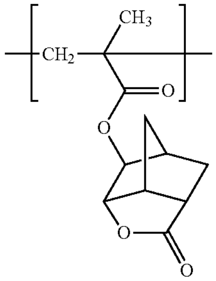

(a3-2-2)

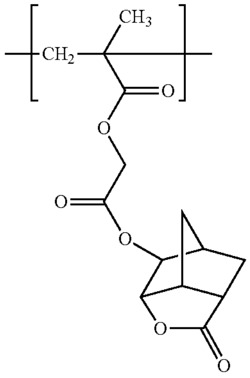

-continued (a3-2x-1)

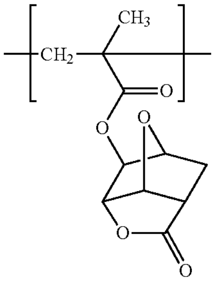

(a3-2x-2)

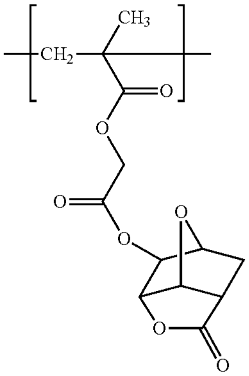

(a3-3-1)

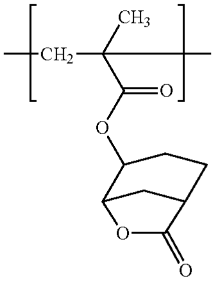

(a3-3-2)

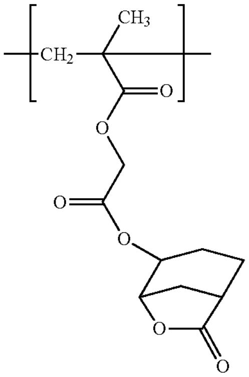

(a3-4-1)

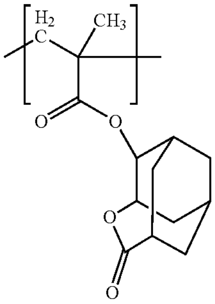

-continued
(a3-4-2)
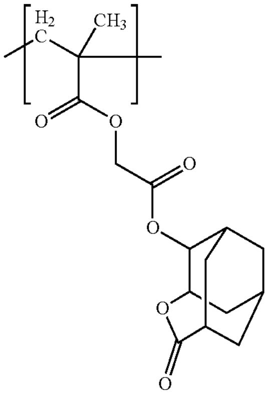
(a3-4-3)
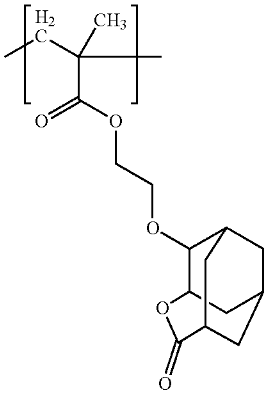
(a3-4-4)
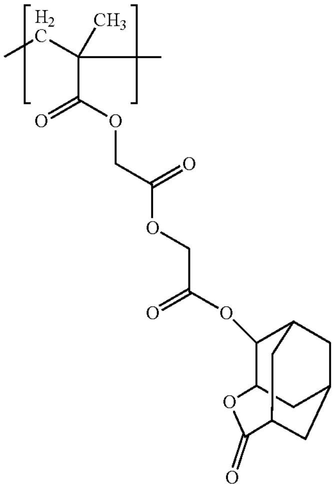
-continued
(a3-4-5)
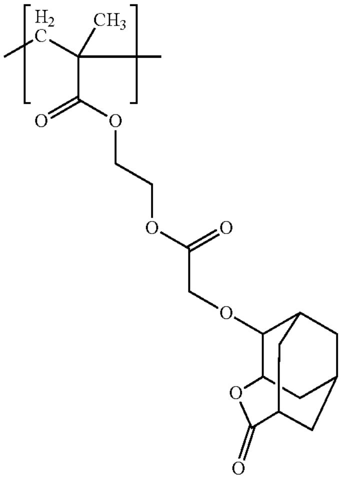
(a3-4-6)
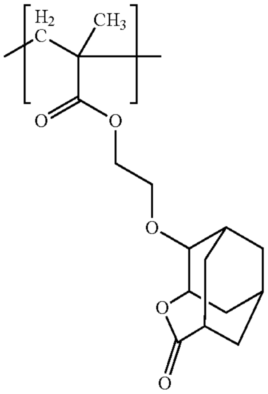
(a3-4-7)
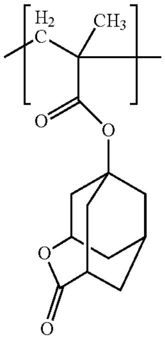

-continued (a3-4-8)

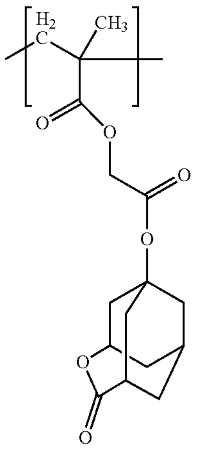

(a3-4-9)

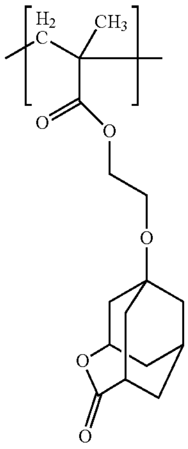

(a3-4-10)

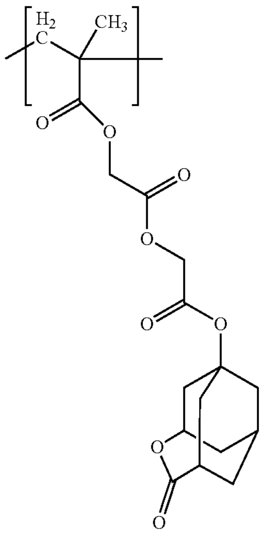

-continued (a3-4-11)

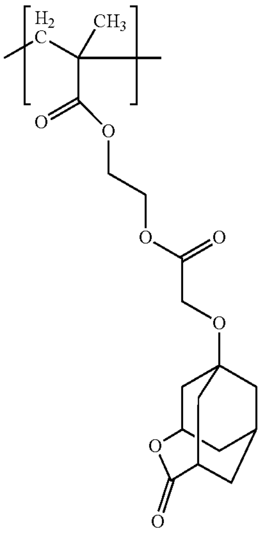

(a3-4-12)

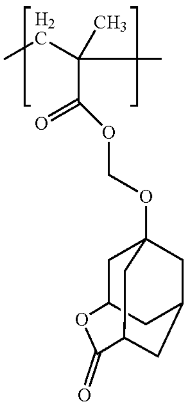

When the resin (A) or the like contains the structural unit (a3), the total content thereof is usually 1 mol % or more, preferably 3 mol % or more, based on the total structural units of the resin (A). more preferably 5 mol % or more, still more preferably 10 mol % or more. Also, it is 70 mol % or less, preferably 65 mol % or less, and more preferably 60 mol % or less. Specifically, it is 1 to 70 mol %, preferably 3 to 65 mol %, more preferably 5 to 60 mol %.

Further, the content of structural unit (a3-1) structural unit (a3-2), structural unit (a3-3) or structural unit (a3-4) is On the other hand, it is preferably 1 mol % or more, more preferably 3 mol % or more, and still more preferably 5 mol % or more. Also, it is preferably 60 mol % or less, more preferably 55 mol % or less, and still more preferably 50 mol % or less. Specifically, it is preferably 1 to 60 mol %, more preferably 3 to 50 mol %, and even more preferably 5 to 50 mol %.

<Structural Unit (a4)>

Examples of the structural unit (a4) include the following structural unit:

(a4)

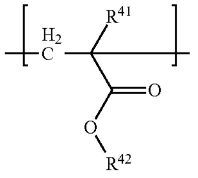

wherein, in formula (a4), $R^{41}$ represents a hydrogen atom or a methyl group, and $R^{42}$ represents a saturated hydrocarbon group having 1 to 24 carbon atoms which has a halogen atom, and —$CH_2$— included in the saturated hydrocarbon group may be replaced by —O— or —CO—.

Examples of the chain saturated hydrocarbon group represented by $R^{42}$ include a chain saturated hydrocarbon group and a monocyclic or polycyclic alicyclic saturated hydrocarbon group, and groups formed by combining these groups.

Examples of the chain saturated hydrocarbon group include a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group.

Examples of the monocyclic or polycyclic alicyclic saturated hydrocarbon group include cycloalkyl groups such as a cyclopentyl group, a cyclohexyl group, a cycloheptyl group and a cyclooctyl group; and polycyclic alicyclic saturated hydrocarbon groups such as a decahydronaphthyl group, an adamantyl group, a norbornyl group, and the following groups (* represents a bonding site).

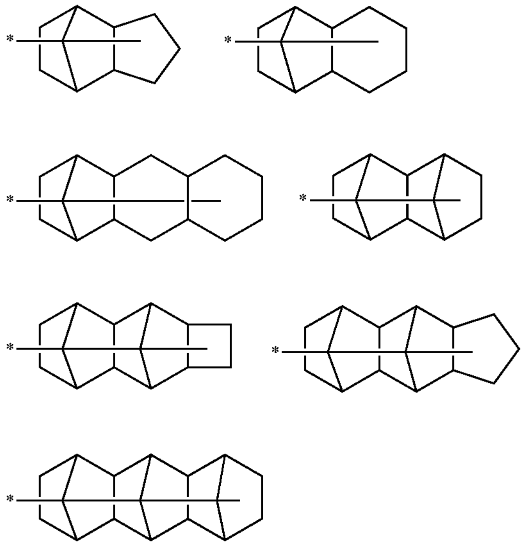

Examples of the group formed by combination include groups formed by combining one or more alkyl groups or one or more alkanediyl groups with one or more alicyclic saturated hydrocarbon groups, and include an alkanediyl group-alicyclic saturated hydrocarbon group, an alicyclic saturated hydrocarbon group-alkyl group, an alkanediyl group-alicyclic saturated hydrocarbon group-alkyl group and the like.

Examples of the structural unit (a4) include a structural unit represented by formula (a4-0), a structural unit represented by formula (a4-1), and a structural unit represented by formula (a4-4):

(a4-0)

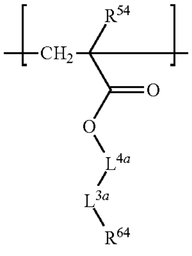

wherein, in formula (a4-0), $R^{54}$ represents a hydrogen atom or a methyl group, $L^{4a}$ represents a single bond or an alkanediyl group having 1 to 4 carbon atoms, $L^{3a}$ represents a perfluoroalkanediyl group having 1 to 8 carbon atoms or a perfluorocycloalkanediyl group having 3 to 12 carbon atoms, and $R^{64}$ represents a hydrogen atom or a fluorine atom.

Examples of the alkanediyl group in $L^{4a}$ include linear alkanediyl groups such as a methylene group, an ethylene group, a propane-1,3-diyl group and a butane-1,4-diyl group; and branched alkanediyl groups such as an ethane-1,1-diyl group, a propane-1,2-diyl group, a butane-1,3-diyl group, a 2-methylpropane-1,3-diyl group and a 2-methylpropane-1,2-diyl group.

Examples of the perfluoroalkanediyl group in $L^3$a include a difluoromethylene group, a perfluoroethylene group, a perfluoroethylfluoromethylene group, a perfluoropropane-1,3-diyl group, a perfluoropropane-1,2-diyl group, a perfluoropropane-2,2-diyl group, a perfluorobutane-1,4-diyl group, a perfluorobutane-2,2-diyl group, a perfluorobutane-1,2-diyl group, a perfluoropentane-1,5-diyl group, a perfluoropentane-2,2-diyl group, a perfluoropentane-3,3-diyl group, a perfluorohexane-1,6-diyl group, a perfluorohexane-2,2-diyl group, a perfluorohexane-3,3-diyl group, a perfluoroheptane-1,7-diyl group, a perfluoroheptane-2,2-diyl group, a perfluoroheptane-3,4-diyl group, a perfluoroheptane-4,4-diyl group, a perfluorooctane-1,8-diyl group, a perfluorooctane-2,2-diyl group, a perfluorooctane-3,3-diyl group, a perfluorooctane-4,4-diyl group and the like.

Examples of the perfluorocycloalkanediyl group in $L^3$a include a perfluorocyclohexanediyl group, a perfluorocyclopentanediyl group, a perfluorocycloheptanediyl group, a perfluoroadamantanediyl group and the like.

$L^{4a}$ is preferably a single bond, a methylene group or an ethylene group, and more preferably a single bond or a methylene group.

$L^{3a}$ is preferably a perfluoroalkanediyl group having 1 to 6 carbon atoms, and more preferably a perfluoroalkanediyl group having 1 to 3 carbon atoms.

Examples of the structural unit (a4-0) include the following structural units, and structural units in which a methyl group corresponding to $R^{54}$ in the structural unit (a4-0) in the following structural units is substituted with a hydrogen atom:

-continued
(a4-0-1)
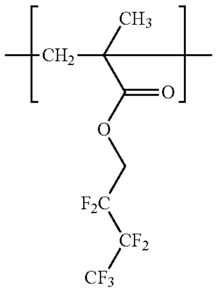
(a4-0-2)
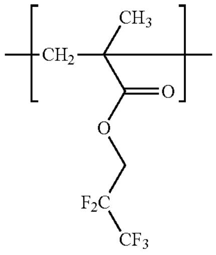
(a4-0-3)
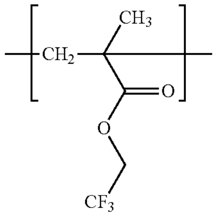
(a4-0-4)
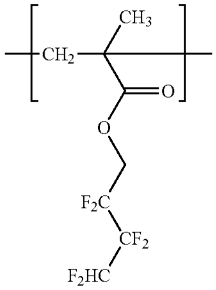
(a4-0-5)
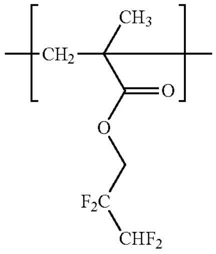
(a4-0-6)
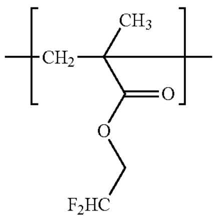
(a4-0-7)
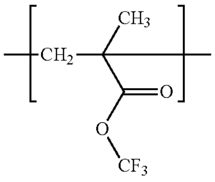
(a4-0-8)
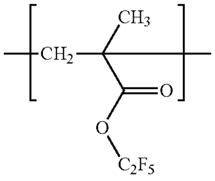
(a4-0-9)
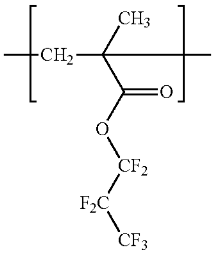
(a4-0-10)
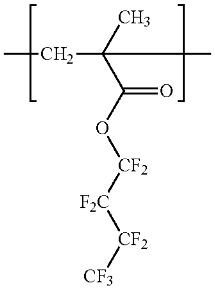
(a4-0-11)
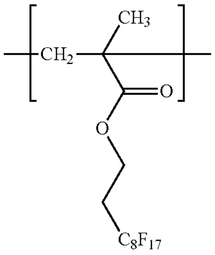
(a4-0-12)
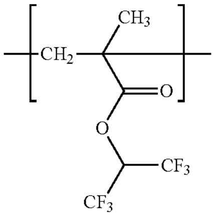

-continued (a4-0-13)

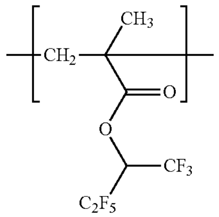

(a4-0-14)

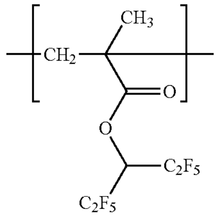

(a4-0-15)

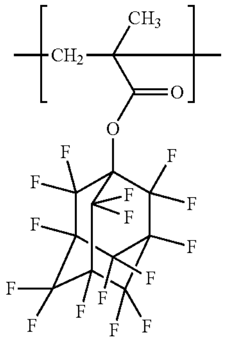

(a4-0-16)

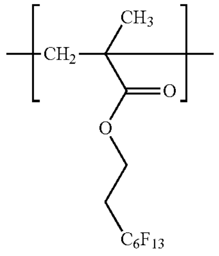

Examples of the structural unit (a4) include a structural unit represented by formula (a4-1):

(a4-1)

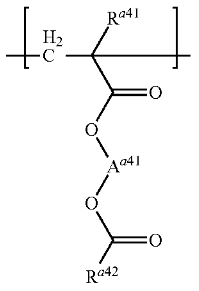

wherein, in formula (a4-1), $R^{a41}$ represents a hydrogen atom or a methyl group, $R^{a42}$ represents a saturated hydrocarbon group having 1 to 20 carbon atoms which may have a substituent, and —$CH_2$— included in the saturated hydrocarbon group may be replaced by —O— or —CO—, $A^{a41}$ represents an alkanediyl group having 1 to 6 carbon atoms which may have a substituent or a group represented by formula (a-g1), in which at least one of $A^{a41}$ and $R^{a42}$ has, as a substituent, a halogen atom (preferably a fluorine atom):

(a-g1)

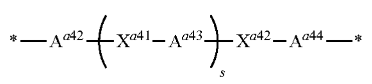

[in which, in formula (a-g1), s represents 0 or 1, $A^{a42}$ and $A^{a44}$ each independently represent a divalent saturated hydrocarbon group having 1 to 5 carbon atoms which may have a substituent, $A^{a43}$ represents a single bond or a divalent saturated hydrocarbon group having 1 to 5 carbon atoms which may have a substituent, $X^{a41}$ and $X^{a42}$ each independently represent —O—, —CO—, —CO—O— or —O—CO—, in which the total number of carbon atoms of $A^{a42}$, $A^{a43}$, $A^{a44}$, $X^{a41}$ and $X^{a42}$ is 7 or less], and

* represents a bonding site and * at the right side represents a bonding site to —O—CO—$R^{a42}$.

Examples of the saturated hydrocarbon group in $R^{a42}$ include a chain hydrocarbon group and a monocyclic or polycyclic alicyclic hydrocarbon group, and groups formed by combining these groups.

Examples of the chain hydrocarbon group include a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group.

Examples of the monocyclic or polycyclic saturated alicyclic hydrocarbon group include cycloalkyl groups such as a cyclopentyl group, a cyclohexyl group, a cycloheptyl group and a cyclooctyl group; and polycyclic alicyclic hydrocarbon groups such as a decahydronaphthyl group, an adamantyl group, a norbornyl group, and the following groups (* represents a bonding site).

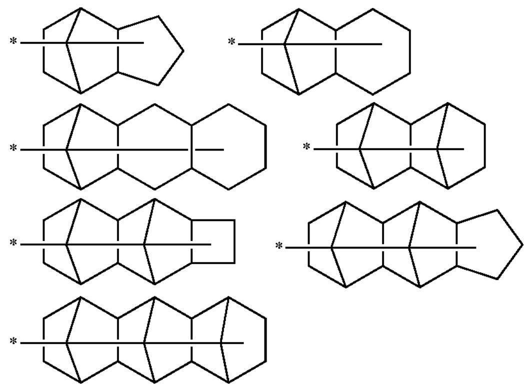

Examples of the group formed by combination include groups formed by combining one or more alkyl groups or one or more alkanediyl groups with one or more saturated alicyclic hydrocarbon groups, for example, an -alkanediyl group-saturated alicyclic hydrocarbon group, a -saturated alicyclic hydrocarbon group-alkyl group, an -alkanediyl group-saturated alicyclic hydrocarbon group-alkyl group and the like.

Examples of the substituent possessed by $R^{a42}$ include at least one selected from the group consisting of a halogen atom and the group consisting of the group represented by formula (a-g3). Examples of the halogen atom include a fluorine atom, a chlorine atom, a bromine atom and an iodine atom, and a fluorine atom is preferable:

$$*—X^{a43}\text{-}A^{a45} \quad \text{(a-g3)}$$

wherein, in formula (a-g3), $X^{a43}$ represents an oxygen atom, a carbonyl group, *—O—CO— or *—CO—O—, $A^{a45}$ represents a saturated hydrocarbon group having 1 to 17 carbon atoms which may have a halogen atom, and

* represents a bonding site to $R^{a42}$.

In $R^{a42}$—$X^{a43}$-$A^{a45}$, when $R^{a42}$ has no halogen atom, $A^{a45}$ represents a saturated hydrocarbon group having 1 to 17 carbon atoms having at least one halogen atom.

Examples of the saturated hydrocarbon group in $A^{a45}$ include alkyl groups such as a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group; monocyclic alicyclic hydrocarbon groups such as a cyclopentyl group, a cyclohexyl group, a cycloheptyl group and a cyclooctyl group; and polycyclic alicyclic hydrocarbon groups such as a decahydronaphthyl group, an adamantyl group, a norbornyl group and the following groups (* represents a bonding site).

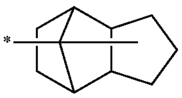
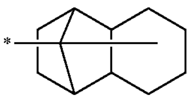
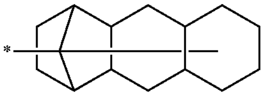
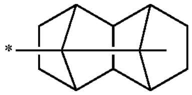
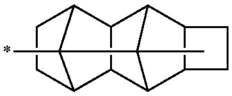
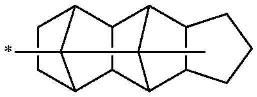
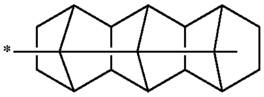

Examples of the group formed by combination include groups obtained by combining one or more alkyl groups or one or more alkanediyl groups with one or more alicyclic hydrocarbon groups, for example, an -alkanediyl group-alicyclic hydrocarbon group, an -alicyclic hydrocarbon group-alkyl group, an -alkanediyl group-alicyclic hydrocarbon group-alkyl group and the like.

$R^{a42}$ is preferably a saturated hydrocarbon group which may have a halogen atom, and more preferably an alkyl group having a halogen atom and/or a saturated hydrocarbon group having a group represented by formula (a-g3).

When $R^{a42}$ is a saturated hydrocarbon group having a halogen atom, a saturated hydrocarbon group having a fluorine atom is preferable, a perfluoroalkyl group or a perfluorocycloalkyl group is more preferable, a perfluoroalkyl group having 1 to 6 carbon atoms is still more preferable, and a perfluoroalkyl group having 1 to 3 carbon atoms is particularly preferable. Examples of the perfluoroalkyl group include a perfluoromethyl group, a perfluoroethyl group, a perfluoropropyl group, a perfluorobutyl group, a perfluoropentyl group, a perfluorohexyl group, a perfluoroheptyl group and a perfluorooctyl group. Examples of the perfluorocycloalkyl group include a perfluorocyclohexyl group and the like.

When $R^{a42}$ is a saturated hydrocarbon group having a group represented by formula (a-g3), the total number of carbon atoms of $R^{a42}$ is preferably 15 or less, and more preferably 12 or less, including the number of carbon atoms included in the group represented by formula (a-g3). When having the group represented by formula (a-g3) as the substituent, the number thereof is preferably 1.

When $R^{a42}$ is a saturated hydrocarbon group having the group represented by formula (a-g3), $R^{a42}$ is still more preferably a group represented by formula (a-g2):

$$*\text{-}A^{a46}\text{-}X^{a44}\text{-}A^{a47} \quad \text{(a-g2)}$$

wherein, in formula (a-g2), $A^{a46}$ represents a divalent saturated hydrocarbon group having 1 to 17 carbon atoms which may have a halogen atom, $X^{a44}$ represents —O—CO— or —CO—O— (** represents a bonding site to $A^{a46}$), $A^{a47}$ represents a saturated hydrocarbon group having 1 to 17 carbon atoms which may have a halogen atom, the total number of carbon atoms of $A^{a46}$, $A^{a47}$ and $X^{a44}$ is 18 or less, and at least one of $A^{a46}$ and $A^{a47}$ has at least one halogen atom, and

* represents a bonding site to a carbonyl group.

In some embodiments, the number of carbon atoms of the saturated hydrocarbon group as for $A^{a46}$ is preferably 1 to 6, and more preferably 1 to 3.

In some embodiments, the number of carbon atoms of the saturated hydrocarbon group as for $A^{a47}$ is preferably 4 to 15, and more preferably 5 to 12, and $A^{a47}$ is still more preferably a cyclohexyl group or an adamantyl group.

Preferred structures of the group represented by formula (a-g2) are the following structures (* represents a bonding site to a carbonyl group).

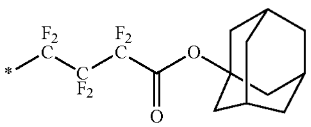
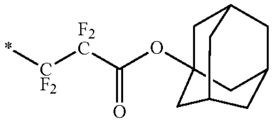
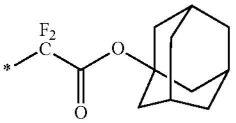
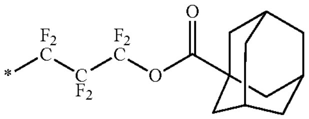
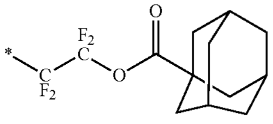
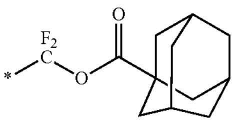

Examples of the alkanediyl group in $A^{a41}$ include linear alkanediyl groups such as a methylene group, an ethylene group, a propane-1,3-diyl group, a butane-1,4-diyl group, a pentane-1,5-diyl group and a hexane-1,6-diyl group; and branched alkanediyl groups such as a propane-1,2-diyl group, a butane-1,3-diyl group, a 2-methylpropane-1,2-diyl group, a 1-methylbutane-1,4-diyl group and a 2-methylbutane-1,4-diyl group.

Examples of the substituent in the alkanediyl group represented by $A^{a41}$ include a hydroxy group and an alkoxy group having 1 to 6 carbon atoms.

$A^{a41}$ is preferably an alkanediyl group having 1 to 4 carbon atoms, more preferably an alkanediyl group having 2 to 4 carbon atoms, and still more preferably an ethylene group.

Examples of the divalent saturated hydrocarbon group represented by $A^{a42}$, $A^{a43}$ and $A^{a44}$ in the group represented by formula (a-g1) include a linear or branched alkanediyl group and a monocyclic divalent alicyclic saturated hydrocarbon group, and divalent saturated hydrocarbon groups formed by combining an alkanediyl group and a divalent alicyclic saturated hydrocarbon group. Specific examples thereof include a methylene group, an ethylene group, a propane-1,3-diyl group, a propane-1,2-diyl group, a butane-1,4-diyl group, a 1-methylpropane-1,3-diyl group, a 2-methylpropane-1,3-diyl group, a 2-methylpropane-1,2-diyl group and the like.

Examples of the substituent of the divalent saturated hydrocarbon group represented by $A^{a42}$, $A^{a43}$ and $A^{a44}$ include a hydroxy group and an alkoxy group having 1 to 6 carbon atoms.

s is preferably 0.

In the group represented by formula (a-g1), examples of the group in which $X^{a42}$ is —O—, —CO—, —CO—O— or —O—CO— include the following groups. In the following exemplification, * and  each represent a bonding site, and  represents a bonding site to —O—CO—$R^{a42}$.

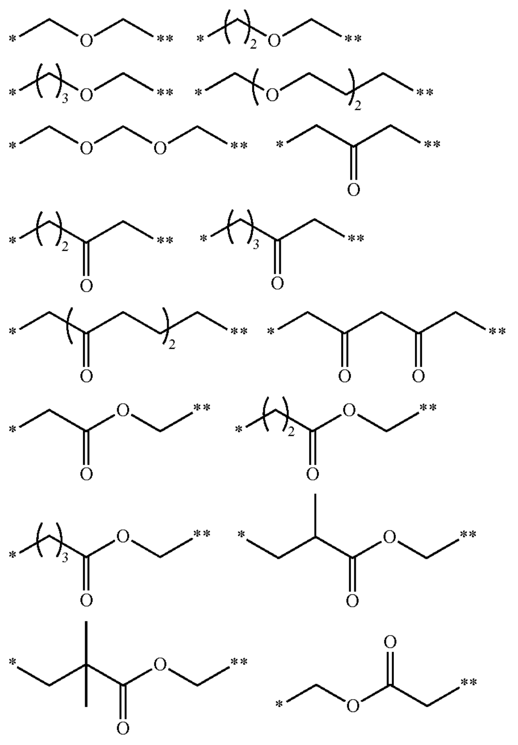

-continued

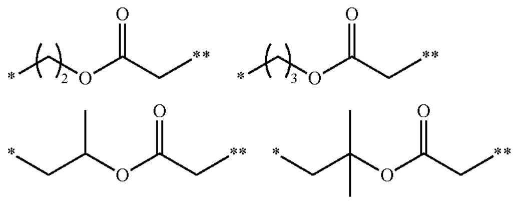

Examples of the structural unit represented by formula (a4-1) include the following structural units, and structural units in which a methyl group corresponding to $A^{a41}$ in the structural unit represented by formula (a4-1) in the following structural units is substituted with a hydrogen atom.

(a4-1-1)

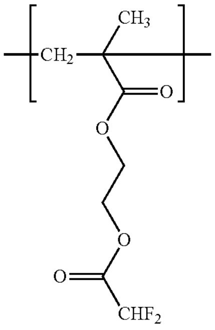

(a4-1-2)

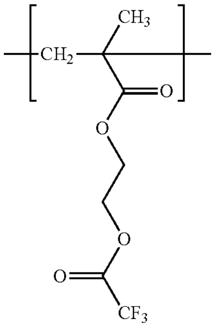

(a4-1-3)

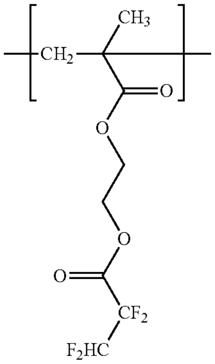

-continued
(a4-1-4)
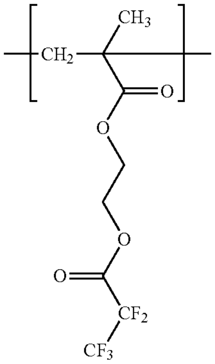
(a4-1-5)
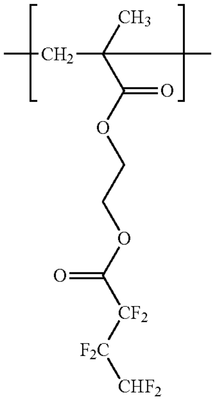
(a4-1-6)
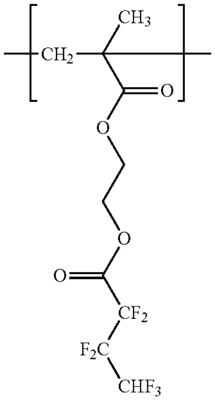
(a4-1-7)
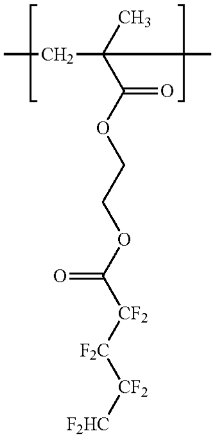
-continued
(a4-1-8)
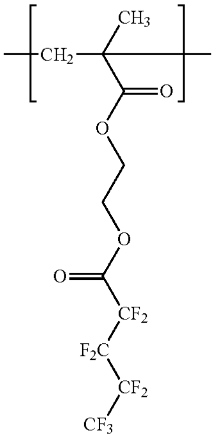
(a4-1-9)
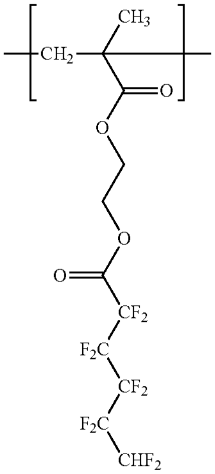
(a4-1-10)
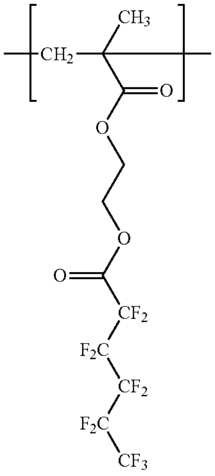

-continued
(a4-1-11)
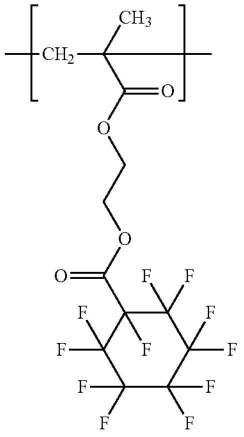
(a4-1′-1)
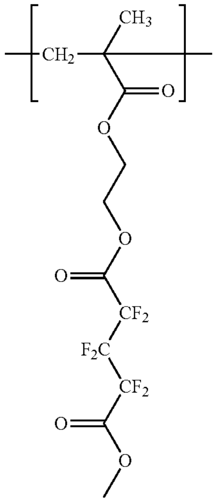
(a4-1′-2)
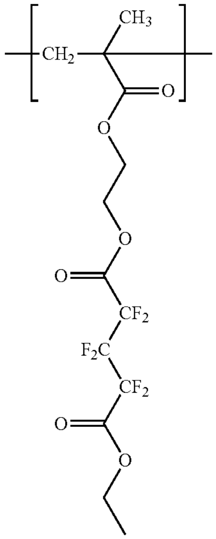
-continued
(a4-1′-3)
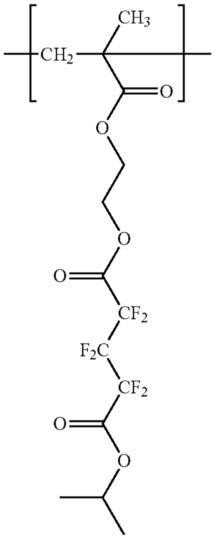
(a4-1′-4)
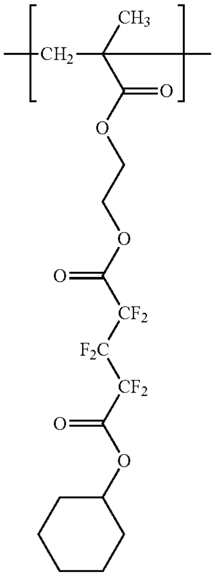

-continued
(a4-1'-5)
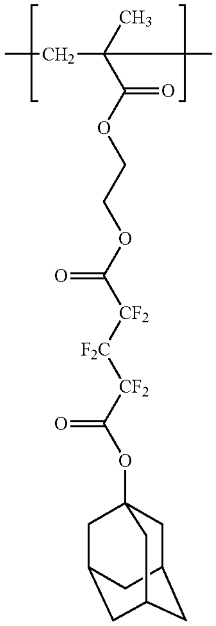
(a4-1'-6)
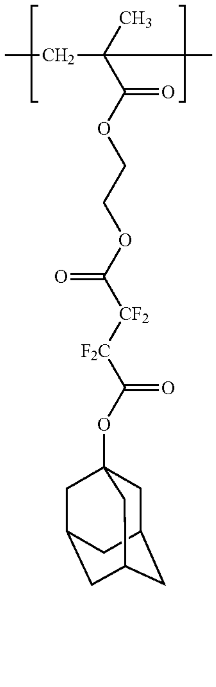
-continued
(a4-1'-7)
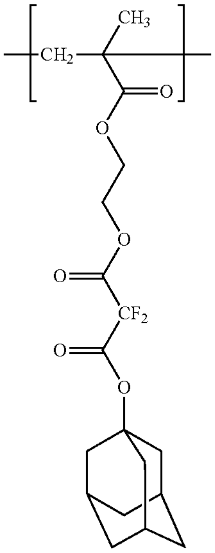
(a4-1'-8)
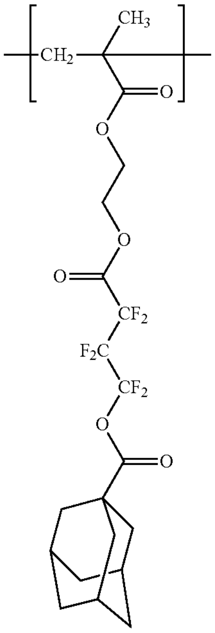

-continued (a4-1'-9)

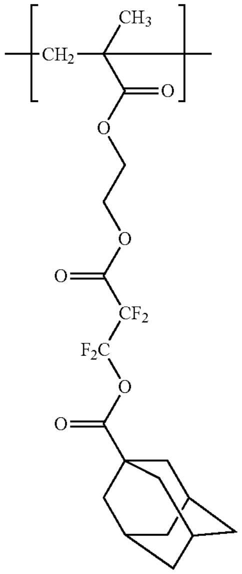

(a4-1'-10)

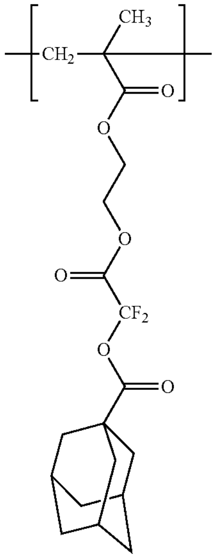

(a4-1'-11)

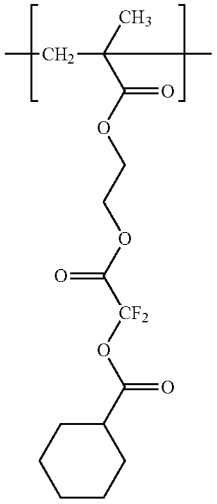

Examples of the structural unit (a4) include a structural unit represented by formula (a4-2) and a structural unit represented by formula (a4-3):

(a4-2)

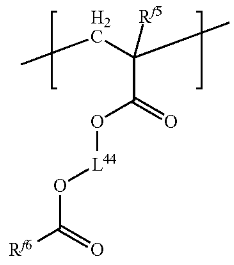

wherein, in formula (a4-2), $R^{f5}$ represents a hydrogen atom or a methyl group, $L^{44}$ represents an alkanediyl group having 1 to 6 carbon atoms, and $-CH_2-$ included in the alkanediyl group may be replaced by $-O-$ or $-CO-$, $R^{f6}$ represents a saturated hydrocarbon group having 1 to 20 carbon atoms having a fluorine atom, and the upper limit of the total number of carbon atoms as for $L^{44}$ and $R^{f6}$ is 21.

Examples of the alkanediyl group having 1 to 6 carbon atoms as for $L^{44}$ include the same groups as mentioned for $A^{a41}$.

Examples of the saturated hydrocarbon group as for $R^{f6}$ include the same groups as mentioned for $R^{42}$.

The alkanediyl group in $L^{44}$ is preferably an alkanediyl group having 2 to 4 carbon atoms, and more preferably an ethylene group.

The structural unit represented by formula (a4-2) includes, for example, structural units represented by formula (a4-1-1) to formula (a4-1-11). A structural unit in which a methyl group corresponding to $R^{f5}$ in the structural unit (a4-2) is substituted with a hydrogen atom is also exemplified as the structural unit represented by formula (a4-2).

(a4-3)

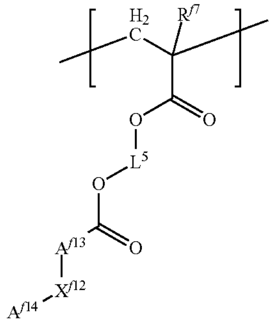

wherein, in formula (a4-3), $R^{f7}$ represents a hydrogen atom or a methyl group, $L^5$ represents an alkanediyl group having 1 to 6 carbon atoms, $A^{f13}$ represents a divalent saturated hydrocarbon group having 1 to 18 carbon atoms which may have a fluorine atom, $X^{f12}$ represents $*-O-CO-$ or $*-CO-O-$ (* represents a bonding site to $A^{f13}$), $A^{f14}$ represents a saturated hydrocarbon group having 1 to 17 carbon atoms which may have a fluorine atom, and at least one of $A^{f13}$ and $A^{f14}$ has a fluorine atom, and the upper limit of the total number of carbon atoms of $L^5$, $A^{f13}$ and $A^{f14}$ is 20.

Examples of the alkanediyl group in $L^5$ include those which are the same as mentioned as for the alkanediyl group as for $A^{a41}$.

The divalent saturated hydrocarbon group which may have a fluorine atom in $A^{f13}$ is preferably a divalent chain saturated hydrocarbon group which may have a fluorine atom and a divalent alicyclic saturated hydrocarbon group which may have a fluorine atom, and more preferably a perfluoroalkanediyl group.

Examples of the divalent chain saturated hydrocarbon group which may have a fluorine atom include alkanediyl groups such as a methylene group, an ethylene group, a propanediyl group, a butanediyl group and a pentanediyl group; and perfluoroalkanediyl groups such as a difluoromethylene group, a perfluoroethylene group, a perfluoropropanediyl group, a perfluorobutanediyl group and a perfluoropentanediyl group.

The divalent alicyclic saturated hydrocarbon group which may have a fluorine atom may be either monocyclic or polycyclic. Examples of the monocyclic group include a cyclohexanediyl group and a perfluorocyclohexanediyl group. Examples of the polycyclic group include an adamantanediyl group, a norbornanediyl group, a perfluoroadamantanediyl group and the like.

Examples of the saturated hydrocarbon group and the saturated hydrocarbon group which may have a fluorine atom as for $A^{f14}$ include the same groups as mentioned as for $R^{a42}$. Of these groups, preferred are fluorinated alkyl groups such as a trifluoromethyl group, a difluoromethyl group, a methyl group, a perfluoroethyl group, a 2,2,2-trifluoroethyl group, a 1,1,2,2-tetrafluoroethyl group, an ethyl group, a perfluoropropyl group, a 2,2,3,3,3-pentafluoropropyl group, a propyl group, a perfluorobutyl group, a 1,1,2,2,3,3,4,4-octafluorobutyl group, a butyl group, a perfluoropentyl group, a 2,2,3,3,4,4,5,5,5-nonafluoropentyl group, a pentyl group, a hexyl group, a perfluorohexyl group, a heptyl group, a perfluoroheptyl group, an octyl group and a perfluorooctyl group; a cyclopropylmethyl group, a cyclopropyl group, a cyclobutylmethyl group, a cyclopentyl group, a cyclohexyl group, a perfluorocyclohexyl group, an adamantyl group, an adamantylmethyl group, an adamantyldimethyl group, a norbornyl group, a norbornylmethyl group, a perfluoroadamantyl group, a perfluoroadamantylmethyl group and the like.

In formula (a4-3), $L^5$ is preferably an ethylene group. The divalent saturated hydrocarbon group as for $A^{f13}$ is preferably a group including a divalent chain saturated hydrocarbon group having 1 to 6 carbon atoms and a divalent alicyclic saturated hydrocarbon group having 3 to 12 carbon atoms, and more preferably a divalent chain saturated hydrocarbon group having 2 to 3 carbon atoms.

The saturated hydrocarbon group as for $A^{f14}$ is preferably a group which has a chain saturated hydrocarbon group having 3 to 12 carbon atoms and an alicyclic saturated hydrocarbon group having 3 to 12 carbon atoms, and more preferably a group which has a chain saturated hydrocarbon group having 3 to 10 carbon atoms and an alicyclic saturated hydrocarbon group having 3 to 10 carbon atoms. Of these groups, $A^{f14}$ is preferably a group which has an alicyclic saturated hydrocarbon group having 3 to 12 carbon atoms, and more preferably a cyclopropylmethyl group, a cyclopentyl group, a cyclohexyl group, a norbornyl group and an adamantyl group.

The structural unit represented by formula (a4-3) includes, for example, structural units represented by formula (a4-1'-1) to formula (a4-1'-11). A structural unit in which a methyl group corresponding to $R^{f7}$ in the structural unit (a4-3) is substituted with a hydrogen atom is also exemplified as the structural unit represented by formula (a4-3).

It is also possible to exemplify, as the structural unit (a4), a structural unit represented by formula (a4-4):

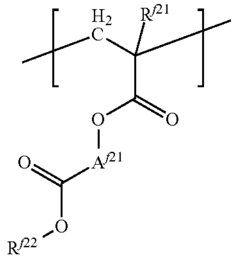

(a4-4)

wherein, in formula (a4-4), $R^{f21}$ represents a hydrogen atom or a methyl group, $A^{f21}$ represents $-(CH_2)_{j1}-$, $-(CH_2)_{j2}-O-(CH_2)_{j3}-$ or $-(CH_2)_{j4}-CO-O-(CH_2)_{j5}-$, j1 to j5 each independently represent an integer of 1 to 6, and $R^{f22}$ represents a saturated hydrocarbon group having 1 to 10 carbon atoms having a fluorine atom.

Examples of the saturated hydrocarbon group of $R^{f22}$ include those which are the same as the saturated hydrocarbon group represented by $R^{a42}$. $R^{f22}$ is preferably an alkyl group having 1 to 10 carbon atoms which has a fluorine atom or an alicyclic hydrocarbon group having 1 to 10 carbon atoms which has a fluorine atom, more preferably an alkyl group having 1 to 10 carbon atoms which has a fluorine atom, and still more preferably an alkyl group having 1 to 6 carbon atoms which has a fluorine atom.

In formula (a4-4), $A^{f21}$ is preferably $-(CH_2)_{j1}-$, more preferably an ethylene group or a methylene group, and still more preferably a methylene group.

The structural unit represented by formula (a4-4) includes, for example, the following structural units and structural units in which a methyl group corresponding to $R^{f21}$ in the structural unit (a4-4) is substituted with a hydrogen atom in structural units represented by the following formulas.

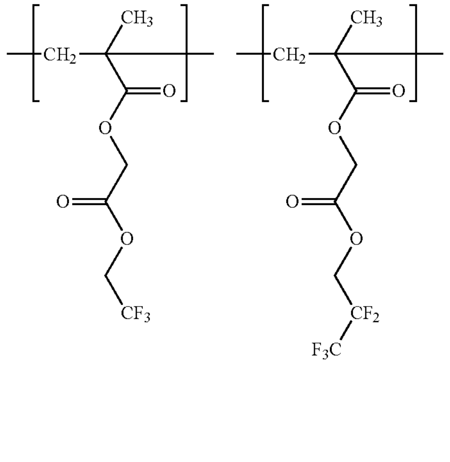

-continued
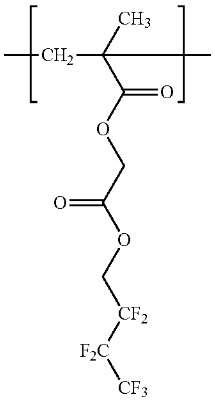
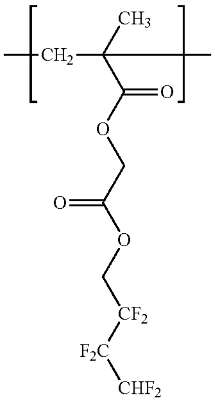
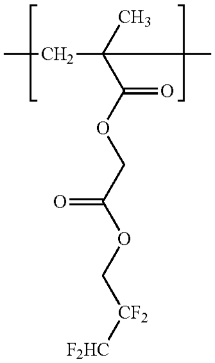
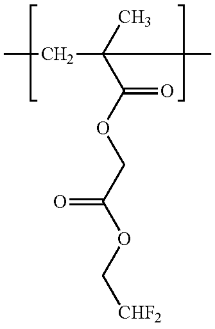
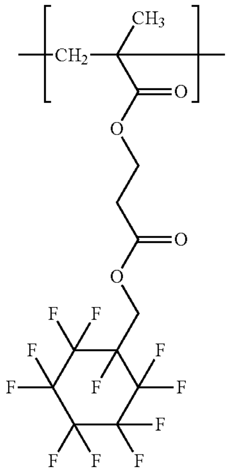
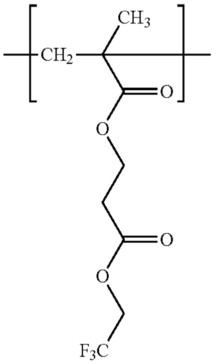
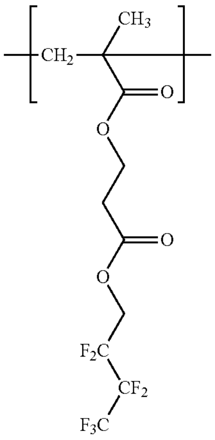
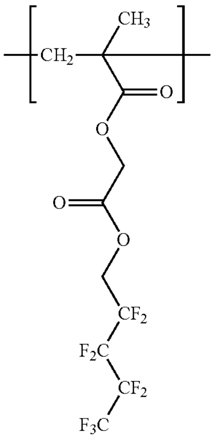
-continued
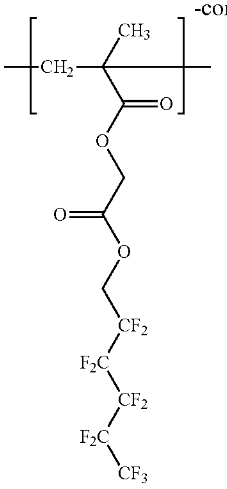
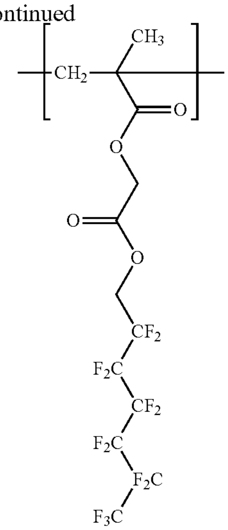
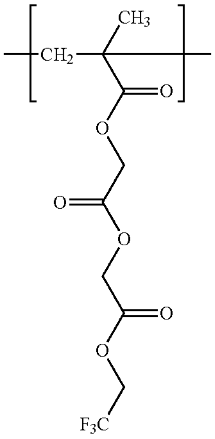
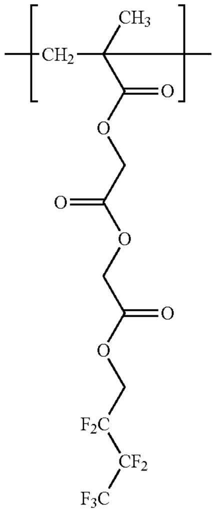
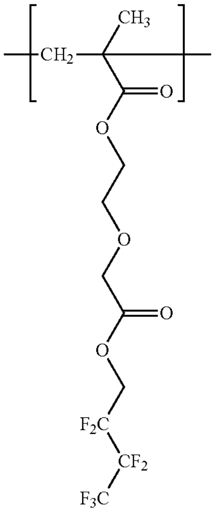
When the resin (A) includes the structural unit (a4), the content is preferably 1 to 20 mol %, more preferably 2 to 15 mol %, and still more preferably 3 to 10 mol %, based on all structural units of the resin (A).
<Structural Unit (a5)>
Examples of a non-leaving hydrocarbon group possessed by the structural unit (a5) include groups having a linear, branched or cyclic hydrocarbon group. Of these, the structural unit (a5) is preferably a group having an alicyclic hydrocarbon group.

The structural unit (a5) includes, for example, a structural unit represented by formula (a5-1):

(a5-1)

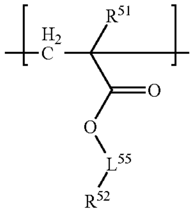

wherein, in formula (a5-1), $R^{51}$ represents a hydrogen atom or a methyl group, $R^{52}$ represents an alicyclic hydrocarbon group having 3 to 18 carbon atoms, and a hydrogen atom included in the alicyclic hydrocarbon group may be substituted with an aliphatic hydrocarbon group having 1 to 8 carbon atoms, and $L^{55}$ represents a single bond or a divalent saturated hydrocarbon group having 1 to 18 carbon atoms, and —$CH_2$— included in the saturated hydrocarbon group may be replaced by —O— or —CO—.

The alicyclic hydrocarbon group in $R^{52}$ may be either monocyclic or polycyclic. The monocyclic alicyclic hydrocarbon group includes, for example, a cyclopropyl group, a cyclobutyl group, a cyclopentyl group and a cyclohexyl group. The polycyclic alicyclic hydrocarbon group includes, for example, an adamantyl group and a norbornyl group.

The aliphatic hydrocarbon group having 1 to 8 carbon atoms includes, for example, alkyl groups such as a methyl group, an ethyl group, a propyl group, an isopropyl group, a butyl group, a sec-butyl group, a tert-butyl group, a pentyl group, a hexyl group, an octyl group and a 2-ethylhexyl group.

Examples of the alicyclic hydrocarbon group having a substituent includes a 3-methyladamantyl group and the like.

$R^{52}$ is preferably an unsubstituted alicyclic hydrocarbon group having 3 to 18 carbon atoms, and more preferably an adamantyl group, a norbornyl group or a cyclohexyl group.

Examples of the divalent saturated hydrocarbon group in $L^{55}$ include a divalent chain saturated hydrocarbon group and a divalent alicyclic saturated hydrocarbon group, and a divalent chain saturated hydrocarbon group is preferable.

The divalent chain saturated hydrocarbon group includes, for example, alkanediyl groups such as a methylene group, an ethylene group, a propanediyl group, a butanediyl group and a pentanediyl group.

The divalent alicyclic saturated hydrocarbon group may be either monocyclic or polycyclic. Examples of the monocyclic alicyclic saturated hydrocarbon group include cycloalkanediyl groups such as a cyclopentanediyl group and a cyclohexanediyl group. Examples of the polycyclic divalent alicyclic saturated hydrocarbon group include an adamantanediyl group and a norbornanediyl group.

The group in which —$CH_2$— included in the divalent saturated hydrocarbon group represented by $L^{55}$ is replaced by —O— or —CO— includes, for example, groups represented by formula (L1-1) to formula (L1-4). In the following formulas, * and ** each represent a bonding site, and * represents a bonding site to an oxygen atom.

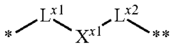

(L1-1)

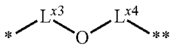

(L1-2)

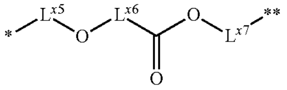

(L1-3)

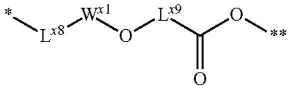

(L1-4)

In formula (L1-1), $X^{x1}$ represents *—O—CO— or *—CO—O— (* represents a bonding site to $L^{x1}$), $L^{x1}$ represents a divalent aliphatic saturated hydrocarbon group having 1 to 16 carbon atoms, $L^{x2}$ represents a single bond or a divalent aliphatic saturated hydrocarbon group having 1 to 15 carbon atoms, and the total number of carbon atoms of $L^{x1}$ and $L^{x2}$ is 16 or less.

In formula (L1-2), $L^{x3}$ represents a divalent aliphatic saturated hydrocarbon group having 1 to 17 carbon atoms, $L^{x4}$ represents a single bond or a divalent aliphatic saturated hydrocarbon group having 1 to 16 carbon atoms, and the total number of carbon atoms of $L^{x3}$ and $L^{x4}$ is 17 or less.

In formula (L1-3), $L^{x5}$ represents a divalent aliphatic saturated hydrocarbon group having 1 to 15 carbon atoms, $L^{x6}$ and $L^{x7}$ each independently represent a single bond or a divalent aliphatic saturated hydrocarbon group having 1 to 14 carbon atoms, and the total number of carbon atoms of $L^{x5}$, $L^{x6}$ and $L^{x7}$ is 15 or less.

In formula (L1-4), $L^{x8}$ and $L^{x9}$ represent a single bond or a divalent aliphatic saturated hydrocarbon group having 1 to 12 carbon atoms, $W^{x1}$ represents a divalent alicyclic saturated hydrocarbon group having 3 to 15 carbon atoms, and the total number of carbon atoms of $L^{x8}$, $L^{x9}$ and $W^{x1}$ is 15 or less.

$L^{x1}$ is preferably a divalent aliphatic saturated hydrocarbon group having 1 to 8 carbon atoms, and more preferably a methylene group or an ethylene group.

$L^{x2}$ is preferably a single bond or a divalent aliphatic saturated hydrocarbon group having 1 to 8 carbon atoms, and more preferably a single bond.

$L^{x3}$ is preferably a divalent aliphatic saturated hydrocarbon group having 1 to 8 carbon atoms.

$L^{x4}$ is preferably a single bond or a divalent aliphatic saturated hydrocarbon group having 1 to 8 carbon atoms.

$L^{x5}$ is preferably a divalent aliphatic saturated hydrocarbon group having 1 to 8 carbon atoms, and more preferably a methylene group or an ethylene group.

$L^{x6}$ is preferably a single bond or a divalent aliphatic saturated hydrocarbon group having 1 to 8 carbon atoms, and more preferably a methylene group or an ethylene group.

$L^{x7}$ is preferably a single bond or a divalent aliphatic saturated hydrocarbon group having 1 to 8 carbon atoms.

$L^{x8}$ is preferably a single bond or a divalent aliphatic saturated hydrocarbon group having 1 to 8 carbon atoms, and more preferably a single bond or a methylene group.

$L^{x9}$ is preferably a single bond or a divalent aliphatic saturated hydrocarbon group having 1 to 8 carbon atoms, and more preferably a single bond or a methylene group.

$W^{x1}$ is preferably a divalent alicyclic saturated hydrocarbon group having 3 to 10 carbon atoms, and more preferably a cyclohexanediyl group or an adamantanediyl group.

The group represented by formula (L1-1) includes, for example, the following divalent groups.

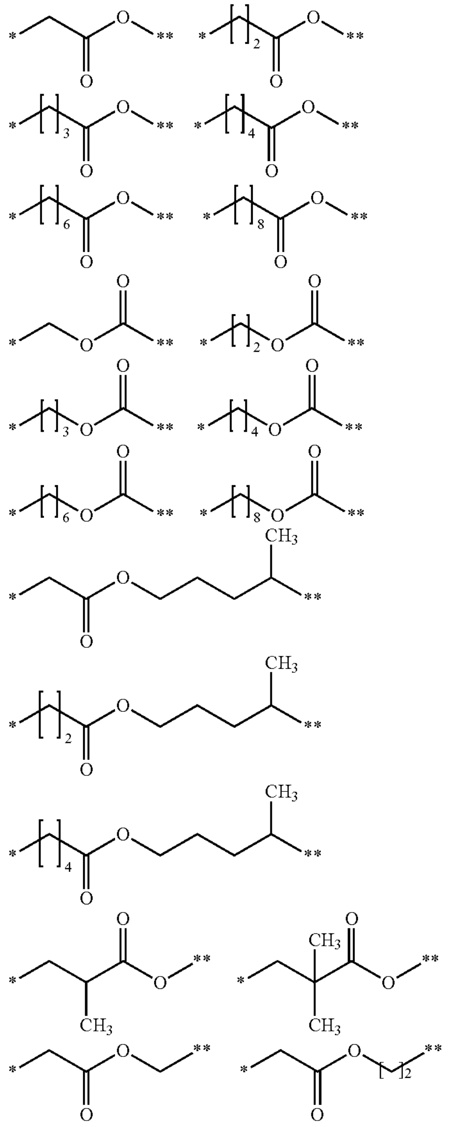

The group represented by formula (L1-2) includes, for example, the following divalent groups.

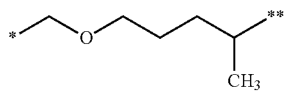

-continued

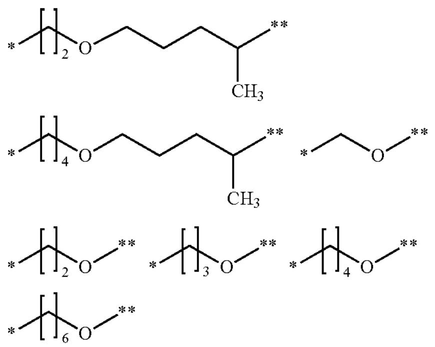

The group represented by formula (L1-3) includes, for example, the following divalent groups.

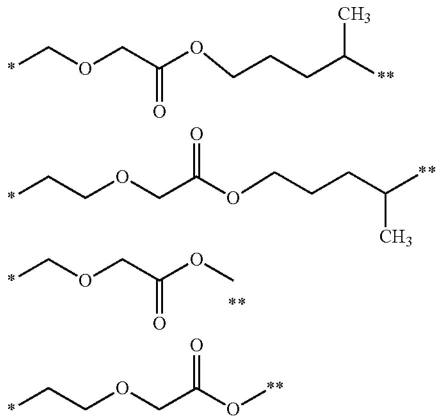

The group represented by formula (L1-4) includes, for example, the following divalent groups.

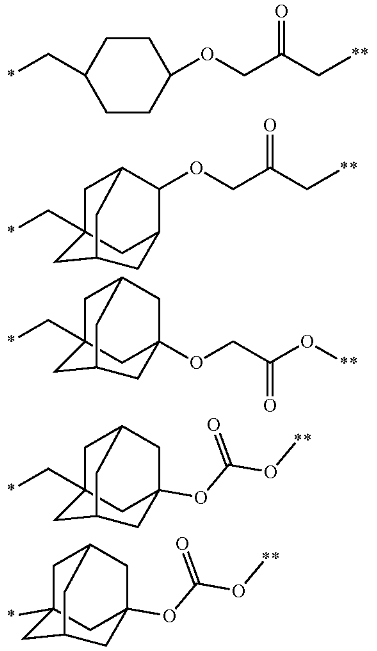

-continued
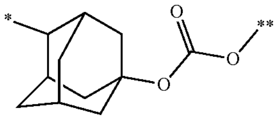
$L^{55}$ is preferably a single bond or a group represented by formula (L1-1).
Examples of the structural unit (a5-1) include the following structural units and structural units in which a methyl group corresponding to $R^{51}$ in the structural unit (a5-1) in the following structural units is substituted with a hydrogen atom.
(a5-1-1)
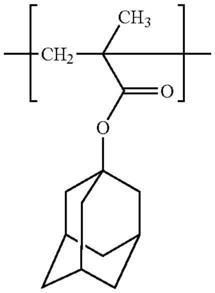
(a5-1-2)
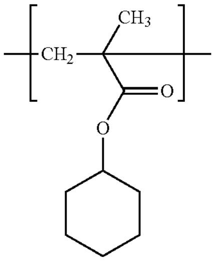
(a5-1-3)
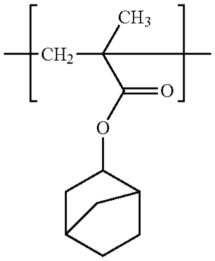
(a5-1-4)
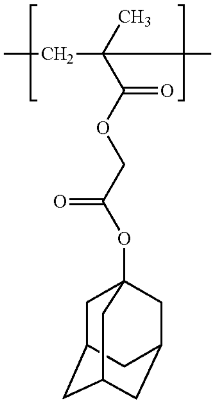
-continued
(a5-1-5)
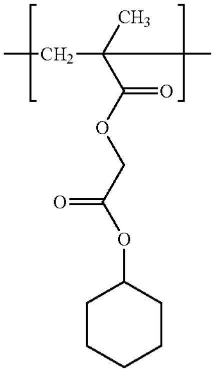
(a5-1-6)
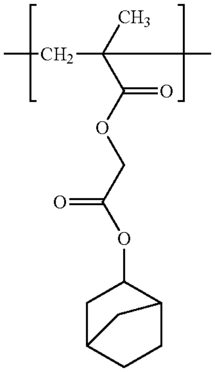
(a5-1-7)
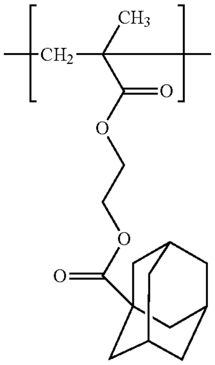
(a5-1-8)
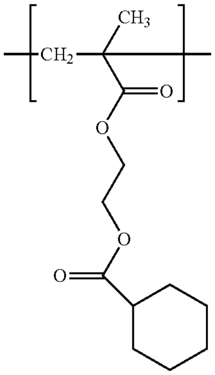

-continued
(a5-1-9)
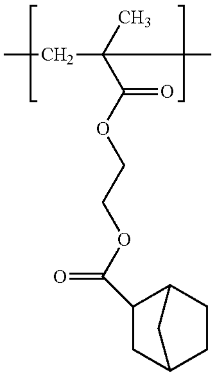
(a5-1-10)
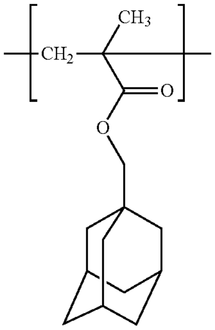
(a5-1-11)
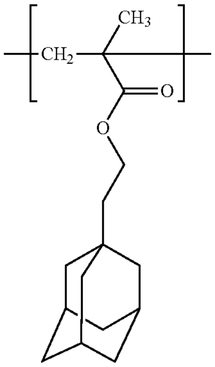
(a5-1-12)
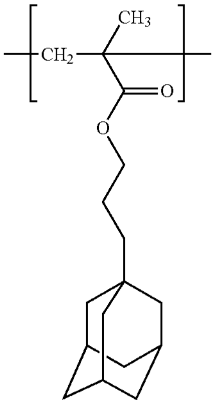
-continued
(a5-1-13)
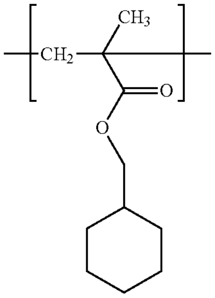
(a5-1-14)
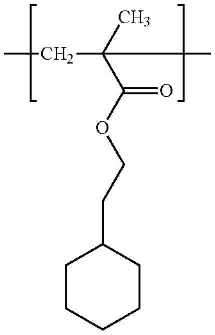
(a5-1-15)
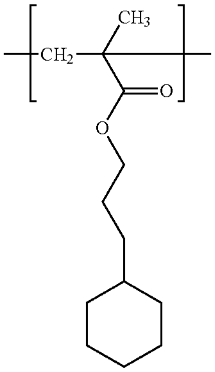
(a5-1-16)
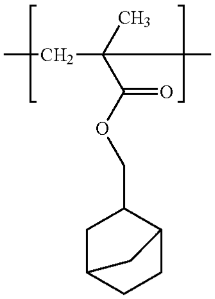

-continued (a5-1-17)

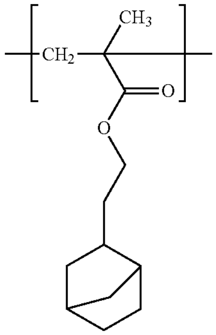

(a5-1-18)

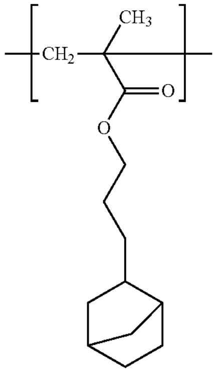

When the resin (A) includes the structural unit (a5), the content is preferably 1 to 30 mol %, more preferably 2 to 20 mol %, and still more preferably 3 to 15 mol %, based on all structural units of the resin (A).

<Structural Unit (a6)>

The structural unit (a6) is a structural unit having an $—SO_2—$ group, and it is preferable to have an $—SO_2—$ group in a side chain.

The structural unit having an $—SO_2—$ group may have a linear structure having an $—SO_2—$ group, a branched structure having an $—SO_2—$ group, or a cyclic structure (monocyclic and polycyclic structure) having an $—SO_2—$ group. The structural unit is preferably a structural unit which has a cyclic structure having an $—SO_2—$ group, and more preferably a structural unit which has a cyclic structure (sultone ring) having $—SO_2—O—$.

Examples of the sultone ring include rings represented by the following formula ($T^1$-1), formula ($T^1$-2), formula ($T^1$-3) and formula ($T^1$-4). The bonding site can be any position in groups shown below. The sultone ring may be monocyclic, and is preferably polycyclic. The polycyclic sultone ring means a bridged ring which has $—SO_2—O—$ as an atomic group constituting the ring, and examples thereof include rings represented by formula ($T^1$-1) and formula ($T^1$-2). The sultone ring may have, as the atomic group constituting the ring, a heteroatom, in addition to $—SO_2—O—$, like the ring represented by formula ($T^1$-2). Examples of the heteroatom include an oxygen atom, a sulfur atom or a nitrogen atom, and an oxygen atom is preferable.

($T^1$-1)

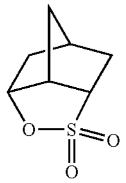

($T^1$-2)

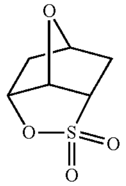

($T^1$-3)

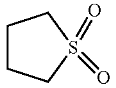

($T^1$-4)

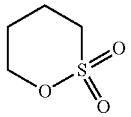

The sultone ring may have a substituent, and examples of the substituent include an alkyl group having 1 to 12 carbon atoms which may have a halogen atom or a hydroxy group, a halogen atom, a hydroxy group, a cyano group, an alkoxy group having 1 to 12 carbon atoms, an aryl group having 6 to 12 carbon atoms, an aralkyl group having 7 to 12 carbon atoms, a glycidyloxy group, an alkoxycarbonyl group having 2 to 12 carbon atoms and an alkylcarbonyl group having 2 to 4 carbon atoms.

Examples of the halogen atom include a fluorine atom, a chlorine atom, a bromine atom and an iodine atom.

Examples of the alkyl group include a methyl group, an ethyl group, a propyl group, a butyl group, a pentyl group, a hexyl group, an octyl group and a decyl group, and the alkyl group is preferably an alkyl group having 1 to 6 carbon atoms, and more preferably a methyl group.

Examples of the alkyl group having a halogen atom include a trifluoromethyl group, a perfluoroethyl group, a perfluoropropyl group, a perfluoroisopropyl group, a perfluorobutyl group, a perfluorosec-butyl group, a perfluoro-tert-butyl group, a perfluoropentyl group, a perfluorohexyl group, a trichloromethyl group, a tribromomethyl group and a triiodomethyl group, and a trifluoromethyl group is preferable.

Examples of the alkyl group having a hydroxy group include hydroxyalkyl groups such as a hydroxymethyl group and a 2-hydroxyethyl group.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the aryl group include a phenyl group, a naphthyl group, an anthryl group, a p-methylphenyl group, a p-tert-butylphenyl group, a p-adamantylphenyl group, a tolyl group, a xylyl group, a cumyl group, a mesityl group, a biphenyl group, a phenanthryl group, a 2,6-diethylphenyl group and a 2-methyl-6-ethylphenyl group.

Examples of the aralkyl group include a benzyl group, a phenethyl group, a phenylpropyl group, a naphthylmethyl group and a naphthylethyl group.

Examples of the alkoxycarbonyl group include groups in which an alkoxy group is bonded with a carbonyl group, such as a methoxycarbonyl group or an ethoxycarbonyl group, and preferably include an alkoxycarbonyl group having 6 or less carbon atoms and more preferably include a methoxycarbonyl group.

Examples of the alkylcarbonyl group include an acetyl group, a propionyl group and a butyryl group.

From the viewpoint that it is easy to produce a monomer from which the structural unit (a6) is derived, a sultone ring having no substituent is preferable.

The sultone ring is preferably a ring represented by the following formula (T1'):

(T1')

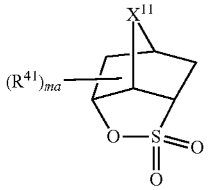

wherein, in formula (T1'), $X^{11}$ represents an oxygen atom, a sulfur atom or a methylene group, $R^{41}$ represents an alkyl group having 1 to 12 carbon atoms which may have a halogen atom or a hydroxy group, a halogen atom, a hydroxy group, a cyano group, an alkoxy group having 1 to 12 carbon atoms, an aryl group having 6 to 12 carbon atoms, an aralkyl group having 7 to 12 carbon atoms, a glycidyloxy group, an alkoxycarbonyl group having 2 to 12 carbon atoms, or an alkylcarbonyl group having 2 to 4 carbon atoms, ma represents an integer of 0 to 9, and when ma is 2 or more, a plurality of $R^{41}$ may be the same or different, and the bonding site may be any position.

$X^{11}$ is preferably an oxygen atom or a methylene group, and more preferably a methylene group.

Examples of $R^{41}$ include those which are the same as the substituent of the above-mentioned sultone ring, and an alkyl group having 1 to 12 carbon atoms which may have a halogen atom or a hydroxy group is preferable.

ma is preferably 0 or 1, and more preferably 0.

Examples of the ring represented by formula (T1') include the following rings. The bonding site may be any position.

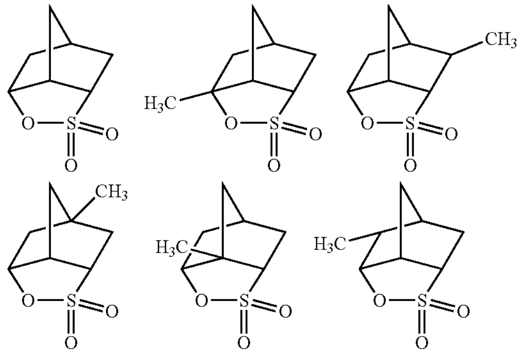

-continued

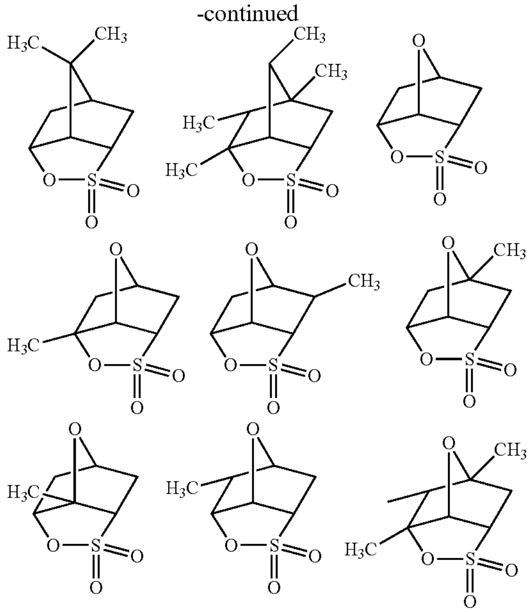

It is preferable that the structural unit having a sultone ring has the following groups. * in the following groups represents a bonding site.

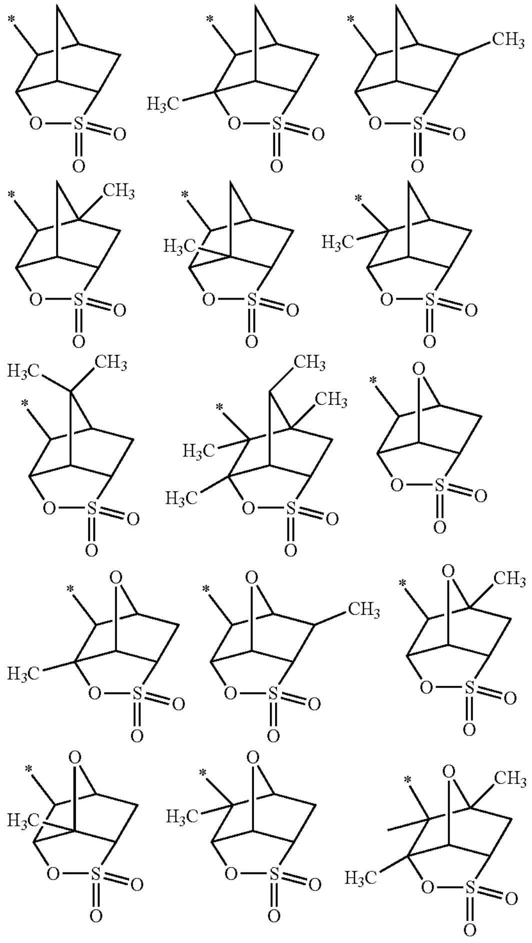

It is preferable that the structural unit having an —$SO_2$— group further has a group derived from a polymerizable group. Examples of the polymerizable group include a vinyl group, an acryloyl group, a methacryloyl group, an acryloyloxy group, a methacryloyloxy group, an acryloylamino group, a methacryloylamino group, an acryloylthio group, a methacryloylthio group and the like.

Particularly, the monomer from which the structural unit (a6) is derived is preferably a monomer having an ethylenically unsaturated bond, and more preferably a (meth)acrylic monomer.

The structural unit (a6) is preferably a structural unit represented by formula (Ix):

(Ix)

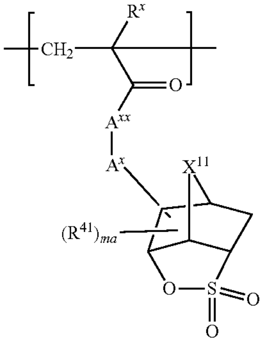

wherein, in formula (Ix), $R^x$ represents an alkyl group having 1 to 6 carbon atoms which may have a halogen atom, a hydrogen atom or a halogen atom, $A^{xx}$ represents an oxygen atom, —N($R^c$)— or a sulfur atom, $A^x$ represents a single bond or a divalent saturated hydrocarbon group having 1 to 18 carbon atoms, and —$CH_2$— included in the saturated hydrocarbon group may be replaced by —O—, —CO— or —N($R^d$)—, $X^{11}$, $R^{41}$ and ma have the same meanings as above, and $R^c$ and $R^d$ each independently represent a hydrogen atom or an alkyl group having 1 to 6 carbon atoms.

Examples of the halogen atom as for $R^x$ include a fluorine atom, a chlorine atom, a bromine atom and an iodine atom.

Examples of the alkyl group as for $R^x$ include a methyl group, an ethyl group, an n-propyl group, an isopropyl group, an n-butyl group, a sec-butyl group, a tert-butyl group, an n-pentyl group and an n-hexyl group, and an alkyl group having 1 to 4 carbon atoms is preferable, and a methyl group or an ethyl group is more preferable.

Examples of the alkyl group having a halogen atom as for $R^x$ include a trifluoromethyl group, a perfluoroethyl group, a perfluoropropyl group, a perfluoroisopropyl group, a perfluorobutyl group, a perfluorosec-butyl group, a perfluoro-tert-butyl group, a perfluoropentyl group, a perfluorohexyl group, a trichloromethyl group, a tribromomethyl group and a triiodomethyl group.

$R^x$ is preferably a hydrogen atom or an alkyl group having 1 to 4 carbon atoms, more preferably a hydrogen atom, a methyl group or an ethyl group, and still more preferably a hydrogen atom or a methyl group.

Examples of the divalent saturated hydrocarbon group as for $A^x$ include a linear alkanediyl group, a branched alkanediyl group and a monocyclic or polycyclic divalent alicyclic saturated hydrocarbon group, and the divalent saturated hydrocarbon group may be those obtained by combining two or more of these groups.

Specific examples thereof include linear alkanediyl groups such as a methylene group, an ethylene group, a propane-1,3-diyl group, a propane-1,2-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, a heptadecane-1,17-diyl group, an ethane-1,1-diyl group, a propane-1,1-diyl group and a propane-2,2-diyl group;

branched alkanediyl groups such as a butane-1,3-diyl group, a 2-methylpropane-1,3-diyl group, a 2-methylpropane-1,2-diyl group, a pentane-1,4-diyl group and a 2-methylbutane-1,4-diyl group;

monocyclic divalent alicyclic saturated hydrocarbon groups which are cycloalkanediyl groups such as a cyclobutane-1,3-diyl group, a cyclopentane-1,3-diyl group, a cyclohexane-1,4-diyl group and a cyclooctane-1,5-diyl group; and polycyclic divalent alicyclic saturated hydrocarbon groups such as a norbornane-1,4-diyl group, a norbornane-2,5-diyl group, an adamantane-1,5-diyl group and an adamantane-2,6-diyl group.

Examples of the structural unit (a6) include the following structural units.

(a6-1)

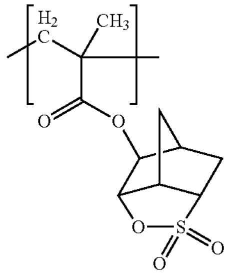

(a6-2)

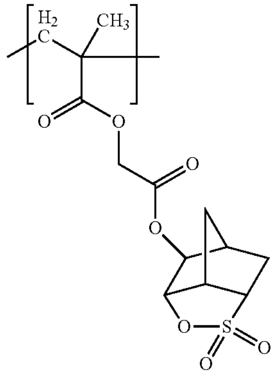

-continued
(a6-3)
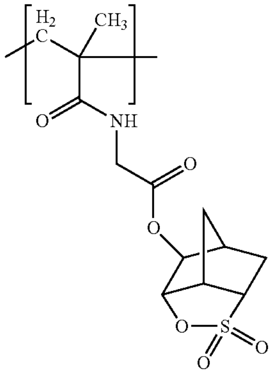
(a6-4)
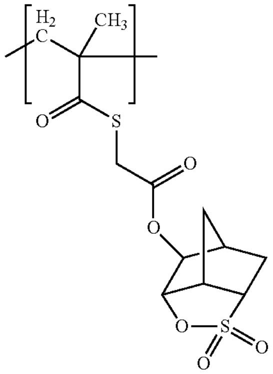
(a6-5)
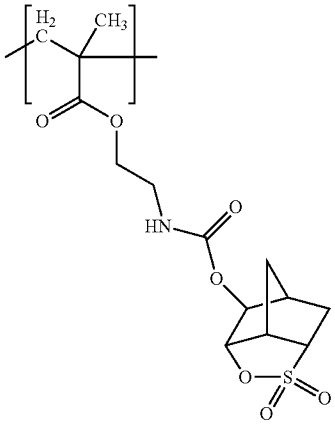
(a6-6)
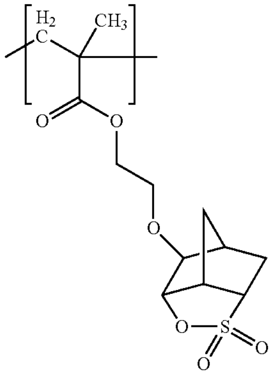
-continued
(a6-7)
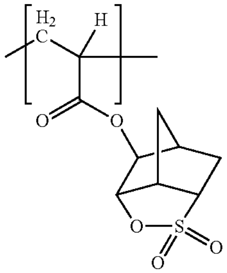
(a6-8)
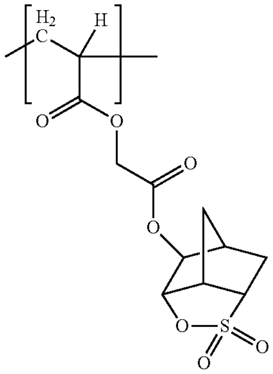
(a6-9)
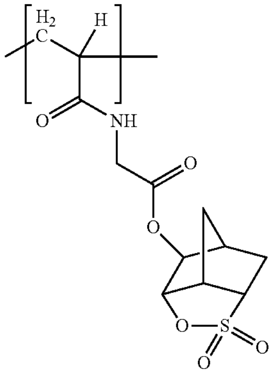
(a6-10)
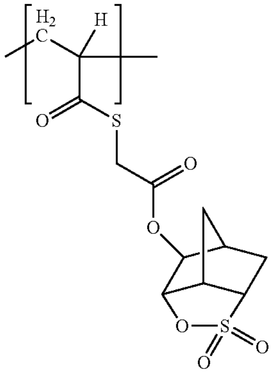

-continued (a6-11)

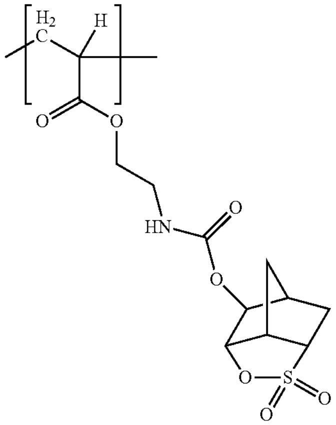

(a6-12)

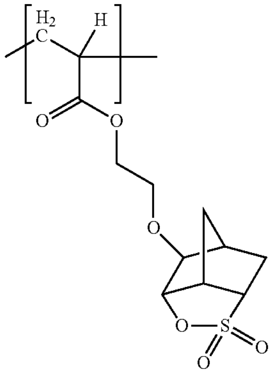

Of these, structural units represented by formula (a6-1), formula (a6-2), formula (a6-6), formula (a6-7), formula (a6-8) and formula (a6-12) are preferable, and structural units represented by formula (a6-1), formula (a6-2), formula (a6-7) and (a6-8) are more preferable.

When the resin (A) includes the structural unit (a6), the content is preferably 1 to 50 mol %, more preferably 2 to 40 mol %, and still more preferably 3 to 30 mol %, based on all structural units of the resin (A).

<Structural Unit (II)>

The resin (A) may further include a structural unit which is decomposed upon exposure to radiation to generate an acid (hereinafter sometimes referred to as “structural unit (II)”). Specific examples of the structural unit (II) include the structural units mentioned in JP 2016-79235 A, and a structural unit having a sulfonate group or a carboxylate group and an organic cation in a side chain or a structural unit having a sulfonio group and an organic anion in a side chain are preferable.

The structural unit having a sulfonate group or a carboxylate group and an organic cation in a side chain is preferably a structural unit represented by formula (II-2-A'):

(II-2-A')

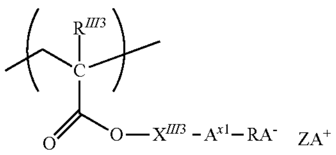

wherein, in formula (II-2-A'), $X^{III3}$ represents a divalent saturated hydrocarbon group having 1 to 18 carbon atoms, —$CH_2$— included in the saturated hydrocarbon group may be replaced by —O—, —S— or —CO—, and a hydrogen atom included in the saturated hydrocarbon group may be substituted with a halogen atom, an alkyl group having 1 to 6 carbon atoms which may have a halogen atom, or a hydroxy group, $A^{x1}$ represents an alkanediyl group having 1 to 8 carbon atoms, and a hydrogen atom included in the alkanediyl group may be substituted with a fluorine atom or a perfluoroalkyl group having 1 to 6 carbon atoms, $RA^-$ represents a sulfonate group or a carboxylate group, $R^{III3}$ represents a hydrogen atom, a halogen atom, or an alkyl group having 1 to 6 carbon atoms which may have a halogen atom, and $ZA^+$ represents an organic cation.

Examples of the halogen atom represented by $R^{III3}$ include a fluorine atom, a chlorine atom, a bromine atom and an iodine atom.

Examples of the alkyl group having 1 to 6 carbon atoms which may have a halogen atom represented by $R^{III3}$ include those which are the same as the alkyl group having 1 to 6 carbon atoms which may have a halogen atom represented by $R^{a8}$.

Examples of the alkanediyl group having 1 to 8 carbon atoms represented by $A^{x1}$ include a methylene group, an ethylene group, a propane-1,3-diyl group, a butane-1,4-diyl group, a pentane-1,5-diyl group, a hexane-1,6-diyl group, an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group, a 2-methylbutane-1,4-diyl group and the like.

Examples of the perfluoroalkyl group having 1 to 6 carbon atoms which may be substituted in $A^{x1}$ include a trifluoromethyl group, a perfluoroethyl group, a perfluoropropyl group, a perfluoroisopropyl group, a perfluorobutyl group, a perfluorosec-butyl group, a perfluorotert-butyl group, a perfluoropentyl group, a perfluorohexyl group and the like.

Examples of the divalent saturated hydrocarbon group having 1 to 18 carbon atoms represented by $X^{III3}$ include a linear or branched alkanediyl group, a monocyclic or a polycyclic divalent alicyclic saturated hydrocarbon group, or a combination thereof.

Specific examples thereof include linear alkanediyl groups such as a methylene group, an ethylene group, a propane-1,3-diyl group, a propane-1,2-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group and a dodecane-1,12-diyl group; branched alkanediyl groups such as a butane-1,3-diyl group, a 2-methylpropane-1,3-diyl group, a 2-methylpropane-1,2-diyl group, a pentane-1,4-diyl group and a 2-methylbutane-1,4-diyl group; cycloalkanediyl groups such as a cyclobutane-1,3-diyl group, a cyclopentane-1,3-diyl group, a cyclohexane-1,4-diyl group and a cyclooctane-1,5-diyl group; and divalent polycyclic alicyclic saturated hydrocarbon groups such as a norbornane-1,4-diyl group, a norbornane-2,5-diyl group, an adamantane-1,5-diyl group and an adamantane-2,6-diyl group.

Those in which —$CH_2$— included in the saturated hydrocarbon group are replaced by —O—, —S— or —CO— include, for example, divalent groups represented by formula (X1) to formula (X53). Before replacing —$CH_2$— included in the saturated hydrocarbon group by —O—, —S— or —CO—, the number of carbon atoms is 17 or less. In the following formulas, * and ** represent a bonding site, and * represents a bond to $A^{x1}$.
(X1)
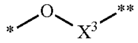
(X2)
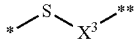
(X3)
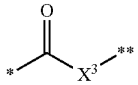
(X4)
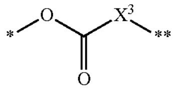
(X5)
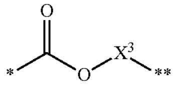
(X6)
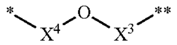
(X7)
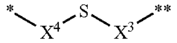
(X8)
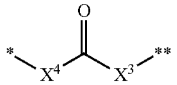
(X9)
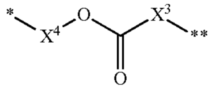
(X10)
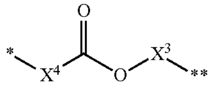
(X11)
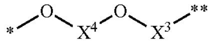
(X12)
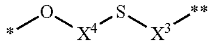
(X13)
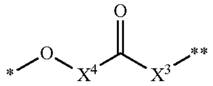
(X14)
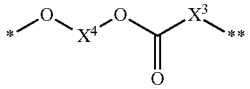
(X15)
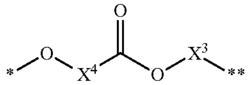
(X16)
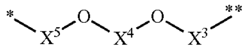
(X17)
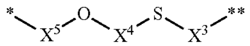
(X18)
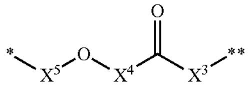
-continued
(X19)
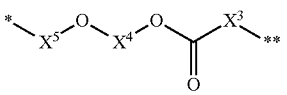
(X20)
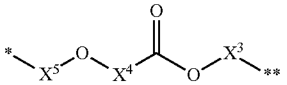
(X21)
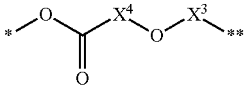
(X22)
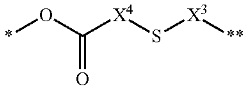
(X23)
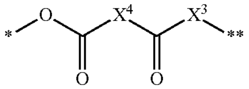
(X24)
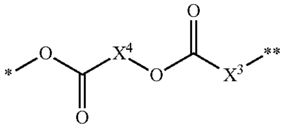
(X25)
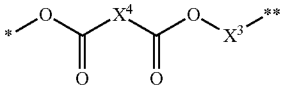
(X26)
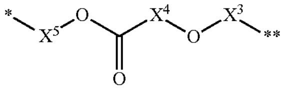
(X27)
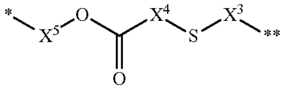
(X28)
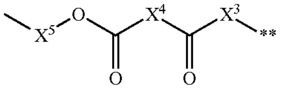
(X29)
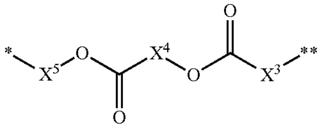
(X30)
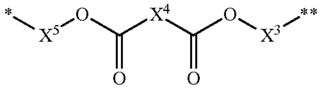
(X31)
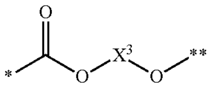
(X32)
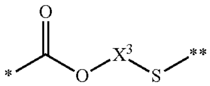

-continued (X33)

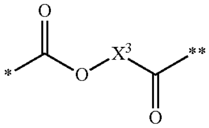

(X34)

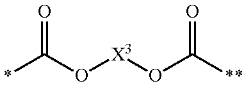

(X35)

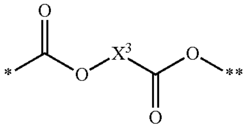

(X36)

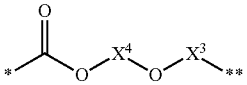

(X37)

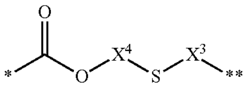

(X38)

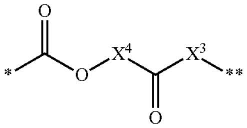

(X39)

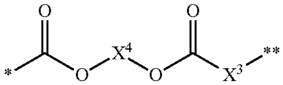

(X40)

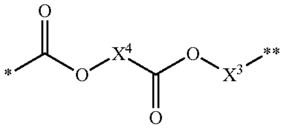

(X41)

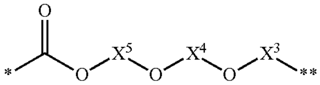

(X42)

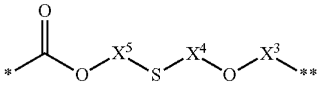

(X43)

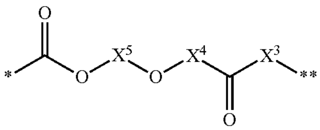

(X44)

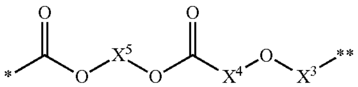

(X45)

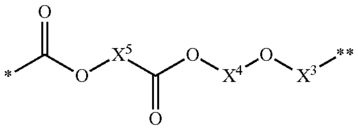

-continued (X46)

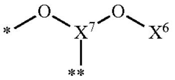

(X47)

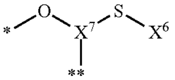

(X48)

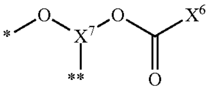

(X49)

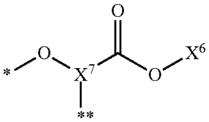

(X50)

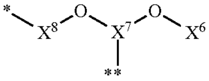

(X51)

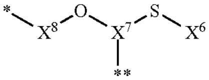

(X52)

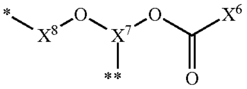

(X53)

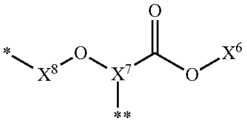

$X^3$ represents a divalent saturated hydrocarbon group having 1 to 16 carbon atoms.

$X^4$ represents a divalent saturated hydrocarbon group having 1 to 15 carbon atoms.

$X^5$ represents a divalent saturated hydrocarbon group having 1 to 13 carbon atoms.

$X^6$ represents a divalent saturated hydrocarbon group having 1 to 14 carbon atoms.

$X^7$ represents a trivalent saturated hydrocarbon group having 1 to 14 carbon atoms.

$X^8$ represents a divalent saturated hydrocarbon group having 1 to 13 carbon atoms.

Examples of $ZA^+$ in formula (II-2-A') include those which are the same as the cation $Z1^+$ in the salt represented by formula (B1)

The structural unit represented by formula (II-2-A') is preferably a structural unit represented by formula (II-2-A):

(II-2-A)

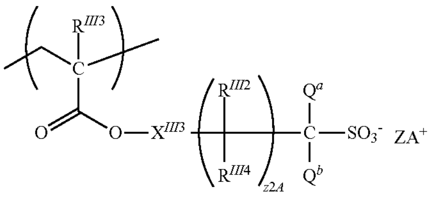

wherein, in formula (II-2-A), $R^{III3}$ $X^{III3}$ and $ZA^+$ are the same as defined above, z2A represents an integer of 0 to 6, $R^{III2}$ and $R^{III4}$ each independently represent a hydrogen atom, a fluorine atom or a perfluoroalkyl group having 1 to 6 carbon atoms, and when z2A is 2 or more, a plurality of $R^{III2}$ and $R^{III4}$ may be the same or different form each other, and $Q^a$ and $Q^b$ each independently represent a fluorine atom or a perfluoroalkyl group having 1 to 6 carbon atoms.

Examples of the perfluoroalkyl group having 1 to 6 carbon atoms represented by $R^{III2}$, $R^{III4}$, $Q^a$ and $Q^b$ include those which are the same as the perfluoroalkyl group having 1 to 6 carbon atoms represented by $Q^{b1}$.

The structural unit represented by formula (II-2-A) is preferably a structural unit represented by formula (II-2-A-1)

(II-2-A-1)

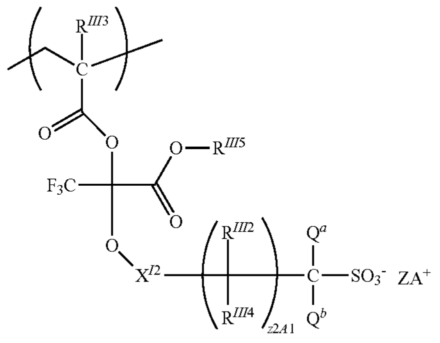

wherein, in formula (II-2-A-1), $R^{III2}$, $R^{III3}$, $R^{III4}$, $Q^a$, $Q^b$ and $ZA^+$ are the same as defined above, $R^{III5}$ represents a saturated hydrocarbon group having 1 to 12 carbon atoms, z2A1 represents an integer of 0 to 6, and $X^{I2}$ represents a divalent saturated hydrocarbon group having 1 to 11 carbon atoms, —$CH_2$— included in the saturated hydrocarbon group may be replaced by —O—, —S— or —CO—, and a hydrogen atom included in the saturated hydrocarbon group may be substituted with a halogen atom or a hydroxy group.

Examples of the saturated hydrocarbon group having 1 to 12 carbon atoms represented by $R^{III5}$ include linear or branched alkyl groups such as a methyl group, an ethyl group, a propyl group, an isopropyl group, a butyl group, a sec-butyl group, a tert-butyl group, a pentyl group, a hexyl group, a heptyl group, an octyl group, a nonyl group, a decyl group, an undecyl group and a dodecyl group.

Examples of the divalent saturated hydrocarbon group represented by $X^{I2}$ include those which are the same as the divalent saturated hydrocarbon group represented by $X^{III3}$.

The structural unit represented by formula (II-2-A-1) is more preferably a structural unit represented by formula (II-2-A-2):

(II-2-A-2)

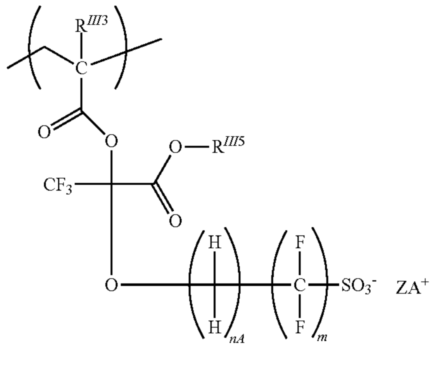

wherein, in formula (II-2-A-2), $R^{III3}$, $R^{III5}$ and $ZA^+$ are the same as defined above, and m and nA each independently represent 1 or 2.

The structural unit represented by formula (II-2-A') includes, for example, the following structural units, structural units in which a group corresponding to a methyl group of $R^{III3}$ is substituted with an alkyl group having 1 to 6 carbon atoms which may have a hydrogen atom, a halogen atom (e.g., fluorine atom) or a halogen atom (e.g., trifluoromethyl group, etc.) and the structural units mentioned in WO 2012/050015 A. $ZA^+$ represents an organic cation.

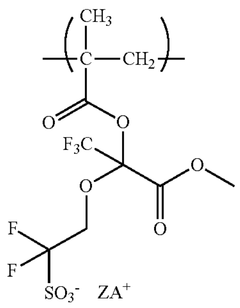

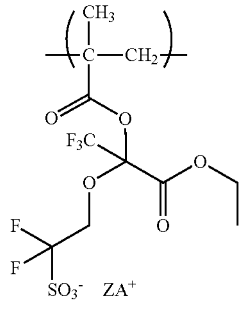

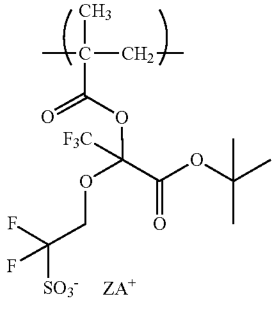

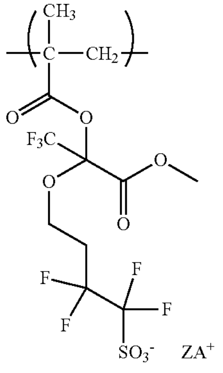

-continued

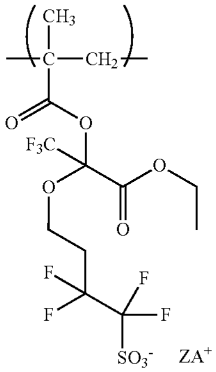

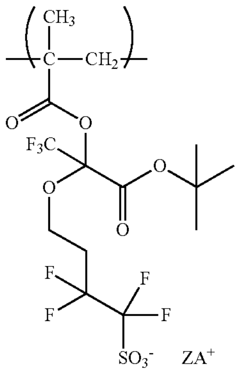

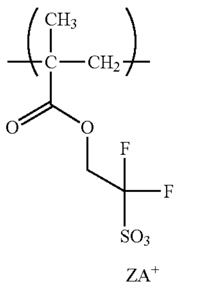

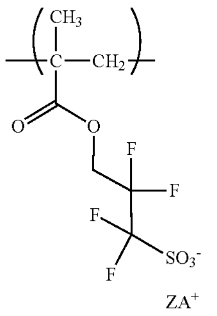

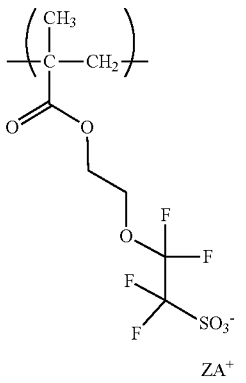

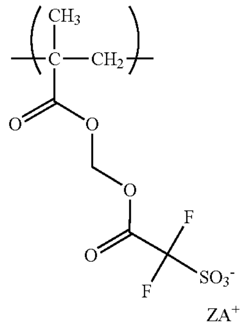

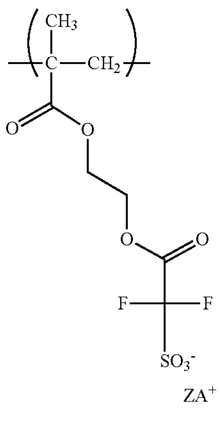

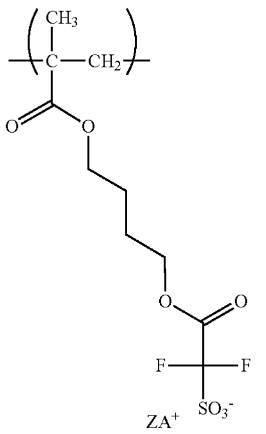

The structural unit having a sulfonio group and an organic anion in a side chain is preferably a structural unit represented by formula (II-1-1):

(II-1-1)

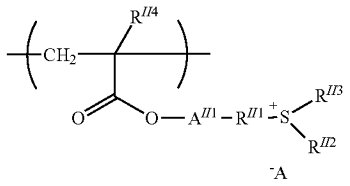

wherein, in formula (II-1-1), $A^{II1}$ represents a single bond or a divalent linking group, $R^{II1}$ represents a divalent aromatic hydrocarbon group having 6 to 18 carbon atoms, $R^{II2}$ and $R^{II3}$ each independently represent a hydrocarbon group having 1 to 18 carbon atoms, and $R^{II2}$ and $R^{II3}$ may be bonded to each other to form a ring together with sulfur atoms to which $R^{II2}$ and $R^{II3}$ are bonded, $R^{II4}$ represents a hydrogen atom, a halogen atom, or an alkyl group having 1 to 6 carbon atoms which may have a halogen atom, and $A^-$ represents an organic anion.

Examples of the divalent aromatic hydrocarbon group having 6 to 18 carbon atoms represented by $R^{II1}$ include a phenylene group and a naphthylene group.

Examples of the hydrocarbon group represented by $R^{II2}$ and $R^{II3}$ include an alkyl group, an alicyclic hydrocarbon group, an aromatic hydrocarbon group, and groups obtained by combining these groups.

Examples of the halogen atom represented by $R^{II4}$ include a fluorine atom, a chlorine atom, a bromine atom and an iodine atom.

Examples of the alkyl group having 1 to 6 carbon atoms which may have a halogen atom represented by $R^{II4}$ include those which are the same as the alkyl group having 1 to 6 carbon atoms which may have a halogen atom represented by $R^{a8}$.

Examples of the divalent linking group represented by $A^{II1}$ include a divalent saturated hydrocarbon group having 1 to 18 carbon atoms, and $—CH_2—$ included in the divalent saturated hydrocarbon group may be replaced by —O—, —S— or —CO—. Specific examples thereof include those which are the same as the divalent saturated hydrocarbon group having 1 to 18 carbon atoms represented by $X^{111}3$.

Examples of the structural unit including a cation in formula (II-1-1) include the following structural units and structural units in which a group corresponding to a methyl group of $R^{II4}$ is substituted with a hydrogen atom, a fluorine atom, a trifluoromethyl group and the like.

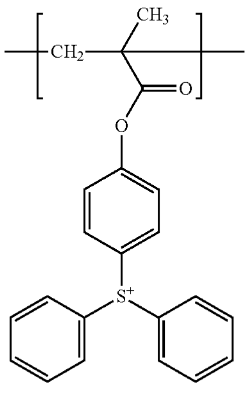

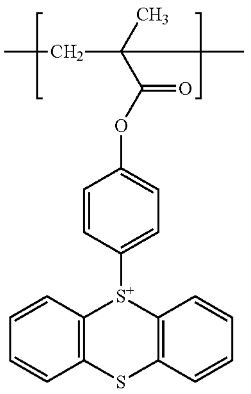

-continued

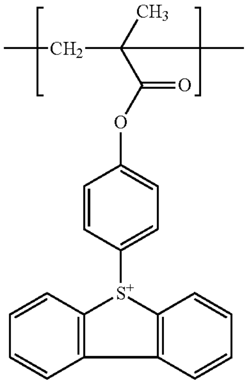

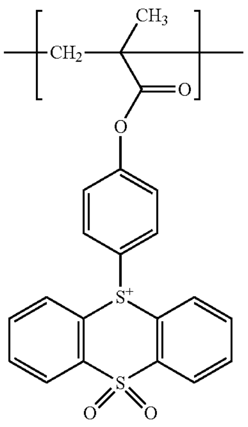

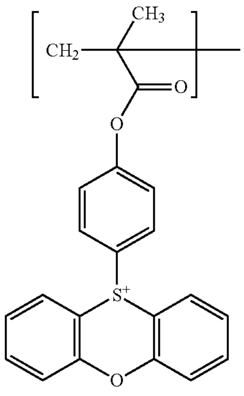

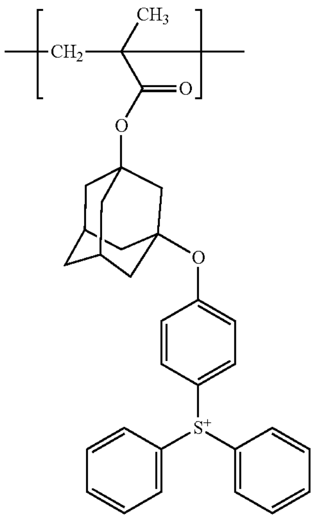

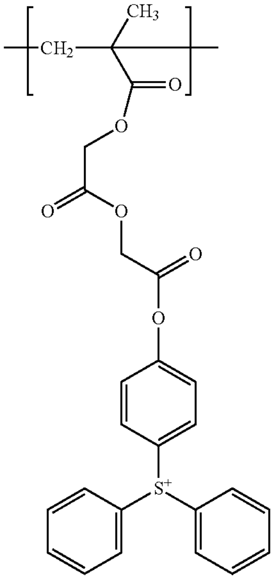

-continued

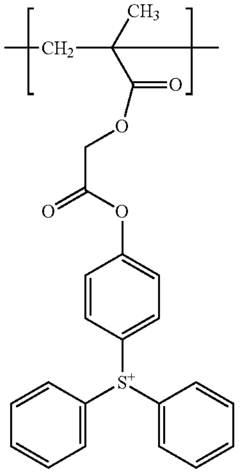

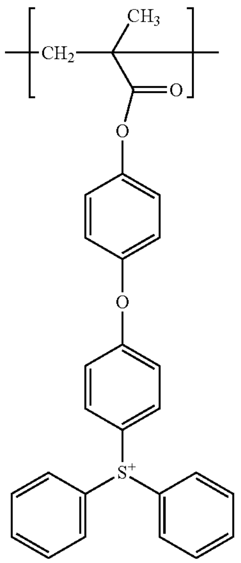

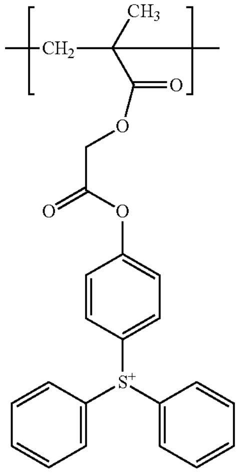

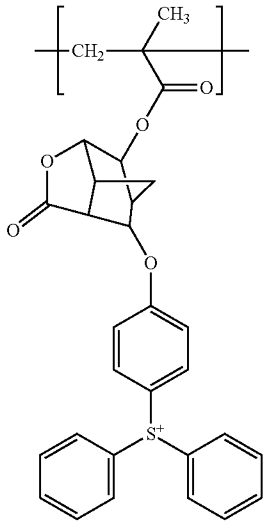

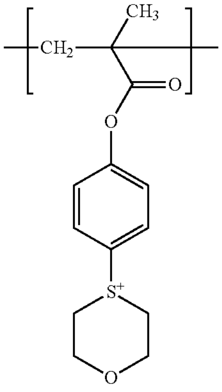

Examples of the organic anion represented by $A^-$ include a sulfonic acid anion, a sulfonylimide anion, a sulfonylmethide anion and a carboxylic acid anion. The organic anion represented by $A^-$ is preferably a sulfonic acid anion, and the sulfonic acid anion is more preferably an anion included in the below-mentioned salt represented by formula (B1).

Examples of the sulfonylimide anion include the followings.

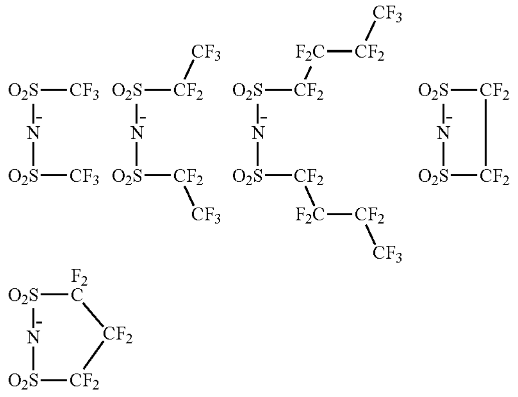
Examples of the sulfonylmethide anion include the followings.
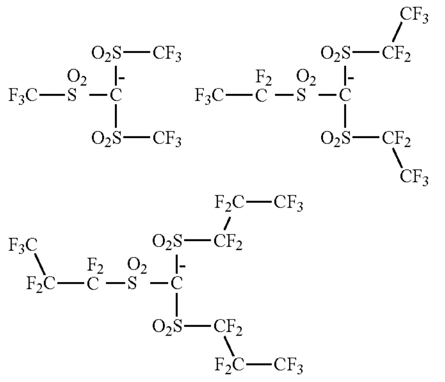
Examples of the carboxylic acid anion include the followings.
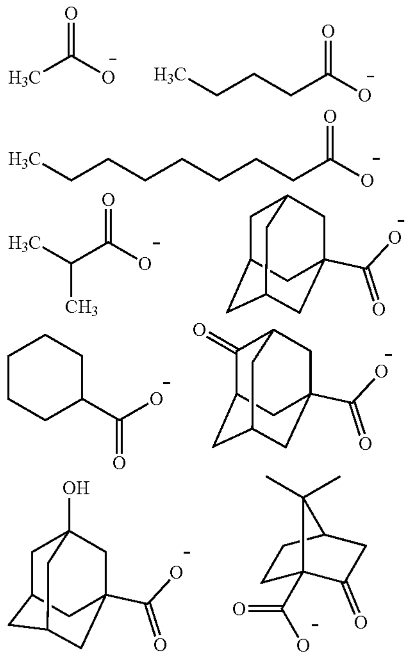
-continued
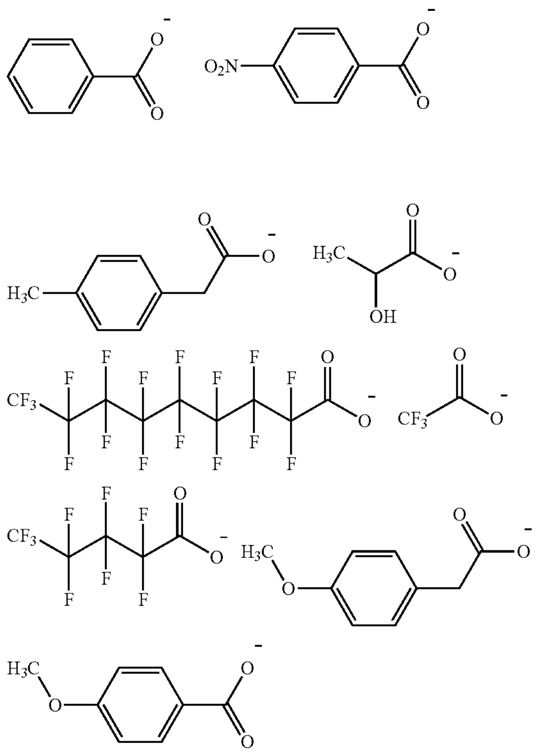
Examples of the structural unit represented by formula (II-1-1) include structural units shown below.
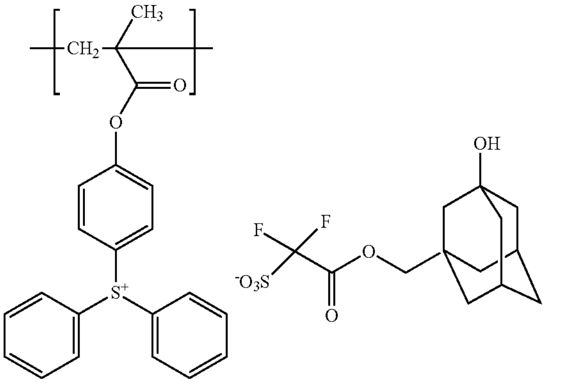
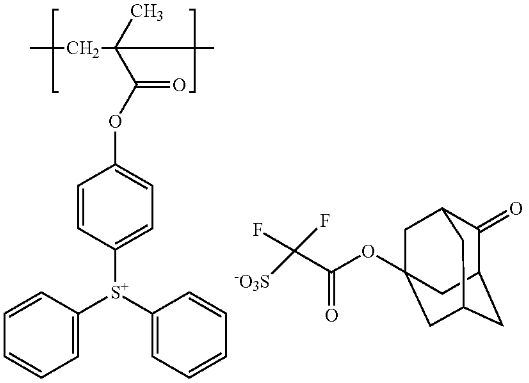

-continued

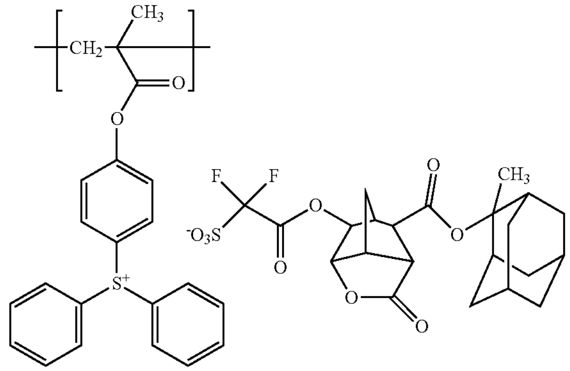

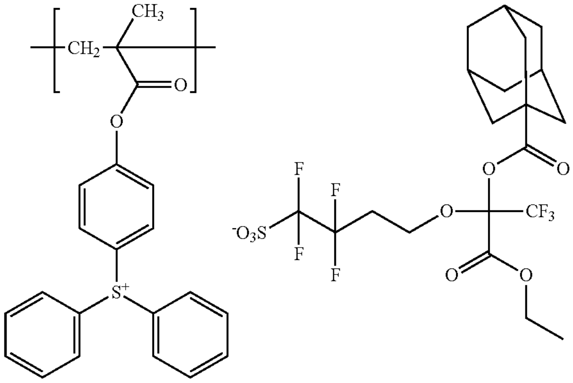

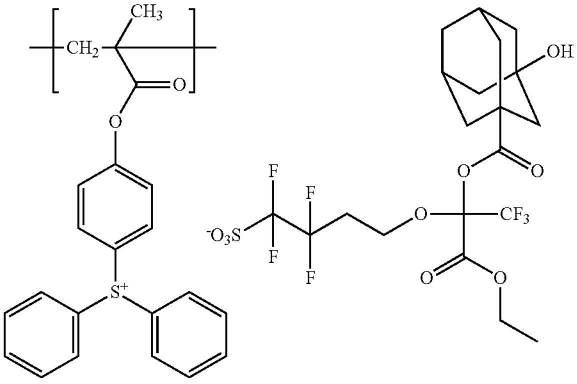

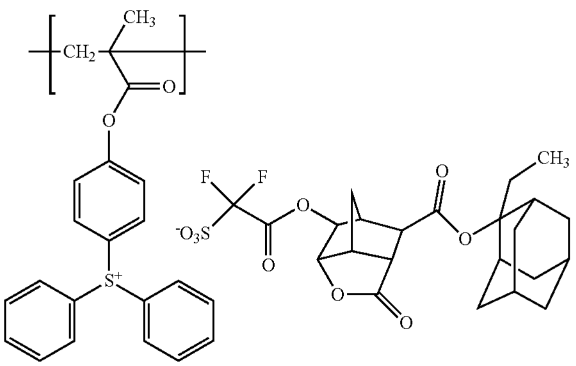

-continued

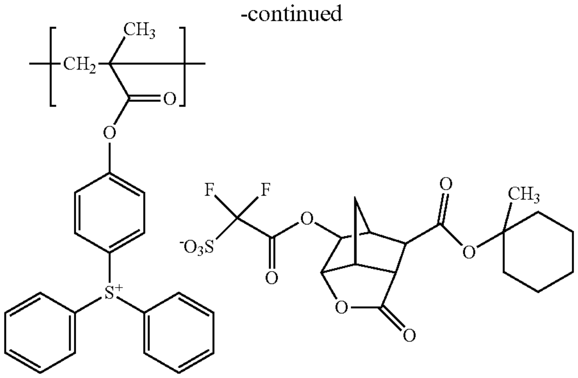

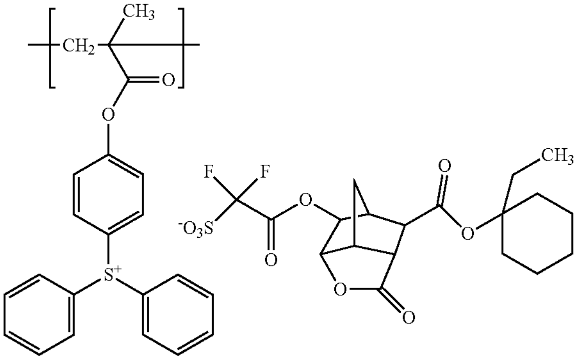

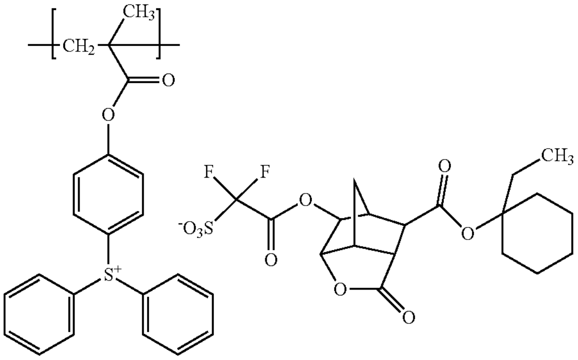

When the structural unit (II) is included in the resin (A), the content of the structural unit (II) is preferably 1 to 20 mol %, more preferably 2 to 15 mol %, and still more preferably 3 to 10 mol %, based on all structural units of the resin (A).

The resin (A) may include structural units other than the structural units mentioned above, and examples of such structural unit include structural units well-known in the art.

The resin (A) is preferably a resin including a structural unit (a1). Particularly, the resin (Ap) is more preferably a resin composed of a structural unit (IP), a structural unit (a1) and a structural unit (s), that is, a copolymer of a salt (I), a monomer (a1) and a monomer (s). The resin (A) including no structural unit (IP) is preferably a resin composed of a structural unit (a1) and a structural unit (s).

The structural unit (a1) is preferably at least one selected from the group consisting of a structural unit (a1-0), a structural unit (a1-1) and a structural unit (a1-2) (preferably the structural unit having a cyclohexyl group and a cyclopentyl group), more preferably at least two, and still more preferably at least two selected from the group consisting of a structural unit (a1-1) and a structural unit (a1-2).

The structural unit (s) is preferably at least one selected from the group consisting of a structural unit (a2) and a structural unit (a3). The structural unit (a2) is preferably a structural unit (a2-1) or a structural unit (a2-A). The structural unit (a3) is preferably at least one selected from the group consisting of a structural unit represented by formula (a3-1), a structural unit represented by formula (a3-2) and a structural unit represented by formula (a3-4).

The respective structural units constituting the resin (A) may be used alone, or two or more structural units may be used in combination. Using a monomer from which these structural units are derived, it is possible to produce by a known polymerization method (e.g. radical polymerization method). The content of the respective structural units included in the resin (A) can be adjusted according to the amount of the monomer used in the polymerization.

The weight-average molecular weight of the resin (A) is preferably 2,000 or more (more preferably 2,500 or more, and still more preferably 3,000 or more), and 50,000 or less (more preferably 30,000 or less, and still more preferably 15,000 or less). In the present specification, the weight-average molecular weight is a value determined by gel permeation chromatography under the conditions mentioned in Examples. The structural unit (IP) may constitute a dimer, a trimer, and a compound having a weight-average molecular weight of less than 2,000.

[Carboxylic Acid Generator]

The carboxylic acid generator of the present disclosure is a carboxylic acid generator including a carboxylate (I) or a structural unit (IP). The structural unit (IP) can be included as a compound or a resin obtained by polymerizing a plurality thereof. The carboxylate (I) or structural unit (IP) of the present disclosure can act as a carboxylic acid generator in the resist composition. When using the carboxylate (I) as the carboxylic acid generator in the resist composition, the carboxylic acid generator may include the carboxylate (I) alone, or two or more thereof. When using the structural unit (IP) as the carboxylic acid generator in the resist composition, the compound or resin including the structural unit (IP) may be used alone or in combination of two or more thereof. The carboxylic acid generator of the present disclosure may include both the carboxylate (I) and structural unit (IP).

As mentioned later, the carboxylic acid generator of the present disclosure may further include an acid generator known in the resist field other than the carboxylate (I) (hereinafter sometimes referred to as "acid generator (B)") and/or a carboxylate known in the resist field other than the carboxylate (I). The acid generator (B) may be used alone, or in combination of two or more thereof.

When the carboxylic acid generator includes the acid generator (B), a ratio of the content of the carboxylate (I) to that of the acid generator (B) (mass ratio; carboxylate (I):acid generator (B)) is usually 1:99 to 100:0, preferably 1:99 to 99:1, more preferably 2:98 to 98:2, still more preferably 5:95 to 95:5, yet more preferably 15:85 to 85:15, and particularly preferably 10:90 to 40:60.

[Resist Composition]

The resist composition of the present disclosure includes the carboxylic acid generator of the present disclosure. The carboxylic acid generator here may be a resin (Ap) including a structural unit (IP). That is, the resist composition of the present disclosure may include at least one of an acid generator including a structural unit (IP) and a carboxylate (I) or including a structural unit (IP) and a carboxylate (I). The structural unit (IP) may be in a form of either compound or resin. In other words, the resist composition of the present disclosure may include, as the carboxylic acid generator, a resin and/or a resin (Ap), and a carboxylate (I). The resist composition of the present disclosure preferably include a resin including a structural unit (a1) having an acid-labile group. That is, the resist composition more preferably includes (a) a carboxylate (I) and a resin (A), (b) a resin (Ap) including a structural unit (IP) and a structural unit (a1) having an acid-labile group, or (c) a resin (Ap) including a structural unit (IP) and a resin (A). Of these, the resist composition is preferably the resist composition (b). Two or more resins (A) and/or resins (Ap) may be included.

It is preferable that the resist composition of the present disclosure further includes an acid generator known in the resist field (hereinafter sometimes referred to as "acid generator (B)", a quencher (hereinafter sometimes referred to as "quencher (C)") and/or a solvent (hereinafter sometimes referred to as "solvent (E)").

<Carboxylic Acid Generator>

The content of the carboxylate (I) of the present disclosure is preferably about 0.01 to 15% by mass, more preferably about 0.001 to 10% by mass, still more preferably about 0.001 to 8% by mass, and yet more preferably about 0.005 to 7% by mass, based on the solid content of the resist composition.

The content of the resin (Ap) of the present disclosure is preferably 80% by mass or more 99% by mass or less, and more preferably 90% by mass or more 99% by mass or less, based on the solid content of the resist composition.

<Resin other than Resin (A)>

The resist composition of the present disclosure may use a resin (Ap) in combination with a resin other than the resin (A).

Examples of the resin (Ap) and the resin other than the resin (A) include a resin (AX) including the same structural unit as that of the resin (A), except that no structural unit (a1) is included in the above-mentioned resin (A), a resin including a structural unit (a4) and/or a structural unit (a5) (including neither structural unit (IP) nor structural unit (a1), hereinafter sometimes referred to as "resin (X)") and the like.

Examples of the resin (AX) include a resin including a structural unit (a2), and a resin including a structural unit (a2-A) is preferable. In the resin (AX), the content of the structural unit (a2-A) is preferably 5 mol % or more, more preferably 10 mol % or more, and still more preferably 15 mol % or more, and is preferably 80 mol % or less, and more preferably 70 mol % or less, based on the total of all structural units of the resin (AX).

Examples of the structural unit, which may be further included in the resin (X), include a structural unit (a2), a structural unit (a3) and structural units derived from other known monomers. Particularly, the resin (X) is preferably a resin composed only of a structural unit (a4) and/or a structural unit (a5), and more preferably a resin composed only of a structural unit (a4).

When the resin (X) includes a structural unit (a4), the content of the structural unit (a4) is 20 mol % or more, preferably 30 mol % or more, more preferably 40 mol % or more, and still more preferably 45 mol % or more, based on the total of all structural units of the resin (X). The content is also 100 mol % or less, preferably 80 mol % or less, more preferably 70 mol % or less, still more preferably 60 mol % or less, and yet more preferably 55 mol % or less. Specifically, the content is 20 to 100 mol %, preferably 20 to 80 mol %, more preferably 30 to 70 mol %, still more preferably 40 to 60 mol %, and yet more preferably 45 to 55 mol %. When the resin (X) includes a structural unit (a5), the content of the structural unit (a5) is 20 mol % or more, preferably 30 mol % or more, more preferably 40 mol % or more, and still more preferably 45 mol % or more, based on the total of all structural units of the resin (X). The content is also 100 mol % or less, preferably 80 mol % or less, more preferably 70 mol % or less, still more preferably 60 mol % or less, and yet more preferably 55 mol % or less. Specifically, the content is 20 to 100 mol %, preferably 20 to 80 mol %, more preferably 30 to 70 mol %, still more preferably 40 to 60 mol %, and yet more preferably 45 to 55 mol %. When the resin (X) includes a structural unit (a4) and a structural unit (a5), the total content of the structural unit (a4) and the structural unit (a5) is 40 mol % or more, preferably 60 mol % or more, more preferably 70 mol % or more, and still more preferably 80 mol % or more, based on the total of all structural units of the resin (X). The content is also 100 mol % or less. Specifically, the content is 40 to 100 mol %, preferably 60 to 100 mol %, more preferably 70 to 100 mol %, and still more preferably 80 to 100 mol %.

The respective structural unit constituting the resin (AX) and the resin (X) may be used alone, or two or more structural units may be used in combination. Using a monomer from which these structural units are derived, it is possible to produce by a known polymerization method (e.g. radical polymerization method). The content of the respective structural units included in the resin (AX) and the resin (X) can be adjusted according to the amount of the monomer used in the polymerization.

The weight-average molecular weight of the resin (AX) and the resin (X) is preferably 6,000 or more (more preferably 7,000 or more) and 80,000 or less (more preferably 60,000 or less). The measurement means of the weight-average molecular weight of the resin (AX) and the resin (X) is the same as in the case of the resin (A).

When the resist composition of the present disclosure includes the resin (X), the content is preferably 1 to 60 part by mass, more preferably 1 to 50 part by mass, still more preferably 1 to 40 part by mass, yet more preferably 1 to 30 part by mass, and further preferably 1 to 8 part by mass, based on 100 part by mass of the resin (A).

The content of the resin (A) in the resist composition is preferably 80% by mass or more and 99% by mass or less, and more preferably 90% by mass or more and 99% by mass or less, based on the solid component of the resist composition. When including resins other than the resin (A), the total content of the resin (A) and resins other than the resin (A) is preferably 80% by mass or more and 99% by mass or less, and more preferably 90% by mass or more and 99% by mass or less, based on the solid component of the resist composition. The solid component of the resist composition and the content of the resin thereto can be measured by a known analysis means such as liquid chromatography or gas chromatography.

<Acid Generator (B)>

Either nonionic or ionic acid generator may be used as the acid generator (B). Examples of the nonionic acid generator include sulfonate esters (e.g., 2-nitrobenzyl ester, aromatic sulfonate, oxime sulfonate, N-sulfonyloxyimide, sulfonyloxyketone, diazonaphthoquinone 4-sulfonate), sulfones (e.g., disulfone, ketosulfone, sulfonyldiazomethane) and the like. Typical examples of the ionic acid generator include onium salts containing an onium cation (e.g., diazonium salt, phosphonium salt, sulfonium salt, iodonium salt). Examples of the anion of the onium salt include sulfonic acid anion, sulfonylimide anion, sulfonylmethide anion and the like.

Specific examples of the acid generator (B) include compounds generating an acid upon exposure to radiation mentioned in JP 63-26653 A, JP 55-164824 A, JP 62-69263 A, JP 63-146038 A, JP 63-163452 A, JP 62-153853 A, JP 63-146029 A, U.S. Pat. Nos. 3,779,778, 3,849,137, DE Patent No. 3914407 and EP Patent No. 126,712. Compounds produced by a known method may also be used. Two or more acid generators (B) may also be used in combination.

The acid generator (B) is preferably a salt represented by formula (B1) (hereinafter sometimes referred to as "acid generator (B1)"):

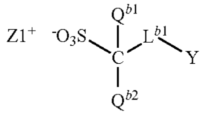

(B1)

wherein, in formula (B1), $Q^{b1}$ and $Q^{b2}$ each independently represent a hydrogen atom, a fluorine atom, a perfluoroalkyl group having 1 to 6 carbon atoms or an alkyl group having 1 to 6 carbon atoms.

$L^{b1}$ represents a divalent saturated hydrocarbon group having 1 to 24 carbon atoms, —$CH_2$— included in the divalent saturated hydrocarbon group may be replaced by —O— or —CO—, and a hydrogen atom included in the divalent saturated hydrocarbon group may be substituted with a fluorine atom or a hydroxy group, Y represents a methyl group which may have a substituent or an alicyclic hydrocarbon group having 3 to 24 carbon atoms which may have a substituent, and —$CH_2$— included in the alicyclic hydrocarbon group may be replaced by —O—, —S—, —$SO_2$— or —CO—, and $Z1^+$ represents an organic cation.

Examples of the perfluoroalkyl group represented by $Q^{b1}$ and $Q^{b2}$ include a trifluoromethyl group, a perfluoroethyl group, a perfluoropropyl group, a perfluoroisopropyl group, a perfluorobutyl group, a perfluorosec-butyl group, a perfluorotert-butyl group, a perfluoropentyl group and a perfluorohexyl group.

Examples of the alkyl group represented by $Q^{b1}$ and $Q^{b2}$ include a methyl group, an ethyl group, a propyl group, an isopropyl group, a butyl group, a sec-butyl group, a tert-butyl group, a pentyl group, a hexyl group and the like.

The acid generator (B) is preferably a fluorine-containing acid generator. Preferably either one of $Q^{b1}$ and $Q^{b2}$ is a fluorine atom or a perfluoroalkyl group, more preferably both are each independently fluorine atoms or perfluoroalkyl groups, still more preferably both are each independently fluorine atoms or trifluoromethyl groups, and yet more preferably both are each independently fluorine atoms.

Examples of the divalent saturated hydrocarbon group in $L^{b1}$ include a linear alkanediyl group, a branched alkanediyl group, and a monocyclic or polycyclic divalent alicyclic saturated hydrocarbon group, or the divalent saturated hydrocarbon group may be a group formed by combining two or more of these groups.

Specific examples thereof include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group;

branched alkanediyl groups such as an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group and a 2-methylbutane-1,4-diyl group;

monocyclic divalent alicyclic saturated hydrocarbon groups which are cycloalkanediyl groups such as a cyclobutane-1,3-diyl group, a cyclopentane-1,3-diyl group, a cyclohexane-1,4-diyl group and a cyclooctane-1,5-diyl group; and polycyclic divalent alicyclic saturated hydrocarbon groups such as a norbornane-1,4-diyl group, a norbornane-2,5-diyl group, an adamantane-1,5-diyl group and an adamantane-2,6-diyl group.

The group in which $—CH_2—$ included in the divalent saturated hydrocarbon group represented by $L^{b1}$ is replaced by —O— or —CO— includes, for example, a group represented by any one of formula (b1-1) to formula (b1-3). In groups represented by formula (b1-1) to formula (b1-3) and groups represented by formula (b1-4) to formula (b1-11) which are specific examples thereof, * and ** represent a bonding site, and * represents a bond to —Y.

(b1-1)

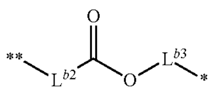

(b1-2)

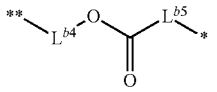

(b1-3)

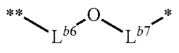

In formula (b1-1), $L^{b2}$ represents a single bond or a divalent saturated hydrocarbon group having 1 to 22 carbon atoms, and a hydrogen atom included in the saturated hydrocarbon group may be substituted with a fluorine atom, $L^{b3}$ represents a single bond or a divalent saturated hydrocarbon group having 1 to 22 carbon atoms, a hydrogen atom included in the saturated hydrocarbon group may be substituted with a fluorine atom or a hydroxy group, and $—CH_2—$ included in the saturated hydrocarbon group may be replaced by —O— or —CO—, and the total number of carbon atoms of $L^{b2}$ and $L^{b3}$ is 22 or less.

In formula (b1-2), $L^{b4}$ represents a single bond or a divalent saturated hydrocarbon group having 1 to 22 carbon atoms, and a hydrogen atom included in the saturated hydrocarbon group may be substituted with a fluorine atom, $L^{b5}$ represents a single bond or a divalent saturated hydrocarbon group having 1 to 22 carbon atoms, a hydrogen atom included in the saturated hydrocarbon group may be substituted with a fluorine atom or a hydroxy group, and $—CH_2—$ included in the saturated hydrocarbon group may be replaced by —O— or —CO—, and the total number of carbon atoms of $L^{b4}$ and $L^{b5}$ is 22 or less.

In formula (b1-3), $L^{b6}$ represents a single bond or a divalent saturated hydrocarbon group having 1 to 23 carbon atoms, a hydrogen atom included in the saturated hydrocarbon group may be substituted with a fluorine atom or a hydroxy group, $L^{b7}$ represents a single bond or a divalent saturated hydrocarbon group having 1 to 23 carbon atoms, a hydrogen atom included in the saturated hydrocarbon group may be substituted with a fluorine atom or a hydroxy group, and $—CH_2—$ included in the saturated hydrocarbon group may be replaced by —O— or —CO—, in which the total number of carbon atoms of $L^{b6}$ and $L^{b7}$ is 23 or less.

In groups represented by formula (b1-1) to formula (b1-3), when $—CH_2—$ included in the saturated hydrocarbon group is replaced by —O— or —CO—, the number of carbon atoms before replacement is taken as the number of carbon atoms of the saturated hydrocarbon group.

Examples of the divalent saturated hydrocarbon group include those which are the same as the divalent saturated hydrocarbon group of $L^{b1}$ $L^{b2}$ is preferably a single bond, a methylene group, $—CH(CF_3)—$, $—C(CF_3)_2—$.

$L^{b3}$ is preferably a divalent saturated hydrocarbon group having 1 to 4 carbon atoms.

$L^{b4}$ is preferably a divalent saturated hydrocarbon group having 1 to 8 carbon atoms, and a hydrogen atom included in the divalent saturated hydrocarbon group may be substituted with a fluorine atom.

$L^{b5}$ is preferably a single bond or a divalent saturated hydrocarbon group having 1 to 8 carbon atoms.

$L^{b6}$ is preferably a single bond or a divalent saturated hydrocarbon group having 1 to 4 carbon atoms, and a hydrogen atom included in the saturated hydrocarbon group may be substituted with a fluorine atom.

$L^{b7}$ is preferably a single bond or a divalent saturated hydrocarbon group having 1 to 18 carbon atoms, a hydrogen atom included in the saturated hydrocarbon group may be substituted with a fluorine atom or a hydroxy group, and $—CH_2—$ included in the divalent saturated hydrocarbon group may be replaced by —O— or —CO—.

The group in which $—CH_2—$ included in the divalent saturated hydrocarbon group represented by $L^{b1}$ is replaced by —O— or —CO— is preferably a group represented by formula (b1-1) or formula (b1-3).

Examples of the group represented by formula (b1-1) include groups represented by formula (b1-4) to formula (b1-8).

(b1-4)

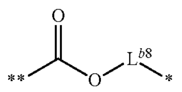

(b1-5)

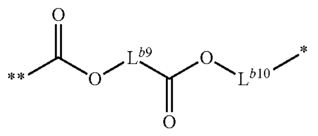

(b1-6)

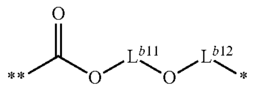

-continued (b1-7)

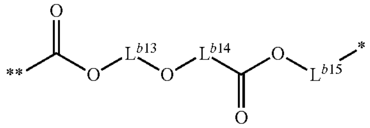

(b1-8)

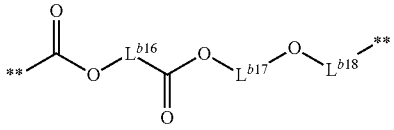

In formula (b1-4), $L^{b8}$ represents a single bond or a divalent saturated hydrocarbon group having 1 to 22 carbon atoms, and a hydrogen atom included in the saturated hydrocarbon group may be substituted with a fluorine atom or a hydroxy group.

In formula (b1-5), $L^{b9}$ represents a divalent saturated hydrocarbon group having 1 to 20 carbon atoms, and —$CH_2$— included in the divalent saturated hydrocarbon group may be replaced by —O— or —CO—.

$L^{b10}$ represents a single bond or a divalent saturated hydrocarbon group having 1 to 19 carbon atoms, and a hydrogen atom included in the divalent saturated hydrocarbon group may be substituted with a fluorine atom or a hydroxy group, and the total number of carbon atoms of $L^{b9}$ and $L^{b10}$ is 20 or less.

In formula (b1-6), $L^{b11}$ represents a divalent saturated hydrocarbon group having 1 to 21 carbon atoms, $L^{b12}$ represents a single bond or a divalent saturated hydrocarbon group having 1 to 20 carbon atoms, and a hydrogen atom included in the divalent saturated hydrocarbon group may be substituted with a fluorine atom or a hydroxy group, and the total number of carbon atoms of $L^{b12}$ and $L^{b12}$ is 21 or less.

In formula (b1-7), $L^{b13}$ represents a divalent saturated hydrocarbon group having 1 to 19 carbon atoms, $L^{b14}$ represents a single bond or a divalent saturated hydrocarbon group having 1 to 18 carbon atoms, and —$CH_2$— included in the divalent saturated hydrocarbon group may be replaced by —O— or —CO—, $L^{b15}$ represents a single bond or a divalent saturated hydrocarbon group having 1 to 18 carbon atoms, and a hydrogen atom included in the divalent saturated hydrocarbon group may be substituted with a fluorine atom or a hydroxy group, and the total number of carbon atoms of $L^{b13}$ to $L^{b15}$ is 19 or less.

In formula (b1-8), $L^{b16}$ represents a divalent saturated hydrocarbon group having 1 to 18 carbon atoms, and —$CH_2$— included in the divalent saturated hydrocarbon group may be replaced by —O— or —CO—, $L^{b17}$ represents a divalent saturated hydrocarbon group having 1 to 18 carbon atoms, $L^{b18}$ represents a single bond or a divalent saturated hydrocarbon group having 1 to 17 carbon atoms, and a hydrogen atom included in the divalent saturated hydrocarbon group may be substituted with a fluorine atom or a hydroxy group, and in which the total number of carbon atoms of $L^{b16}$ to $L^{b18}$ is 19 or less.

$L^{b8}$ is preferably a divalent saturated hydrocarbon group having 1 to 4 carbon atoms.

$L^{b9}$ is preferably a divalent saturated hydrocarbon group having 1 to 8 carbon atoms.

$L^{b10}$ is preferably a single bond or a divalent saturated hydrocarbon group having 1 to 19 carbon atoms, and more preferably a single bond or a divalent saturated hydrocarbon group having 1 to 8 carbon atoms.

$L^{b11}$ is preferably a divalent saturated hydrocarbon group having 1 to 8 carbon atoms.

$L^{b12}$ is preferably a single bond or a divalent saturated hydrocarbon group having 1 to 8 carbon atoms.

$L^{b13}$ is preferably a divalent saturated hydrocarbon group having 1 to 12 carbon atoms.

$L^{b14}$ is preferably a single bond or a divalent saturated hydrocarbon group having 1 to 6 carbon atoms.

$L^{b15}$ is preferably a single bond or a divalent saturated hydrocarbon group having 1 to 18 carbon atoms, and more preferably a single bond or a divalent saturated hydrocarbon group having 1 to 8 carbon atoms.

$L^{b16}$ is preferably a divalent saturated hydrocarbon group having 1 to 12 carbon atoms.

$L^{b17}$ is preferably a divalent saturated hydrocarbon group having 1 to 6 carbon atoms.

$L^{b18}$ is preferably a single bond or a divalent saturated hydrocarbon group having 1 to 17 carbon atoms, and more preferably a single bond or a divalent saturated hydrocarbon group having 1 to 4 carbon atoms.

Examples of the group represented by formula (b1-3) include groups represented by formula (b1-9) to formula (b1-11).

(b1-9)

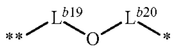

(b1-10)

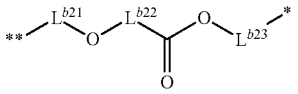

(b1-11)

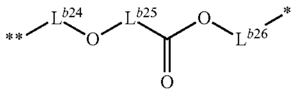

In formula (b1-9), $L^{b19}$ represents a single bond or a divalent saturated hydrocarbon group having 1 to 23 carbon atoms, and a hydrogen atom included in the saturated hydrocarbon group may be substituted with a fluorine atom, $L^{b20}$ represents a single bond or a divalent saturated hydrocarbon group having 1 to 23 carbon atoms, and a hydrogen atom included in the saturated hydrocarbon group may be substituted with a fluorine atom, a hydroxy group or an alkylcarbonyloxy group, —$CH_2$— included in the alkylcarbonyloxy group may be replaced by —O— or —CO—, and a hydrogen atom included in the alkylcarbonyloxy group may be substituted with a hydroxy group, and the total number of carbon atoms of $L^{b19}$ and $L^{b20}$ is 23 or less.

In formula (b1-10), $L^{b21}$ represents a single bond or a divalent saturated hydrocarbon group having 1 to 21 carbon atoms, and a hydrogen atom included in the saturated hydrocarbon group may be substituted with a fluorine atom, $L^{b22}$ represents a single bond or a divalent saturated hydrocarbon group having 1 to 21 carbon atoms, $L^{b23}$ represents a single bond or a divalent saturated hydrocarbon group having 1 to 21 carbon atoms, and a hydrogen atom included in the saturated hydrocarbon group may be substituted with a fluorine atom, a hydroxy group or an alkylcarbonyloxy group, $—CH_2—$ included in the alkylcarbonyloxy group may be replaced by —O— or —CO—, and a hydrogen atom included in the alkylcarbonyloxy group may be substituted with a hydroxy group, and the total number of carbon atoms of $L^{b21}$, $L^{b22}$ and $L^{b23}$ is 21 or less.

In formula (b1-11), $L^{b24}$ represents a single bond or a divalent saturated hydrocarbon group having 1 to 20 carbon atoms, and a hydrogen atom included in the saturated hydrocarbon group may be substituted with a fluorine atom, $L^{b25}$ represents a divalent saturated hydrocarbon group having 1 to 21 carbon atoms, $L^{b26}$ represents a single bond or a divalent saturated hydrocarbon group having 1 to 20 carbon atoms, a hydrogen atom included in the saturated hydrocarbon group may be substituted with a fluorine atom, a hydroxy group or an alkylcarbonyloxy group, $—CH_2—$ included in the alkylcarbonyloxy group may be replaced by —O— or —CO—, and a hydrogen atom included in the alkylcarbonyloxy group may be substituted with a hydroxy group, the total number of carbon atoms of $L^{b24}$, $L^{b25}$ and $L^{b26}$ is 21 or less.

In groups represented by formula (b1-9) to formula (b1-11), when a hydrogen atom included in the saturated hydrocarbon group is substituted with an alkylcarbonyloxy group, the number of carbon atoms before substitution is taken as the number of carbon atoms of the saturated hydrocarbon group.

Examples of the alkylcarbonyloxy group include an acetyloxy group, a propionyloxy group, a butyryloxy group, a cyclohexylcarbonyloxy group, an adamantylcarbonyloxy group and the like.

Examples of the group represented by formula (b1-4) include the followings.

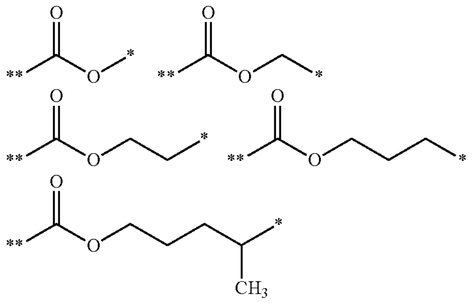

Examples of the group represented by formula (b1-5) include the followings.

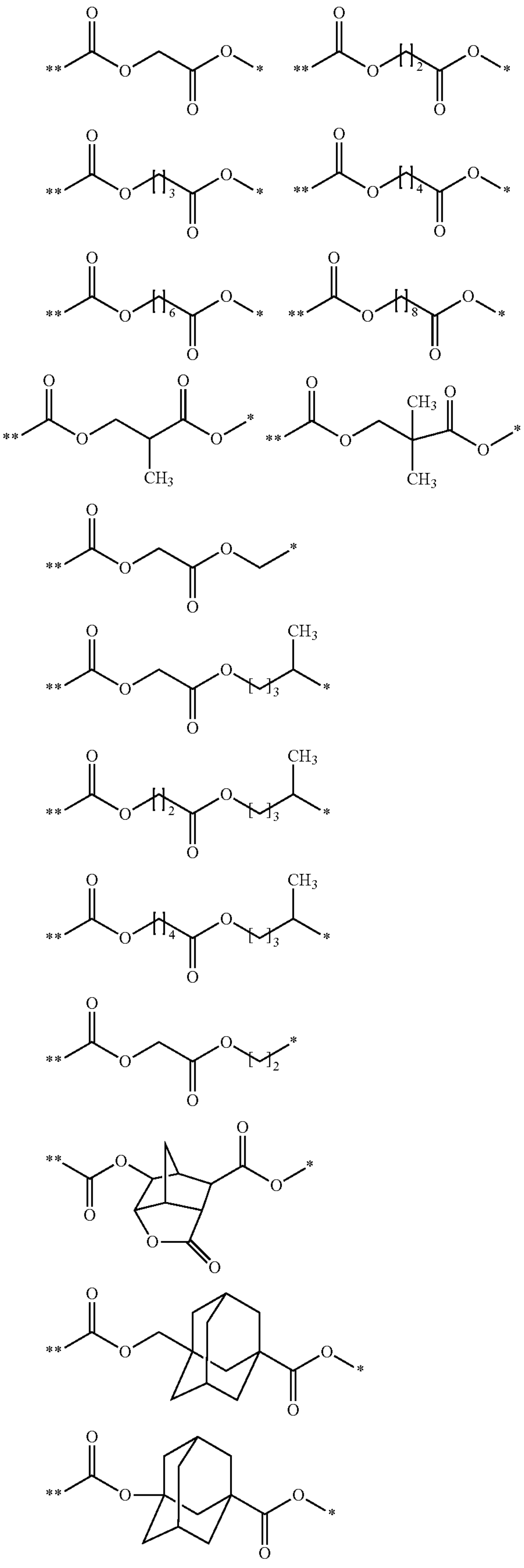

-continued
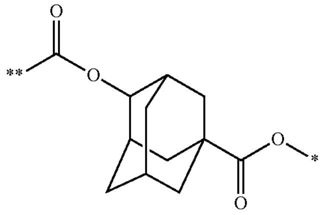
Examples of the group represented by formula (b1-6) include the followings.
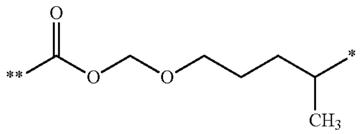
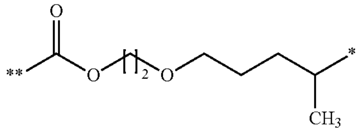
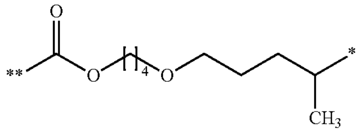
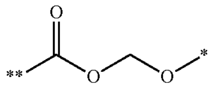
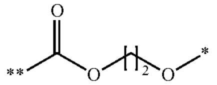
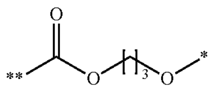
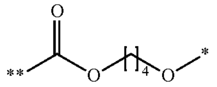
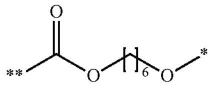
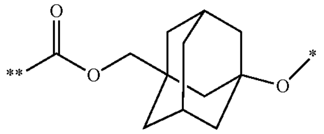
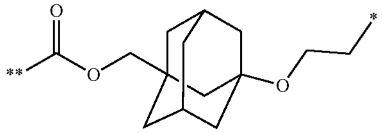
Examples of the group represented by formula (b1-7) include the followings.
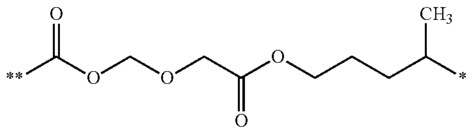
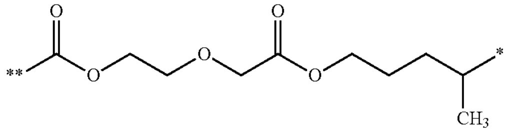
-continued
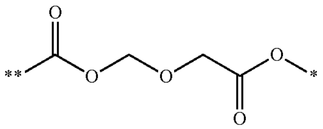
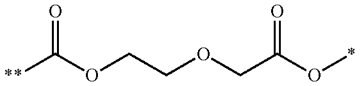
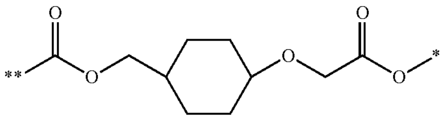
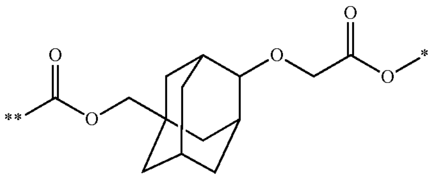
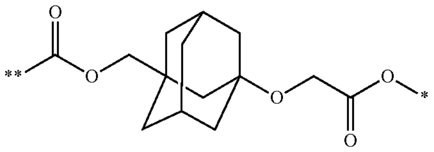
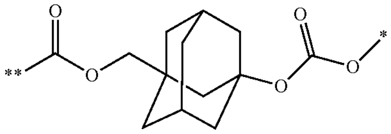
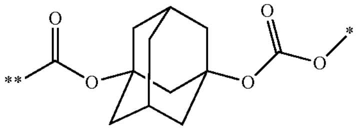
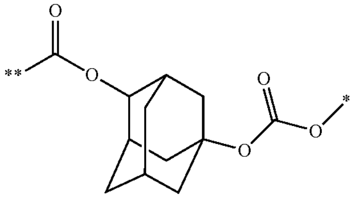
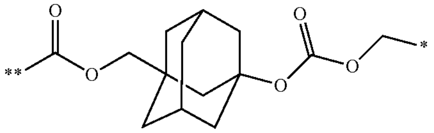
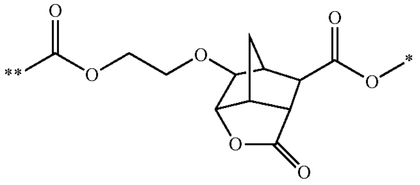
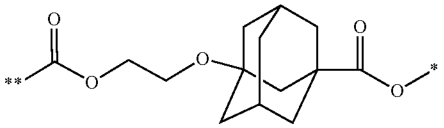
Examples of the group represented by formula (b1-8) include the followings.

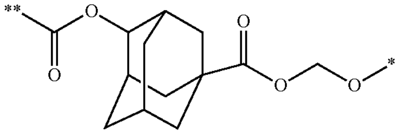
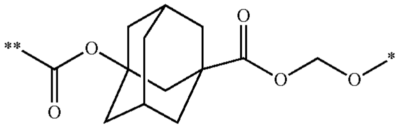
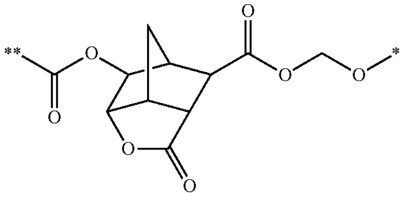
Examples of the group represented by formula (b1-2) include the followings.
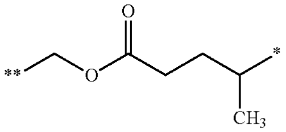
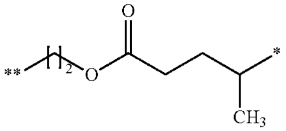
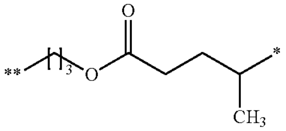
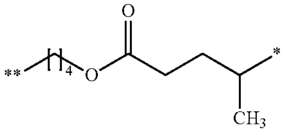
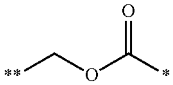
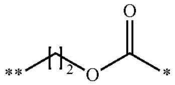
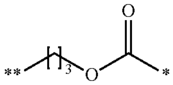
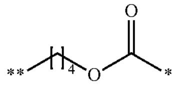
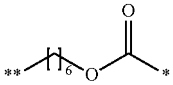
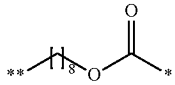
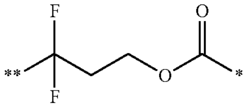
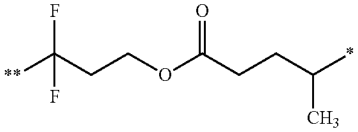
Examples of the group represented by formula (b1-9) include the followings.
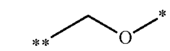
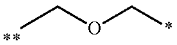
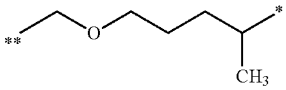
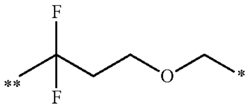
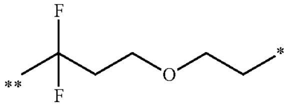
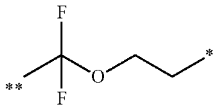
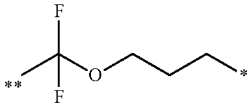
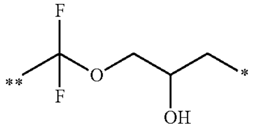
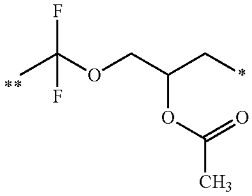
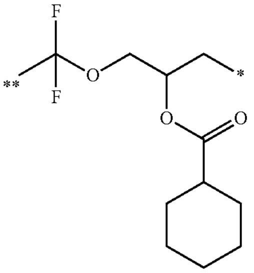
Examples of the group represented by formula (b1-10) include the followings.
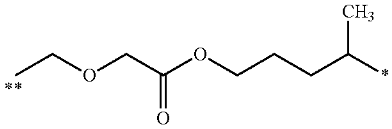
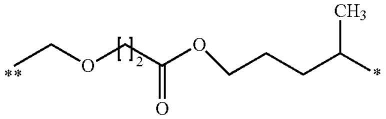
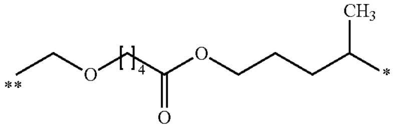
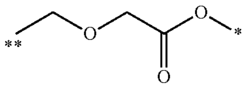
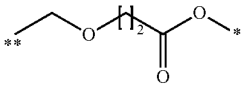
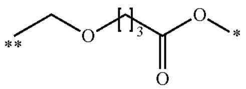
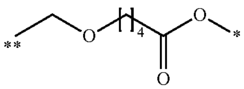
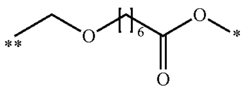
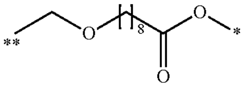
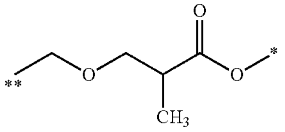
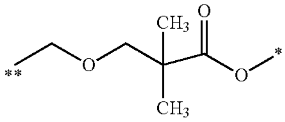

-continued
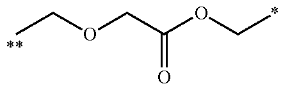
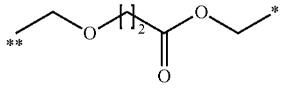
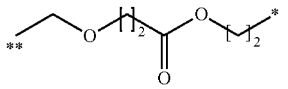
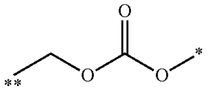
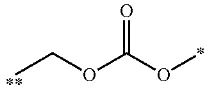
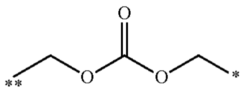
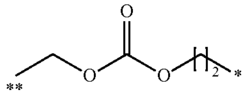
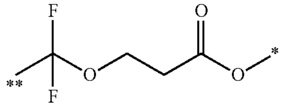
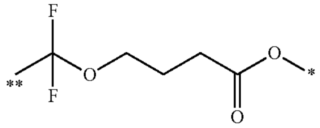
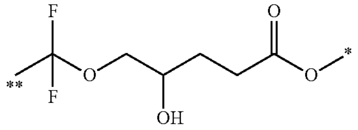
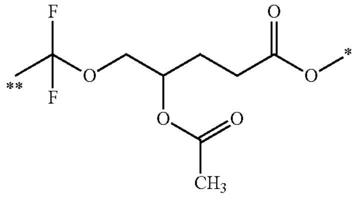
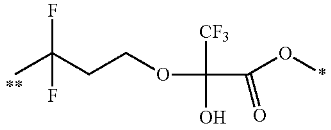
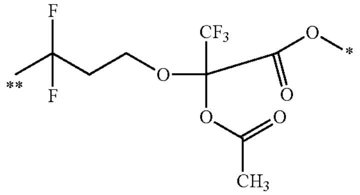
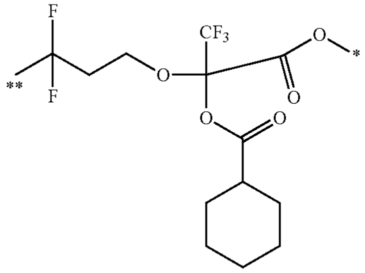
-continued
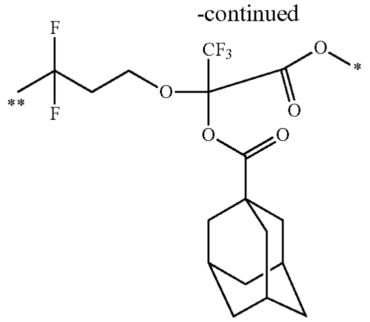
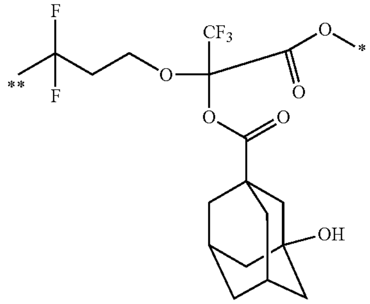
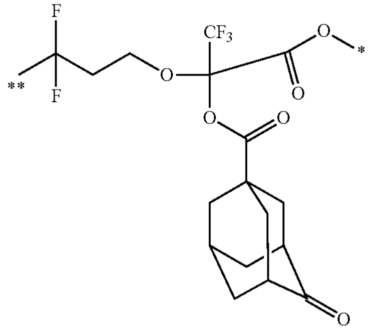
Examples of the group represented by formula (b1-11) include the followings.
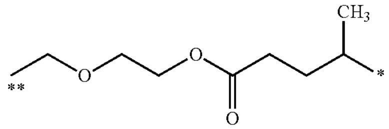
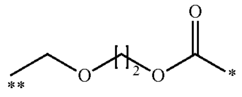
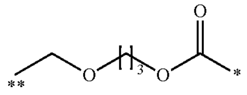
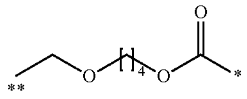
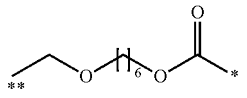
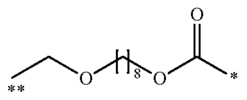

-continued

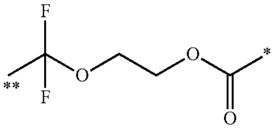

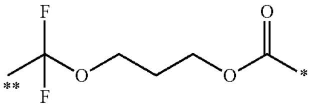

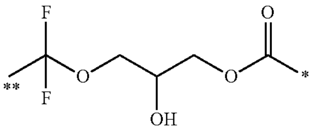

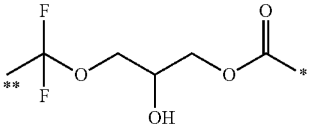

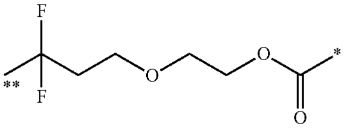

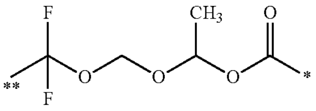

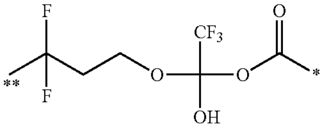

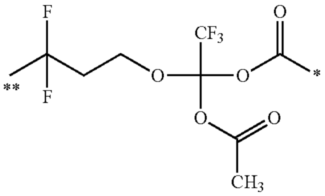

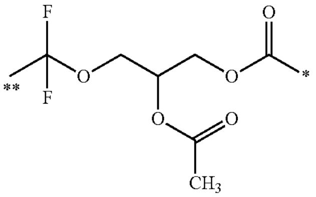

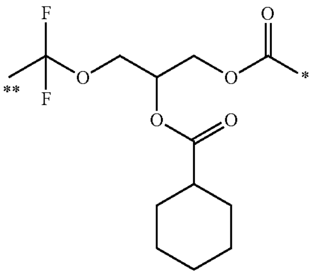

-continued

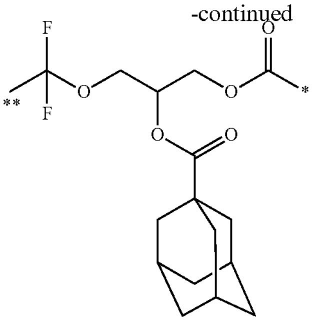

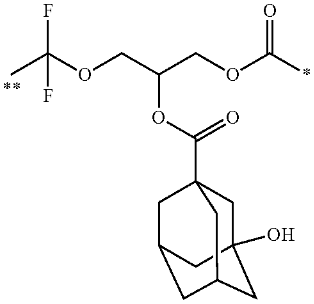

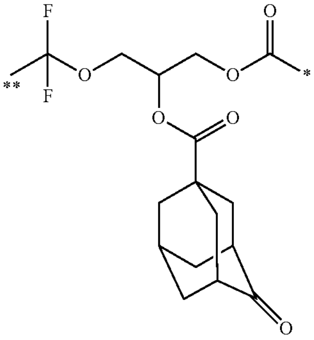

Examples of the alicyclic hydrocarbon group represented by Y include groups represented by formula (Y1) to formula (Y11) and formula (Y36) to formula (Y38).

When —$CH_2$— included in the alicyclic hydrocarbon group represented by Y is replaced by O—, —S—, —$SO_2$— or —CO—, the number may be 1, or 2 or more. Examples of such group include groups represented by formula (Y12) to formula (Y35) and formula (Y39) to formula (Y43). —O— or —CO— of these groups of groups represented by formula (Y12) to formula (Y35) and formula (Y39) to formula (Y43) may be replaced by —S— or —$SO_2$—.

(Y1)

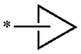

(Y2)

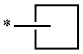

(Y3)

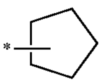

(Y4)

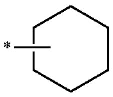

-continued
(Y5)
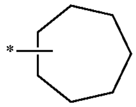
(Y6)
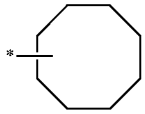
(Y7)
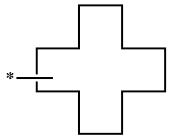
(Y8)
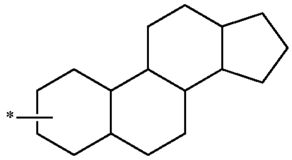
(Y9)
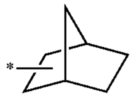
(Y10)
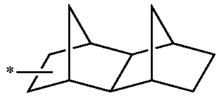
(Y11)
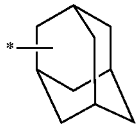
(Y12)
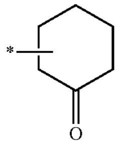
(Y13)
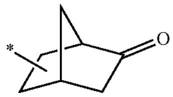
(Y14)
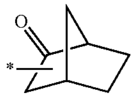
(Y15)
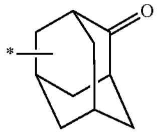
(Y16)
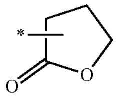
-continued
(Y17)
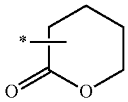
(Y18)
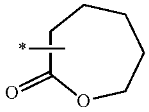
(Y19)
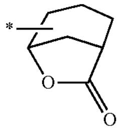
(Y20)
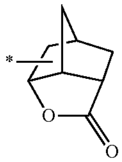
(Y21)
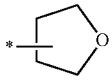
(Y22)
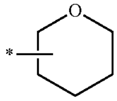
(Y23)
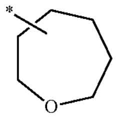
(Y24)
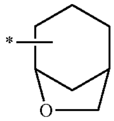
(Y25)
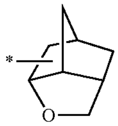
(Y26)
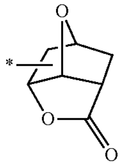
(Y27)
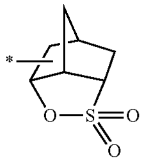

-continued (Y28)

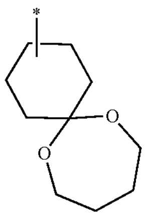

(Y29)

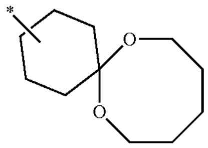

(Y30)

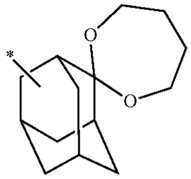

(Y31)

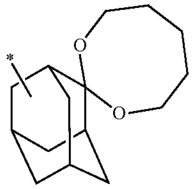

(Y32)

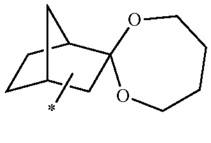

(Y33)

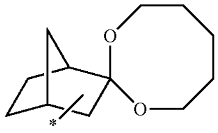

(Y34)

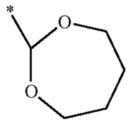

(Y35)

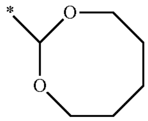

(Y36)

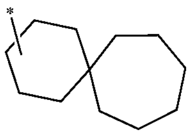

-continued (Y37)

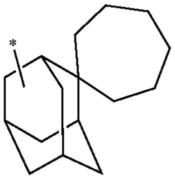

(Y38)

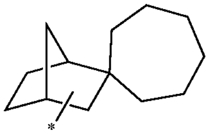

(Y39)

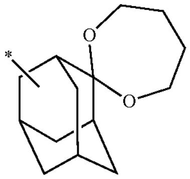

(Y40)

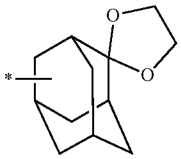

(Y41)

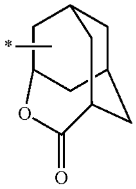

(Y42)

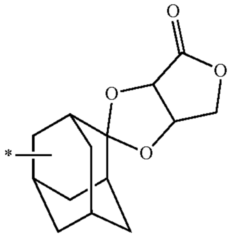

(Y43)

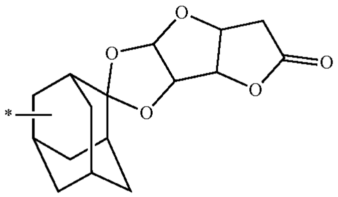

The alicyclic hydrocarbon group represented by Y is preferably a group represented by any one of formula (Y1) to formula (Y20), formula (Y26), formula (Y27), formula (Y30), formula (Y31) and formula (Y39) to formula (Y43), more preferably a group represented by formula (Y11), formula (Y15), formula (Y16), formula (Y20), formula (Y26), formula (Y27), formula (Y30), formula (Y31), formula (Y39), formula (Y40), formula (Y42) or formula (Y43), and still more preferably a group represented by formula (Y11), formula (Y15), formula (Y20), formula (Y26), formula (Y27), formula (Y30), formula (Y31), formula (Y39), formula (Y40), formula (Y42) or formula (Y43).

When the alicyclic hydrocarbon group represented by Y is a spiro ring containing an oxygen atom, such as formula (Y28) to formula (Y35), formula (Y39) to formula (Y40), formula (Y42), formula (Y43), etc., the alkanediyl group between two oxygen atoms preferably has one or more fluorine atoms. Of alkanediyl groups included in a ketal structure, it is preferable that a methylene group adjacent to the oxygen atom is not substituted with a fluorine atom.

Examples of the substituent of the methyl group represented by Y include a halogen atom, a hydroxy group, an alicyclic hydrocarbon group having 3 to 16 carbon atoms, an aromatic hydrocarbon group having 6 to 18 carbon atoms, a glycidyloxy group, a $—(CH_2)_{ja}—CO—O—R^{b1}$ group or a $—(CH_2)_{ja}—O—CO—R^{b1}$ group (wherein $R^{b1}$ represents an alkyl group having 1 to 16 carbon atoms, an alicyclic hydrocarbon group having 3 to 16 carbon atoms, an aromatic hydrocarbon group having 6 to 18 carbon atoms, or a group obtained by combining these groups, $—CH_2—$ included in the alkyl group and the alicyclic hydrocarbon group may be replaced by —O—, $—SO_2—$ or —CO—, a hydrogen atom included in the alkyl group, the alicyclic hydrocarbon group and the aromatic hydrocarbon group may be substituted with a hydroxy group or a fluorine atom, and ja represents an integer of 0 to 4).

Examples of the substituent of the alicyclic hydrocarbon group represented by Y include a halogen atom, a hydroxy group, an alkyl group having 1 to 16 carbon atoms which may be substituted with a hydroxy group ($—CH_2—$ included in the alkyl group may be replaced by —O— or —CO—), an alicyclic hydrocarbon group having 3 to 16 carbon atoms, an aromatic hydrocarbon group having 6 to 18 carbon atoms, an aralkyl group having 7 to 21 carbon atoms, a glycidyloxy group, a $—(CH_2)_{ja}—CO—O—R^{b1}$ group or a $—(CH_2)_{ja}—O—CO—R^{b1}$ group (wherein $R^{b1}$ represents an alkyl group having 1 to 16 carbon atoms, an alicyclic hydrocarbon group having 3 to 16 carbon atoms, an aromatic hydrocarbon group having 6 to 18 carbon atoms, or a group obtained by combining these groups, $—CH_2—$ included in the alkyl group and the alicyclic hydrocarbon group may be replaced by —O—, $—SO_2—$ or —CO—, a hydrogen atom included in the alkyl group, the alicyclic hydrocarbon group and the aromatic hydrocarbon group may be substituted with a hydroxy group or a fluorine atom, and ja represents an integer of 0 to 4).

Examples of the halogen atom include a fluorine atom, a chlorine atom, a bromine atom and an iodine atom.

Examples of the alicyclic hydrocarbon group include a cyclopentyl group, a cyclohexyl group, a methylcyclohexyl group, a dimethylcyclohexyl group, a cycloheptyl group, a cyclooctyl group, a norbornyl group, an adamantyl group and the like. The alicyclic hydrocarbon group may have a chain hydrocarbon group, and examples thereof include a methylcyclohexyl group, a dimethylcyclohexyl group and the like. In some embodiments, the number of carbon atoms of the alicyclic hydrocarbon group is preferably 3 to 12, and more preferably 3 to 10.

Examples of the aromatic hydrocarbon group include aryl groups such as a phenyl group, a naphthyl group, an anthryl group, a biphenyl group and a phenanthryl group. The aromatic hydrocarbon group may have a chain hydrocarbon group or an alicyclic hydrocarbon group, and an aromatic hydrocarbon group which has a chain hydrocarbon group having 1 to 18 carbon atoms (a tolyl group, a xylyl group, a cumenyl group, a mesityl group, a p-methylphenyl group, a p-ethylphenyl group, a p-tert-butylphenyl group, a 2,6-diethylphenyl group, a 2-methyl-6-ethylphenyl group, etc.), and an aromatic hydrocarbon group which has an alicyclic hydrocarbon group having 3 to 18 carbon atoms (a p-adamantylphenyl group, a p-cyclohexylphenyl group, etc.) are preferable. In some embodiments, the number of carbon atoms of the aromatic hydrocarbon group is preferably 6 to 14, and more preferably 6 to 10.

Examples of the alkyl group include a methyl group, an ethyl group, a propyl group, an isopropyl group, a butyl group, a sec-butyl group, a tert-butyl group, a pentyl group, a hexyl group, a heptyl group, a 2-ethylhexyl group, an octyl group, a nonyl group, a decyl group, an undecyl group, a dodecyl group and the like. In some embodiments, the number of carbon atoms of the alkyl group is preferably 1 to 12, more preferably 1 to 6, and still more preferably 1 to 4.

Examples of the alkyl group substituted with a hydroxy group include hydroxyalkyl groups such as a hydroxymethyl group and a hydroxyethyl group.

Examples of the aralkyl group include a benzyl group, a phenethyl group, a phenylpropyl group, a naphthylmethyl group and a naphthylethyl group.

Examples of the group in which $—CH_2—$ included in the alkyl group is replaced by —O—, $—SO_2—$ or —CO— include an alkoxy group, an alkylsulfonyl group, an alkoxycarbonyl group, an alkylcarbonyl group, an alkylcarbonyloxy group, or a group obtained by combining these groups.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group. In some embodiments, the number of carbon atoms of the alkoxy group is preferably 1 to 12, more preferably 1 to 6, and still more preferably 1 to 4.

Examples of the alkylsulfonyl group include a methylsulfonyl group, an ethylsulfonyl group, a propylsulfonyl group and the like. In some embodiments, the number of carbon atoms of the sulfonyl group is preferably 1 to 12, more preferably 1 to 6, and still more preferably 1 to 4.

Examples of the alkoxycarbonyl group include a methoxycarbonyl group, an ethoxycarbonyl group, a butoxycarbonyl group and the like. In some embodiments, the number of carbon atoms of the alkoxycarbonyl group is preferably 2 to 12, more preferably 2 to 6, and still more preferably 2 to 4.

Examples of the alkylcarbonyl group include an acetyl group, a propionyl group and a butyryl group. In some embodiments, the number of carbon atoms of the alkylcarbonyl group is preferably 2 to 12, more preferably 2 to 6, and still more preferably 2 to 4.

Examples of the alkylcarbonyloxy group include an acetyloxy group, a propionyloxy group, a butyryloxy group and the like. In some embodiments, the number of carbon atoms of the alkylcarbonyloxy group is preferably 2 to 12, more preferably 2 to 6, and still more preferably 2 to 4.

Examples of the combined group include a group obtained by combining an alkoxy group with an alkyl group, a group obtained by combining an alkoxy group with an alkoxy group, a group obtained by combining an alkoxy group with an alkylcarbonyl group, a group obtained by combining an alkoxy group with an alkylcarbonyloxy group and the like.

Examples of the group obtained by combining an alkoxy group with an alkyl group include alkoxyalkyl groups such as a methoxymethyl group, a methoxyethyl group, an ethoxyethyl group and an ethoxymethyl group. In some embodiments, the number of carbon atoms of the alkoxyalkyl group is preferably 2 to 12, more preferably 2 to 6, and still more preferably 2 to 4.

Examples of the group obtained by combining an alkoxy group with an alkoxy group include alkoxyalkoxy groups such as a methoxymethoxy group, a methoxyethoxy group, an ethoxymethoxy group and an ethoxyethoxy group. In some embodiments, the number of carbon atoms of the alkoxyalkoxy group is preferably 2 to 12, more preferably 2 to 6, and still more preferably 2 to 4.

Examples of the group obtained by combining an alkoxy group with an alkylcarbonyl group include alkoxyalkylcarbonyl groups such as a methoxyacetyl group, a methoxypropionyl group, an ethoxyacetyl group and an ethoxypropionyl group. In some embodiments, the number of carbon atoms of the alkoxyalkylcarbonyl group is preferably 3 to 13, more preferably 3 to 7, and still more preferably 3 to 5.

Examples of the group obtained by combining an alkoxy group with an alkylcarbonyloxy group include alkoxyalkylcarbonyloxy groups such as a methoxyacetyloxy group, a methoxypropionyloxy group, an ethoxyacetyloxy group and an ethoxypropionyloxy group. In some embodiments, the number of carbon atoms of the alkoxyalkylcarbonyloxy group is preferably 3 to 13, more preferably 3 to 7, and still more preferably 3 to 5.

Examples of the group in which $-CH_2-$ included in the alicyclic hydrocarbon group is replaced by $-O-$, $-SO_2-$ or $-CO-$ include groups represented by formula (Y12) to formula (Y35) and formula (Y39) to formula (Y43).

Y is preferably an alicyclic hydrocarbon group having 3 to 24 carbon atoms which may have a substituent, more preferably an alicyclic hydrocarbon group having 3 to 20 carbon atoms which may have a substituent, still more preferably an alicyclic hydrocarbon group having 3 to 18 carbon atoms which may have a substituent, and yet more preferably an adamantyl group which may have a substituent, or a norbornyl group, and $-CH_2-$ constituting the alicyclic hydrocarbon group, the adamantyl group or the norbornyl group may be replaced by $-CO-$, $-SO_2-$ or $-CO-$. Specifically, the followings are exemplified.

(Y100)

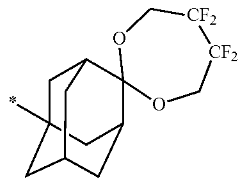

(Y101)

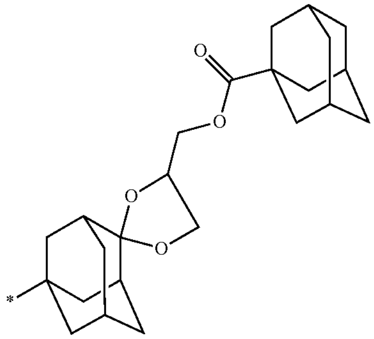

-continued (Y102)

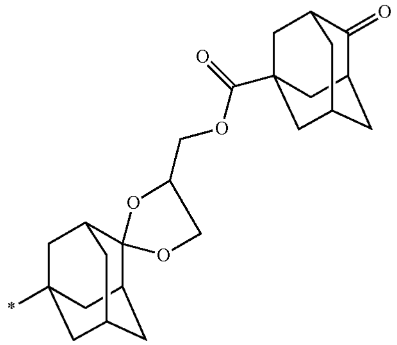

(Y103)

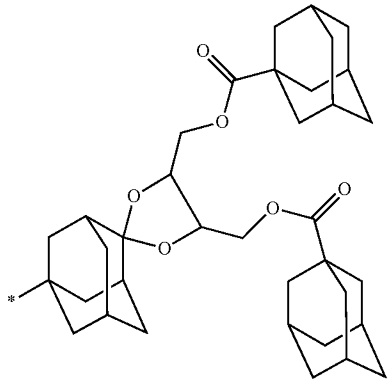

(Y104)

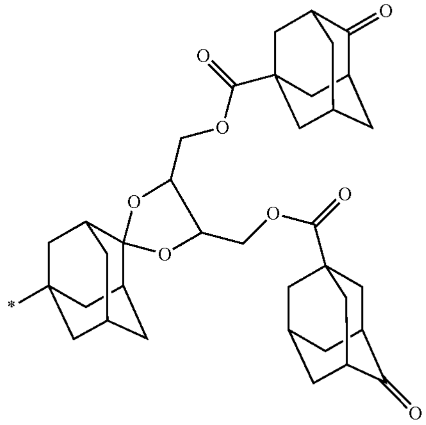

(Y105)

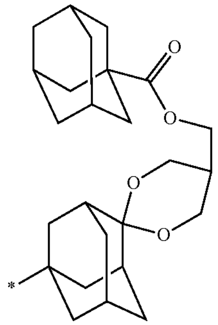

-continued
(Y106)
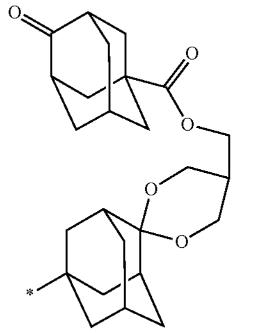
(Y107)
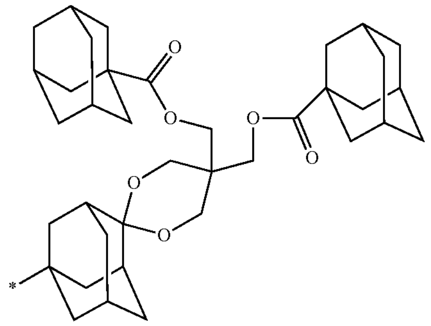
(Y108)
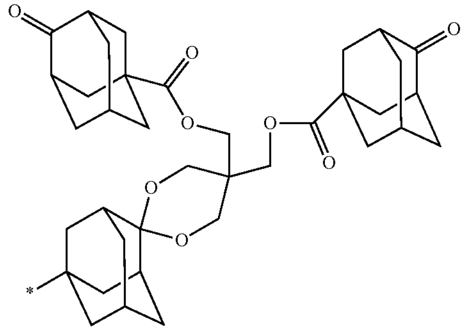
(Y109)
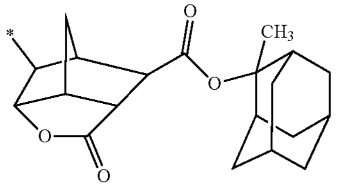
(Y110)
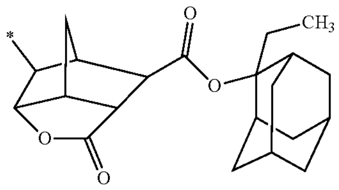
(Y111)
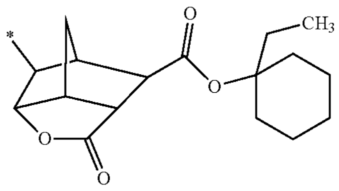
-continued
(Y42)
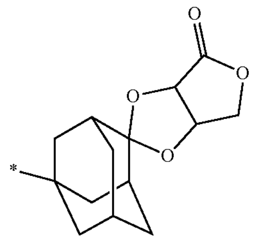
(Y112)
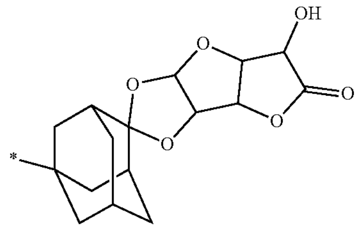
(Y113)
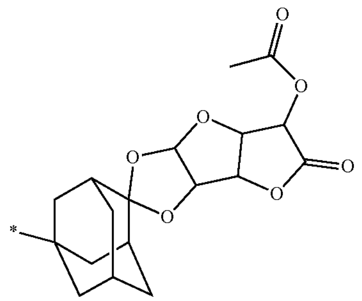
(Y114)
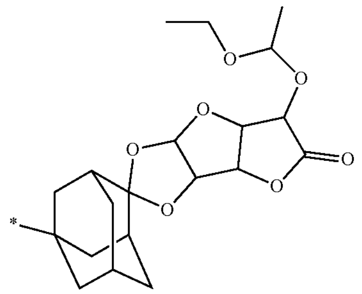
(Y115)
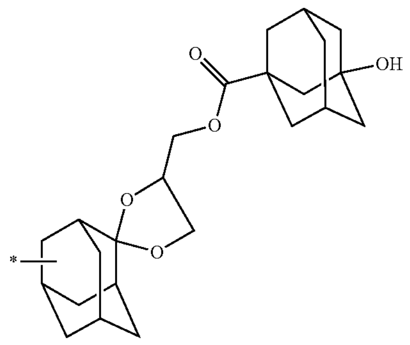

-continued
(Y116)
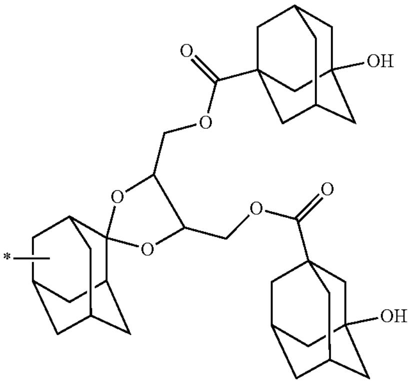
(Y11)
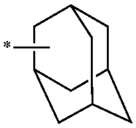
(Y4)
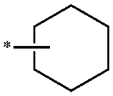
(Y117)
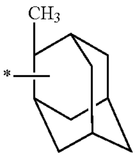
(Y118)
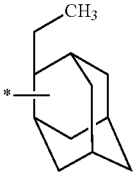
(Y119)
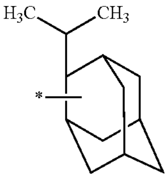
(Y120)
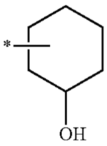
(Y121)
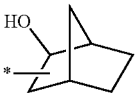
(Y122)
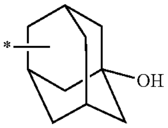
-continued
(Y123)
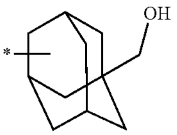
(Y15)
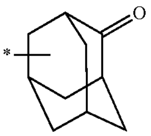
(Y124)
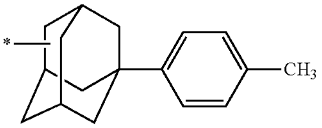
(Y125)
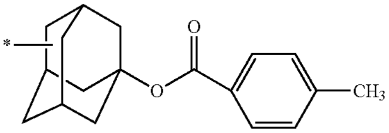
(Y126)
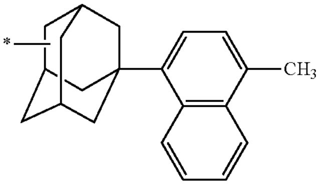
(Y127)
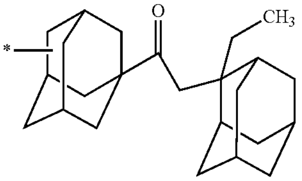
(Y128)
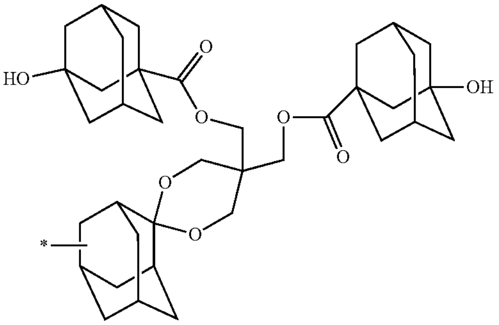

-continued
(Y129)
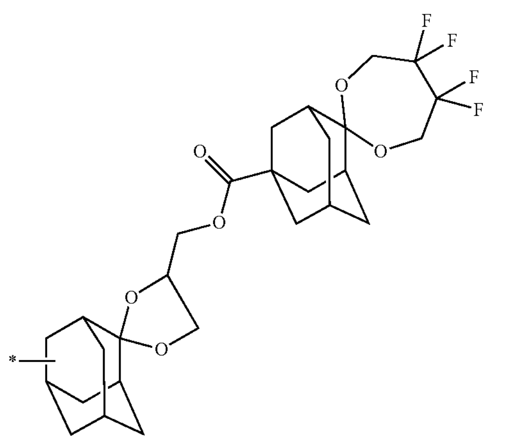
(Y130)
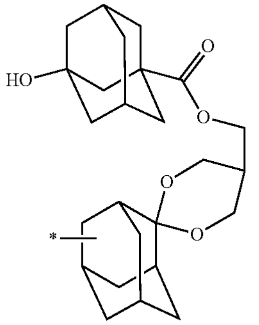
(Y131)
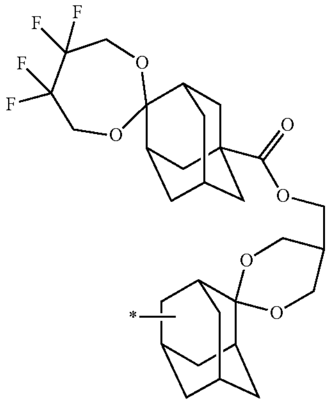
(Y132)
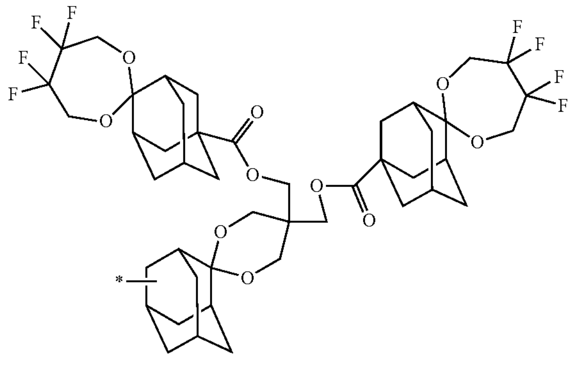
-continued
(Y133)
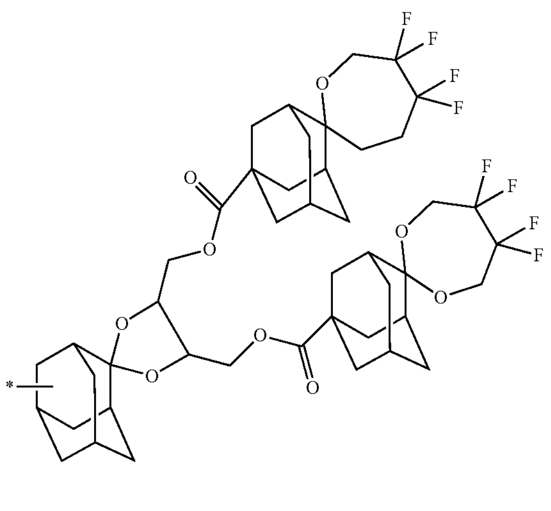
(Y134)
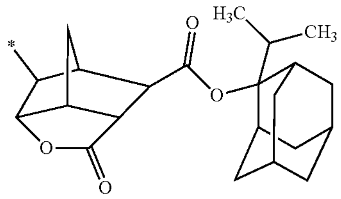
(Y135)
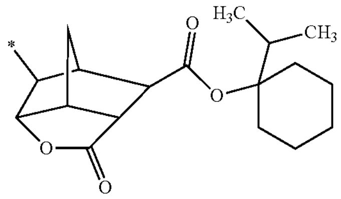
(Y136)
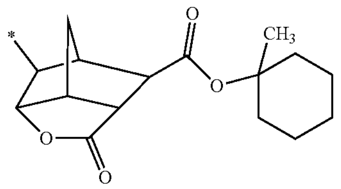
(Y137)
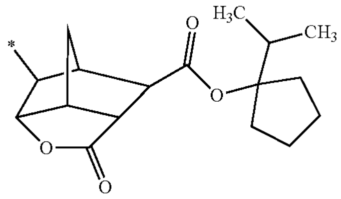
(Y138)
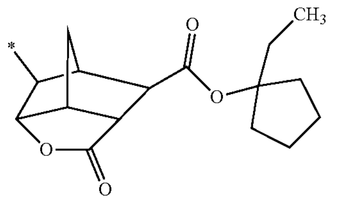

-continued (Y139)

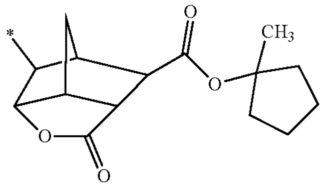

Of these, Y is preferably an adamantyl group, a hydroxyadamantyl group, an oxoadamantyl group, a norbornanelactone group, or groups represented by formula (Y42), formula (Y100) to formula (Y114) and formula (Y134) to formula (Y139).

The anion in the salt represented by formula (B1) is preferably anions represented by formula (B1-A-1) to formula (B1-A-65) [hereinafter sometimes referred to as "anion (B1-A-1)" according to the number of formula], and more preferably anion represented by any one of formula (B1-A-1) to formula (B1-A-4), formula (B1-A-9), formula (B1-A-10), formula (B1-A-24) to formula (B1-A-33), formula (B1-A-36) to formula (B1-A-40) and formula (B1-A-47) to formula (B1-A-65).

(B1-A-1)

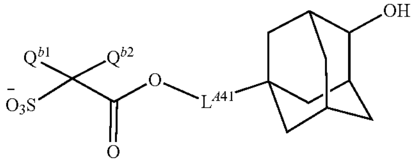

(B1-A-2)

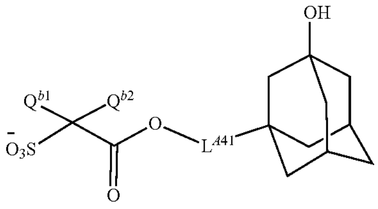

(B1-A-3)

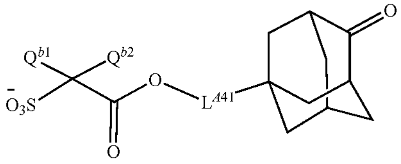

(B1-A-4)

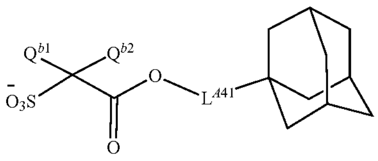

(B1-A-5)

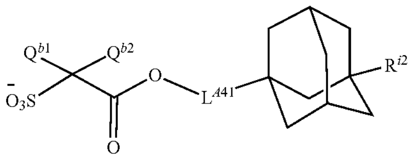

-continued (B1-A-6)

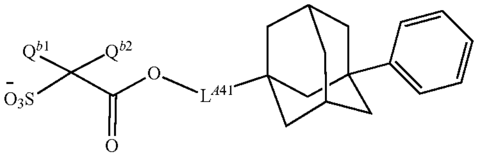

(B1-A-7)

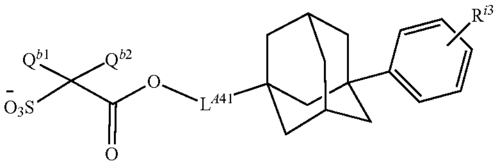

(B1-A-8)

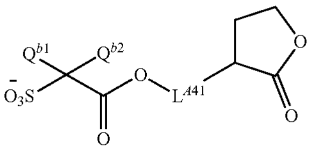

(B1-A-9)

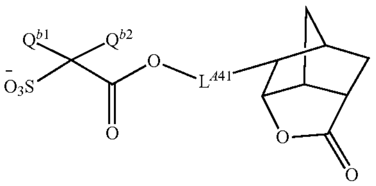

(B1-A-10)

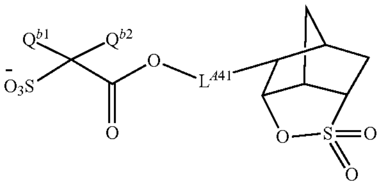

(B1-A-11)

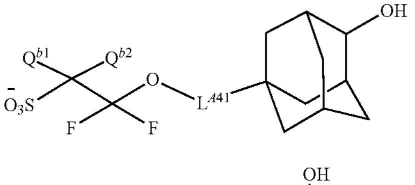

(B1-A-12)

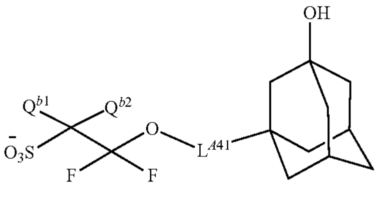

(B1-A-13)

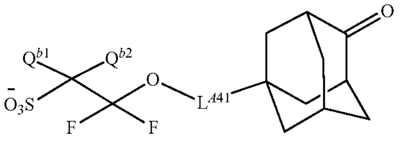

(B1-A-14)

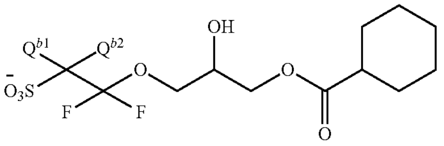

-continued
(B1-A-15)
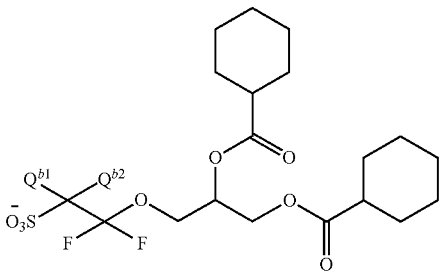
(B1-A-16)
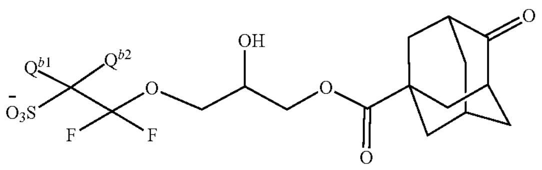
(B1-A-17)
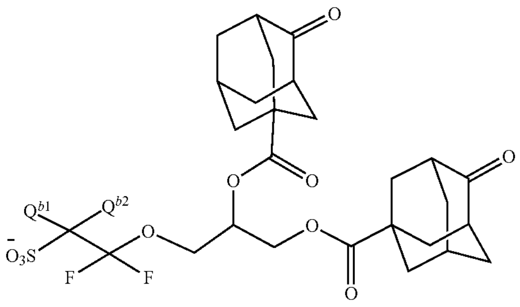
(B1-A-18)
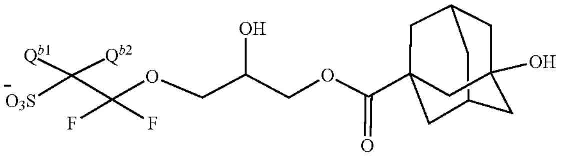
(B1-A-19)
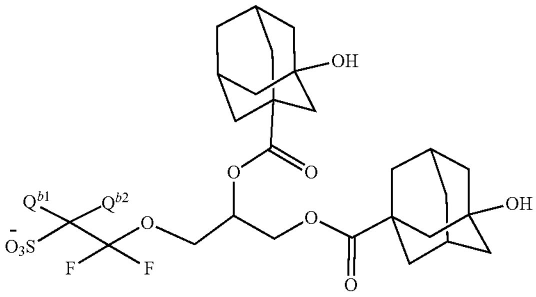
(B1-A-20)
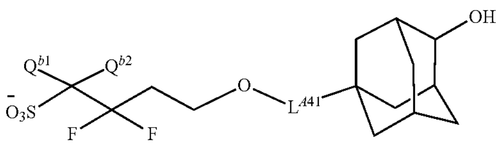
-continued
(B1-A-21)
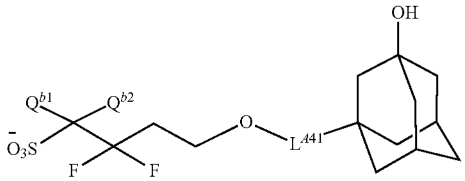
(B1-A-22)
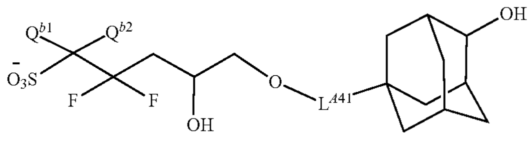
(B1-A-23)
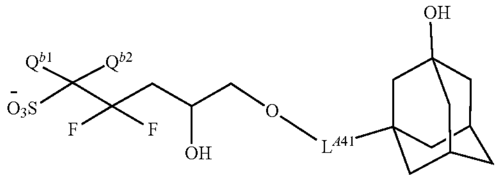
(B1-A-24)
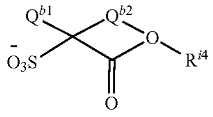
(B1-A-25)
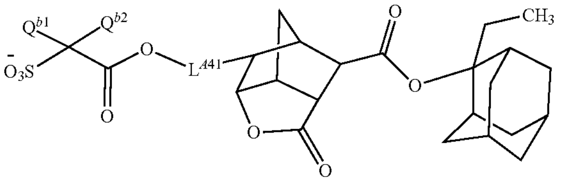
(B1-A-26)
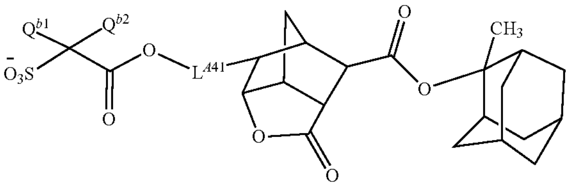
(B1-A-27)
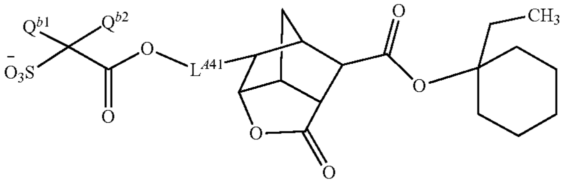

-continued
(B1-A-28)
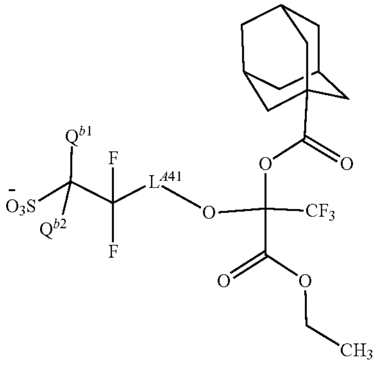
(B1-A-29)
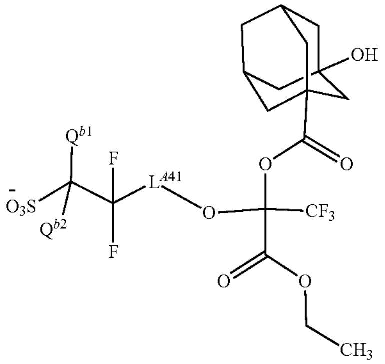
(B1-A-30)
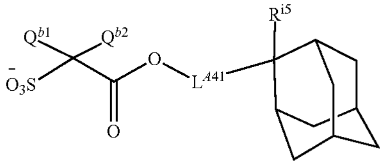
(B1-A-31)
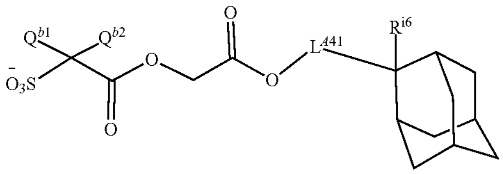
(B1-A-32)
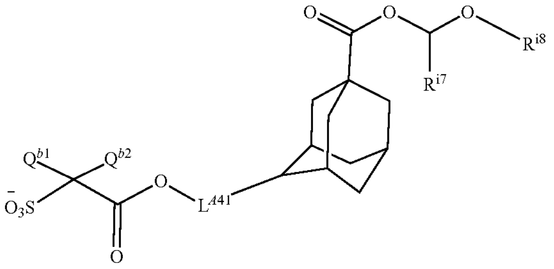
-continued
(B1-A-33)
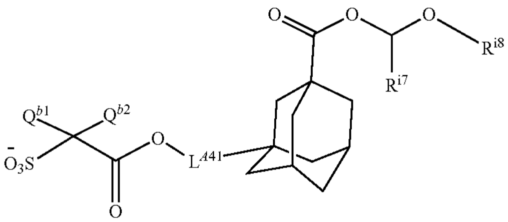
(B1-A-34)
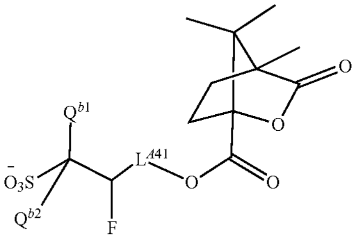
(B1-A-35)
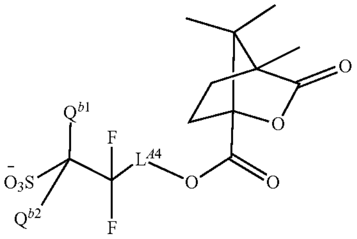
(B1-A-36)
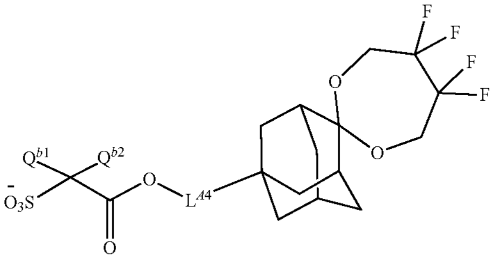
(B1-A-37)
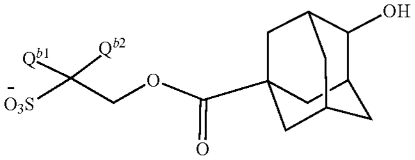
(B1-A-38)
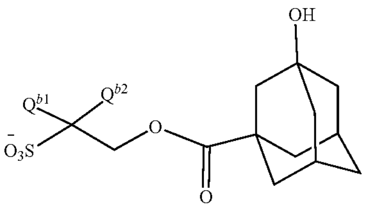
(B1-A-39)
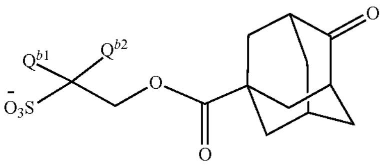

-continued
(B1-A-40)
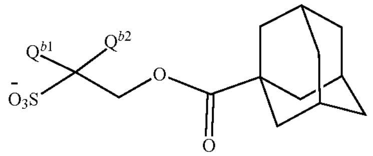
(B1-A-41)
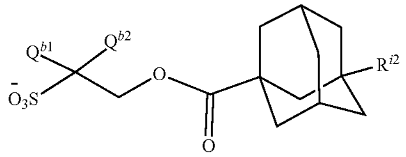
(B1-A-42)
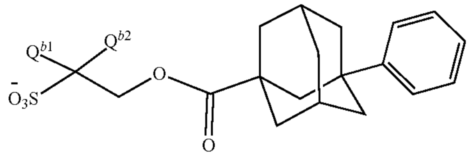
(B1-A-43)
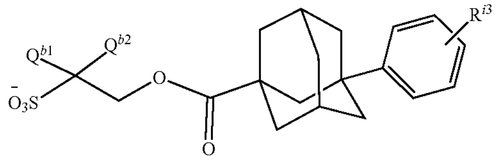
(B1-A-44)
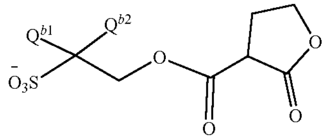
(B1-A-45)
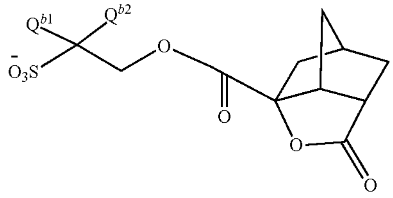
(B1-A-46)
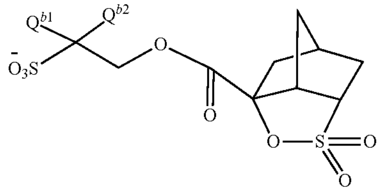
(B1-A-47)
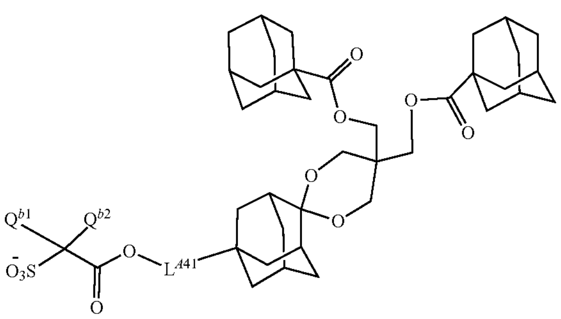
-continued
(B1-A-48)
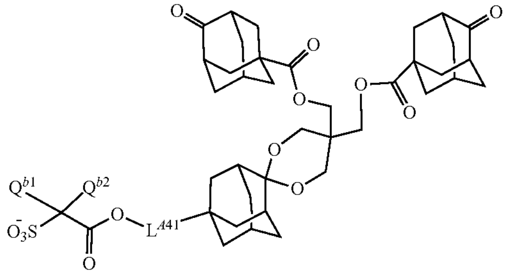
(B1-A-49)
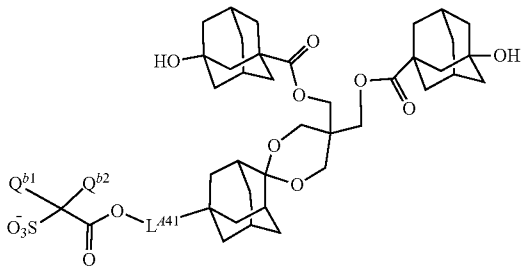
(B1-A-50)
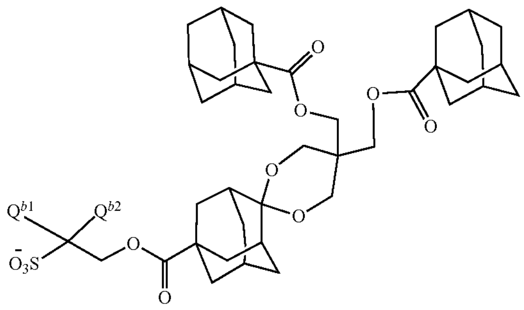
(B1-A-51)
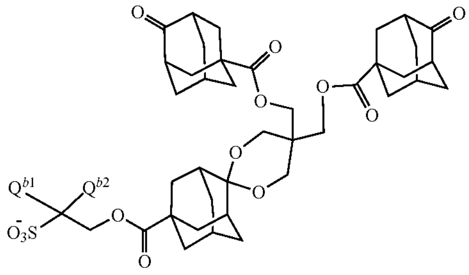
(B1-A-52)
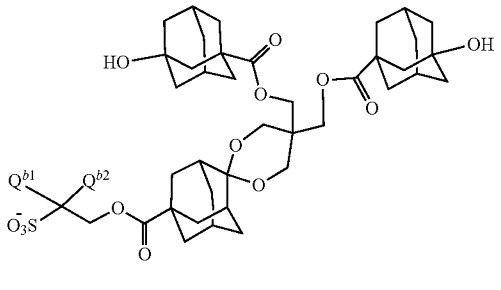

-continued
(B1-A-53)
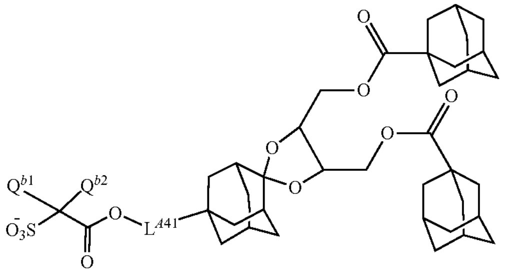
(B1-A-54)
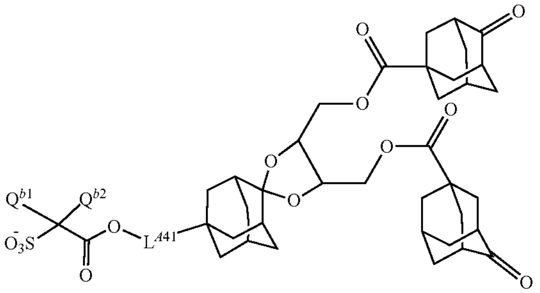
(B1-A-55)
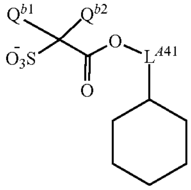
(B1-A-56)
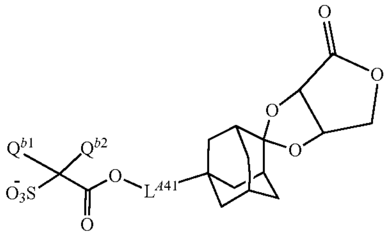
(B1-A-57)
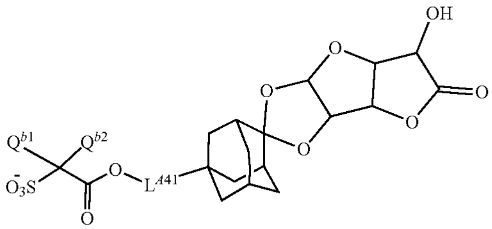
(B1-A-58)
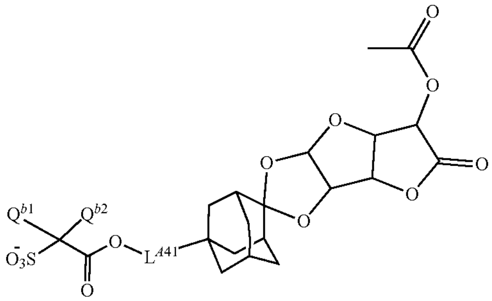
-continued
(B1-A-59)
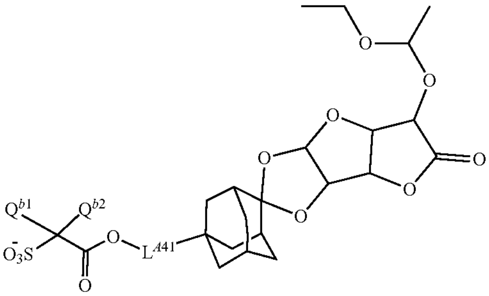
(B1-A-60)
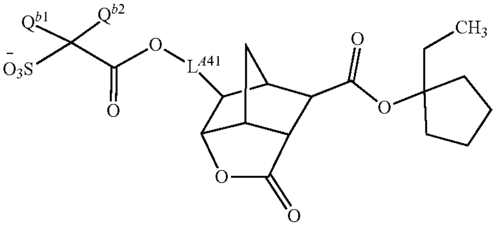
(B1-A-61)
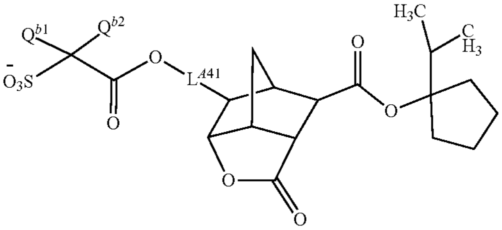
(B1-A-62)
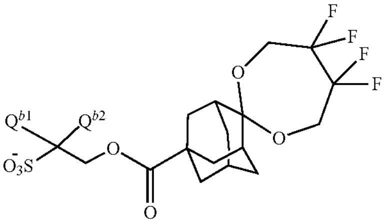
(B1-A-63)
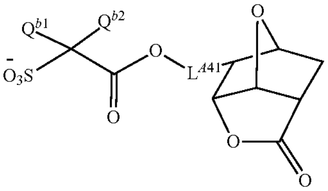
(B1-A-64)
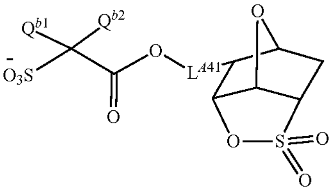

-continued (B1-A-65)

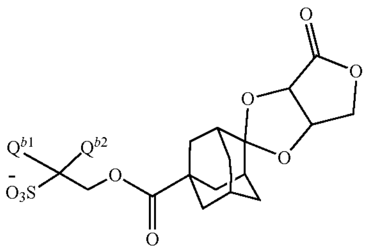

$R^{i2}$ to $R^{i7}$ each independently represent, for example, an alkyl group having 1 to 4 carbon atoms, and preferably a methyl group or an ethyl group. $R^{i8}$ is, for example, a chain hydrocarbon group having 1 to 12 carbon atoms, preferably an alkyl group having 1 to 4 carbon atoms, an alicyclic hydrocarbon group having 5 to 12 carbon atoms, or a group formed by combining these groups, and more preferably a methyl group, an ethyl group, a cyclohexyl group or an adamantyl group. $L^{A41}$ is a single bond or an alkanediyl group having 1 to 4 carbon atoms. $Q^{b1}$ and $Q^{b2}$ are the same as defined above.

Specific examples of the anion in the salt represented by formula (B1) include anions mentioned in JP 2010-204646 A.

The anion in the salt represented by formula (B1) preferably includes anions represented by formula (B1a -1) to formula (B1a -43).

(B1a-1)

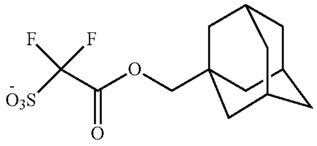

(B1a-2)

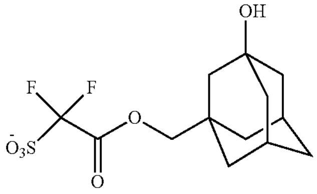

(B1a-3)

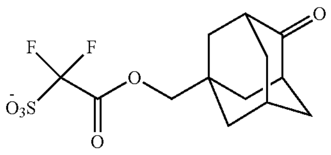

(B1a-4)

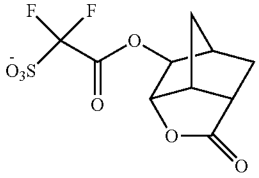

-continued (B1a-5)

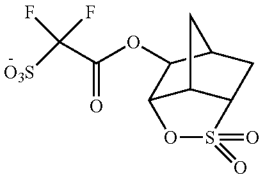

(B1a-6)

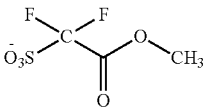

(B1a-7)

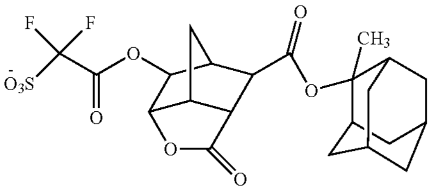

(B1a-8)

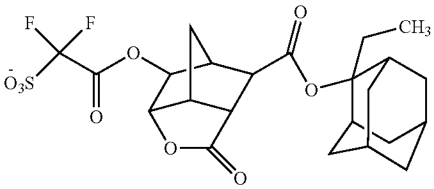

(B1a-9)

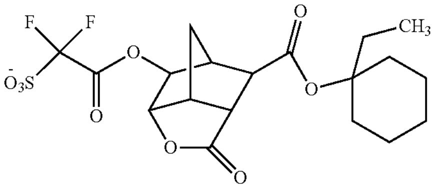

(B1a-10)

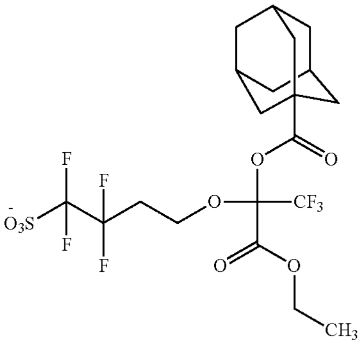

(B1a-11)

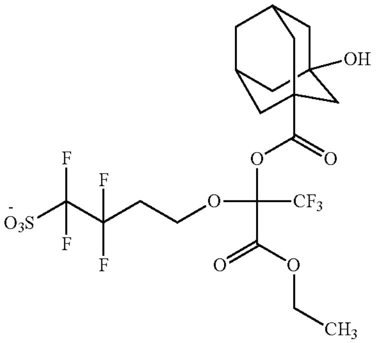

-continued
(B1a-12)
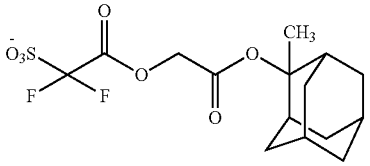
(B1a-13)
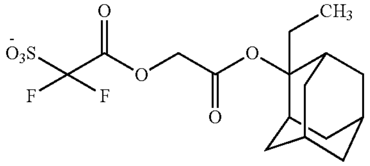
(B1a-14)
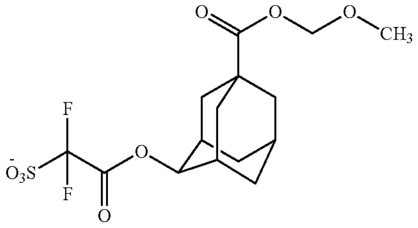
(B1a-15)
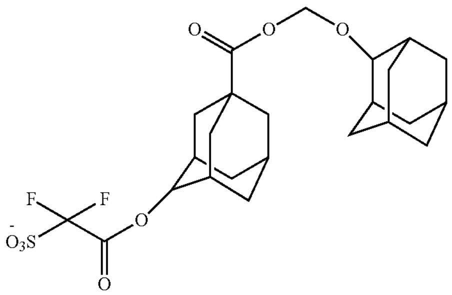
(B1a-16)
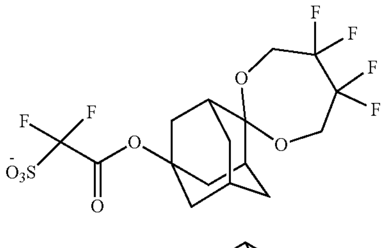
(B1a-17)
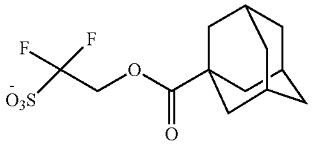
(B1a-18)
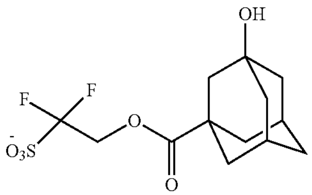
(B1a-19)
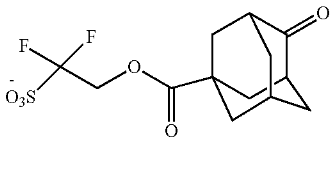
-continued
(B1a-20)
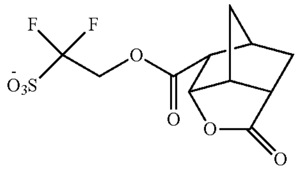
(B1a-21)
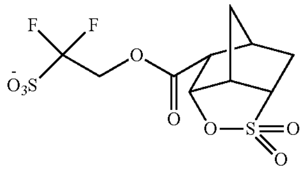
(B1a-22)
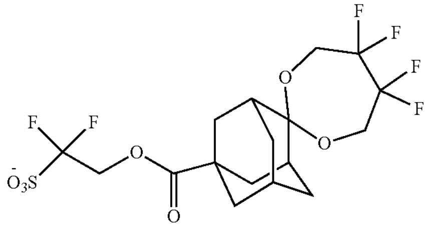
(B1a-23)
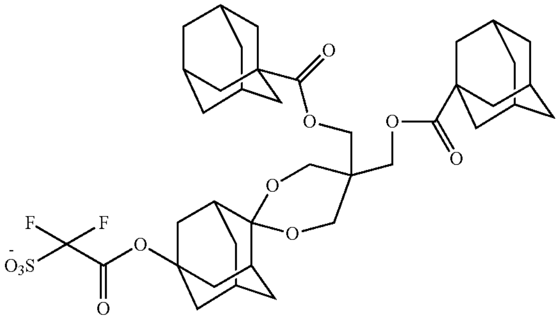
(B1a-24)
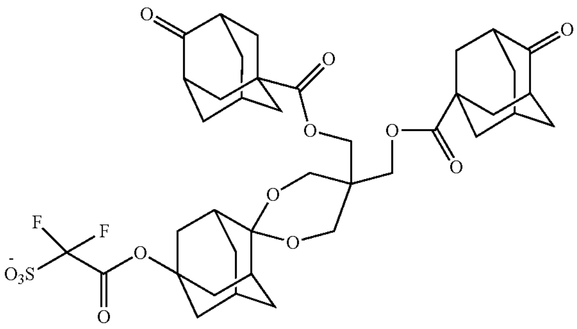
(B1a-25)
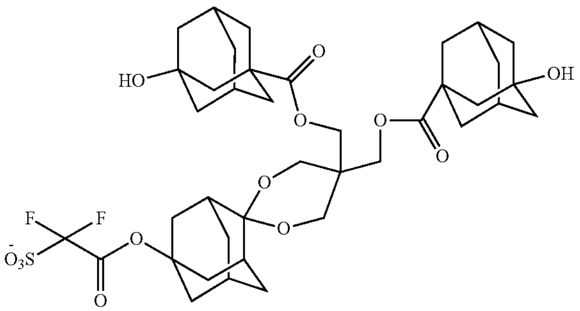

-continued
(B1a-26)
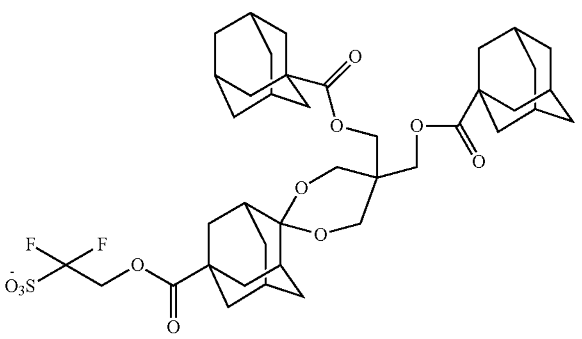
(B1a-27)
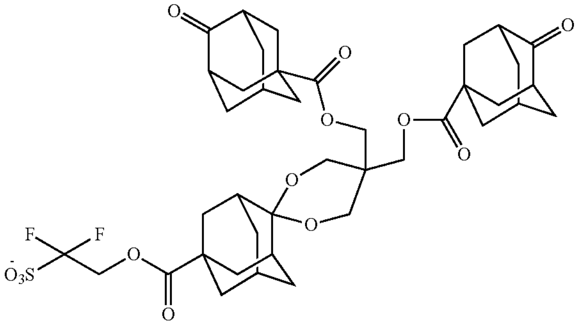
(B1a-28)
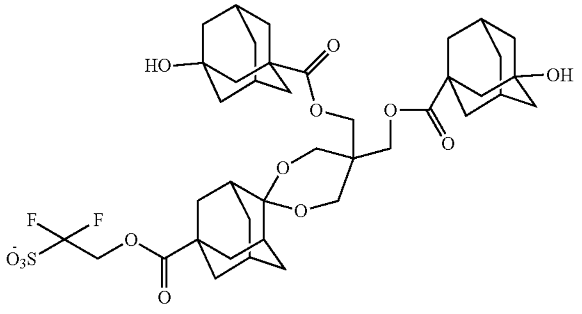
(B1a-29)
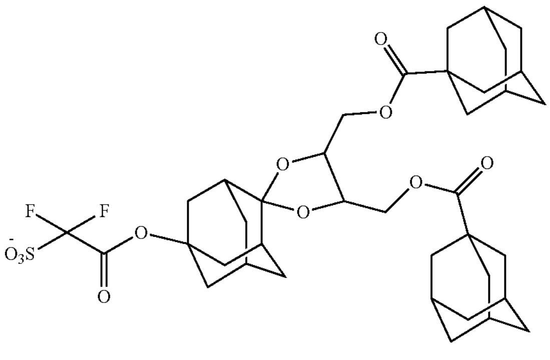
-continued
(B1a-30)
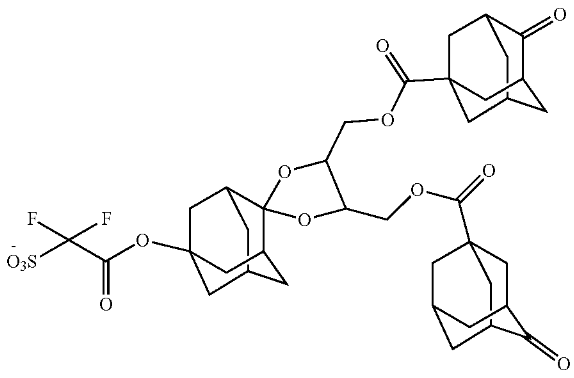
(B1a-31)
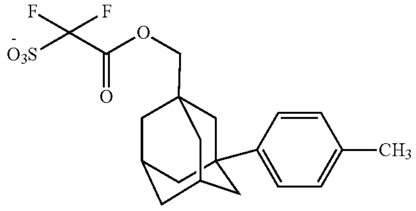
(B1a-32)
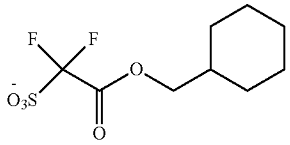
(B1a-33)
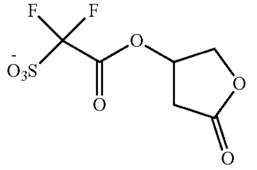
(B1a-34)
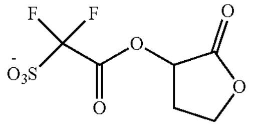
(B1a-35)
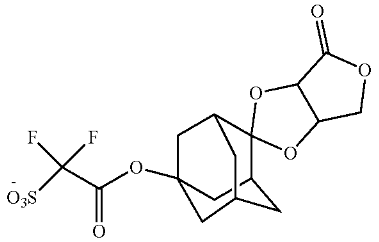
(B1a-36)
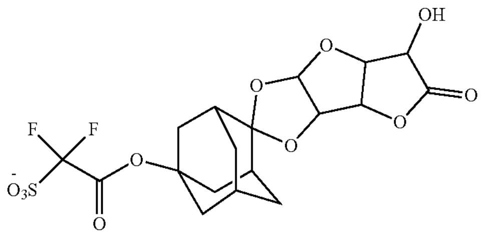

-continued (B1a-37)

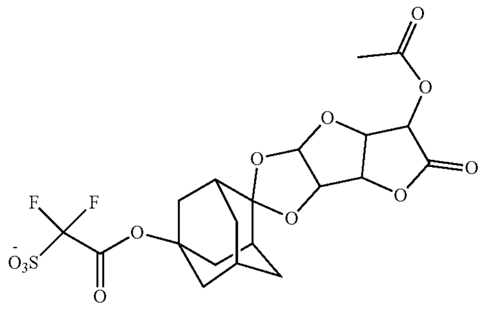

(B1a-38)

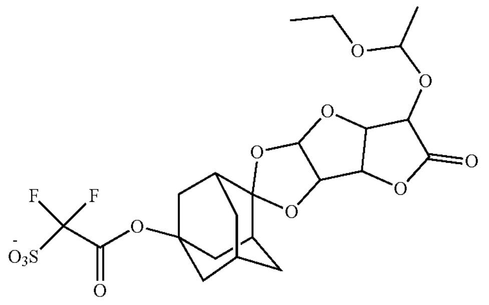

(B1a-39)

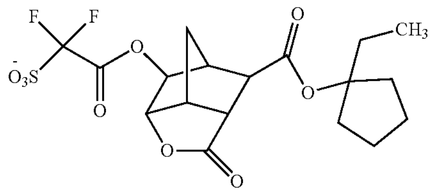

(B1a-40)

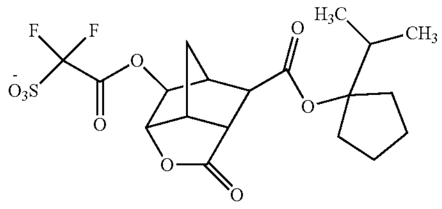

(B1a-41)

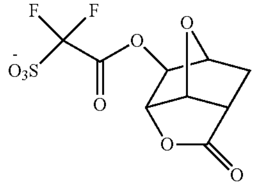

(B1a-42)

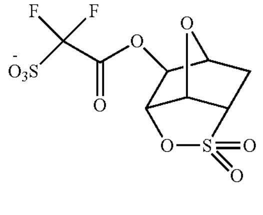

-continued (B1a-43)

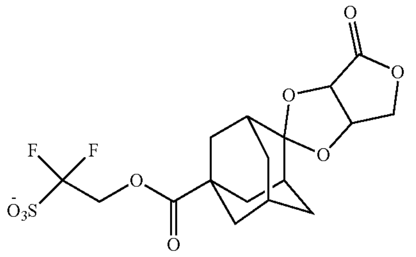

Of these, anion represented by any one of formula (B1a -1) to formula (B1a -3), formula (B1a -7) to formula (B1a -16), formula (B1a -18), formula (B1a -19) and formula (B1a -22) to formula (B1a -38) is preferable.

Examples of the sulfonylimide anion include the followings.

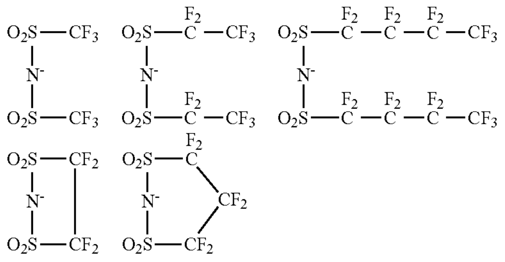

Examples of the sulfonylmethide anion include the followings.

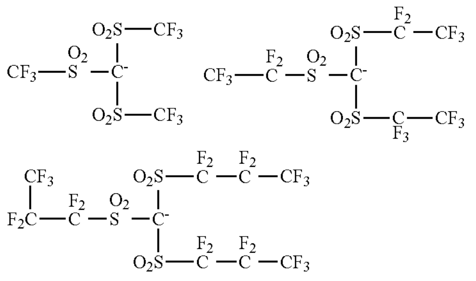

Examples of the organic cation of $Z^+$ include an organic onium cation, an organic sulfonium cation, an organic iodonium cation, an organic ammonium cation, a benzothiazolium cation and an organic phosphonium cation. Of these, an organic sulfonium cation and an organic iodonium cation are preferable, and an aryl sulfonium cation is more preferable. Specific examples thereof include a cation represented by any one of formula (b2-1) to formula (b2-4) (hereinafter sometimes referred to as "cation (b2-1)" according to the number of formula).

(b2-1)

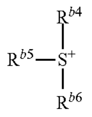

-continued (b2-2)

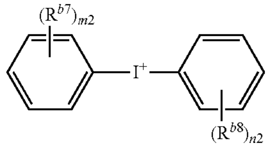

(b2-3)

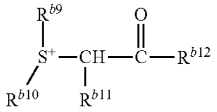

(b2-4)

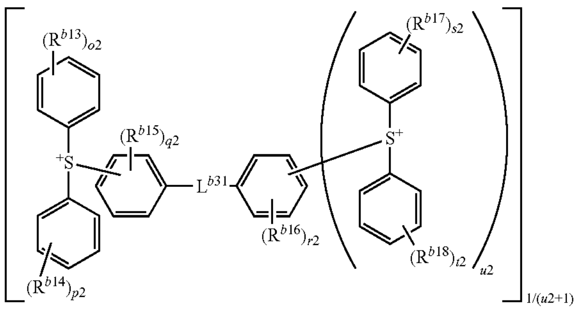

In formula (b2-1) to formula (b2-4), $R^{b4}$ to $R^{b6}$ each independently represent a chain hydrocarbon group having 1 to 30 carbon atoms, an alicyclic hydrocarbon group having 3 to 36 carbon atoms or an aromatic hydrocarbon group having 6 to 36 carbon atoms, a hydrogen atom included in the chain hydrocarbon group may be substituted with a hydroxy group, an alkoxy group having 1 to 12 carbon atoms, an alicyclic hydrocarbon group having 3 to 12 carbon atoms or an aromatic hydrocarbon group having 6 to 18 carbon atoms, a hydrogen atom included in the alicyclic hydrocarbon group may be substituted with a halogen atom, an aliphatic hydrocarbon group having 1 to 18 carbon atoms, an alkylcarbonyl group having 2 to 4 carbon atoms or a glycidyloxy group, and a hydrogen atom included in the aromatic hydrocarbon group may be substituted with a halogen atom, a hydroxy group, an aliphatic hydrocarbon group having 1 to 18 carbon atoms, an alkyl fluoride group having 1 to 12 carbon atoms or an alkoxy group having 1 to 12 carbon atoms.

$R^{b4}$ and $R^{b5}$ may be bonded to each other to form a ring together with sulfur atoms to which $R^{b4}$ and $R^{b5}$ are bonded, and $—CH_2—$ included in the ring may be replaced by —O—, —S— or —CO—, $R^{b7}$ and $R^{b8}$ each independently represent a halogen atom, a hydroxy group, an aliphatic hydrocarbon group having 1 to 12 carbon atoms or an alkoxy group having 1 to 12 carbon atoms, m2 and n2 each independently represent an integer of 0 to 5, when m2 is 2 or more, a plurality of $R^{b7}$ may be the same or different, and when n2 is 2 or more, a plurality of $R^{b8}$ may be the same or different, $R^{b9}$ and $R^{b10}$ each independently represent a chain hydrocarbon group having 1 to 36 carbon atoms or an alicyclic hydrocarbon group having 3 to 36 carbon atoms, $R^{b9}$ and $R^{b10}$ may be bonded to each other to form a ring together with sulfur atoms to which $R^{b9}$ and $R^{b10}$ are bonded, and $—CH_2—$ included in the ring may be replaced by —O—, —S— or —CO—, $R^{b11}$ represents a hydrogen atom, a chain hydrocarbon group having 1 to 36 carbon atoms, an alicyclic hydrocarbon group having 3 to 36 carbon atoms or an aromatic hydrocarbon group having 6 to 18 carbon atoms, $R^{b12}$ represents a chain hydrocarbon group having 1 to 12 carbon atoms, an alicyclic hydrocarbon group having 3 to 18 carbon atoms or an aromatic hydrocarbon group having 6 to 18 carbon atoms, a hydrogen atom included in the chain hydrocarbon group may be substituted with an aromatic hydrocarbon group having 6 to 18 carbon atoms, a hydrogen atom included in the aromatic hydrocarbon group may be substituted with an alkoxy group having 1 to 12 carbon atoms or an alkylcarbonyloxy group having 1 to 12 carbon atoms, $R^{b11}$ and $R^{b12}$ may be bonded to each other to form a ring, including —CH—CO— to which $R^{b11}$ and $R^{b12}$ are bonded, and $—CH_2—$ included in the ring may be replaced by —O—, —S— or —CO—, $R^{b13}$ to $R^{b18}$ each independently represent a halogen atom, a hydroxy group, an aliphatic hydrocarbon group having 1 to 12 carbon atoms, an alkyl fluoride group having 1 to 12 carbon atoms or an alkoxy group having 1 to 12 carbon atoms, $L^{b31}$ represents a sulfur atom or an oxygen atom, o2, p2, s2 and t2 each independently represent an integer of 0 to 5, q2 and r2 each independently represent an integer of 0 to 4, u2 represents 0 or 1, and when o2 is 2 or more, a plurality of $R^{b13}$ are the same or different, when p2 is 2 or more, a plurality of $R^{b14}$ are the same or different, when q2 is 2 or more, a plurality of $R^{b15}$ are the same or different, when r2 is 2 or more, a plurality of $R^{b16}$ are the same or different, when s2 is 2 or more, a plurality of $R^{b17}$ are the same or different, and when t2 is 2 or more, a plurality of $R^{b18}$ are the same or different.

The aliphatic hydrocarbon group represents a chain hydrocarbon group and an alicyclic hydrocarbon group.

Examples of the chain hydrocarbon group include alkyl groups such as a methyl group, an ethyl group, a propyl group, an isopropyl group, a butyl group, a sec-butyl group, a tert-butyl group, a pentyl group, a hexyl group, an octyl group and a 2-ethylhexyl group.

Particularly, the chain hydrocarbon group of $R^{b9}$ to $R^{b12}$ preferably has 1 to 12 carbon atoms.

The alicyclic hydrocarbon group may be either monocyclic or polycyclic, and examples of the monocyclic alicyclic hydrocarbon group include cycloalkyl groups such as a cyclopropyl group, a cyclobutyl group, a cyclopentyl group, a cyclohexyl group, a cycloheptyl group, a cyclooctyl group and a cyclodecyl group. Examples of the polycyclic alicyclic hydrocarbon group include a decahydronaphthyl group, an adamantyl group, a norbornyl group and the following groups.

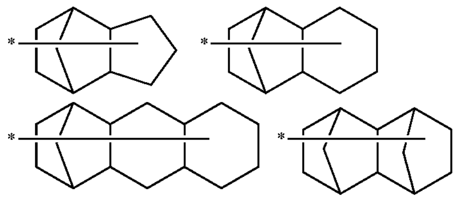

-continued

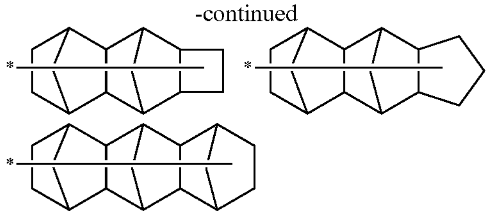

Particularly, the alicyclic hydrocarbon group of $R^{b9}$ to $R^{b12}$ preferably has 3 to 18 carbon atoms, and more preferably 4 to 12 carbon atoms.

Examples of the alicyclic hydrocarbon group in which a hydrogen atom is substituted with an aliphatic hydrocarbon group include a methylcyclohexyl group, a dimethylcyclohexyl group, a 2-methyladamantan-2-yl group, a 2-ethyladamantan-2-yl group, a 2-isopropyladamantan-2-yl group, a methylnorbornyl group, an isobornyl group and the like. In the alicyclic hydrocarbon group in which a hydrogen atom is substituted with an aliphatic hydrocarbon group, the total number of carbon atoms of the alicyclic hydrocarbon group and the aliphatic hydrocarbon group is preferably 20 or less.

The alkyl fluoride group represents an alkyl group having 1 to 12 carbon atoms which has a fluorine atom, and examples thereof include a fluoromethyl group, a difluoromethyl group, a trifluoromethyl group, a perfluorobutyl group and the like. In some embodiments, the number of carbon atoms of the alkyl fluoride group is preferably 1 to 9, more preferably 1 to 6, still more preferably 1 to 4.

Examples of the aromatic hydrocarbon group include aryl groups such as a phenyl group, a biphenyl group, a naphthyl group and a phenanthryl group. The aromatic hydrocarbon group may have a chain hydrocarbon group or an alicyclic hydrocarbon group, and examples thereof include an aromatic hydrocarbon group having a chain hydrocarbon group (a tolyl group, a xylyl group, a cumenyl group, a mesityl group, a p-ethylphenyl group, a p-tert-butylphenyl group, a 2,6-diethylphenyl group, a 2-methyl-6-ethylphenyl group, etc.) and an aromatic hydrocarbon group having an alicyclic hydrocarbon group (a p-cyclohexylphenyl group, a p-adamantylphenyl group, etc.). When the aromatic hydrocarbon group has a chain hydrocarbon group or an alicyclic hydrocarbon group, a chain hydrocarbon group having 1 to 18 carbon atoms and an alicyclic hydrocarbon group having 3 to 18 carbon atoms are preferable.

Examples of the aromatic hydrocarbon group in which a hydrogen atom is substituted with an alkoxy group include a p-methoxyphenyl group and the like.

Examples of the chain hydrocarbon group in which a hydrogen atom is substituted with an aromatic hydrocarbon group include aralkyl groups such as a benzyl group, a phenethyl group, a phenylpropyl group, a trityl group, a naphthylmethyl group and a naphthylethyl group.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the alkylcarbonyl group include an acetyl group, a propionyl group and a butyryl group.

Examples of the halogen atom include a fluorine atom, a chlorine atom, a bromine atom and an iodine atom.

Examples of the alkylcarbonyloxy group include a methylcarbonyloxy group, an ethylcarbonyloxy group, a propylcarbonyloxy group, an isopropylcarbonyloxy group, a butylcarbonyloxy group, a sec-butylcarbonyloxy group, a tert-butylcarbonyloxy group, a pentylcarbonyloxy group, a hexylcarbonyloxy group, an octylcarbonyloxy group and a 2-ethylhexylcarbonyloxy group.

The ring formed by bonding $R^{b4}$ and $R^{b5}$ each other, together with sulfur atoms to which $R^{b4}$ and $R^{b5}$ are bonded, may be a monocyclic, polycyclic, aromatic, nonaromatic, saturated or unsaturated ring. This ring includes a ring having 3 to 18 carbon atoms and is preferably a ring having 4 to 18 carbon atoms. The ring containing a sulfur atom includes a 3-membered to 12-membered ring and is preferably a 3-membered to 7-membered ring and includes, for example, the following rings and the like. * represents a bonding site.

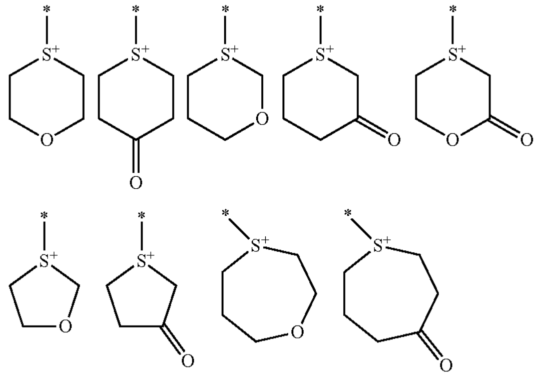

The ring formed by combining $R^{b9}$ and $R^{b10}$ together may be a monocyclic, polycyclic, aromatic, nonaromatic, saturated or unsaturated ring. This ring includes a 3-membered to 12-membered ring and is preferably a 3-membered to 7-membered ring. The ring includes, for example, a thiolan-1-ium ring (tetrahydrothiophenium ring), a thian-1-ium ring, a 1,4-oxathian-4-ium ring and the like.

The ring formed by combining $R^{b11}$ and $R^{b12}$ together may be a monocyclic, polycyclic, aromatic, nonaromatic, saturated or unsaturated ring. This ring includes a 3-membered to 12-membered ring and is preferably a 3-membered to 7-membered ring. Examples thereof include an oxocycloheptane ring, an oxocyclohexane ring, an oxonorbornane ring, an oxoadamantane ring and the like.

Of cation (b2-1) to cation (b2-4), a cation (b2-1) is preferable.

Examples of the cation (b2-1) include the following cations.

(b2-c-1)

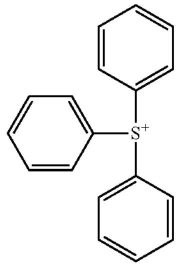

-continued
(b2-c-2)
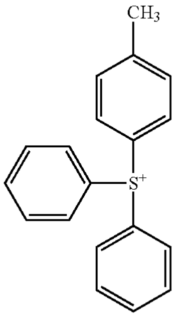
(b2-c-3)
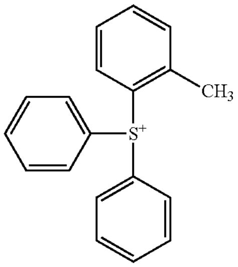
(b2-c-4)
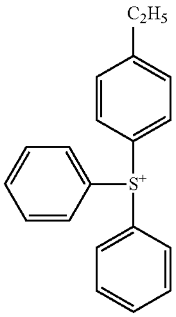
(b2-c-5)
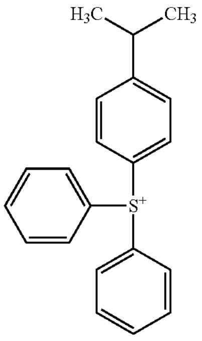
(b2-c-6)
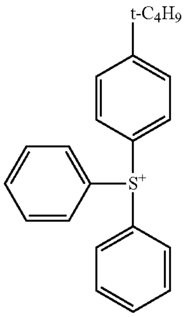
-continued
(b2-c-7)
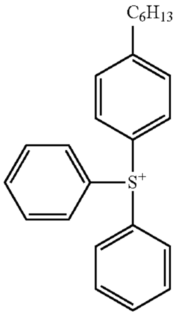
(b2-c-8)
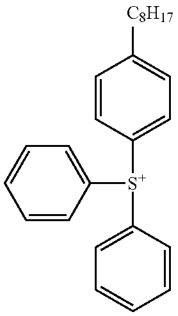
(b2-c-9)
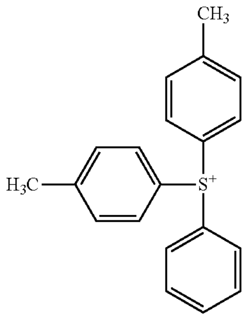
(b2-c-10)
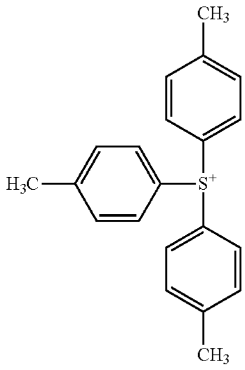
(b2-c-11)
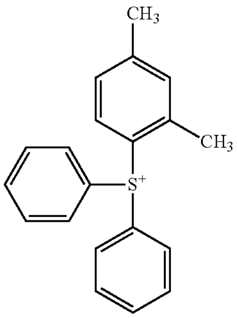

-continued
(b2-c-12)
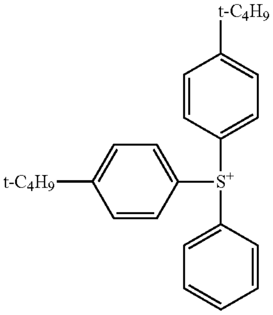
(b2-c-13)
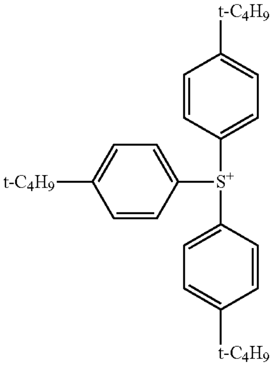
(b2-c-14)
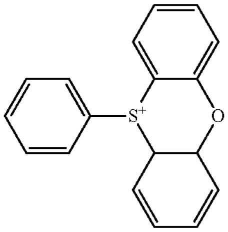
(b2-c-15)
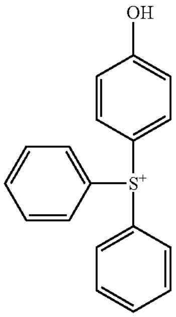
(b2-c-16)
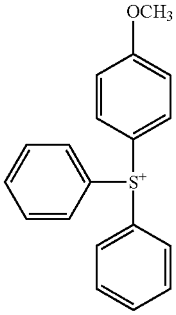
-continued
(b2-c-17)
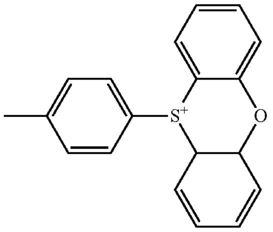
(b2-c-18)
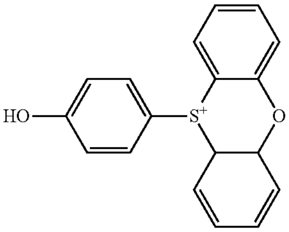
(b2-c-19)
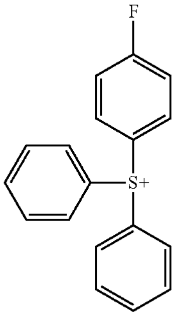
(b2-c-20)
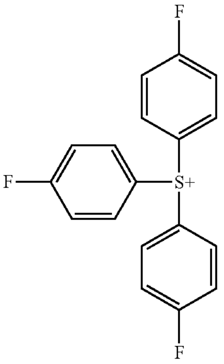
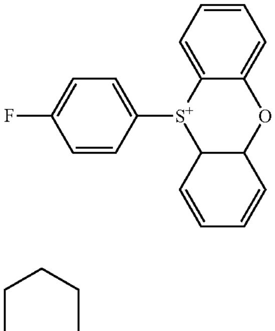
(b2-c-21)
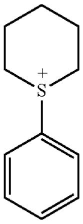

-continued
(b2-c-22)
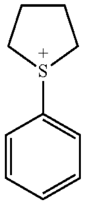
(b2-c-23)
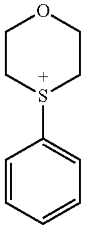
(b2-c-24)
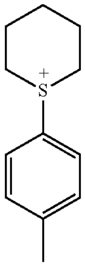
(b2-c-25)
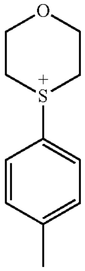
(b2-c-26)
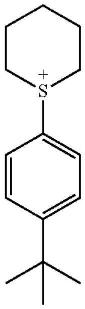
(b2-c-27)
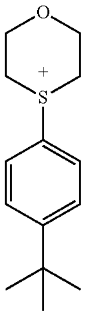
-continued
(b2-c-47)
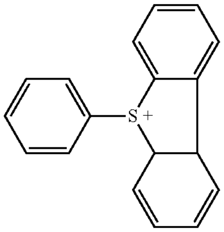
(b2-c-48)
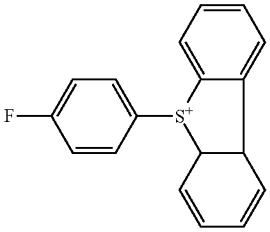
(b2-c-49)
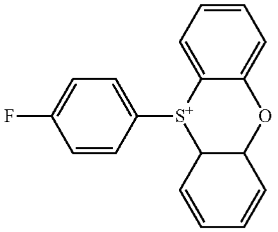
(b2-c-51)
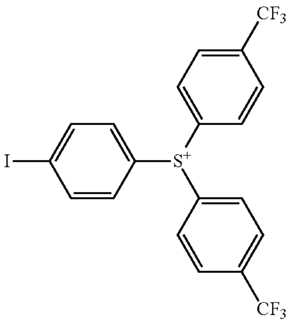
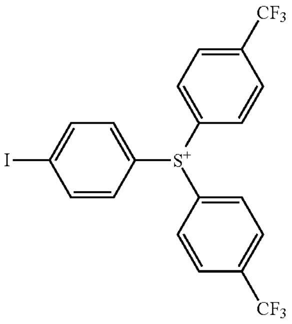

-continued
(b2-c-52)
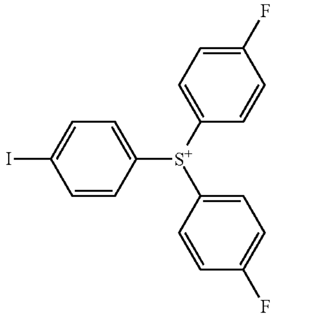
(b2-c-53)
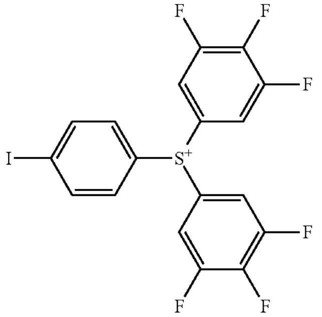
Examples of the cation (b2-2) include the following cations.
(b2-c-28)
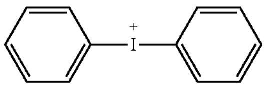
(b2-c-29)
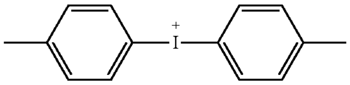
(b2-c-30)
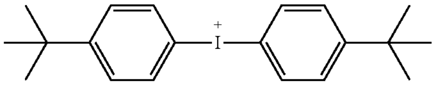
(b2-c-50)
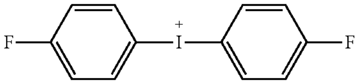
Examples of the cation (b2-3) include the following cations.
(b2-c-31)
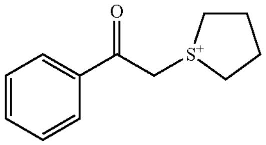
(b2-c-32)
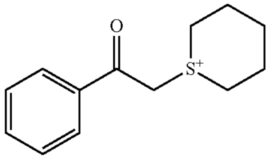
-continued
(b2-c-33)
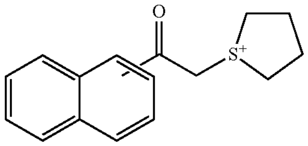
(b2-c-34)
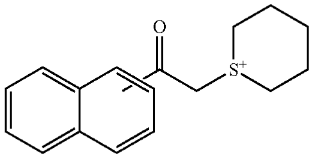
Examples of the cation (b2-4) include the following cations.
(b2-c-35)
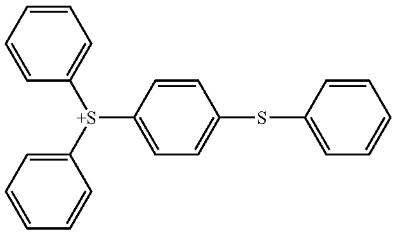
(b2-c-36)
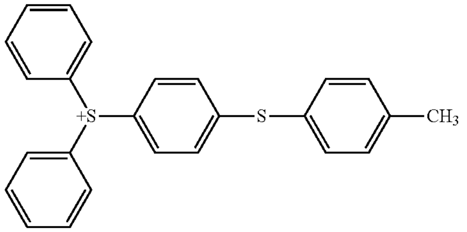
(b2-c-37)
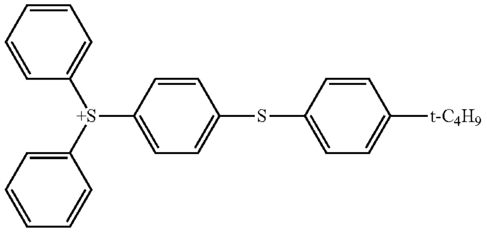
(b2-c-38)
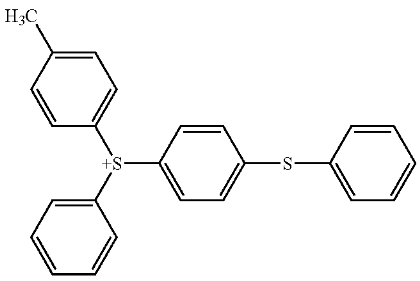

-continued
(b2-c-39)
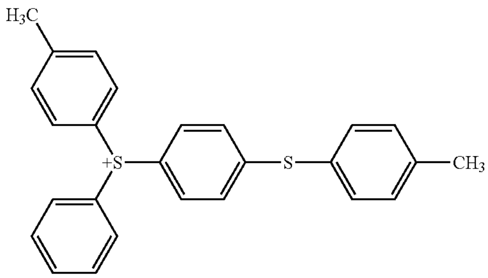
(b2-c-40)
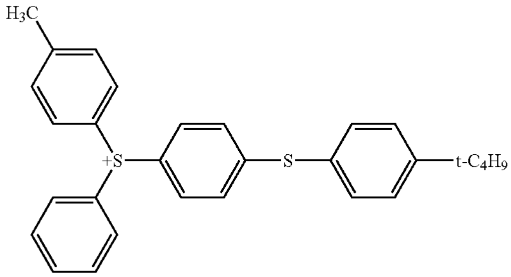
(b2-c-41)
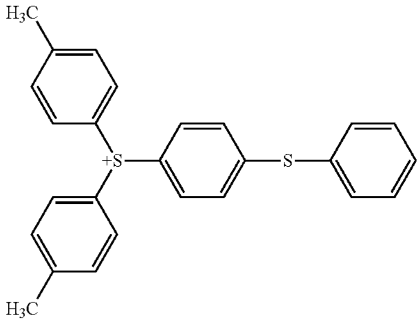
(b2-c-42)
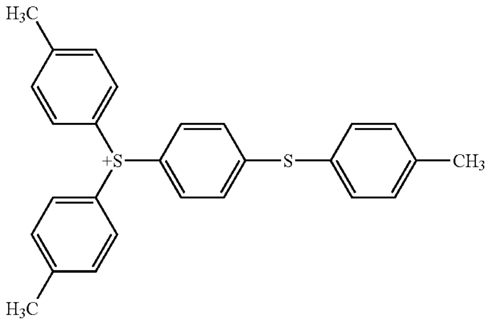
(b2-c-43)
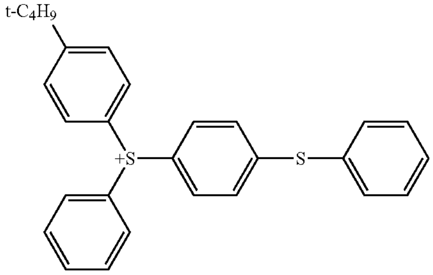
-continued
(b2-c-44)
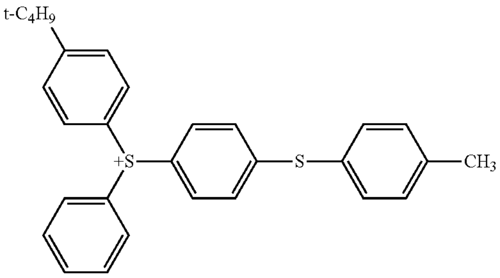
(b2-c-45)
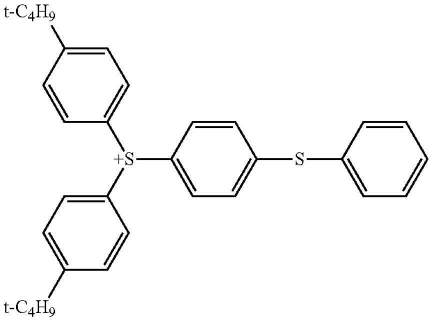
(b2-c-46)
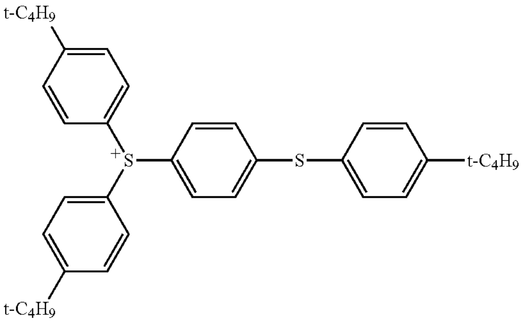
(b2-c-54)
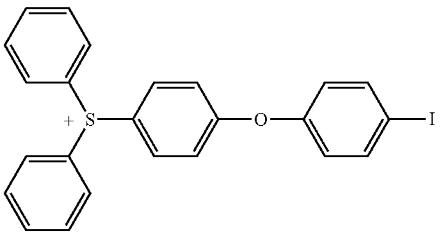

-continued (b2-c-55)

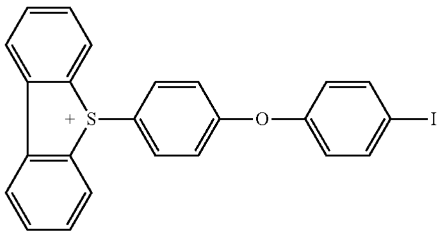

(b2-c-56)

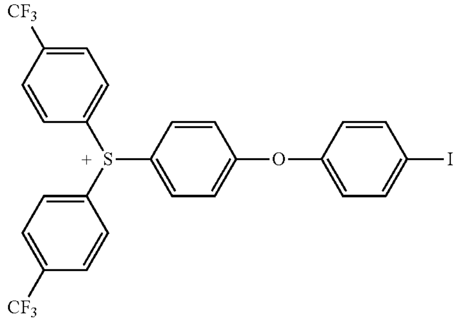

-continued (b2-c-57)

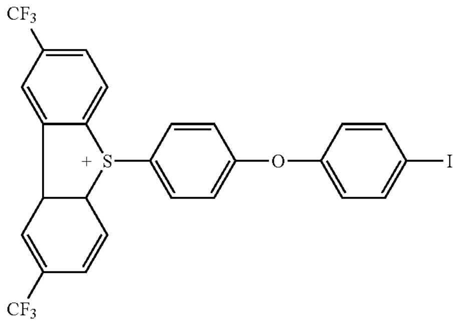

The acid generator (B) is a combination of the anion mentioned above and the organic cation mentioned above, and these can be optionally combined. The acid generator (B) preferably includes a combination of anion represented by any one of formula (B1a -1) to formula (B1a -3), formula (B1a -7) to formula (B1a -16), formula (B1a -18), formula (B1a -19) and formula (B1a -22) to formula (B1a -38) with a cation (b2-1), a cation (b2-2), a cation (b2-3) or a cation (b2-4).

The acid generator (B) preferably includes those represented by formula (B1-1) to formula (B1-60), and of these acid generators, those containing an arylsulfonium cation are preferable and those represented by formula (B1-1) to formula (B1-3), formula (B1-5) to formula (B1-7), formula (B1-11) to formula (B1-14), formula (B1-20) to formula (B1-26), formula (B1-29) and formula (B1-31) to formula (B1-60) are particularly preferable.

(B1-1)

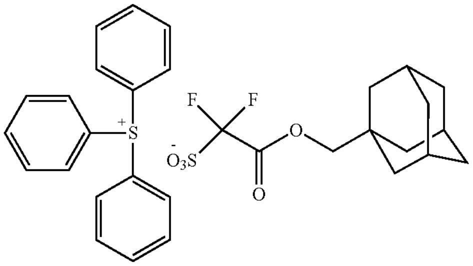

(B1-2)

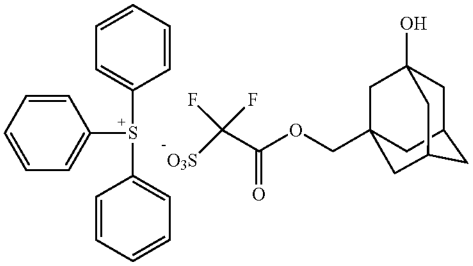

(B1-3)

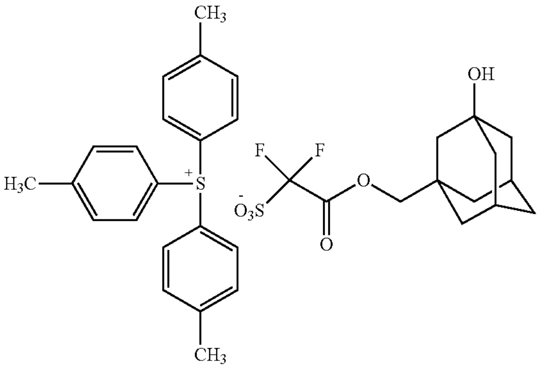

(B1-4)

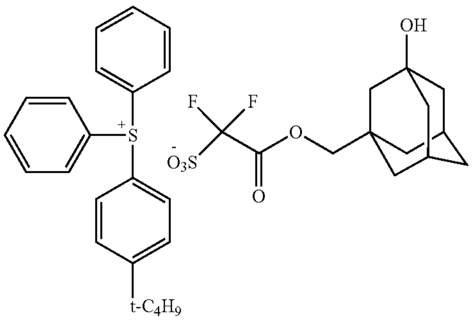

-continued
(B1-5)
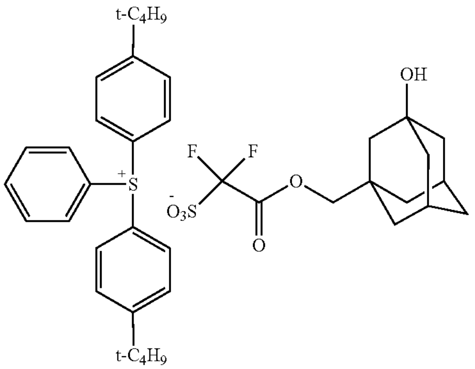
(B1-6)
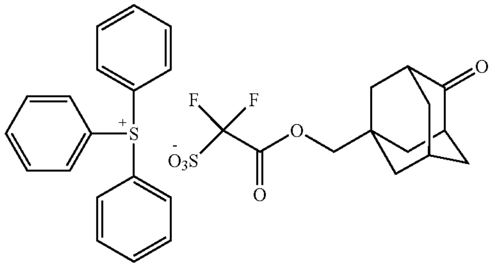
(B1-7)
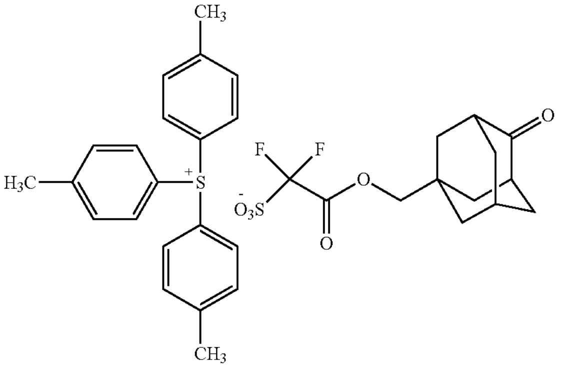
(B1-8)
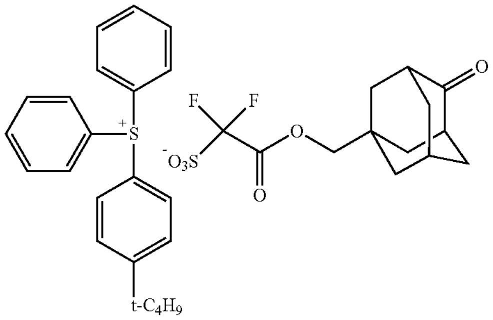
(B1-9)
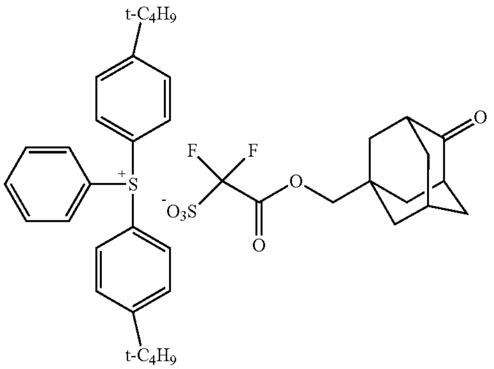
(B1-10)
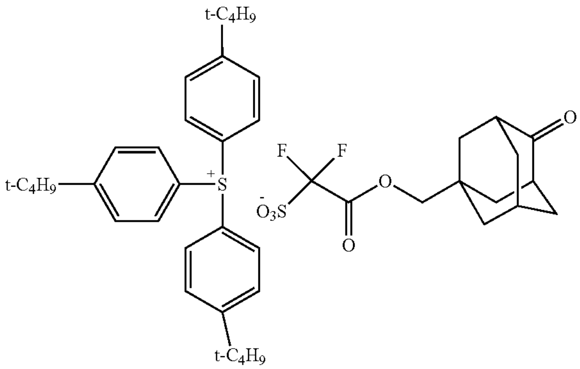
(B1-11)
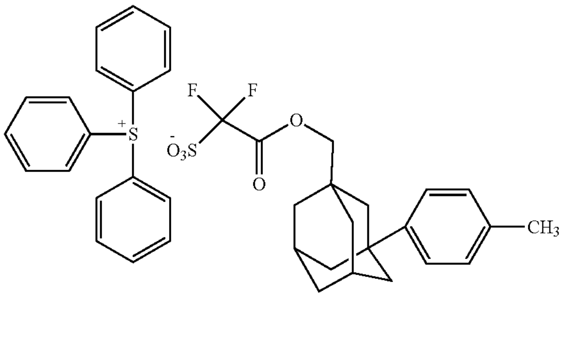
(B1-12)
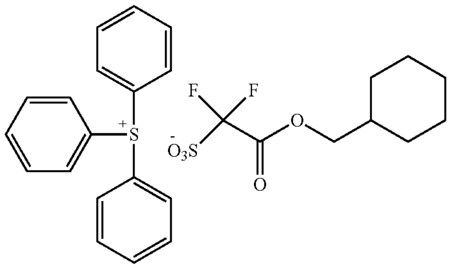

-continued
(B1-13)
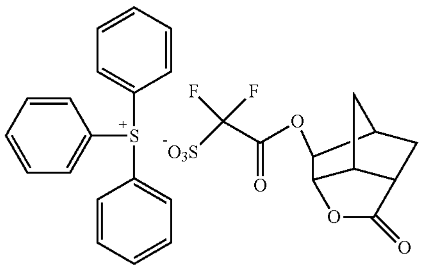
(B1-14)
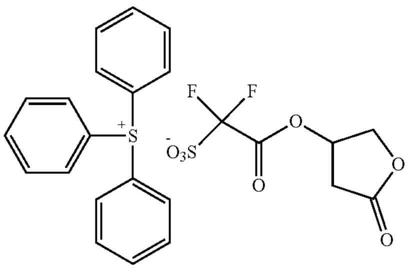
(B1-15)
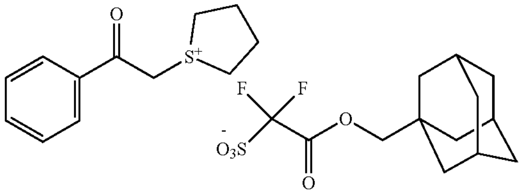
(B1-16)
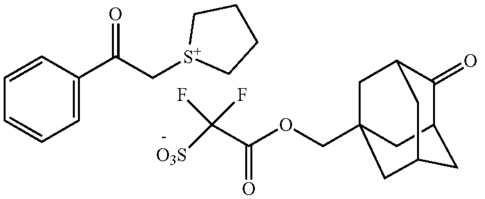
(B1-17)
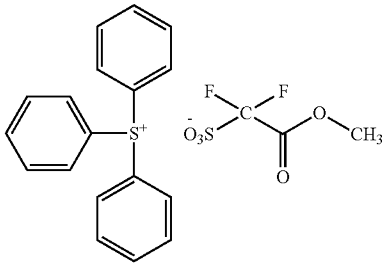
(B1-18)
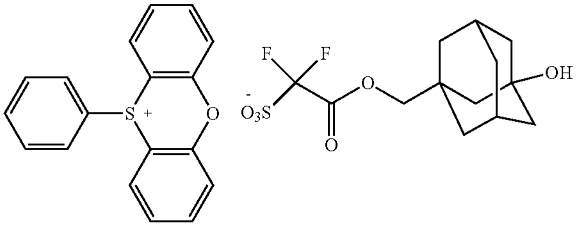
(B1-19)
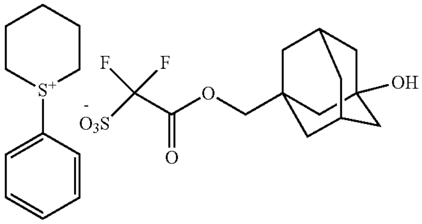
(B1-20)
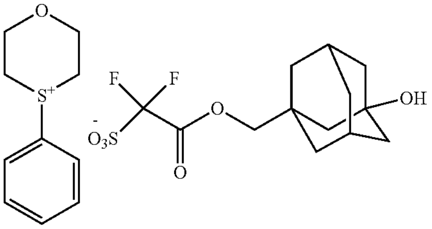
(B1-21)
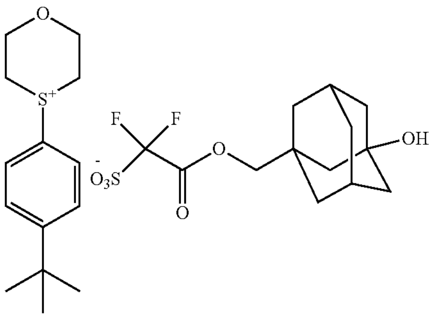
(B1-22)
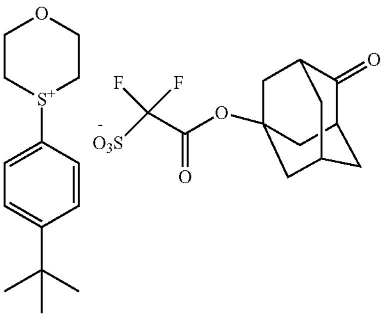

-continued
(B1-23)
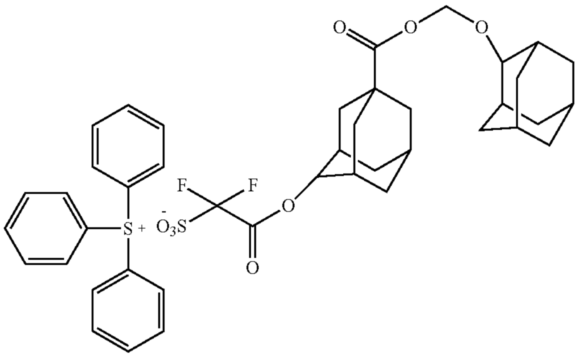
(B1-24)
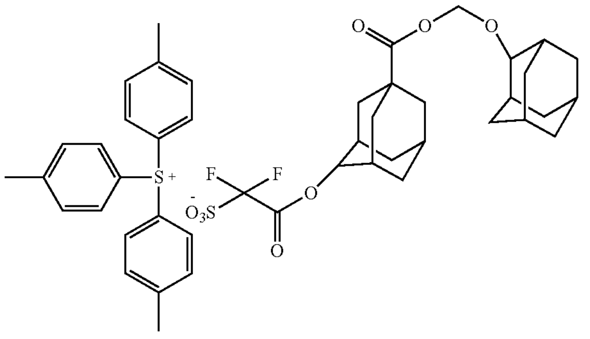
(B1-25)
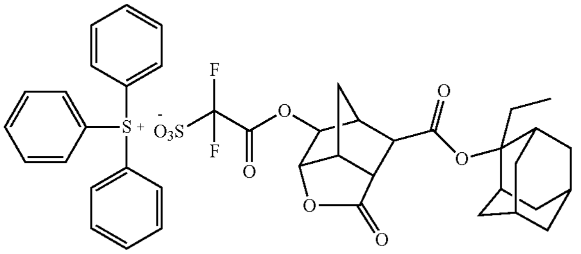
(B1-26)
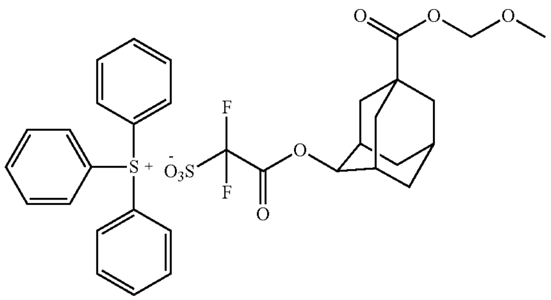
(B1-27)
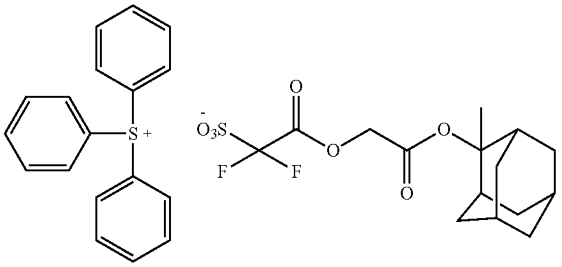
(B1-28)
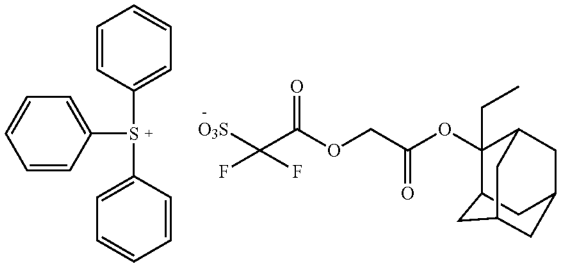
(B1-29)
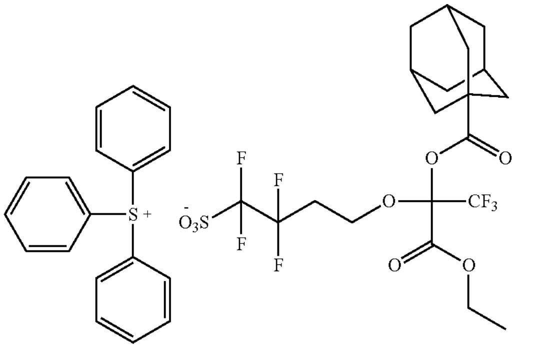
(B1-30)
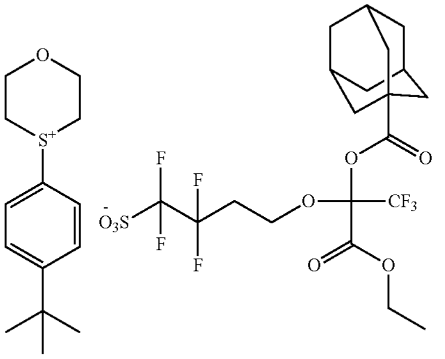

-continued
(B1-31)
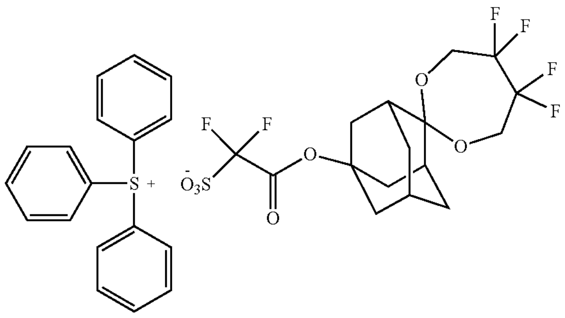
(B1-32)
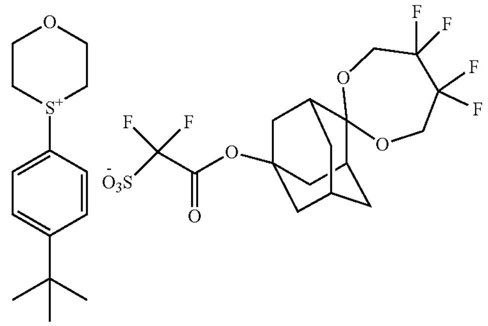
(B1-33)
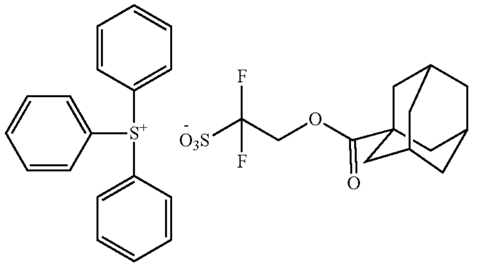
(B1-34)
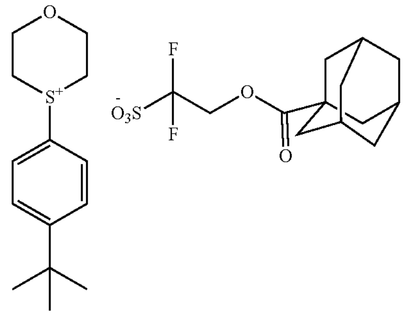
(B1-35)
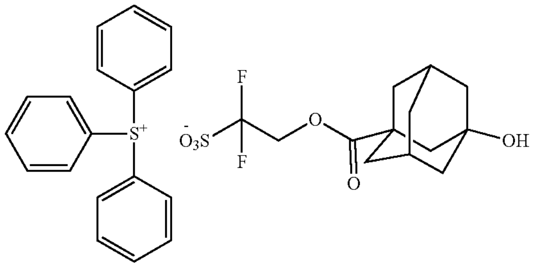
(B1-36)
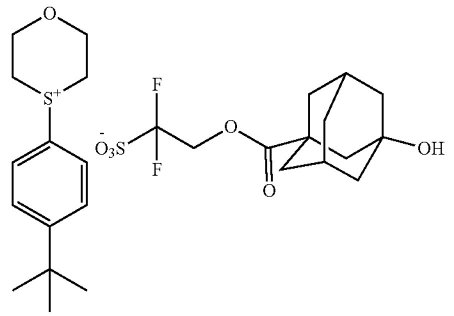
(B1-37)
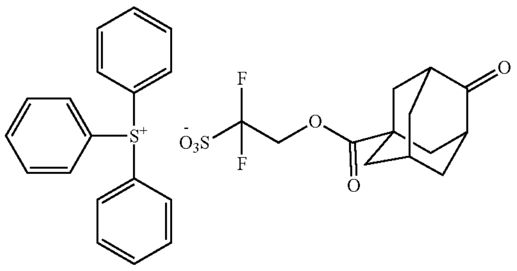
(B1-38)
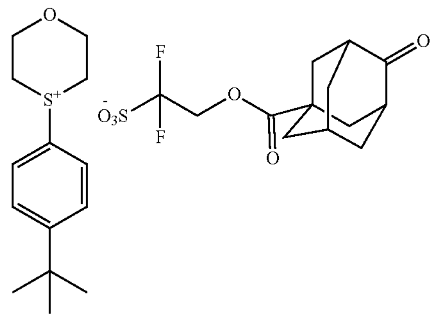

-continued
(B1-39)
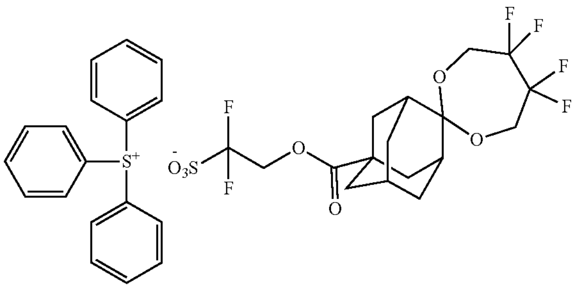
(B1-40)
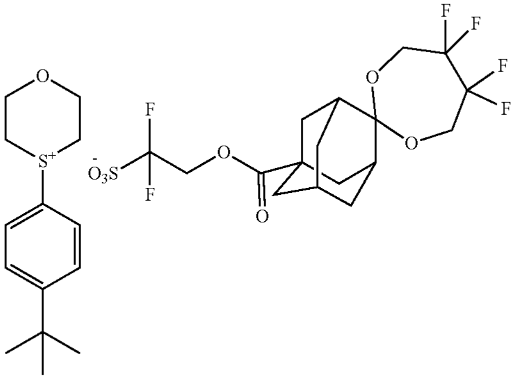
(B1-41)
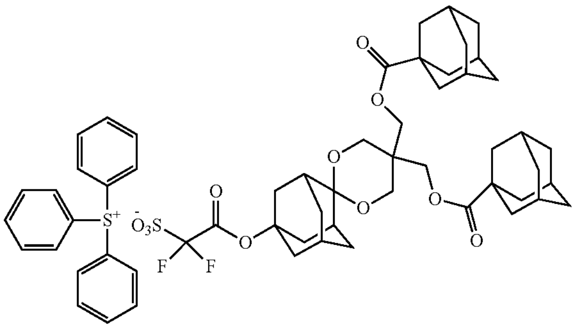
(B1-42)
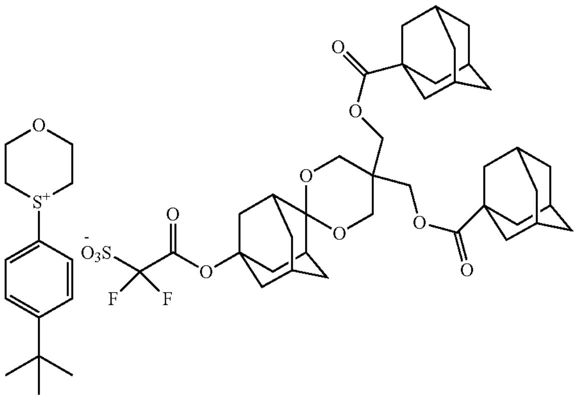
(B1-43)
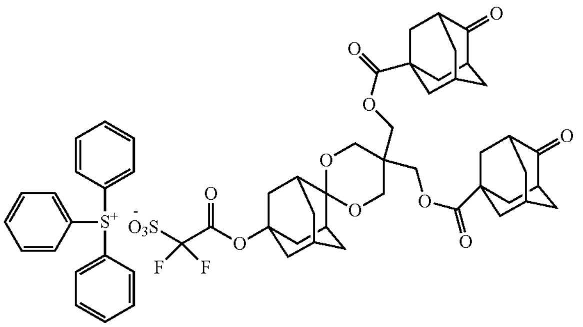
(B1-44)
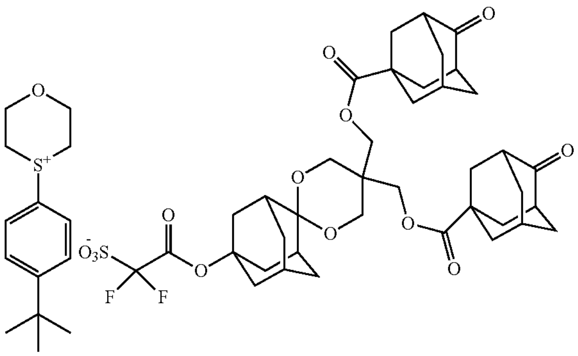
(B1-45)
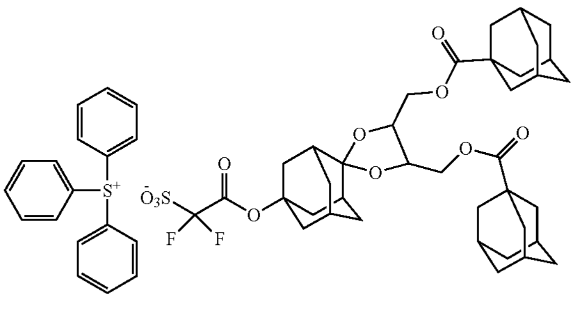
(B1-46)
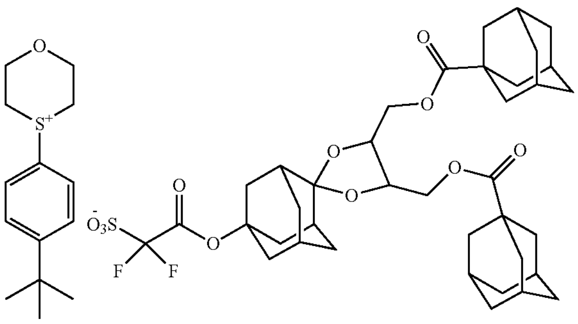

-continued
(B1-47)
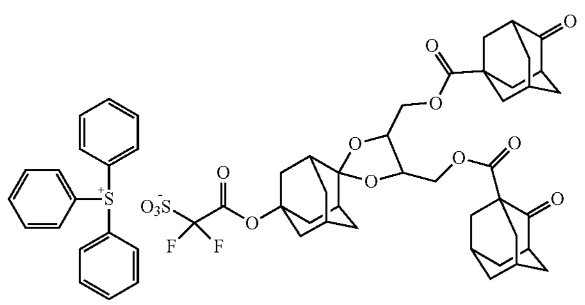
(B1-48)
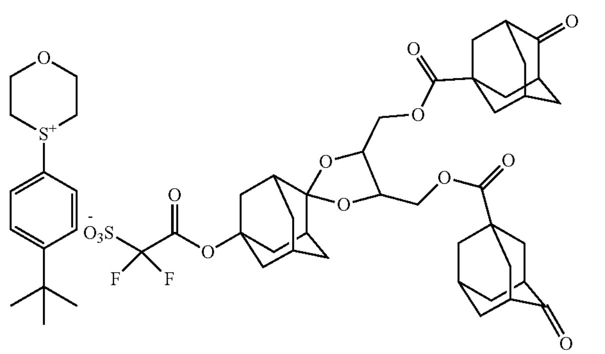
(B1-49)
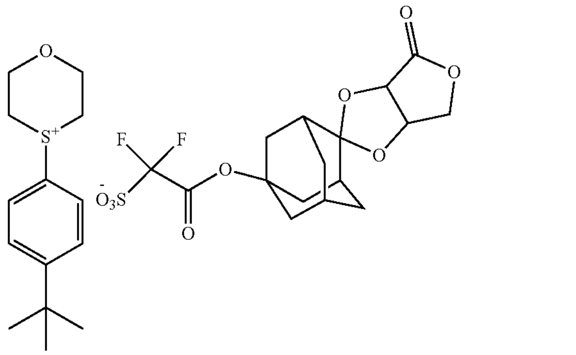
(B1-50)
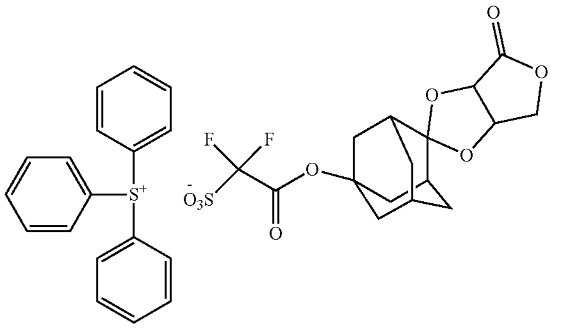
(B1-51)
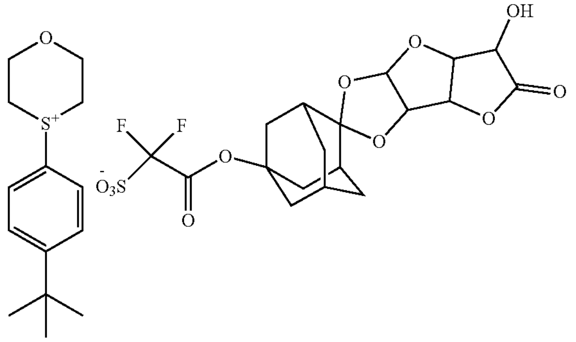
(B1-52)
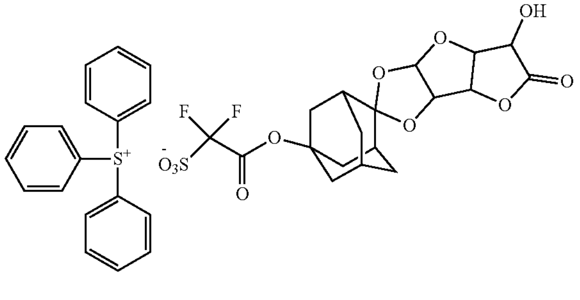
(B1-53)
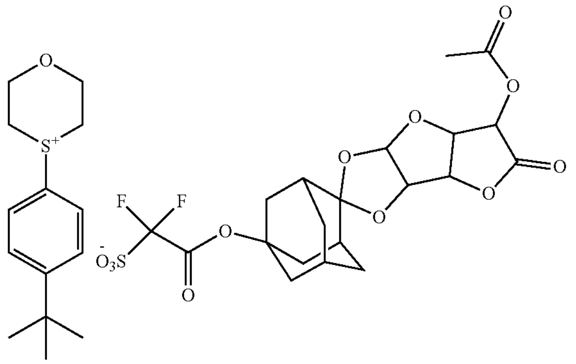
(B1-54)
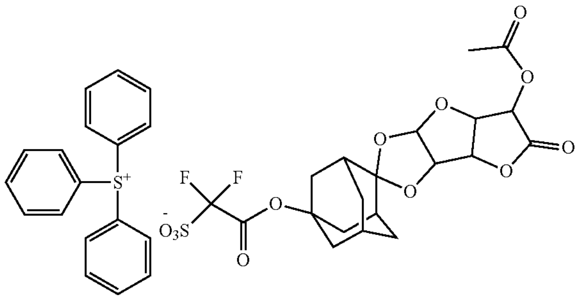

-continued (B1-55)

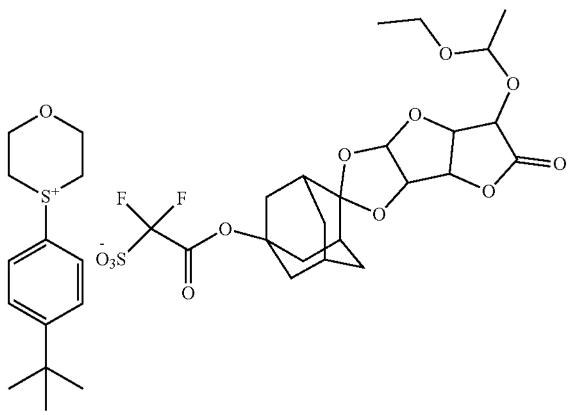

(B1-56)

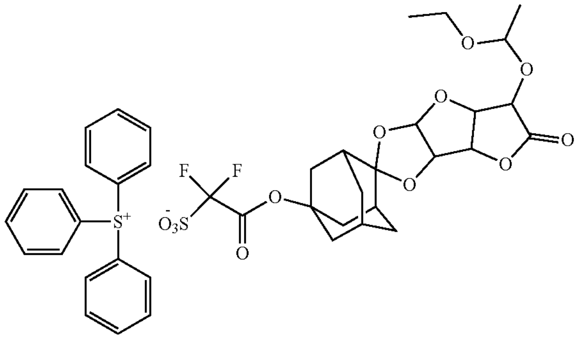

(B1-57)

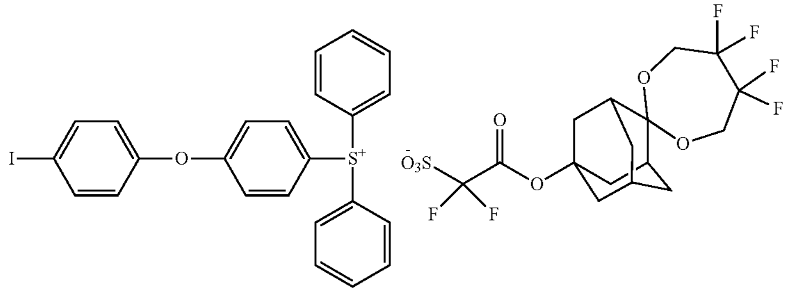

(B1-58)

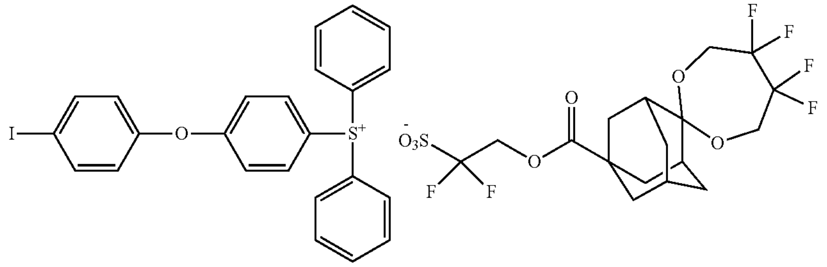

(B1-59)

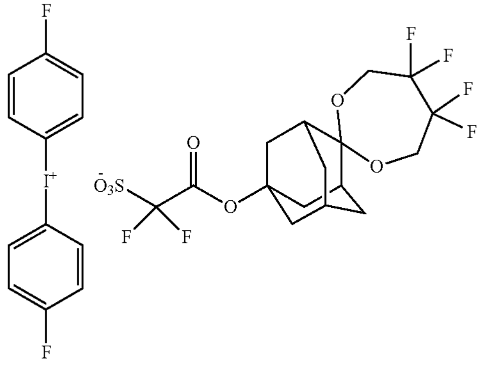

(B1-60)

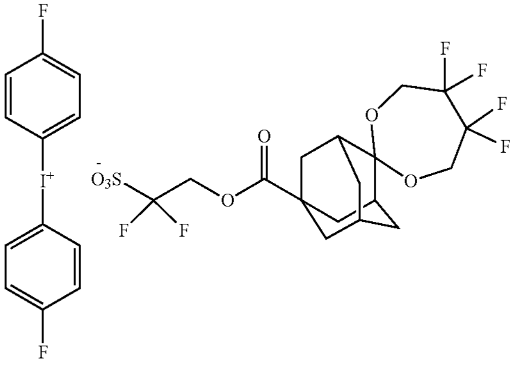

In the resist composition of the present disclosure, the content of the acid generator is preferably 0.1% by mass or more and 99.9% by mass or less, more preferably 1% by mass or more and 45% by mass or less, still more preferably 1% by mass or more and 40% by mass or less, and yet preferably 3% by mass or more and 40% by mass or less, based on the solid content of the resist composition. When including the resin (A), the content of the acid generator is preferably 1 part by mass or more and 45 part by mass or less, more preferably 1 part by mass or more and 40 part by mass or less, and still more preferably 3 part by mass or more and 35 part by mass or less, based on 100 part by mass of the resin (A).

<Solvent (E)>

The content of the solvent (E) in the resist composition is usually 90% by mass or more and 99.9% by mass or less, preferably 92% by mass or more and 99% by mass or less, and more preferably 94% by mass or more and 99% by mass or less. The content of the solvent (E) can be measured, for example, by a known analysis means such as liquid chromatography or gas chromatography.

Examples of the solvent (E) include glycol ether esters such as ethylcellosolve acetate, methylcellosolve acetate and propylene glycol monomethyl ether acetate; glycol ethers such as propylene glycol monomethyl ether; esters such as ethyl lactate, butyl acetate, amyl acetate and ethyl pyruvate; ketones such as acetone, methyl isobutyl ketone, 2-heptanone and cyclohexanone; and cyclic esters such as γ-butyrolactone. The solvent (E) may be used alone, or two or more solvents may be used.

<Quencher (C)>

Examples of the quencher (C) include a salt generating an acid having an acidity lower than that of an acid generated from an acid generator (B), and a basic nitrogen-containing organic compound. The content of the quencher (C) is preferably about 0.01 to 15% by mass, more preferably about 0.01 to 10% by mass, still more preferably about 0.1 to 8% by mass, and yet more preferably about 0.1 to 7% by mass, based on the amount of the solid component of the resist composition.

<Salt Generating Acid Having Acidity Lower than that of Acid Generated from Acid Generator>

The acidity in a salt generating an acid having an acidity lower than that of an acid generated from the acid generator (B) is indicated by the acid dissociation constant (pKa). Regarding the salt generating an acid having an acidity lower than that of an acid generated from the acid generator (B), the acid dissociation constant of an acid generated from the salt usually meets the following inequality: $-3<pKa$, preferably $-1<pKa<7$, and more preferably $0<pKa<5$.

Examples of the salt generating an acid having an acidity lower than that of an acid generated from the acid generator (B) include salts represented by the following formulas, a salt represented by formula (D) mentioned in JP 2015-147926 A (hereinafter sometimes referred to as "weak acid inner salt (D)"), and salts mentioned in JP 2012-229206 A, JP 2012-6908 A, JP 2012-72109 A, JP 2011-39502 A and JP 2011-191745 A. The salt generating an acid having an acidity lower than that of an acid generated from the acid generator (B) is preferably a salt generating a carboxylic acid having an acidity lower than that of an acid generated from the acid generator (B) (salt having a carboxylic acid anion), more preferably a weak acid inner salt (D), and still more preferably a weak acid inner salt (D).

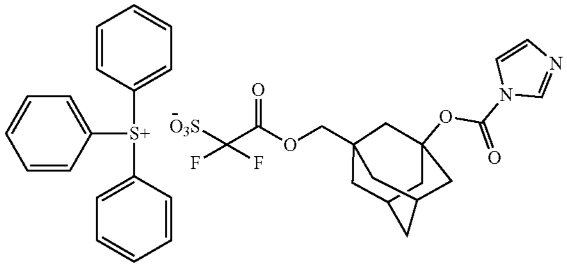

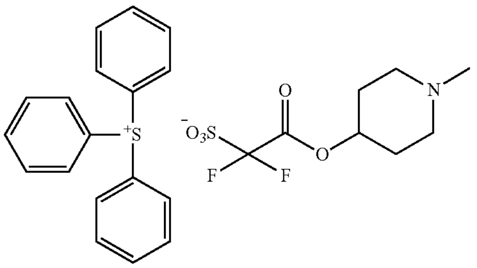

-continued

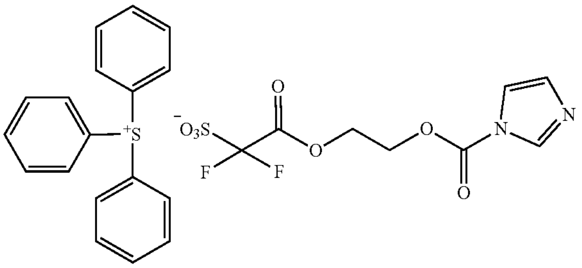

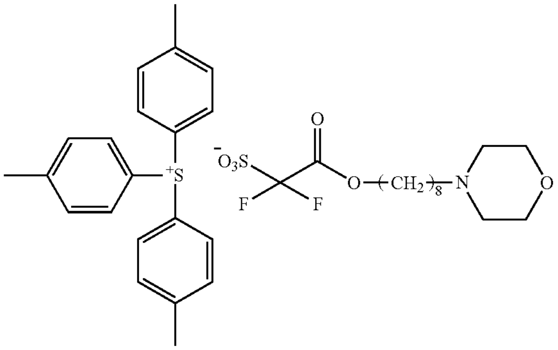

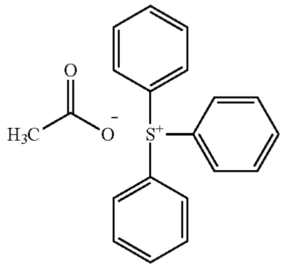

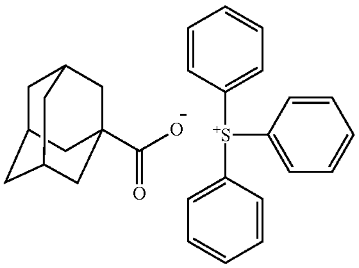

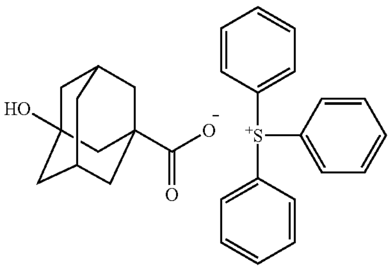

-continued

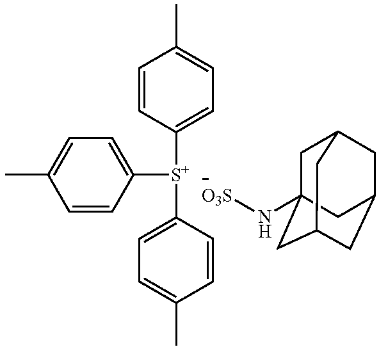

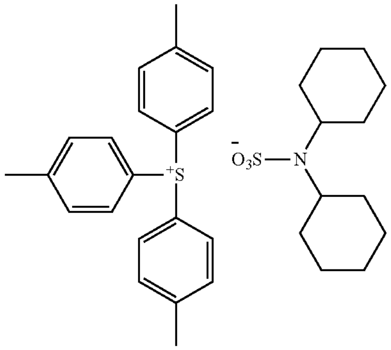

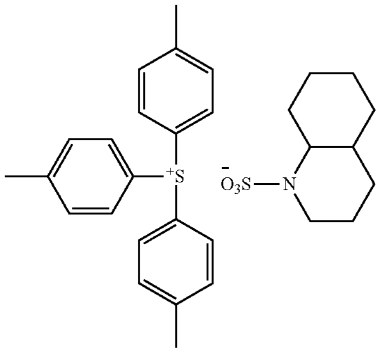

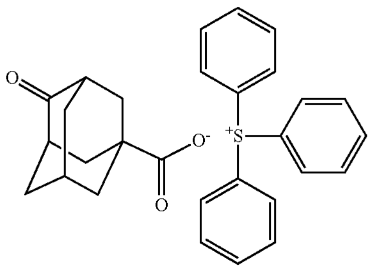

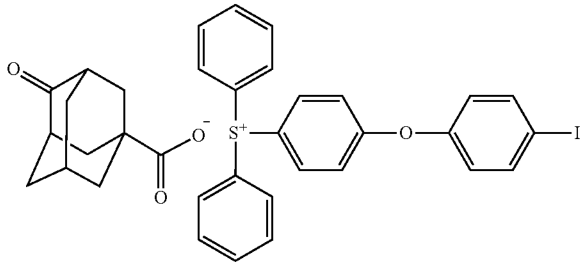

-continued

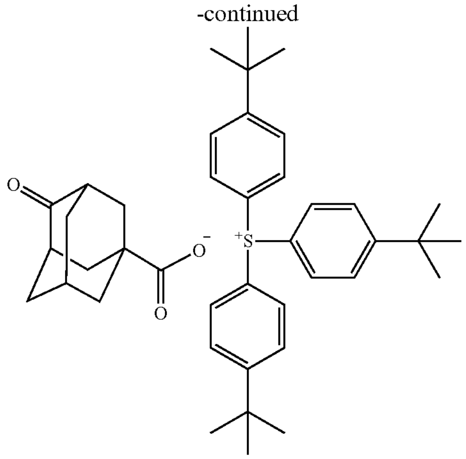

The weak acid inner salt (D) is preferably a diphenyliodonium salt having an iodonium cation to which two phenyl groups are bonded, and a carboxy anion substituted with at least one phenyl group of two phenyl groups bonded to the iodonium cation, and examples thereof include a salt represented by the following formula:

(D)

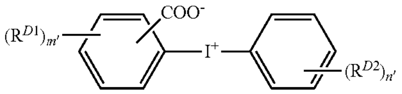

wherein, in formula (D), $R^{D1}$ and $R^{D2}$ each independently represent a hydrocarbon group having 1 to 12 carbon atoms, an alkoxy group having 1 to 6 carbon atoms, an acyl group having 2 to 7 carbon atoms, an acyloxy group having 2 to 7 carbon atoms, an alkoxycarbonyl group having 2 to 7 carbon atoms, a nitro group or a halogen atom, and m' and n' each independently represent an integer of 0 to 4, and when m' is 2 or more, a plurality of $R^{D1}$ may be the same or different, and when n' is 2 or more, a plurality of $R^{D2}$ may be the same or different.

Examples of the hydrocarbon group as for $R^{D1}$ and $R^{D2}$ include a chain hydrocarbon group, an alicyclic hydrocarbon group, an aromatic hydrocarbon group, and a group formed by combining these groups.

Examples of the chain hydrocarbon group include alkyl groups such as a methyl group, an ethyl group, a propyl group, an isopropyl group, a butyl group, an isobutyl group, a tert-butyl group, a pentyl group, a hexyl group, a nonyl group and the like.

The alicyclic hydrocarbon group may be either monocyclic or polycyclic, or may be either saturated or unsaturated. Examples thereof include cycloalkyl groups such as a cyclopropyl group, a cyclobutyl group, a cyclopentyl group, a cyclohexyl group, a cyclononyl group and a cyclododecyl group, a norbornyl group, an adamantyl group and the like.

Examples of the aromatic hydrocarbon group include aryl groups such as a phenyl group, a 1-naphthyl group, a 2-naphthyl group, a 2-methylphenyl group, a 3-methylphenyl group, a 4-methylphenyl group, a 4-ethylphenyl group, a 4-propylphenyl group, a 4-isopropylphenyl group, a 4-butylphenyl group, a 4-t-butylphenyl group, a 4-hexylphenyl group, a 4-cyclohexylphenyl group, an anthryl group, a p-adamantylphenyl group, a tolyl group, a xylyl group, a cumenyl group, a mesityl group, a biphenyl group, a phenanthryl group, a 2,6-diethylphenyl group and a 2-methyl-6-ethylphenyl.

Examples of the group formed by combining these groups include an alkyl-cycloalkyl group, a cycloalkyl-alkyl group, an aralkyl group (e.g., a phenylmethyl group, a 1-phenylethyl group, a 2-phenylethyl group, a 1-phenyl-1-propyl group, a 1-phenyl-2-propyl group, a 2-phenyl-2-propyl group, a 3-phenyl-1-propyl group, a 4-phenyl-1-butyl group, a 5-phenyl-1-pentyl group, a 6-phenyl-1-hexyl group, etc.) and the like.

Examples of the alkoxy group include a methoxy group, an ethoxy group and the like.

Examples of the acyl group include an acetyl group, a propanoyl group, a benzoyl group, a cyclohexanecarbonyl group and the like.

Examples of the acyloxy group include a group obtained by bonding an oxy group (—O—) to the above acyl group.

Examples of the alkoxycarbonyl group include a group obtained by bonding a carbonyl group (—CO—) to the above alkoxy group.

Examples of the halogen atom include a fluorine atom, a chlorine atom, a bromine atom and the like.

Preferably, $R^{D1}$ and $R^{D2}$ each independently represent an alkyl group having 1 to 8 carbon atoms, a cycloalkyl group having 3 to 10 carbon atoms, an alkoxy group having 1 to 6 carbon atoms, an acyl group having 2 to 4 carbon atoms, an acyloxy group having 2 to 4 carbon atoms, an alkoxycarbonyl group having 2 to 4 carbon atoms, a nitro group or a halogen atom.

Preferably, m' and n' are each independently an integer of 0 to 2, and more preferably 0, and when m' is 2 or more, a plurality of $R^{D1}$ may be the same or different, and when n' is 2 or more, a plurality of $R^{D2}$ may be the same or different.

More specifically, the following salts are exemplified.

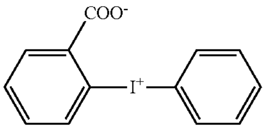

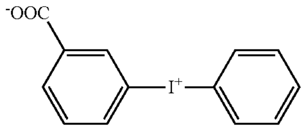

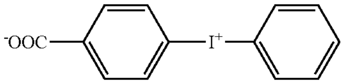

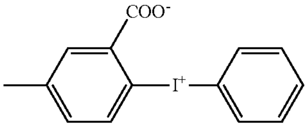

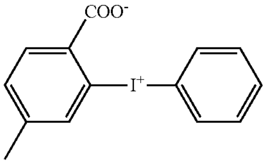

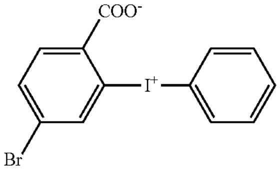

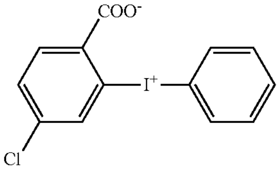

-continued

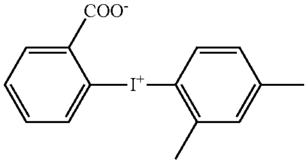

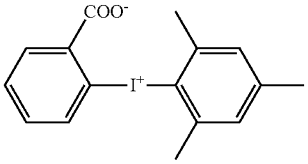

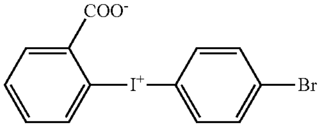

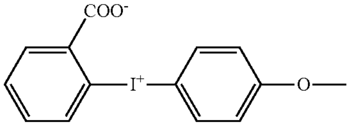

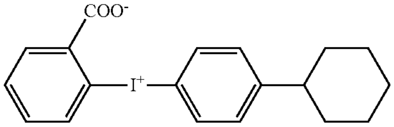

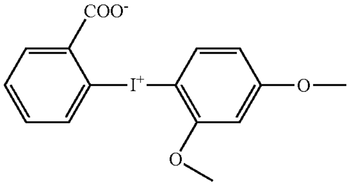

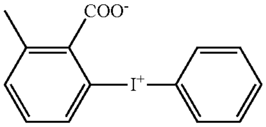

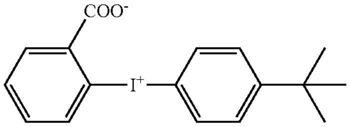

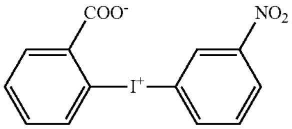

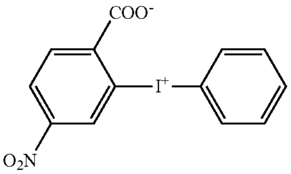

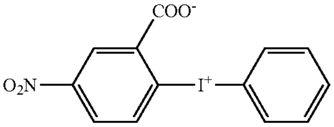

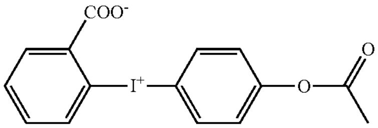

-continued

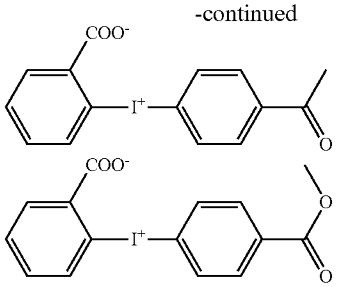

Examples of the basic nitrogen-containing organic compound include amine and an ammonium salt. Examples of the amine include an aliphatic amine and an aromatic amine. Examples of the aliphatic amine include a primary amine, a secondary amine and a tertiary amine.

Examples of the amine include 1-naphthylamine, 2-naphthylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl)propane, 1,2-di(4-pyridyloxy)ethane, di(2-pyridyl)ketone, 4,4'-dipyridyl sulfide, 4,4'-dipyridyl disulfide, 2,2'-dipyridylamine, 2,2'-dipicolylamine, bipyridine and the like, preferably an aromatic amine such as diisopropylaniline, and more preferably 2,6-diisopropylaniline.

Examples of the ammonium salt include tetramethylammonium hydroxide, tetraisopropylammonium hydroxide, tetrabutylammonium hydroxide, tetrahexylammonium hydroxide, tetraoctylammonium hydroxide, phenyltrimethylammonium hydroxide, 3-(trifluoromethyl)phenyltrimethylammonium hydroxide, tetra-n-butylammonium salicylate and choline.

<Other Components>

The resist composition of the present disclosure may also include components other than the components mentioned above (hereinafter sometimes referred to as "other components (F)"). The other components (F) are not particularly limited and it is possible to use various additives known in the resist field, for example, sensitizers, dissolution inhibitors, surfactants, stabilizers and dyes.

<Preparation of Resist Composition>

The resist composition of the present disclosure can be prepared by mixing a carboxylate represented by formula (I) or a resin including a structural unit represented by formula (I-1), and if necessary, a resin (A), an acid generator (B), resins other than the resin (A), a solvent (E), a quencher (C) and other components (F). The order of mixing these components is any order and is not particularly limited. It is possible to select, as the temperature during mixing, appropriate temperature from 10 to 40° C., according to the type of the resin, the solubility in the solvent (E) of the resin and the like. It is possible to select, as the mixing time, appropriate time from 0.5 to 24 hours according to the mixing temperature. The mixing means is not particularly limited and it is possible to use mixing with stirring.

After mixing the respective components, the mixture is preferably filtered through a filter having a pore diameter of about 0.003 to 0.2 μm.

<Method for Producing Resist Pattern>

The method for producing a resist pattern of the present disclosure include:

(1) a step of applying the resist composition of the present disclosure on a substrate, (2) a step of drying the applied composition to form a composition layer, (3) a step of exposing the composition layer, (4) a step of heating the exposed composition layer, and (5) a step of developing the heated composition layer.

The resist composition can be usually applied on a substrate using a conventionally used apparatus, such as a spin coater. Examples of the substrate include inorganic substrates such as a silicon wafer, and organic substrates in which a resist film is formed on the surface. Before applying the resist composition, the substrate may be washed, and an organic antireflection film may be formed on the substrate.

The solvent is removed by drying the applied composition to form a composition layer. Drying is performed by evaporating the solvent using a heating device such as a hot plate (so-called "prebake"), or a decompression device. The heating temperature is preferably 50 to 200° C. and the heating time is preferably 10 to 180 seconds. The pressure during drying under reduced pressure is preferably about 1 to $1.0\times10^5$ Pa.

The composition layer thus obtained is usually exposed using an aligner. The aligner may be a liquid immersion aligner. It is possible to use, as an exposure source, various exposure sources, for example, exposure sources capable of emitting laser beam in an ultraviolet region such as KrF excimer laser (wavelength of 248 nm), ArF excimer laser (wavelength of 193 nm) and $F_2$ excimer laser (wavelength of 157 nm), an exposure source capable of emitting harmonic laser beam in a far-ultraviolet or vacuum ultra violet region by wavelength-converting laser beam from a solid-state laser source (YAG or semiconductor laser), an exposure source capable of emitting electron beam or extreme ultraviolet light (EUV) and the like. In the present specification, such exposure to radiation is sometimes collectively referred to as "exposure". The exposure is usually performed through a mask corresponding to a pattern to be required. When electron beam is used as the exposure source, exposure may be performed by direct writing without using the mask.

The exposed composition layer is subjected to a heat treatment (so-called "post-exposure bake") to promote the deprotection reaction in an acid-labile group. The heating temperature is usually about 50 to 200° C., and preferably about 70 to 150° C. It is also possible to perform a chemical treatment (silylation) which adjusts the hydrophilicity or hydrophobicity of the resin on a surface side of the composition after heating. Before performing the development, the steps of application of the resist composition, drying, exposure and heating may be repeatedly performed on the exposed composition layer.

The heated composition layer is usually developed with a developing solution using a development apparatus. Examples of the developing method include a dipping method, a paddle method, a spraying method, a dynamic dispensing method and the like. The developing temperature is preferably, for example, 5 to 60° C. and the developing time is preferably, for example, 5 to 300 seconds. It is possible to produce a positive resist pattern or negative resist pattern by selecting the type of the developing solution as follows.

When the positive resist pattern is produced from the resist composition of the present disclosure, an alkaline developing solution is used as the developing solution. The alkaline developing solution may be various aqueous alkaline solutions used in this field. Examples thereof include aqueous solutions of tetramethylammonium hydroxide and (2-hydroxyethyl)trimethylammonium hydroxide (commonly known as choline). The surfactant may be contained in the alkaline developing solution.

It is preferable that the developed resist pattern is washed with ultrapure water and then water remaining on the substrate and the pattern is removed.

When the negative resist pattern is produced from the resist composition of the present disclosure, a developing solution containing an organic solvent (hereinafter sometimes referred to as "organic developing solution") is used as the developing solution.

Examples of the organic solvent contained in the organic developing solution include ketone solvents such as 2-hexanone and 2-heptanone; glycol ether ester solvents such as propylene glycol monomethyl ether acetate; ester solvents such as butyl acetate; glycol ether solvents such as propylene glycol monomethyl ether; amide solvents such as N,N-dimethylacetamide; and aromatic hydrocarbon solvents such as anisole.

The content of the organic solvent in the organic developing solution is preferably 90% by mass or more and 100% by mass or less, more preferably 95% by mass or more and 100% by mass or less, and still more preferably the organic developing solution is substantially composed of the organic solvent.

Particularly, the organic developing solution is preferably a developing solution containing butyl acetate and/or 2-heptanone. The total content of butyl acetate and 2-heptanone in the organic developing solution is preferably 50% by mass or more and 100% by mass or less, more preferably 90% by mass or more and 100% by mass or less, and still more preferably the organic developing solution is substantially composed of butyl acetate and/or 2-heptanone.

The surfactant may be contained in the organic developing solution. A trace amount of water may be contained in the organic developing solution.

During development, the development may be stopped by replacing by a solvent with the type different from that of the organic developing solution.

The developed resist pattern is preferably washed with a rinsing solution. The rinsing solution is not particularly limited as long as it does not dissolve the resist pattern, and it is possible to use a solution containing an ordinary organic solvent which is preferably an alcohol solvent or an ester solvent.

After washing, the rinsing solution remaining on the substrate and the pattern is preferably removed.

<Applications>

The resist composition of the present disclosure is suitable as a resist composition for exposure of KrF excimer laser, a resist composition for exposure of ArF excimer laser, a resist composition for exposure of electron beam (EB) or a resist composition for exposure of EUV, particularly a resist composition for exposure of electron beam (EB) or a resist composition for exposure of EUV, and the resist composition is useful for fine processing of semiconductors.

EXAMPLES

The present disclosure will be described more specifically by way of Examples. Percentages and part expressing the contents or amounts used in the Examples are by mass unless otherwise specified.

The weight-average molecular weight is a value determined by gel permeation chromatography. Analysis conditions of gel permeation chromatography are as follows.

Column: TSKgel Multipore IIXL-M×3+guardcolumn (manufactured by TOSOH CORPORATION)

Eluent: tetrahydrofuran

Flow rate: 1.0 mL/min

Detector: RI detector

Column temperature: 40° C.

Injection amount: 100 μl

Molecular weight standards: polystyrene standard (manufactured by TOSOH CORPORATION)

Structures of compounds were confirmed by measuring a molecular ion peak using mass spectrometry (LC is Model 1100, manufactured by Agilent Technologies, Inc., and MASS is Model LC/MSD, manufactured by Agilent Technologies, Inc.). The value of this molecular ion peak in the following Examples is indicated by "MASS".

Example 1: Synthesis of Salt Represented by Formula (I-244)

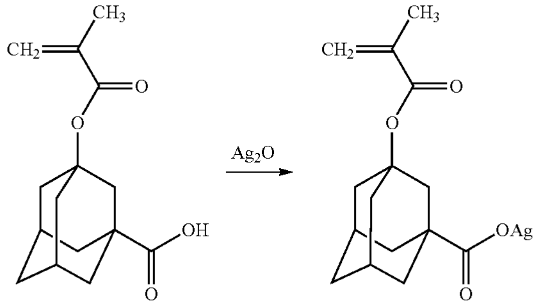

(I-1-a) (I-1-b)

5.28 part of a compound represented by formula (I-1-a), 30 part of acetonitrile and 2.32 part of silver oxide were mixed, followed by stirring at 23° C. for 4 hours and further filtration. To the filter residue thus obtained, 20 part of tert-butyl methyl ether was added, followed by stirring at 23° C. for 30 minutes and further filtration to obtain 5.86 part of a salt represented by formula (I-1-b).

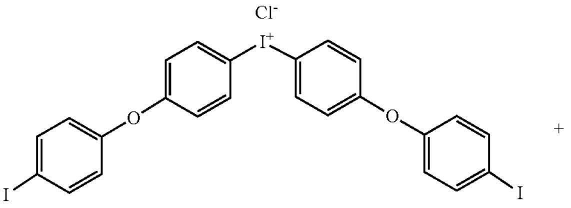

(I-244-c)

-continued

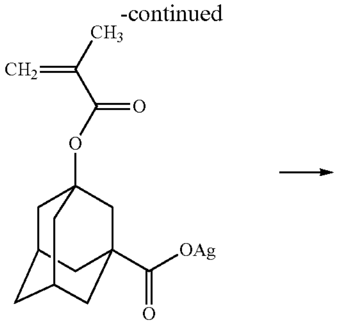

(I-1-b)

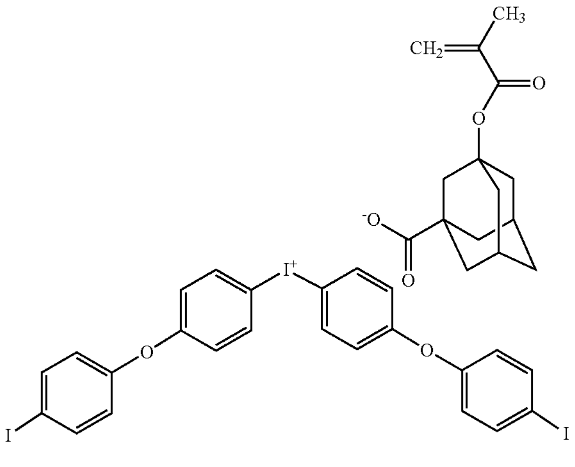

(I-244)

7.53 part of a salt represented by formula (I-244-c), 3.71 part of a salt represented by formula (I-1-b), 20 part of methanol and 10 part of ion-exchanged water were mixed, followed by stirring at 23° C. for 30 minutes. To the mixture thus obtained, 0.44 part of potassium carbonate was added, followed by stirring at 23° C. for 5 hours. To the reaction product thus obtained, 60 part of chloroform and 10 part of ion-exchanged water were added, and after stirring at 23° C. for 30 minutes, the organic layer was isolated through separation. To the organic layer thus obtained, 30 part of ion-exchanged water was added, and after stirring at 23° C. for 30 minutes, the organic layer was isolated through separation. This water washing operation was repeated seven times. The organic layer thus obtained was concentrated and then 30 part of tert-butyl methyl ether was added to the concentrated residue, and after stirring at 23° C. for 30 minutes, the supernatant was removed, followed by concentration to obtain 8.41 part of a salt represented by formula (I-244).

MASS (ESI (+) Spectrum): $M^+$ 716.8

MASS (ESI (−) Spectrum): $M^-$ 263.1

Example 2: Synthesis of Salt Represented by Formula (I-487)

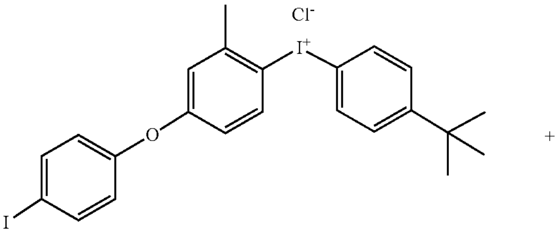

(I-487-c)

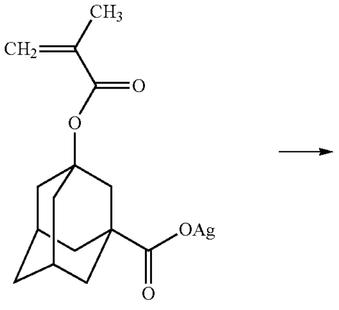

(I-1-b)

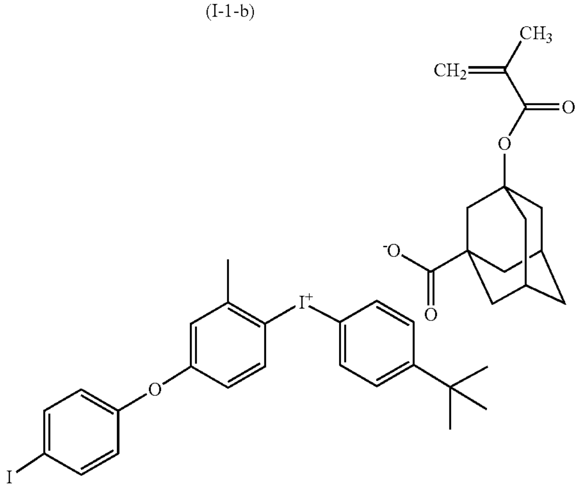

(I-487)

6.05 part of a salt represented by formula (I-487-c), 3.71 part of a salt represented by formula (I-1-b), 20 part of methanol and 10 part of ion-exchanged water were mixed, followed by stirring at 23° C. for 30 minutes. To the mixture thus obtained, 0.44 part of potassium carbonate was added, followed by stirring at 23° C. for 5 hours. To the reaction product thus obtained, 60 part of chloroform and 10 part of ion-exchanged water were added, and after stirring at 23° C. for 30 minutes, the organic layer was isolated through separation. To the organic layer thus obtained, 30 part of ion-exchanged water was added, and after stirring at 23° C. for 30 minutes, the organic layer was isolated through separation. This water washing operation was repeated seven times. The organic layer thus obtained was concentrated and then 30 part of tert-butyl methyl ether was added to the concentrated residue, and after stirring at 23° C. for 30 minutes, the supernatant was removed, followed by concentration to obtain 6.62 part of a salt represented by formula (I-487).

MASS (ESI (+) Spectrum): $M^+$ 569.0

MASS (ESI (−) Spectrum): $M^-$ 263.1

Example 3: Synthesis of Salt Represented by Formula (I-489)

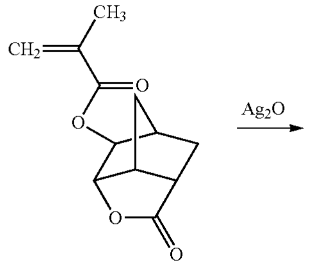

(I-489-a)

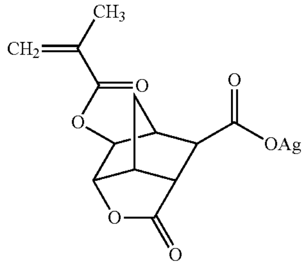

(I-489-b)

5.32 part of a compound represented by formula (I-489-a), 30 part of acetonitrile and 2.32 part of silver oxide were mixed, followed by stirring at 23° C. for 4 hours and further filtration. To the filter residue thus obtained, 20 part of tert-butyl methyl ether was added, followed by stirring at 23° C. for 30 minutes and further filtration to obtain 5.61 part of a salt represented by formula (I-489-b).

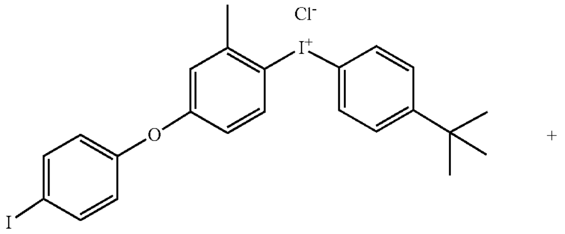

(I-487-c)

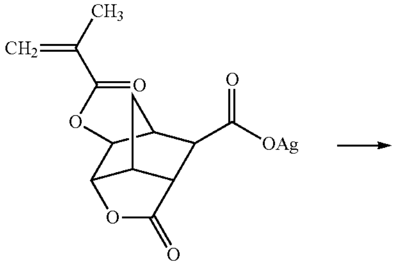

(I-489-b)

-continued

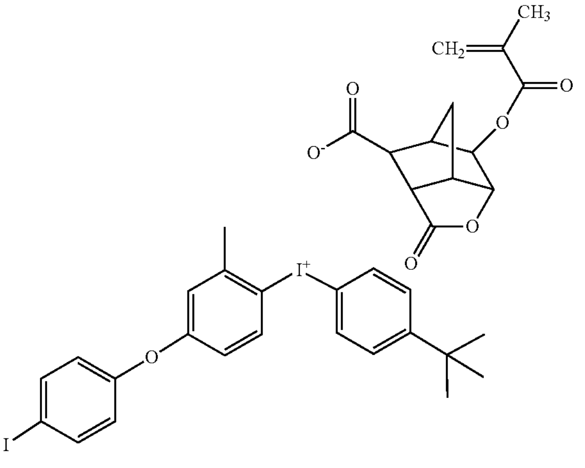

(I-489)

6.05 part of a salt represented by formula (I-487-c), 3.73 part of a salt represented by formula (I-489-b), 20 part of methanol and 10 part of ion-exchanged water were mixed, followed by stirring at 23° C. for 30 minutes. To the mixture thus obtained, 0.44 part of potassium carbonate was added, followed by stirring at 23° C. for 5 hours. To the reaction product thus obtained, 60 part of chloroform and 10 part of ion-exchanged water were added, and after stirring at 23° C. for 30 minutes, the organic layer was isolated through separation. To the organic layer thus obtained, 30 part of ion-exchanged water was added, and after stirring at 23° C. for 30 minutes, the organic layer was isolated through separation. This water washing operation was repeated seven times. The organic layer thus obtained was concentrated and then 30 part of tert-butyl methyl ether was added to the concentrated residue, and after stirring at 23° C. for 30 minutes, the supernatant was removed, followed by concentration to obtain 6.24 part of a salt represented by formula (I-489).

MASS (ESI (+) Spectrum): $M^+$ 569.0

MASS (ESI (−) Spectrum): $M^-$ 265.1

Example 4: Synthesis of Salt Represented by Formula (I-508)

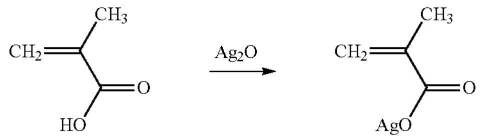

(I-508-a) (I-508-b)

1.72 part of a compound represented by formula (I-508-a), 30 part of acetonitrile and 2.32 part of silver oxide were mixed, followed by stirring at 23° C. for 4 hours and further filtration. To the filter residue thus obtained, 20 part of tert-butyl methyl ether was added, followed by stirring at 23° C. for 30 minutes and further filtration to obtain 3.22 part of a salt represented by formula (I-508-b).

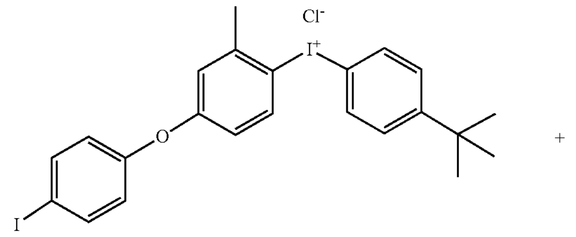

(I-487-c)

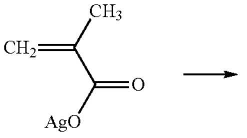

(I-508-b)

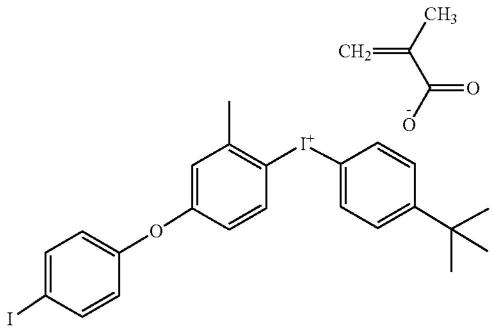

(I-508)

6.05 part of a salt represented by formula (I-487-c), 1.93 part of a salt represented by formula (I-508-b), 20 part of methanol and 10 part of ion-exchanged water were mixed, followed by stirring at 23° C. for 30 minutes. To the mixture thus obtained, 0.44 part of potassium carbonate was added, followed by stirring at 23° C. for 5 hours. To the reaction product thus obtained, 60 part of chloroform and 10 part of ion-exchanged water were added, and after stirring at 23° C. for 30 minutes, the organic layer was isolated through separation. To the organic layer thus obtained, 30 part of ion-exchanged water was added, and after stirring at 23° C. for 30 minutes, the organic layer was isolated through separation. This water washing operation was repeated seven times. The organic layer thus obtained was concentrated and then 30 part of tert-butyl methyl ether was added to the concentrated residue, and after stirring at 23° C. for 30 minutes, the supernatant was removed, followed by concentration to obtain 5.08 part of a salt represented by formula (I-508).

MASS (ESI (+) Spectrum): $M^+$ 569.0

MASS (ESI (−) Spectrum): $M^-$ 85.0

Example 5: Synthesis of Salt Represented by Formula (I-865)

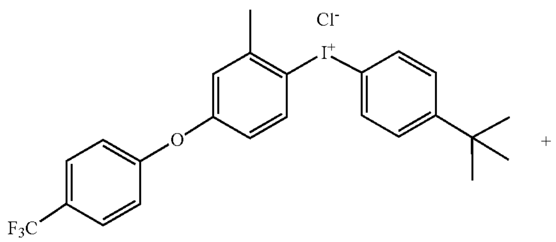

(I-865-c)

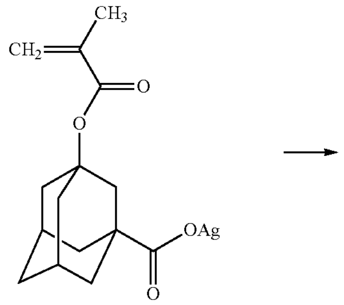

(I-1-b)

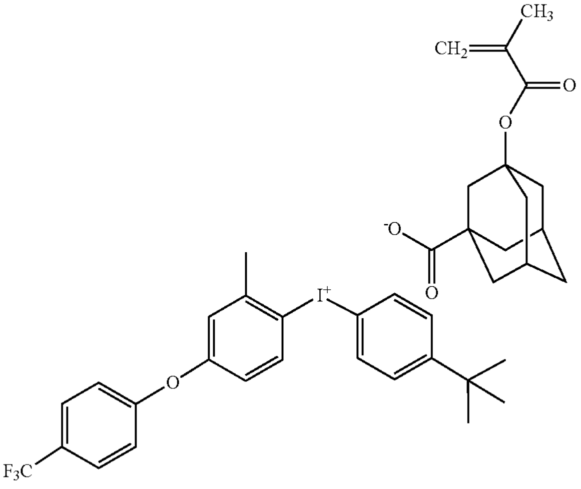

(I-865)

5.47 part of a salt represented by formula (I-865-c), 3.71 part of a salt represented by formula (I-1-b), 20 part of methanol and 10 part of ion-exchanged water were mixed, followed by stirring at 23° C. for 30 minutes. To the mixture thus obtained, 0.44 part of potassium carbonate was added, followed by stirring at 23° C. for 5 hours. To the reaction product thus obtained, 60 part of chloroform and 10 part of ion-exchanged water were added, and after stirring at 23° C. for 30 minutes, the organic layer was isolated through separation. To the organic layer thus obtained, 30 part of ion-exchanged water was added, and after stirring at 23° C. for 30 minutes, the organic layer was isolated through separation. This water washing operation was repeated seven times. The organic layer thus obtained was concentrated and then 30 part of tert-butyl methyl ether was added to the concentrated residue, and after stirring at 23° C. for 30 minutes, the supernatant was removed, followed by concentration to obtain 6.49 part of a salt represented by formula (I-865).

MASS (ESI (+) Spectrum): $M^+$ 511.1

MASS (ESI (−) Spectrum): $M^-$ 263.1

Example 6: Synthesis of Salt Represented by Formula (I-1108)

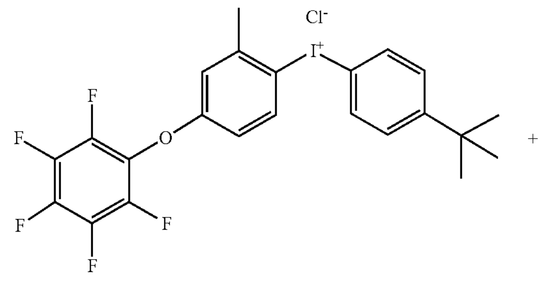

(I-1108-c)

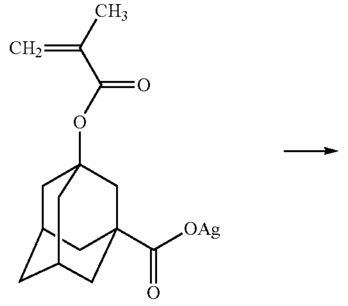

(I-1-b)

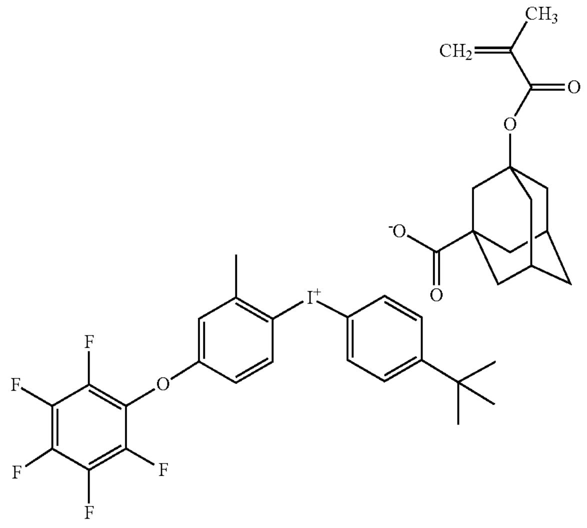

(I-1108)

5.69 part of a salt represented by formula (I-1108-c), 3.71 part of a salt represented by formula (I-1-b), 20 part of methanol and 10 part of ion-exchanged water were mixed, followed by stirring at 23° C. for 30 minutes. To the mixture thus obtained, 0.44 part of potassium carbonate was added, followed by stirring at 23° C. for 5 hours. To the reaction product thus obtained, 60 part of chloroform and 10 part of ion-exchanged water were added, and after stirring at 23° C. for 30 minutes, the organic layer was isolated through separation. To the organic layer thus obtained, 30 part of ion-exchanged water was added, and after stirring at 23° C. for 30 minutes, the organic layer was isolated through separation. This water washing operation was repeated seven times. The organic layer thus obtained was concentrated and then 30 part of tert-butyl methyl ether was added to the concentrated residue, and after stirring at 23° C. for 30 minutes, the supernatant was removed, followed by concentration to obtain 6.53 part of a salt represented by formula (I-1108).

MASS (ESI (+) Spectrum): $M^+$ 533.0

MASS (ESI (−) Spectrum): $M^-$ 263.1

Example 7: Synthesis of Salt Represented by Formula (I-1378)

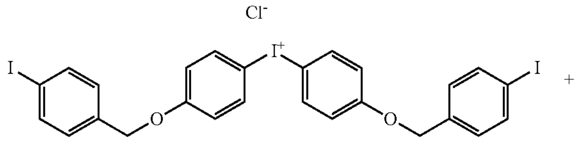

(I-1378-c)

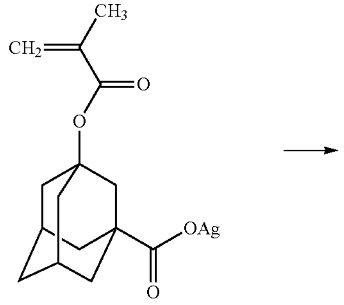

(I-1-b)

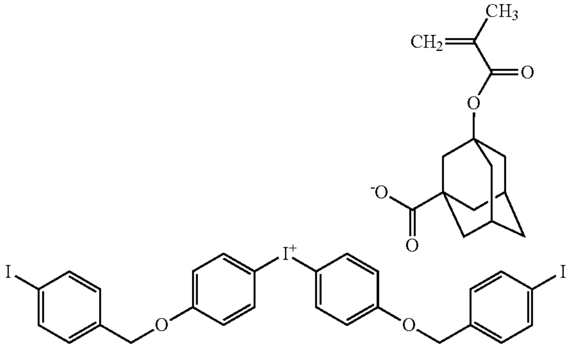

(I-1378)

7.81 part of a salt represented by formula (I-1378-c), 3.71 part of a salt represented by formula (I-1-b), 20 part of methanol and 10 part of ion-exchanged water were mixed, followed by stirring at 23° C. for 30 minutes. To the mixture thus obtained, 0.44 part of potassium carbonate was added, followed by stirring at 23° C. for 5 hours. To the reaction product thus obtained, 60 part of chloroform and 10 part of ion-exchanged water were added, and after stirring at 23° C. for 30 minutes, the organic layer was isolated through separation. To the organic layer thus obtained, 30 part of ion-exchanged water was added, and after stirring at 23° C. for 30 minutes, the organic layer was isolated through separation. This water washing operation was repeated seven times. The organic layer thus obtained was concentrated and then 30 part of tert-butyl methyl ether was added to the concentrated residue, and after stirring at 23° C. for 30 minutes, the supernatant was removed, followed by concentration to obtain 9.01 part of a salt represented by formula (I-1378).

MASS (ESI (+) Spectrum): $M^+$ 744.9

MASS (ESI (−) Spectrum): $M^-$ 263.1

Example 8: Synthesis of Salt Represented by Formula (I-1621)

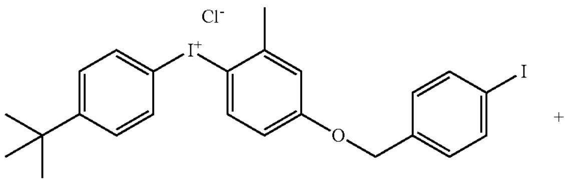

(I-1621-c)

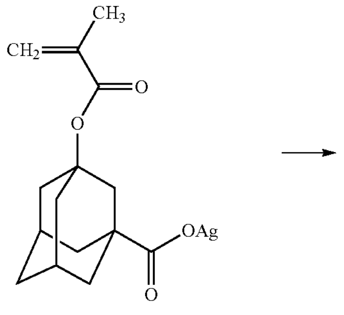

(I-1-b)

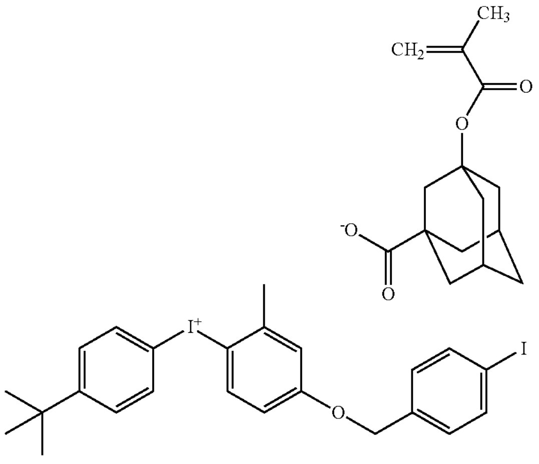

(I-1621)

6.19 part of a salt represented by formula (I-1621-c), 3.71 part of a salt represented by formula (I-1-b), 20 part of methanol and 10 part of ion-exchanged water were mixed, followed by stirring at 23° C. for 30 minutes. To the mixture thus obtained, 0.44 part of potassium carbonate was added, followed by stirring at 23° C. for 5 hours. To the reaction product thus obtained, 60 part of chloroform and 10 part of ion-exchanged water were added, and after stirring at 23° C. for 30 minutes, the organic layer was isolated through separation. To the organic layer thus obtained, 30 part of ion-exchanged water was added, and after stirring at 23° C. for 30 minutes, the organic layer was isolated through separation. This water washing operation was repeated seven times. The organic layer thus obtained was concentrated and then 30 part of tert-butyl methyl ether was added to the concentrated residue, and after stirring at 23° C. for 30 minutes, the supernatant was removed, followed by concentration to obtain 7.36 part of a salt represented by formula (I-1621).

MASS (ESI (+) Spectrum): $M^+$ 583.0

MASS (ESI (−) Spectrum): $M^-$ 263.1

Example 9: Synthesis of Salt Represented by Formula (I-2161)

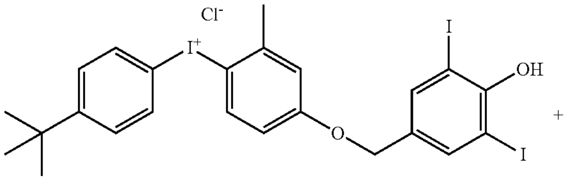

(I-2161-c)

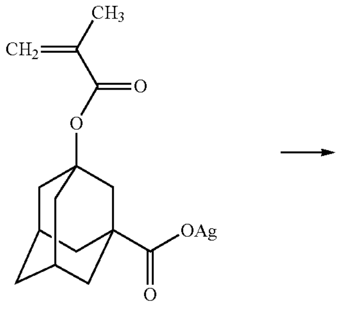

(I-1-b)

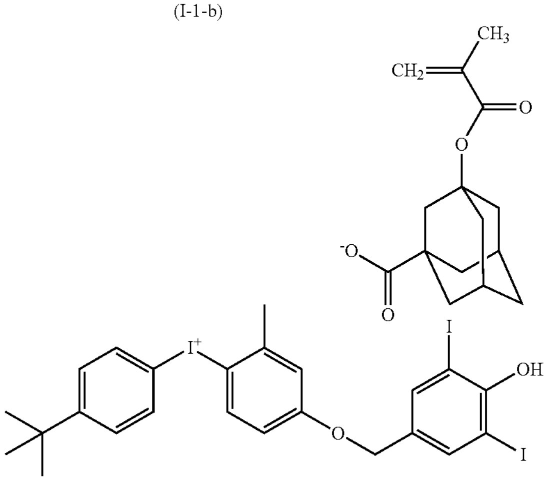

(I-2161)

7.61 part of a salt represented by formula (I-2161-c), 3.71 part of a salt represented by formula (I-1-b), 20 part of methanol and 10 part of ion-exchanged water were mixed, followed by stirring at 23° C. for 30 minutes. To the mixture thus obtained, 0.44 part of potassium carbonate was added, followed by stirring at 23° C. for 5 hours. To the reaction product thus obtained, 60 part of chloroform and 10 part of ion-exchanged water were added, and after stirring at 23° C. for 30 minutes, the organic layer was isolated through separation. To the organic layer thus obtained, 30 part of ion-exchanged water was added, and after stirring at 23° C. for 30 minutes, the organic layer was isolated through separation. This water washing operation was repeated seven times. The organic layer thus obtained was concentrated and then 30 part of tert-butyl methyl ether was added to the concentrated residue, and after stirring at 23° C. for 30 minutes, the supernatant was removed, followed by concentration to obtain 8.29 part of a salt represented by formula (I-2161).

MASS (ESI (+) Spectrum): $M^+$ 724.9

MASS (ESI (−) Spectrum): $M^-$ 263.1

Example 10: Synthesis of Salt Represented by Formula (I-1642)

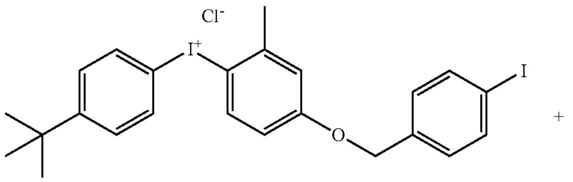

(I-1621-c)

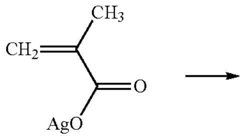

(I-508-b)

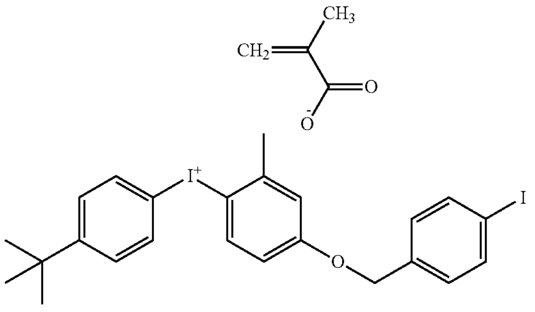

(I-1642)

6.19 part of a salt represented by formula (I-1642-c), 1.93 part of a salt represented by formula (I-508-b), 20 part of methanol and 10 part of ion-exchanged water were mixed, followed by stirring at 23° C. for 30 minutes. To the mixture thus obtained, 0.44 part of potassium carbonate was added, followed by stirring at 23° C. for 5 hours. To the reaction product thus obtained, 60 part of chloroform and 10 part of ion-exchanged water were added, and after stirring at 23° C. for 30 minutes, the organic layer was isolated through separation. To the organic layer thus obtained, 30 part of ion-exchanged water was added, and after stirring at 23° C. for 30 minutes, the organic layer was isolated through separation. This water washing operation was repeated seven times. The organic layer thus obtained was concentrated and then 30 part of tert-butyl methyl ether was added to the concentrated residue, and after stirring at 23° C. for 30 minutes, the supernatant was removed, followed by concentration to obtain 8.29 part of a salt represented by formula (I-1642).

MASS (ESI (+) Spectrum): $M^+$ 583.0

MASS (ESI (−) Spectrum): $M^-$ 85.0

Example 11: Synthesis of Salt Represented by Formula (I-2188)

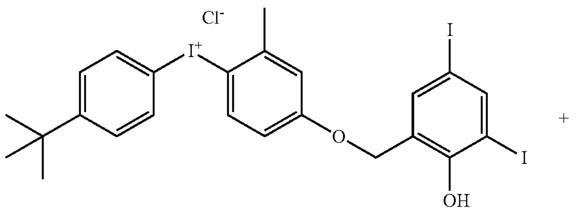

(I-2188-c)

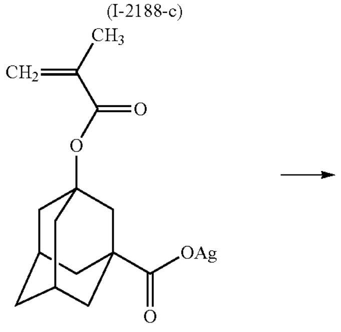

(I-1-b)

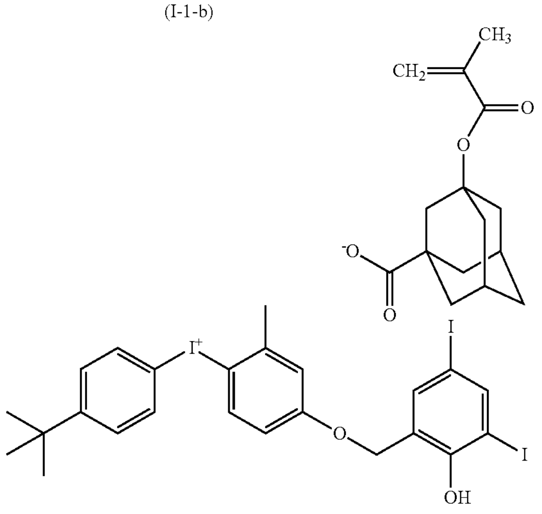

(I-2188)

7.61 part of a salt represented by formula (I-2188-c), 3.71 part of a salt represented by formula (I-1-b), 20 part of methanol and 10 part of ion-exchanged water were mixed, followed by stirring at 23° C. for 30 minutes. To the mixture thus obtained, 0.44 part of potassium carbonate was added, followed by stirring at 23° C. for 5 hours. To the reaction product thus obtained, 60 part of chloroform and 10 part of ion-exchanged water were added, and after stirring at 23° C. for 30 minutes, the organic layer was isolated through separation. To the organic layer thus obtained, 30 part of ion-exchanged water was added, and after stirring at 23° C. for 30 minutes, the organic layer was isolated through separation. This water washing operation was repeated seven times. The organic layer thus obtained was concentrated and then 30 part of tert-butyl methyl ether was added to the concentrated residue, and after stirring at 23° C. for 30 minutes, the supernatant was removed, followed by concentration to obtain 8.18 part of a salt represented by formula (I-2188).

MASS (ESI (+) Spectrum): $M^+$ 724.9
MASS (ESI (−) Spectrum): $M^-$ 263.1
Synthesis of Resin
Compounds (monomers) used in synthesis of a resin (A) are shown below. Hereinafter, these compounds are referred to as "monomer (a1-1-3)" according to the formula number.
(a1-1-3)
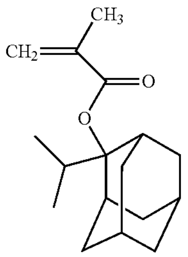
(a1-2-6)
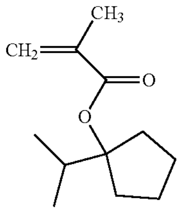
(a2-1-1)
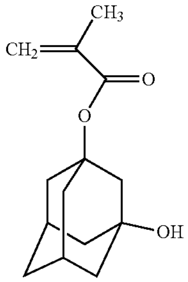
(a3-4-2)
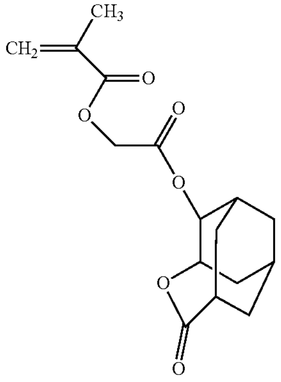
(a4-0-12)
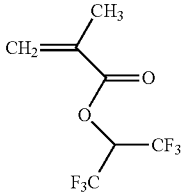
-continued
(a5-1-1)
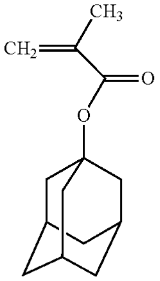
(I-244)
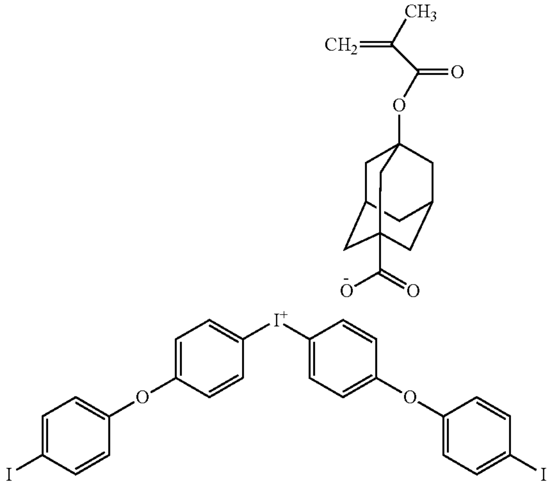
(I-487)
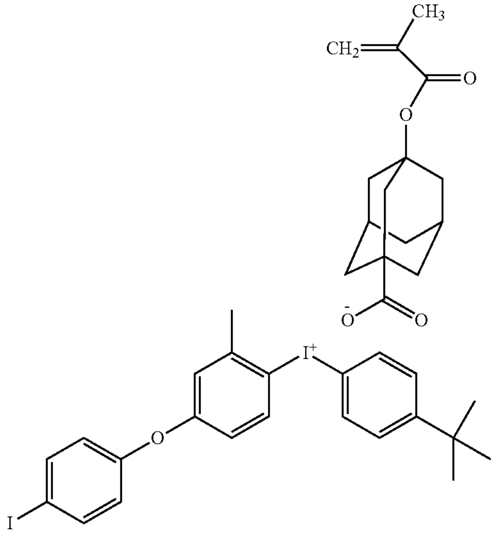

-continued
(I-489)
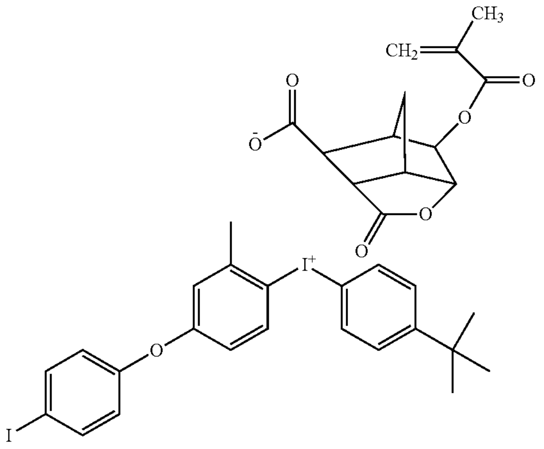
(I-508)
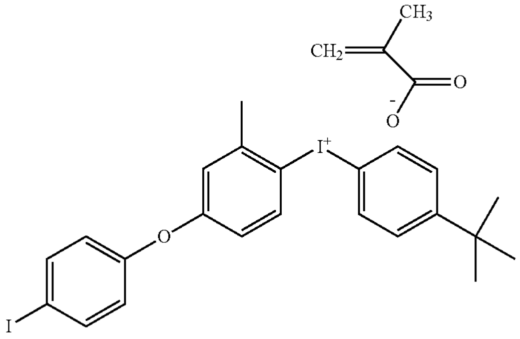
(I-865)
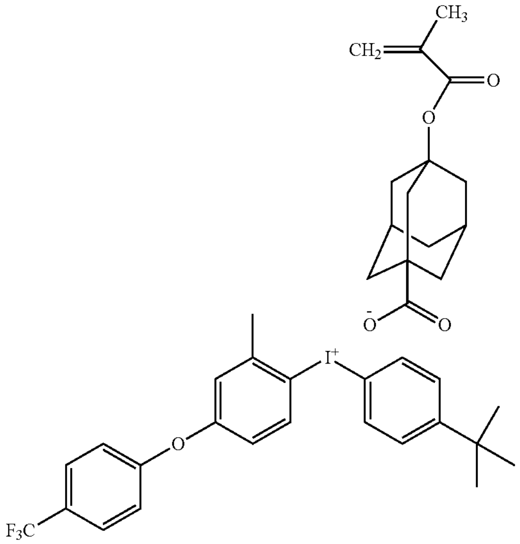
-continued
(I-1108)
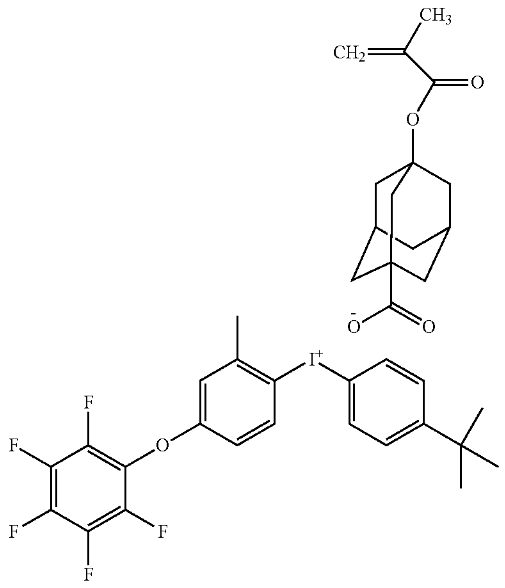
(I-1378 )
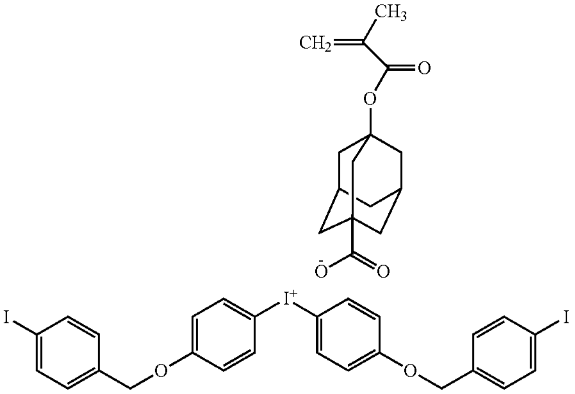
(I-1621)
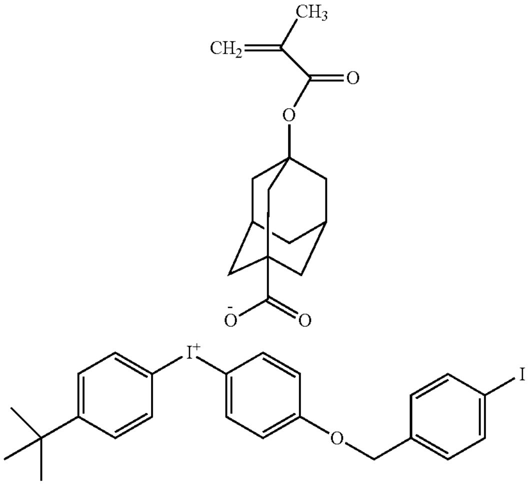

-continued (I-2161)

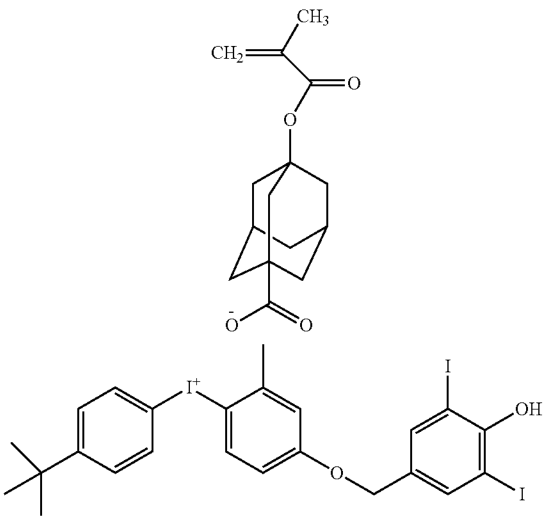

(I-1642)

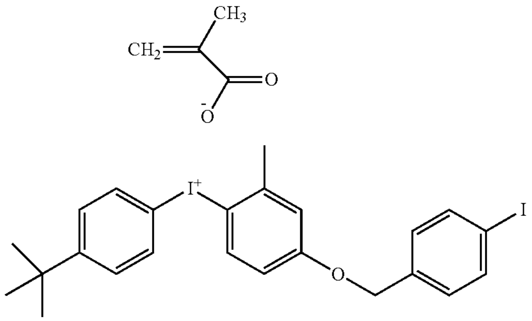

(IX-1)

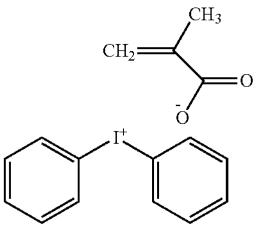

-continued (I-2188)

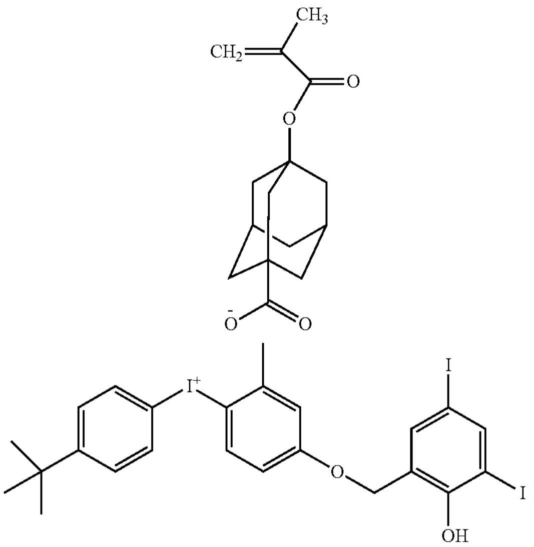

Example 12 [Synthesis of Resin A1]

Using a monomer (a1-1-3), a monomer (a1-2-6), a monomer (a2-1-1), a monomer (a3-4-2) and a monomer (I-244) as monomers, these monomers were mixed in a molar ratio of 45:14:2.5:33.5:5 [monomer (a1-1-3):monomer (a1-2-6): monomer (a2-1-1):monomer (a3-4-2): monomer (I-244)], and then this monomer mixture was mixed with methyl isobutyl ketone in the amount of 1.5 mass times the total mass of all monomers. To the mixture thus obtained, azobisisobutyronitrile and azobis(2,4-dimethylvaleronitrile) as initiators were added in the amounts of 1 mol % and 3 mol % based on the amount of all monomers, followed by heating at 73° C. for about 5 hours. Thereafter, the polymerization reaction solution was poured into a large amount of n-heptane to precipitate a resin, followed by filtration and recovery to obtain a resin A1 having a weight-average molecular weight of about $7.6\times10^3$ in a yield of 63%. This resin A1 has the following structural units.

A1

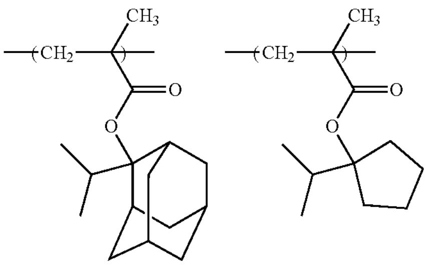

-continued

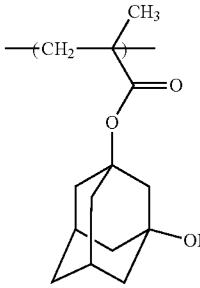

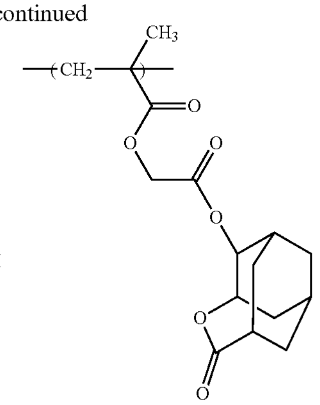

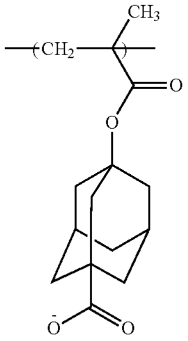

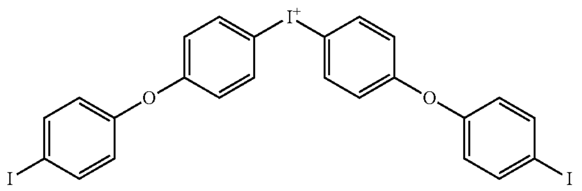

Example 13 [Synthesis of Resin A2]

Using a monomer (a1-1-3), a monomer (a1-2-6), a monomer (a2-1-1), a monomer (a3-4-2) and a monomer (I-487) as monomers, these monomers were mixed in a molar ratio of 45:14:2.5:33.5:5 [monomer (a1-1-3):monomer (a1-2-6): monomer (a2-1-1):monomer (a3-4-2):monomer (I-487)], and then this monomer mixture was mixed with methyl isobutyl ketone in the amount of 1.5 mass times the total mass of all monomers. To the mixture thus obtained, azobisisobutyronitrile and azobis(2,4-dimethylvaleronitrile) as initiators were added in the amounts of 1 mol % and 3 mol % based on the amount of all monomers, followed by heating at 73° C. for about 5 hours. Thereafter, the polymerization reaction solution was poured into a large amount of n-heptane to precipitate a resin, followed by filtration and recovery to obtain a resin A2 having a weight-average molecular weight of about $7.8\times10^3$ in a yield of 68%. This resin A2 has the following structural units.

A2

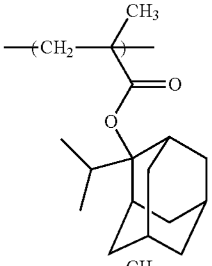

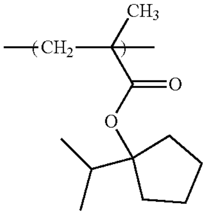

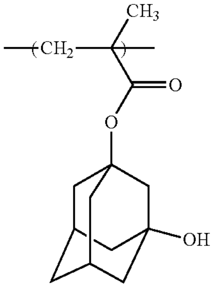

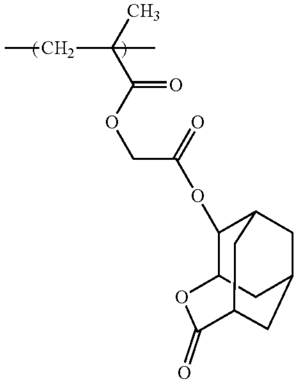

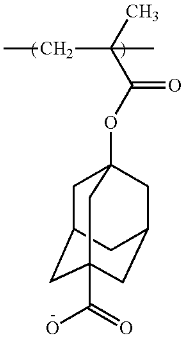

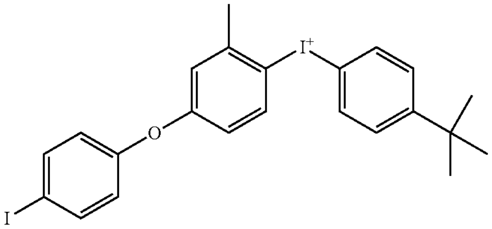

Example 14 [Synthesis of Resin A3]

Using a monomer (a1-1-3), a monomer (a1-2-6), a monomer (a2-1-1), a monomer (a3-4-2) and a monomer (I-489) as monomers, these monomers were mixed in a molar ratio of 45:14:2.5:33.5:5 [monomer (a1-1-3):monomer (a1-2-6): monomer (a2-1-1):monomer (a3-4-2):monomer (I-489)], and then this monomer mixture was mixed with methyl isobutyl ketone in the amount of 1.5 mass times the total mass of all monomers. To the mixture thus obtained, azobisisobutyronitrile and azobis(2,4-dimethylvaleronitrile) as initiators were added in the amounts of 1 mol % and 3 mol % based on the amount of all monomers, followed by heating at 73° C. for about 5 hours. Thereafter, the polymerization reaction solution was poured into a large amount of n-heptane to precipitate a resin, followed by filtration and recovery to obtain a resin A3 having a weight-average molecular weight of about $7.6\times10^3$ in a yield of 69%. This resin A3 has the following structural units.

A3

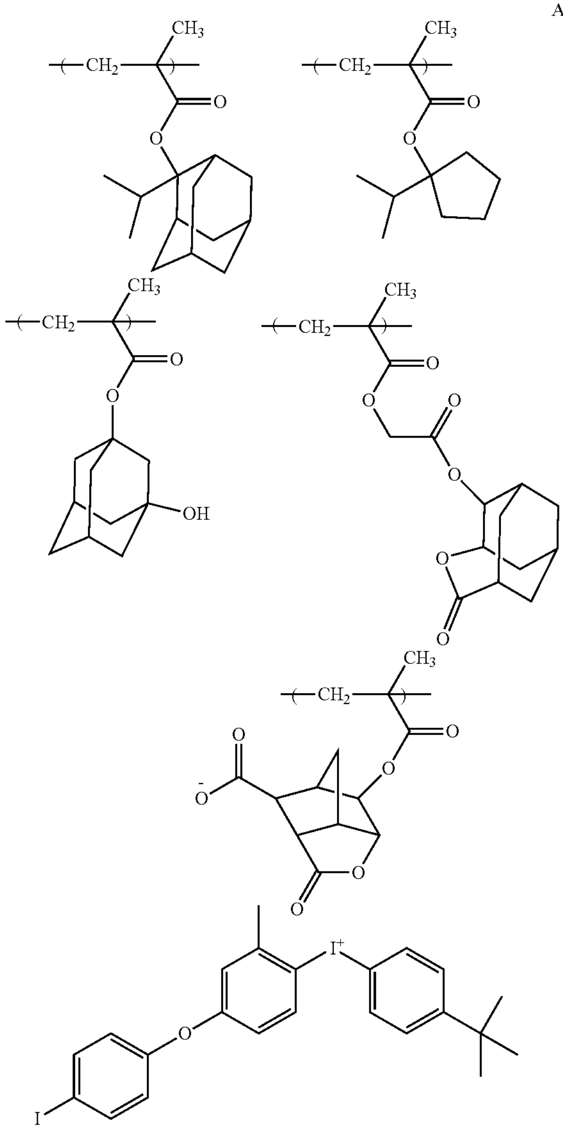

Example 15 [Synthesis of Resin A4]

Using a monomer (a1-1-3), a monomer (a1-2-6), a monomer (a2-1-1), a monomer (a3-4-2) and a monomer (I-508) as monomers, these monomers were mixed in a molar ratio of 45:14:2.5:33.5:5 [monomer (a1-1-3):monomer (a1-2-6): monomer (a2-1-1):monomer (a3-4-2):monomer (I-508)], and then this monomer mixture was mixed with methyl isobutyl ketone in the amount of 1.5 mass times the total mass of all monomers. To the mixture thus obtained, azobisisobutyronitrile and azobis(2,4-dimethylvaleronitrile) as initiators were added in the amounts of 1 mol % and 3 mol % based on the amount of all monomers, followed by heating at 73° C. for about 5 hours. Thereafter, the polymerization reaction solution was poured into a large amount of n-heptane to precipitate a resin, followed by filtration and recovery to obtain a resin A4 having a weight-average molecular weight of about $7.6\times10^3$ in a yield of 61%. This resin A4 has the following structural units.

A4

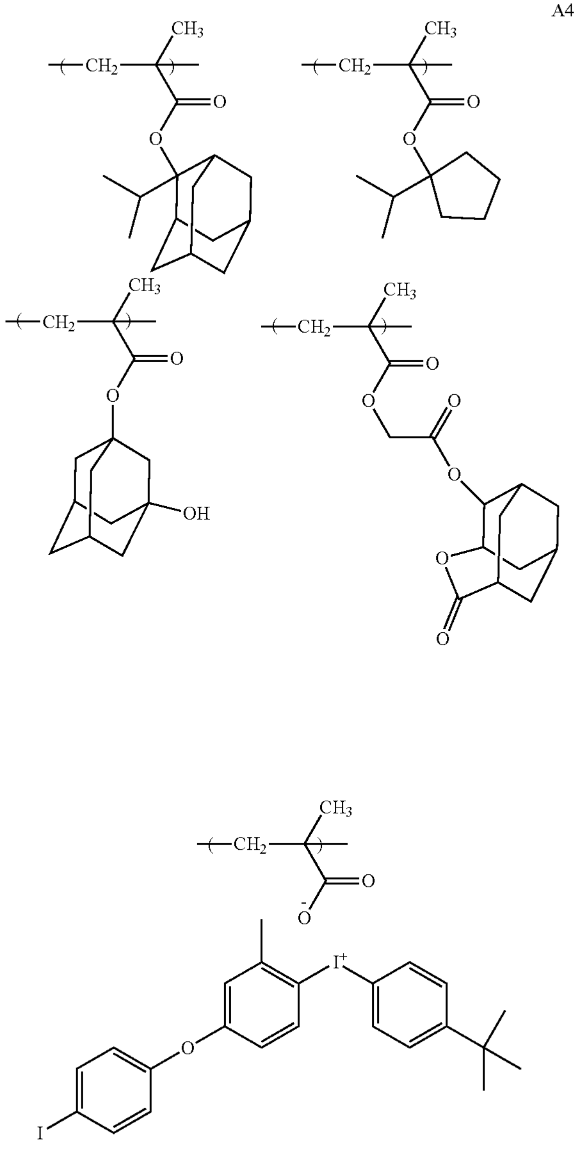

Example 16 [Synthesis of Resin A5]

Using a monomer (a1-1-3), a monomer (a1-2-6), a monomer (a2-1-1), a monomer (a3-4-2) and a monomer (I-865) as monomers, these monomers were mixed in a molar ratio of 45:14:2.5:33.5:5 [monomer (a1-1-3):monomer (a1-2-6): monomer (a2-1-1):monomer (a3-4-2):monomer (I-865)], and then this monomer mixture was mixed with methyl isobutyl ketone in the amount of 1.5 mass times the total mass of all monomers. To the mixture thus obtained, azobisisobutyronitrile and azobis(2,4-dimethylvaleronitrile) as initiators were added in the amounts of 1 mol % and 3 mol % based on the amount of all monomers, followed by heating at 73° C. for about 5 hours. Thereafter, the polymerization reaction solution was poured into a large amount of n-heptane to precipitate a resin, followed by filtration and recovery to obtain a resin A5 having a weight-average molecular weight of about $7.7\times10^3$ in a yield of 66%. This resin A5 has the following structural units.

A5

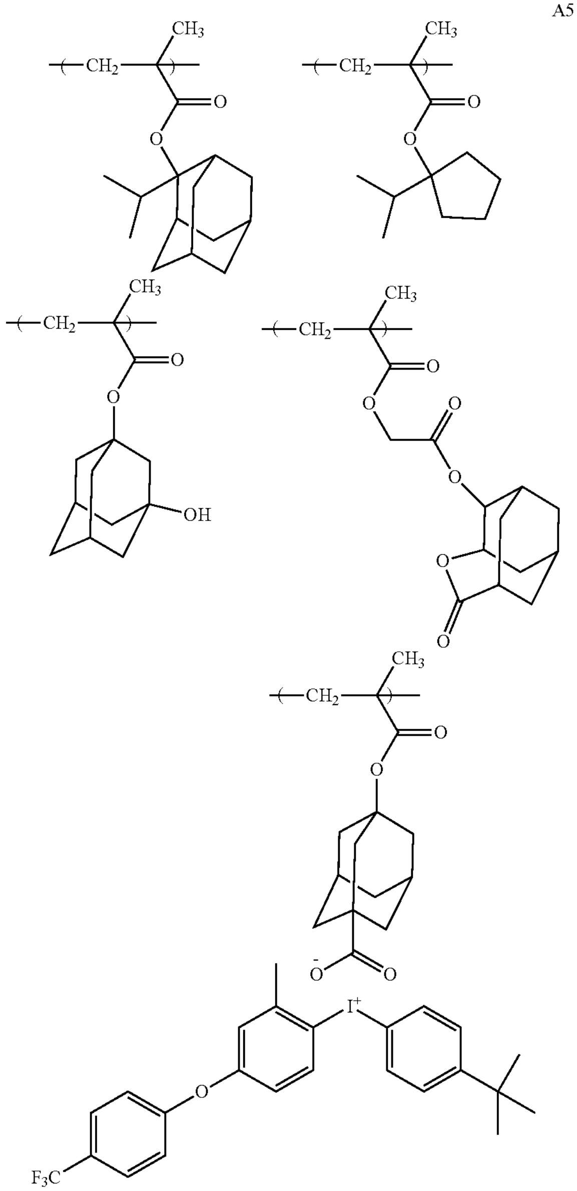

A6

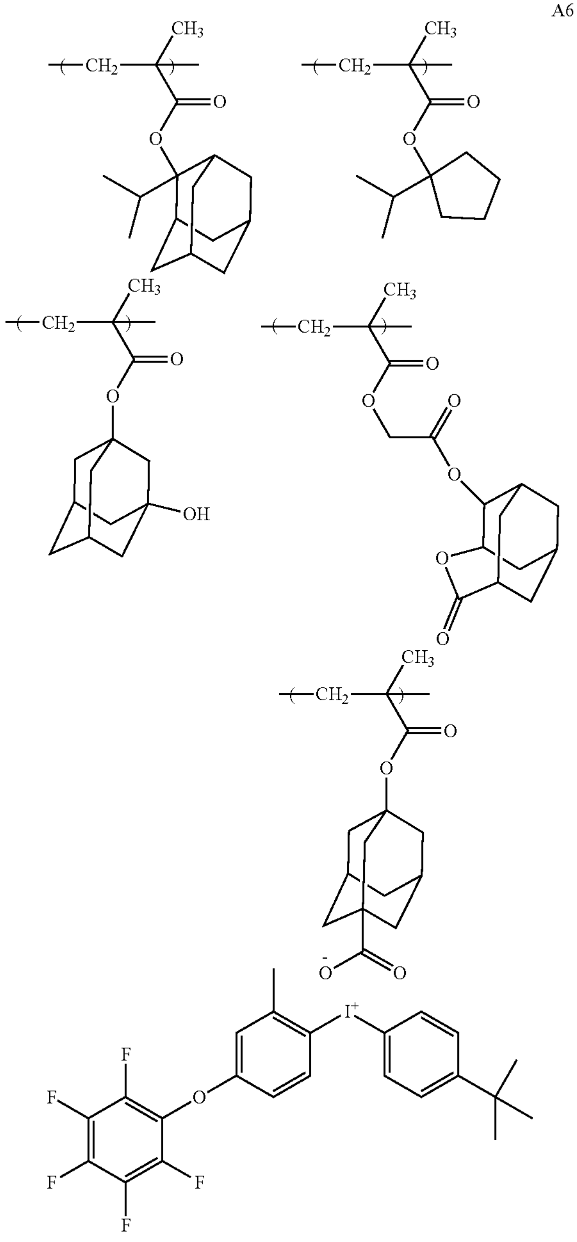

Example 17 [Synthesis of Resin A6]

Using a monomer (a1-1-3), a monomer (a1-2-6), a monomer (a2-1-1), a monomer (a3-4-2) and a monomer (I-1108) as monomers, these monomers were mixed in a molar ratio of 45:14:2.5:33.5:5 [monomer (a1-1-3):monomer (a1-2-6): monomer (a2-1-1):monomer (a3-4-2):monomer (I-1108)], and then this monomer mixture was mixed with methyl isobutyl ketone in the amount of 1.5 mass times the total mass of all monomers. To the mixture thus obtained, azobisisobutyronitrile and azobis(2,4-dimethylvaleronitrile) as initiators were added in the amounts of 1 mol % and 3 mol % based on the amount of all monomers, followed by heating at 73° C. for about 5 hours. Thereafter, the polymerization reaction solution was poured into a large amount of n-heptane to precipitate a resin, followed by filtration and recovery to obtain a resin A6 having a weight-average molecular weight of about $8.0\times10^3$ in a yield of 68%. This resin A6 has the following structural units.

Example 18 [Synthesis of Resin A7]

Using a monomer (a1-1-3), a monomer (a1-2-6), a monomer (a2-1-1), a monomer (a3-4-2) and a monomer (I-1378) as monomers, these monomers were mixed in a molar ratio of 45:14:2.5:33.5:5 [monomer (a1-1-3):monomer (a1-2-6): monomer (a2-1-1):monomer (a3-4-2):monomer (I-1378)], and then this monomer mixture was mixed with methyl isobutyl ketone in the amount of 1.5 mass times the total mass of all monomers. To the mixture thus obtained, azobisisobutyronitrile and azobis(2,4-dimethylvaleronitrile) as initiators were added in the amounts of 1 mol % and 3 mol % based on the amount of all monomers, followed by heating at 73° C. for about 5 hours. Thereafter, the polymerization reaction solution was poured into a large amount of n-heptane to precipitate a resin, followed by filtration and recovery to obtain a resin A6 having a weight-average molecular weight of about $8.0\times10^3$ in a yield of 68%. This resin A6 has the following structural units.

Example 17 [Synthesis of Resin A7]

Using a monomer (a1-1-3), a monomer (a1-2-6), a monomer (a2-1-1), a monomer (a3-4-2) and a monomer (I-1108) as monomers, these monomers were mixed in a molar ratio of 45:14:2.5:33.5:5 [monomer (a1-1-3):monomer (a1-2-6): monomer (a2-1-1):monomer (a3-4-2):monomer (I-1108)], and then this monomer mixture was mixed with methyl isobutyl ketone in the amount of 1.5 mass times the total mass of all monomers. To the mixture thus obtained, azobisisobutyronitrile and azobis(2,4-dimethylvaleronitrile) as initiators were added in the amounts of 1 mol % and 3 mol % based on the amount of all monomers, followed by heating at 73° C. for about 5 hours. Thereafter, the polymerization reaction solution was poured into a large amount of n-heptane to precipitate a resin, followed by filtration and recovery to obtain a resin A7 having a weight-average molecular weight of about $7.9\times10^3$ in a yield of 61%. This resin A7 has the following structural units.

A7

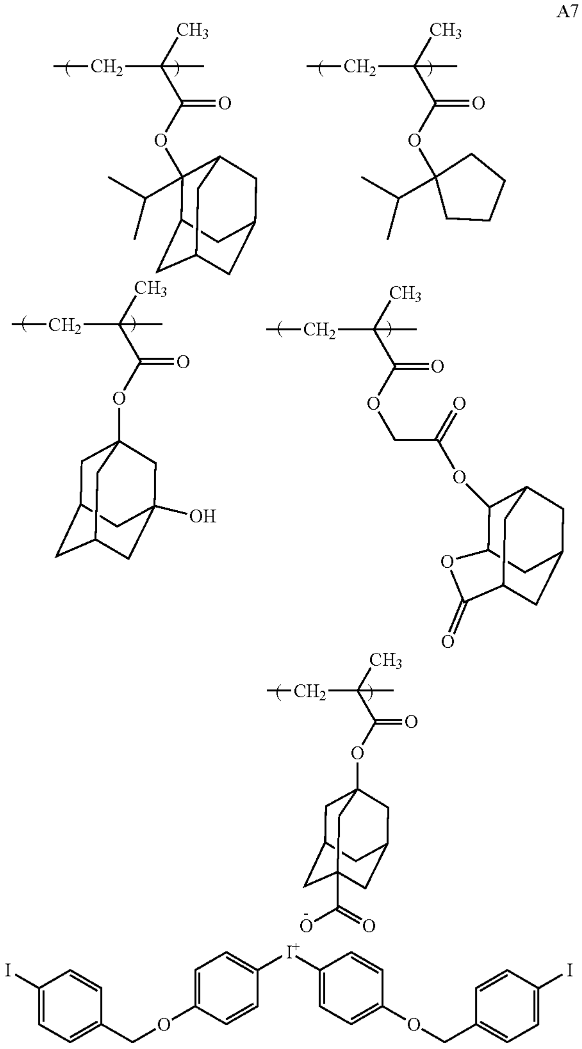

Example 19 [Synthesis of Resin A8]

Using a monomer (a1-1-3), a monomer (a1-2-6), a monomer (a2-1-1), a monomer (a3-4-2) and a monomer (I-1621) as monomers, these monomers were mixed in a molar ratio of 45:14:2.5:33.5:5 [monomer (a1-1-3):monomer (a1-2-6): monomer (a2-1-1):monomer (a3-4-2):monomer (I-1621)], and then this monomer mixture was mixed with methyl isobutyl ketone in the amount of 1.5 mass times the total mass of all monomers. To the mixture thus obtained, azobisisobutyronitrile and azobis(2,4-dimethylvaleronitrile) as initiators were added in the amounts of 1 mol % and 3 mol % based on the amount of all monomers, followed by heating at 73° C. for about 5 hours. Thereafter, the polymerization reaction solution was poured into a large amount of n-heptane to precipitate a resin, followed by filtration and recovery to obtain a resin A8 having a weight-average molecular weight of about $7.7\times10^3$ in a yield of 68%. This resin A8 has the following structural units.

A8

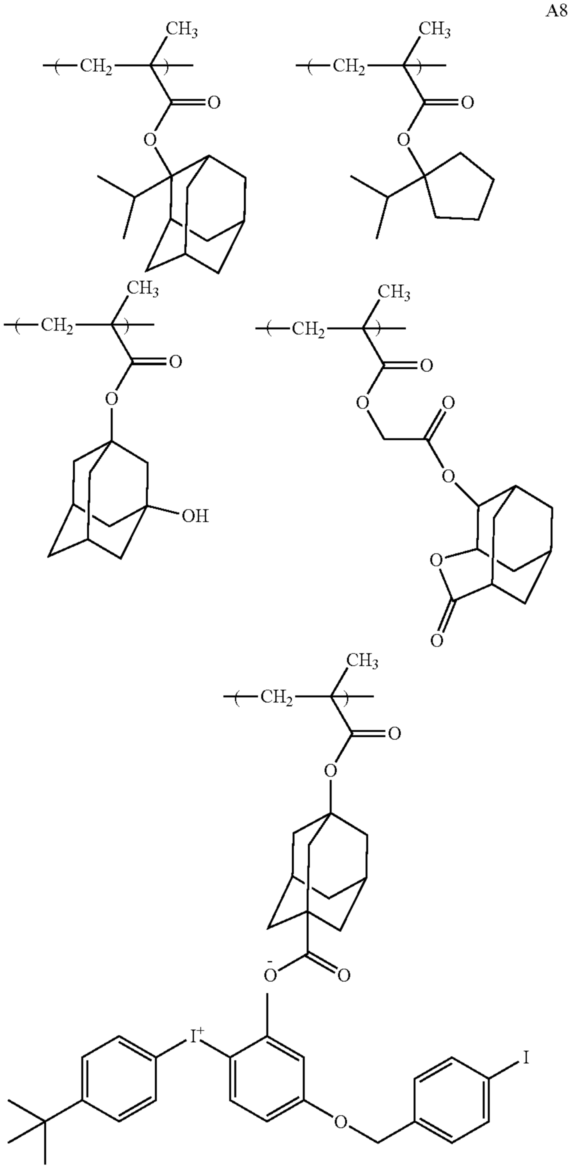

Example 20 [Synthesis of Resin A9]

Using a monomer (a1-1-3), a monomer (a1-2-6), a monomer (a2-1-1), a monomer (a3-4-2) and a monomer (I-2161) as monomers, these monomers were mixed in a molar ratio of 45:14:2.5:33.5:5 [monomer (a1-1-3):monomer (a1-2-6): monomer (a2-1-1):monomer (a3-4-2):monomer (I-2161)], and then this monomer mixture was mixed with methyl isobutyl ketone in the amount of 1.5 mass times the total mass of all monomers. To the mixture thus obtained, azobisisobutyronitrile and azobis(2,4-dimethylvaleronitrile) as initiators were added in the amounts of 1 mol % and 3 mol % based on the amount of all monomers, followed by heating at 73° C. for about 5 hours. Thereafter, the polymerization reaction solution was poured into a large amount of n-heptane to precipitate a resin, followed by filtration and recovery to obtain a resin A9 having a weight-average molecular weight of about $7.5\times10^3$ in a yield of 68%. This resin A9 has the following structural units.

A9

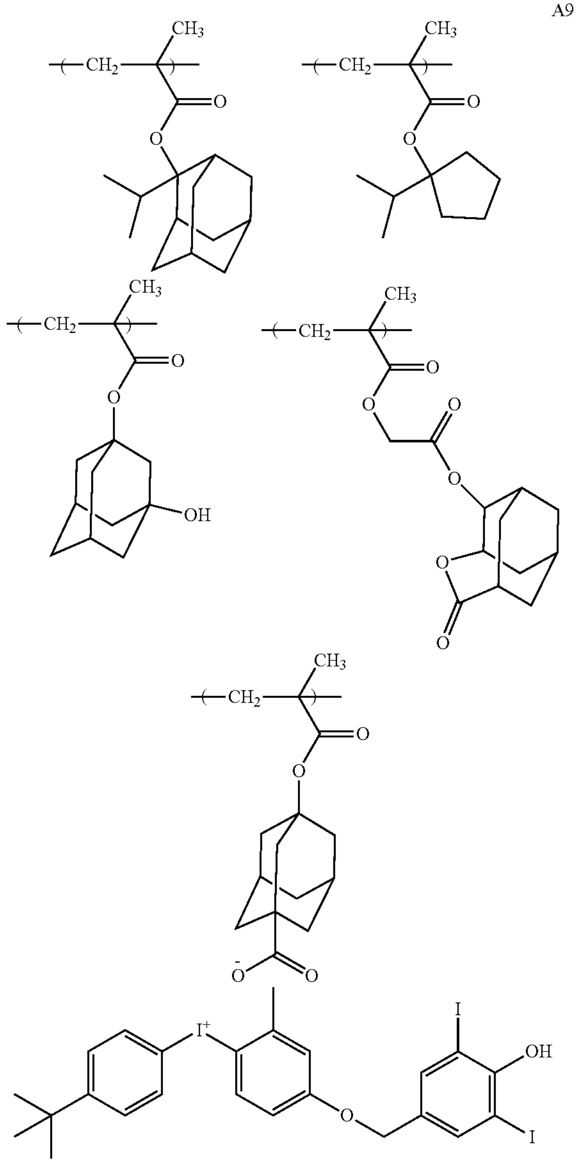

Example 21 [Synthesis of Resin A10]

Using a monomer (a1-1-3), a monomer (a1-2-6), a monomer (a2-1-1), a monomer (a3-4-2) and a monomer (I-1642) as monomers, these monomers were mixed in a molar ratio of 45:14:2.5:33.5:5 [monomer (a1-1-3):monomer (a1-2-6): monomer (a2-1-1):monomer (a3-4-2):monomer (I-1642)], and then this monomer mixture was mixed with methyl isobutyl ketone in the amount of 1.5 mass times the total mass of all monomers. To the mixture thus obtained, azobisisobutyronitrile and azobis(2,4-dimethylvaleronitrile) as initiators were added in the amounts of 1 mol % and 3 mol % based on the amount of all monomers, followed by heating at 73° C. for about 5 hours. Thereafter, the polymerization reaction solution was poured into a large amount of n-heptane to precipitate a resin, followed by filtration and recovery to obtain a resin A10 having a weight-average molecular weight of about $7.6\times10^3$ in a yield of 60%. This resin A10 has the following structural units.

A10

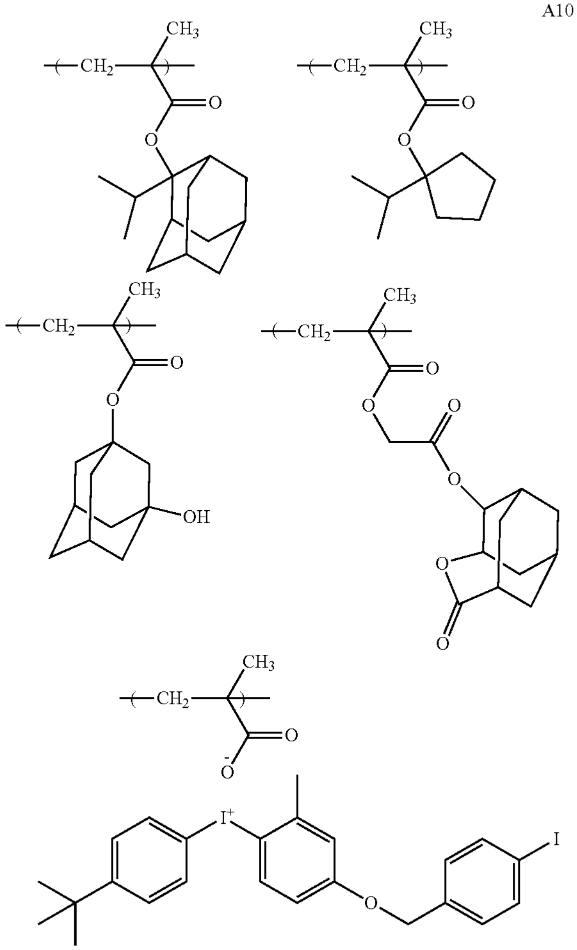

Example 22 [Synthesis of Resin A11]

Using a monomer (a1-1-3), a monomer (a1-2-6), a monomer (a2-1-1), a monomer (a3-4-2) and a monomer (I-2188) as monomers, these monomers were mixed in a molar ratio of 45:14:2.5:33.5:5 [monomer (a1-1-3):monomer (a1-2-6): monomer (a2-1-1):monomer (a3-4-2):monomer (I-2188)], and then this monomer mixture was mixed with methyl isobutyl ketone in the amount of 1.5 mass times the total mass of all monomers. To the mixture thus obtained, azobisisobutyronitrile and azobis(2,4-dimethylvaleronitrile) as initiators were added in the amounts of 1 mol % and 3 mol % based on the amount of all monomers, followed by heating at 73° C. for about 5 hours. Thereafter, the polymerization reaction solution was poured into a large amount of n-heptane to precipitate a resin, followed by filtration and recovery to obtain a resin A11 having a weight-average molecular weight of about $7.6\times10^3$ in a yield of 68%. This resin A11 has the following structural units.

A10

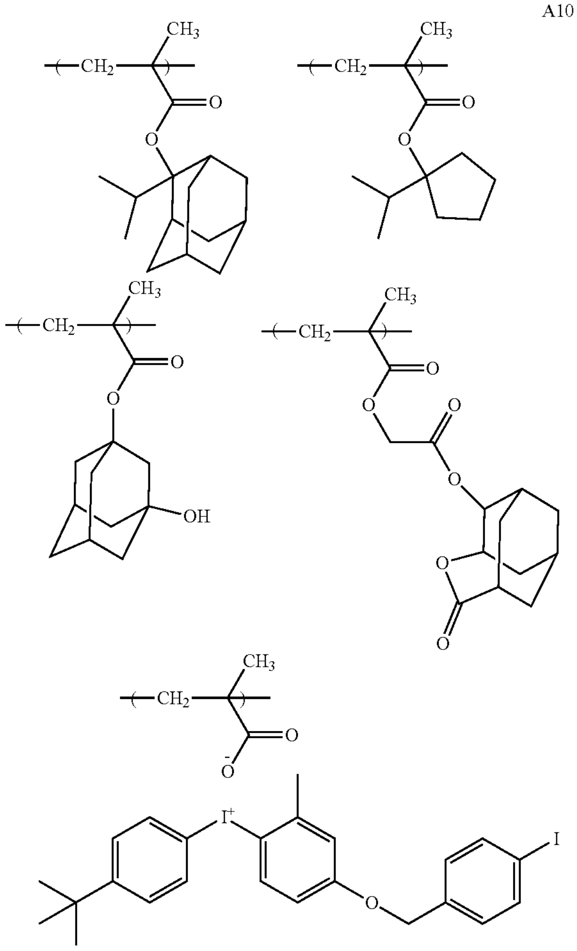

Synthesis Example 1 [Synthesis of Resin AX1]

Using a monomer (a1-1-3), a monomer (a1-2-6), a monomer (a2-1-1), a monomer (a3-4-2) and a monomer (AX-1) as monomers, these monomers were mixed in a molar ratio of 45:14:2.5:33.5:5 [monomer (a1-1-3):monomer (a1-2-6): monomer (a2-1-1):monomer (a3-4-2):monomer (AX-1)], and then this monomer mixture was mixed with methyl isobutyl ketone in the amount of 1.5 mass times the total mass of all monomers. To the mixture thus obtained, azobisisobutyronitrile and azobis(2,4-dimethylvaleronitrile) as initiators were added in the amounts of 1 mol % and 3 mol % based on the amount of all monomers, followed by heating at 73° C. for about 5 hours. Thereafter, the polymerization reaction solution was poured into a large amount of n-heptane to precipitate a resin, followed by filtration and recovery to obtain a resin AX1 having a weight-average molecular weight of about $7.7\times10^3$ in a yield of 60%. This resin AX1 has the following structural units.

AX1

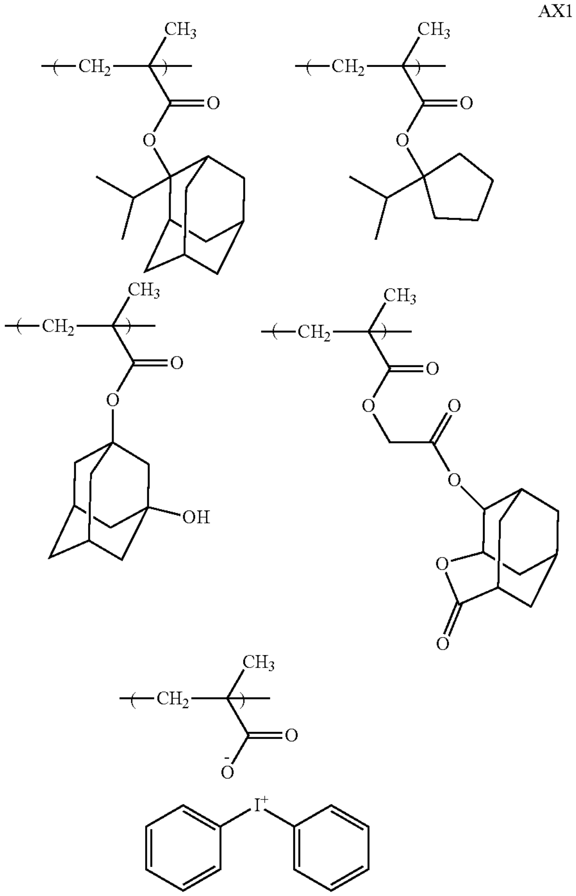

Synthesis Example 2 [Synthesis of Resin AA1]

Using a monomer (a1-1-3), monomer (a1-2-6), monomer (a2-1-1) and monomer (a3-4-2) as monomers, these monomers were mixed in a molar ratio of 45:14:2.5:38.5 [monomer (a1-1-3):monomer (a1-2-6):monomer (a2-1-1):monomer (a3-4-2)], and then propylene glycol monomethyl ether acetate was added in the amount of 1.5 mass times the amount of all monomers to obtain a solution. To the solution thus obtained, azobisisobutyronitrile and azobis(2,4-dimethylvaleronitrile) as initiators were added in the amounts of 1 mol % and 3 mol % based on the amount of all monomers, followed by heating at 73° C. for about 5 hours. The reaction mixture thus obtained was poured into a large amount of a methanol/water mixed solvent to precipitate a resin, followed by filtration of the resin. After performing a reprecipitation operation of pouring a solution, which is obtained by dissolving again the resin thus obtained in propylene glycol monomethyl ether acetate, into a methanol/water mixed solvent to precipitate a resin, followed by filtration of the resin, twice to obtain a resin AA1 having a weight-average molecular weight of about $7.8\times10^3$ in a yield of 69%. This resin AA1 has the following structural units.

AA1

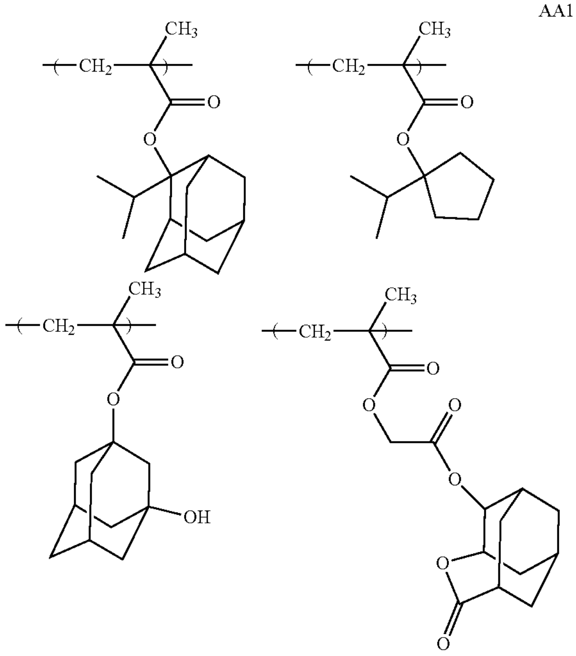

Synthesis Example 3 [Synthesis of Resin X1]

Using a monomer (a5-1-1) and a monomer (a4-0-12) as monomers, these monomers were mixed in a molar ratio of 50:50 [monomer (a5-1-1):monomer (a4-0-12)], and then methyl isobutyl ketone was added in the amount of 1.2 mass times the amount of all monomers to obtain a solution. To the solution thus obtained, azobis(2,4-dimethylvaleronitrile) as initiators was added in the amount of 3 mol % based on the amount of all monomers, followed by heating at 70° C. for about 5 hours. The reaction mixture thus obtained was poured into a large amount of methanol/water mixed solvent to precipitate a resin, followed by filtration of the resin to obtain a resin X1 having a weight-average molecular weight of about 1.0×10$^4$ in a yield of 91%. This resin X1 has the following structural units.

X1

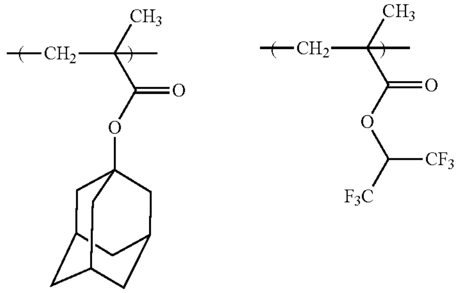

<Preparation of Resist Composition>

As shown in Table 2, the following components were mixed and the mixture thus obtained was filtered through a fluororesin filter having a pore diameter of 0.2 μm to prepare resist compositions.

TABLE 2

| Resist composition | Resin | Acid generator (B) | Carboxylate (I) | Quencher (C) | PB/PEB |
|---|---|---|---|---|---|
| Composition 1 | X1/AA1 = 0.2/10 part | B1-21/B1-22 = 0.90/0.45 part | I-244 = 0.8 part | — | 90° C./85° C. |
| Composition 2 | X1/AA1 = 0.2/10 part | B1-21/B1-22 = 0.90/0.45 part | I-487 = 0.8 part | — | 90° C./85° C. |
| Composition 3 | X1/AA1 = 0.2/10 part | B1-21/B1-22 = 0.90/0.45 part | I-489 = 0.8 part | — | 90° C./85° C. |
| Composition 4 | X1/AA1 = 0.2/10 part | B1-21/B1-22 = 0.90/0.45 part | I-508 = 0.8 part | — | 90° C./85° C. |
| Composition 5 | X1/A1 = 0.2/10 part | B1-21/B1-22 = 0.90/0.45 part | — | D1 = 0.3 part | 90° C./85° C. |
| Composition 6 | X1/A2 = 0.2/10 part | B1-21/B1-22 = 0.90/0.45 part | — | D1 = 0.3 part | 90° C./85° C. |
| Composition 7 | X1/A3 = 0.2/10 part | B1-21/B1-22 = 0.90/0.45 part | — | D1 = 0.3 part | 90° C./85° C. |
| Composition 8 | X1/A4 = 0.2/10 part | B1-21/B1-22 = 0.90/0.45 part | — | D1 = 0.3 part | 90° C./85° C. |
| Composition 9 | X1/A1 = 0.2/10 part | B1-21/B1-22 = 0.90/0.45 part | I-244 = 0.3 part | — | 90° C./85° C. |
| Composition 10 | X1/A2 = 0.2/10 part | B1-21/B1-22 = 0.90/0.45 part | I-487 = 0.3 part | — | 90° C./85° C. |
| Composition 11 | X1/A3 = 0.2/10 part | B1-21/B1-22 = 0.90/0.45 part | I-489 = 0.3 part | — | 90° C./85° C. |
| Composition 12 | XI/A4 = 0.2/10 part | B1-21/B1-22 = 0.90/0.45 part | I-508 = 0.3 part | — | 90° C./85° C. |
| Composition 13 | X1/A1 = 0.2/10 part | B1-21/B1-22 = 0.90/0.45 part | — | — | 90° C./85° C. |
| Composition 14 | X1/A2 = 0.2/10 part | B1-21/B1-22 = 0.90/0.45 part | — | — | 90° C./85° C. |
| Composition 15 | X1/A3 = 0.2/10 part | B1-21/B1-22 = 0.90/0.45 part | — | — | 90° C./85° C. |
| Composition 16 | X1/A4 = 0.2/10 part | B1-21/B1-22 = 0.90/0.45 part | — | — | 90° C./85° C. |
| Composition 17 | X1/AA1 = 0.2/10 part | B1-21/B1-22 = 0.90/0.45 part | I-865 = 0.8 part | — | 90° C./85° C. |
| Composition 18 | X1/A5 = 0.2/10 part | B1-21/B1-22 = 0.90/0.45 part | — | D1 = 0.3 part | 90° C./85° C. |

TABLE 2-continued

| Resist composition | Resin | Acid generator (B) | Carboxylate (I) | Quencher (C) | PB/PEB |
|---|---|---|---|---|---|
| Composition 19 | X1/A5 = 0.2/10 part | B1-21/B1-22 = 0.90/0.45 part | I-865 = 0.3 part | — | 90° C./85° C. |
| Composition 20 | X1/A5 = 0.2/10 part | B1-21/B1-22 = 0.90/0.45 part | — | — | 90° C./85° C. |
| Composition 21 | X1/AA1 = 0.2/10 part | B1-21/B1-22 = 0.90/0.45 part | I-1108 = 0.8 part | — | 90° C./85° C. |
| Composition 22 | X1/A6 = 0.2/10 part | B1-21/B1-22 = 0.90/0.45 part | — | D1 = 0.3 part | 90° C./85° C. |
| Composition 23 | X1/A6 = 0.2/10 part | B1-21/B1-22 = 0.90/0.45 part | I-1108 = 0.3 part | — | 90° C./85° C. |
| Composition 24 | X1/A6 = 0.2/10 part | B1-21/B1-22 = 0.90/0.45 part | — | — | 90° C./85° C. |
| Composition 25 | X1/AA1 = 0.2/10 part | Bl-21/B1-22= 0.90/0.45 part | I-1378 = 0.8 part | — | 90° C./85° C. |
| Composition 26 | X1/AA1 = 0.2/10 part | B1-21/B1-22 = 0.90/0.45 part | I-1621 = 0.8 part | — | 90° C./85° C. |
| Composition 27 | X1/AA1 = 0.2/10 part | B1-21/B1-22 = 0.90/0.45 part | I-2161 = 0.8 part | — | 90° C./85° C. |
| Composition 28 | X1/AA1 = 0.2/10 part | B1-21/B1-22 = 0.90/0.45 part | I-1642 = 0.8 part | — | 90° C./85° C. |
| Composition 29 | X1/A7 = 0.2/10 part | B1-21/B1-22 = 0.90/0.45 part | — | D1 = 0.3 part | 90° C./85° C. |
| Composition 30 | X1/A8 = 0.2/10 part | B1-21/B1-22 = 0.90/0.45 part | — | D1 = 0.3 part | 90° C./85° C. |
| Composition 31 | X1/A9 = 0.2/10 part | B1-21/B1-22 = 0.90/0.45 part | — | D1 = 0.3 part | 90° C./85° C. |
| Composition 32 | X1/A10 = 0.2/10 part | B1-21/B1-22 = 0.90/0.45 part | — | D1 = 0.3 part | 90° C./85° C. |
| Composition 33 | X1/A7 = 0.2/10 part | B1-21/B1-22 = 0.90/0.45 part | I-1378 = 0.3 part | — | 90° C./85° C. |
| Composition 34 | X1/A8 = 0.2/10 part | B1-21/B1-22 = 0.90/0.45 part | I-1621 = 0.3 part | — | 90° C./85° C. |
| Composition 35 | X1/A9 = 0.2/10 part | B1-21/B1-22 = 0.90/0.45 part | I-2161 = 0.3 part | — | 90° C./85° C. |
| Composition 36 | X1/A10 = 0.2/10 part | B1-21/B1-22 = 0.90/0.45 part | I-1642 = 0.3 part | — | 90° C./85° C. |
| Composition 37 | X1/A7 = 0.2/10 part | B1-21/B1-22 = 0.90/0.45 part | — | — | 90° C./85° C. |
| Composition 38 | X1/A8 = 0.2/10 part | B1-21/B1-22 = 0.90/0.45 part | — | — | 90° C./85° C. |
| Composition 39 | X1/A9 = 0.2/10 part | B1-21/B1-22 = 0.90/0.45 part | — | — | 90° C./85° C. |
| Composition 40 | X1/A10 = 0.2/10 part | B1-21/B1-22 = 0.90/0.45 part | — | — | 90° C./85° C. |
| Composition 41 | X1/AA1 = 0.2/10 part | B1-21/B1-22 = 0.90/0.45 part | I-2188 = 0.8 part | — | 90° C./85° C. |
| Composition 42 | X1/A11 = 0.2/10 part | B1-21/B1-22 = 0.90/0.45 part | — | D1 = 0.3 part | 90° C./85° C. |
| Composition 43 | X1/A11 = 0.2/10 part | B1-21/B1-22 = 0.90/0.45 part | I-2188 = 0.3 part | — | 90° C./85° C. |
| Composition 44 | X1/A11 = 0.2/10 part | B1-21/B1-22 = 0.90/0.45 part | — | — | 90° C./85° C. |
| Comparative Composition 1 | X1/AA1 = 0.2/10 part | B1-21/B1-22 = 0.90/0.45 part | — | IX-1 = 0.8 part | 90° C./85° C. |
| Comparative Composition 2 | X1/AX1 = 0.2/10 part | B1-21/B1-22 = 0.90/0.45 part | — | D1 = 0.3 part | 90° C./85° C. |
| Comparative Composition 3 | X1/AX1 = 0.2/10 part | B1-21/B1-22 = 0.90/0.45 part | — | IX-1 = 0.3 part | 90° C./85° C. |
| Comparative Composition 4 | X1/AX1 = 0.2/10 part | B1-21/B1-22 = 0.90/0.45 part | — | — | 90° C./85° C. |

<Resin>

A1 to A6, AA1, AX1, X1: Resins A1 to A6, Resin AA1, Resin AX1, Resin X1

<Acid Generator (B)>

B1-21: Salt represented by Formula (B1-21)

B1-22: Salt represented by Formula (B1-22)

(B1-21)

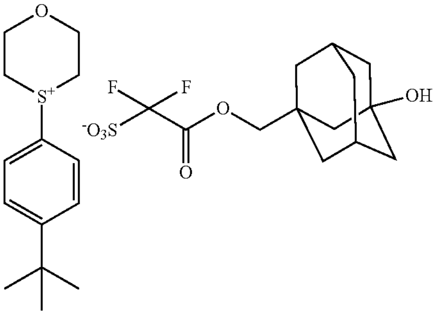

(B1-22)

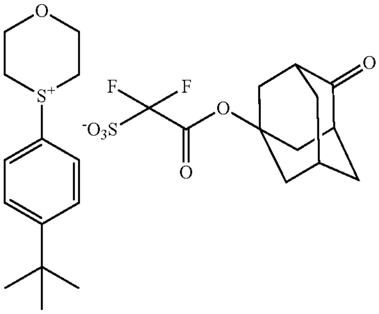

<Carboxylate (I)>

I-244: Salt represented by Formula (I-244)

I-487: Salt represented by Formula (I-487)

I-489: Salt represented by Formula (I-489)

I-508: Salt represented by Formula (I-508)

I-865: Salt represented by Formula (I-865)

I-1108: Salt represented by Formula (I-1108)

I-244: Salt represented by Formula (I-1378)

I-487: Salt represented by Formula (I-1621)

I-489: Salt represented by Formula (I-2161)

I-508: Salt represented by Formula (I-2188)

<Quencher (C)>

IX-1: Carboxylate represented by Formula (B1-25); synthesized by the method mentioned in JP 2011-037834 A (IX-1)

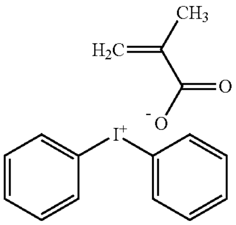

<Weak Acid Inner Salt (D)>

D1: (manufactured by Tokyo Chemical Industry Co., Ltd.)

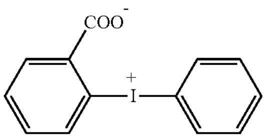

<Solvent>

| | |
|---|---|
| Propylene glycol monomethyl ether acetate | 265 part |
| Propylene glycol monomethyl ether | 20 part |
| 2-Heptanone | 20 part |
| γ-Butyrolactone | 3.5 part |

<Production of Resist Pattern and Evaluation Thereof>

A composition for an organic antireflective film (ARC-29, manufactured by Nissan Chemical Co. Ltd.) was applied onto a silicon wafer and baked under the conditions at 205° C. for 60 seconds to form a 78 nm thick organic antireflective film on the silicon wafer. Then, the above resist composition was applied on the organic antireflective film by coating (spin coating) in such a manner that the thickness of the film after drying became 85 nm. The silicon wafer coated with the resist composition was pre-baked for 60 seconds on a direct hot plate at the temperature mentioned in the "PB" column in Table 2 to form a composition layer. The silicon wafer with the composition layer thus formed thereon was exposed through a mask for forming a contact hole pattern (hole pitch of 90 nm/hole diameter of 55 nm) stepwise with changing exposure dose using an ArF excimer laser stepper for immersion lithography (XT: 1900Gi, manufactured by ASML Ltd.: NA=1.35, 3/4 Annular, XY-polarization). Ultrapure water was used for medium of immersion.

After exposure, post-exposure baking was performed on a hot plate for 60 seconds at the temperature mentioned in the "PEB" column in Table 2. Then, the composition layer on the silicon wafer was subjected to development at 23° C. for 20 seconds by a dynamic dispense method using butyl acetate (manufactured by Tokyo Chemical Industry Co., Ltd.) as a developing solution to obtain a negative resist pattern.

Effective sensitivity was represented as the exposure dose at which the hole diameter formed using the mask became 45 nm in the resist pattern obtained after development.

<Evaluation of Mask Error Factor (MFF)>

Using masks each having a hole diameter (hole dimeter of the translucent part of the mask) of 57 nm, 56 nm, 55 nm, 54 nm and 53 nm (hole pitch is 90 nm in any case), resist patterns were produced at the effective sensitivity. When mask hole dimeters are plotted on the abscissa axis, while diameters of holes of the photoresist patterns formed (transferred) on the substrate by exposure are plotted on the ordinate axis, the slope of a plotted regression line was determined as the MEF value.

The results are shown in Table 3. The numerical value in the Table indicates the MEF value.

TABLE 3

| | Resist composition | MEF |
|---|---|---|
| Example 13 | Composition 1 | 3.72 |
| Example 14 | Composition 2 | 3.63 |
| Example 15 | Composition 3 | 3.61 |
| Example 16 | Composition 4 | 3.89 |
| Example 17 | Composition 5 | 3.62 |

TABLE 3-continued

| | Resist composition | MEF |
|---|---|---|
| Example 18 | Composition 6 | 3.54 |
| Example 19 | Composition 7 | 3.52 |
| Example 20 | Composition 8 | 3.80 |
| Example 21 | Composition 9 | 3.68 |
| Example 22 | Composition 10 | 3.60 |
| Example 23 | Composition 11 | 3.57 |
| Example 24 | Composition 12 | 3.84 |
| Example 25 | Composition 13 | 3.70 |
| Example 26 | Composition 14 | 3.63 |
| Example 27 | Composition 15 | 3.60 |
| Example 28 | Composition 16 | 3.88 |
| Example 29 | Composition 17 | 3.55 |
| Example 30 | Composition 18 | 3.46 |
| Example 31 | Composition 19 | 3.52 |
| Example 32 | Composition 20 | 3.56 |
| Example 33 | Composition 21 | 3.53 |
| Example 34 | Composition 22 | 3.44 |
| Example 35 | Composition 23 | 3.58 |
| Example 36 | Composition 24 | 3.54 |
| Example 37 | Composition 15 | 3.60 |
| Example 38 | Composition 16 | 3.88 |
| Example 39 | Composition 17 | 3.55 |
| Example 40 | Composition 18 | 3.46 |
| Example 41 | Composition 19 | 3.52 |
| Example 42 | Composition 20 | 3.56 |
| Example 43 | Composition 21 | 3.53 |
| Example 44 | Composition 22 | 3.44 |
| Example 45 | Composition 23 | 3.58 |
| Example 46 | Composition 24 | 3.54 |
| Example 47 | Composition 25 | 3.64 |
| Example 48 | Composition 26 | 3.59 |
| Example 49 | Composition 27 | 3.62 |
| Example 50 | Composition 28 | 3.83 |
| Example 51 | Composition 29 | 3.54 |
| Example 52 | Composition 30 | 3.47 |
| Example 53 | Composition 31 | 3.50 |
| Example 54 | Composition 32 | 3.76 |
| Example 55 | Composition 33 | 3.60 |
| Example 56 | Composition 34 | 3.53 |
| Example 57 | Composition 35 | 3.56 |
| Example 58 | Composition 36 | 3.80 |
| Example 59 | Composition 37 | 3.64 |
| Example 60 | Composition 38 | 3.56 |
| Example 61 | Composition 39 | 3.59 |
| Example 62 | Composition 40 | 3.87 |
| Example 63 | Composition 41 | 3.64 |
| Example 64 | Composition 42 | 3.53 |
| Example 65 | Composition 43 | 3.58 |
| Example 66 | Composition 44 | 3.62 |
| Comparative Example 1 | Comparative Composition 1 | 4.07 |
| Comparative Example 2 | Comparative Composition 2 | 3.98 |
| Comparative Example 3 | Comparative Composition 3 | 4.03 |
| Comparative Example 4 | Comparative Composition 4 | 4.05 |

As compared with Comparative Compositions 1 to 4, Compositions 1 to 44 exhibited smaller slope of the plotted regression line, leading to satisfactory evaluation of mask error factor (MEF).

A resist composition including a carboxylate of the present disclosure is capable of obtaining a resist pattern with satisfactory mask error factor (MEF), and is therefore useful for fine processing of semiconductors and is industrially extremely useful.

What claimed is:

1. A carboxylate represented by formula (I) or a structural unit represented by formula (IP):

(I)

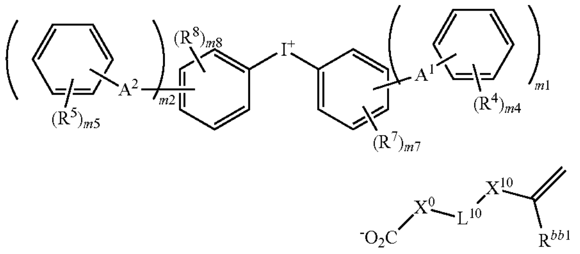

(IP)

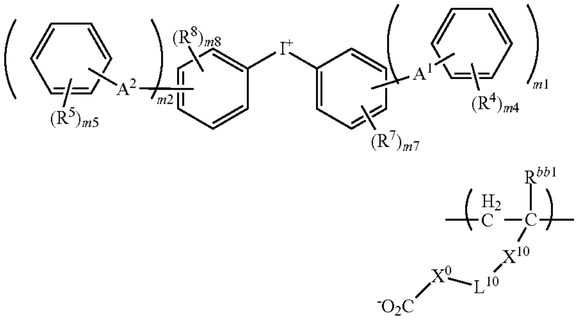

wherein, in formula (I) and formula (IP), $R^4$, $R^5$, and $R^7$ each independently represent a halogen atom, a hydroxy group, a haloalkyl group having 1 to 12 carbon atoms or a hydrocarbon group having 1 to 18 carbon atoms, each of the hydrocarbon group may have a substituent, and a —$CH_2$— included in each of the haloalkyl group and the hydrocarbon group may be replaced by —O—, —CO—, —S— or —$SO_2$—, $R^8$ represents an iodine atom, a fluorine atom, a hydroxy group, an alkyl group having 1 to 4 carbon atoms, a haloalkyl group having 1 to 4 carbon atoms or an alkoxy group having 1 to 3 carbon atoms, when m4 is 1 or more, one $R^4$ of one or more $R^4$s is an iodine atom, $A^1$ and $A^2$ each independently represent a hydrocarbon group having 1 to 20 carbon atoms, each of the hydrocarbon group may have a substituent, and —$CH_2$— included in each of the hydrocarbon group may be replaced by —O—, —CO—, or —S—, m1 represents an integer of 1 to 5, and when m1 is 2 or more, a plurality of groups in parentheses may be the same or different from each other, m2 represents an integer of 0 to 5, and when m2 is 2 or more, a plurality of groups in parentheses may be the same or different from each other, m4 represents an integer of 0 to 5, and when m4 is 2 or more, a plurality of $R^4$ may be the same or different from each other, m5 represents an integer of 0 to 5, and when m5 is 2 or more, a plurality of $R^5$ may be the same or different from each other, m7 represents an integer of 0 to 4, and when m7 is 2 or more, a plurality of $R^7$ may be the same or different from each other, m8 represents an integer of 0 to 5, and when m8 is 2 or more, a plurality of $R^8$ may be the same or different from each other, in which $1<m1+m7<5, 0<m2+m8\leq 5$, $X^0$ represents a single bond or a hydrocarbon group having 1 to 72 carbon atoms which may have a substituent, and —$CH_2$— included in the hydrocarbon group may be replaced by —O—, —S—, —CO—or —$SO_2$—, $R^{bb1}$ represents a hydrogen atom, a halogen atom, or an alkyl group having 1 to 6 carbon atoms which may have a halogen atom, $X^{10}$ represents a single bond, *—O—**, *—CO—O—**, *—O—CO—O—** or *-Ax-Ph-Ay-**, Ph represents a phenylene group which may have a substituent, Ax represents a single bond, an ether bond, an ester bond or a carbonic acid ester bond, Ay represents a single bond, an ether bond, an ester bond or a carbonic acid ester bond,

* represents a bonding site to carbon atoms to which $R^{bb1}$ is bonded,

** represents a bonding site to $L^{10}$, and $L^{10}$ represents a single bond or a hydrocarbon group having 1 to 36 carbon atoms which may have a substituent, and a —$CH_2$—included in each of the hydrocarbon group may be replaced by —O—, —S—, —$SO_2$—or —CO—.

2. The carboxylate according to claim 1, wherein $A^1$ is *—$X^{01}$-$L^{01}$- or *-$L^{01}$-$X^{01}$—, $A^2$ is *—$X^{02}$-$L^{02}$- or *-$L^{02}$-$X^{02}$—, $X^{01}$ and $X^{02}$ each independently represent-O—, —CO—, or —S—, $L^{01}$ and $L^{02}$ each independently represent a single bond or a hydrocarbon group having 1 to 18 carbon atoms, and

*** represents a bonding site to the benzene ring to which It is bonded.

3. The carboxylate according to claim 1, wherein $X^{01}$ and $X^{02}$ are oxygen atoms.

4. The carboxylate according to claim 2, wherein L°1 and $L^{02}$ are each independently a single bond or an alkanediyl group having 1 to 6 carbon atoms.

5. The carboxylate according to claim 1, wherein $X^0$ includes an aliphatic hydrocarbon group having 1 to 72 carbon atoms which may have a substituent and —$CH_2$— included in the aliphatic hydrocarbon group may be replaced by —O—, —S—, —CO—or —$SO_2$—, or an aromatic hydrocarbon group having 6 to 36 carbon atoms which may have a substituent.

6. The carboxylate according to claim 5, wherein $X^0$ includes an alicyclic hydrocarbon group having 3 to 36 carbon atoms which may have a fluorine atom, a perfluoroalkyl group having 1 to 4 carbon atoms or a hydroxy group, and a —$CH_2$—included in the alicyclic hydrocarbon group may be replaced by —O—, —S—, —CO—or —$SO_2$—, a group obtained by combining an alicyclic hydrocarbon group having 3 to 36 carbon atoms with a chain hydrocarbon group having 1 to 18 carbon atoms, and a —$CH_2$—included in the alicyclic hydrocarbon group may be replaced by —O—, —S—, —CO—or —$SO_2$—, a —$CH_2$—included in the chain hydrocarbon group may be replaced by —O—or —CO—, and the alicyclic hydrocarbon group and the chain hydrocarbon group may have a fluorine atom, a perfluoroalkyl group having 1 to 4 carbon atoms or a hydroxy group, or an aromatic hydrocarbon group having 6 to 36 carbon atoms which may have a fluorine atom, a perfluoroalkyl group having 1 to 4 carbon atoms or a hydroxy group.

7. The carboxylate according to claim 5, wherein $X^0$ includes the alicyclic hydrocarbon group, and the alicyclic hydrocarbon group includes;

a cycloalkanediyl group having 5 or 6 carbon atoms, an adamandiyl group, a norbornanediyl group, or a polycyclic alicyclic hydrocarbon group in which a cycloalkanediyl group having 5 or 6 carbon atoms and an adamantanediyl group are spiro-bonded, a —$CH_2$—included in the adamantanediyl group, the norbornanediyl group and the cycloalkanediyl group may be replaced by —O—or —CO—, a —$CH_2$—$CH_2$—included in the adamantanediyl group and the norbornanediyl group may be replaced by —O—CO—, and the cycloalkanediyl group may be an acetal ring.

8. The carboxylate according to claim 1, wherein $X^{10}$ is a single bond or a group represented by any one of formula ($X^1$-1), formula ($X^1$-2') to formula ($X^1$-7') and formula ($X^1$-8):

($X^1$-1)

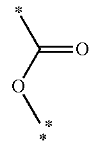

($X^1$-2')

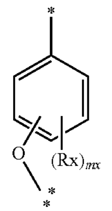

($X^1$-3)'

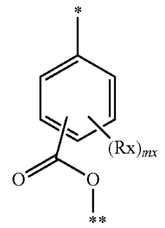

($X^1$-4')

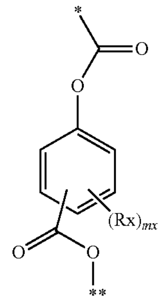

-continued (X[1]-5')

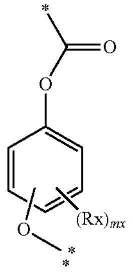

(X[1]-6')

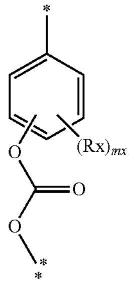

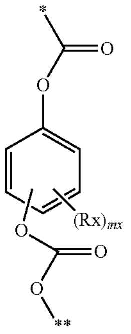

(X[1]-8)

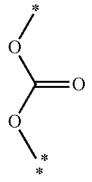

wherein, in formula (X[1]-1), formula (X[1]-2') to formula (X[1]-7') and formula (X[1]-8),

* and  are bonding sites, and  represents a bonding site to $L^{10}$,

Rx represents a halogen atom, a hydroxy group, an alkyl fluoride group having 1 to 6 carbon atoms, an alkyl group having 1 to 18 carbon atoms or an alkoxy group having 1 to 6 carbon atoms, and mx represents an integer of 0 to 4.

9. The carboxylate according to claim 1, wherein $L^{10}$ is a single bond or an alkanediyl group having 1 to 4 carbon atoms, and a —$CH_2$—included in the alkanediyl group may be replaced by —O—or —CO—.

10. A resin comprising a structural unit represented by formula (IP) according to claim 1.

11. The resin according to claim 10, further comprising a structural unit having an acid-labile group.

12. A resist composition comprising the carboxylate according to claim 1 or a resin including a structural unit represented by formula (IP) according to claim 1.

13. The resist composition according to claim 12, further comprising;

a resin including a structural unit having an acid labile group, wherein the acid-labile group includes at least one selected from the group consisting of a structural unit represented by formula (a1-0), a structural unit represented by formula (a1-1) and a structural unit represented by formula (a1-2):

(a1-0)

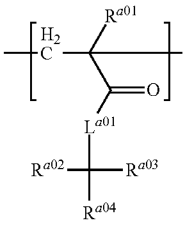

(a1-1)

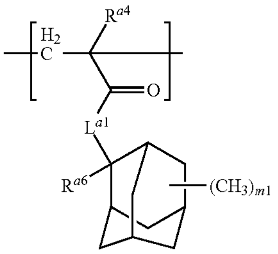

(a1-2)

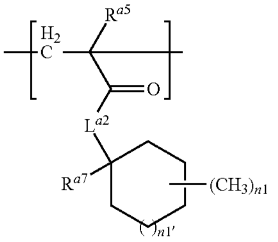

wherein, in formula (a1-0), formula (a1-1) and formula (a1-2), $L^{a01}$, $L^{a1}$ and $L^{a2}$ each independently represent-O—or *—O—($CH_2$) k 1-CO—O—, k1 represents an integer of 1 to 7, and * represents a bonding site to—CO—, $R^{a01}$, $R^{a4}$ and $R^{a5}$ each independently represent a hydrogen atom, a halogen atom, or an alkyl group having 1 to 6 carbon atoms which may have a halogen atom, $R^{a02}$, $R^{a03}$ and $R^{a04}$ each independently represent an alkyl group having 1 to 8 carbon atoms, an alicyclic hydrocarbon group having 3 to 18 carbon atoms, an aromatic hydrocarbon group having 6 to 18 carbon atoms, or a group obtained by combining these groups, $R^{a6}$ and $R^{a7}$ each independently represent an alkyl group having 1 to 8 carbon atoms, an alkenyl group having 2 to 8 carbon atoms, an alicyclic hydrocarbon group having 3 to 18 carbon atoms, an aromatic hydrocarbon group having 6 to 18 carbon atoms, or a group formed by combining these groups, m1 represents an integer of 0 to 14, n1 represents an integer of 0 to 10, and n1' represents an integer of 0 to 3.

14. The resist composition according to claim 12, further comprising:

a resin including a structural unit represented by formula (a2-A):

(a2-A)

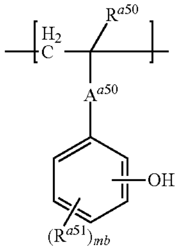

wherein, in formula (a2-A), $R^{a50}$ represents a hydrogen atom, a halogen atom, or an alkyl group having 1 to 6 carbon atoms which may have a halogen atom, $R^{a51}$ represents a halogen atom, a hydroxy group, an alkyl group having 1 to 6 carbon atoms, an alkoxy group having 1 to 6 carbon atoms, an alkoxyalkyl group having 2 to 12 carbon atoms, an alkoxyalkoxy group having 2 to 12 carbon atoms, an alkylcarbonyl group having 2 to 4 carbon atoms, an alkylcarbonyloxy group having 2 to 4 carbon atoms, an acryloyloxy group or a methacryloyloxy group, $A^{a50}$ represents a single bond or $*—X^{a51}—(A^{a52}\text{-}X^{a52})_{nb}—$, and * represents a bond to carbon atoms to which-$R^{a50}$ is bonded, $A^{a52}$ represents an alkanediyl group having 1 to 6 carbon atoms, $x^{a51}$ and $X^{a52}$ each independently represent-O—, —CO—O—or —O—CO—, nb represents 0 or 1, and mb represents an integer of 0 to 4, and when mb is an integer of 2 or more, a plurality of $R^{a51}$ may be the same or different from each other.

15. The resist composition according to claim 12, further comprising:

an acid generator including a salt represented by formula (B1):

(B1)

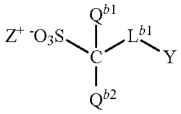

wherein, in formula (B1), $Q^{b1}$ and $Q^{b2}$ each independently represent a hydrogen atom, a fluorine atom, a perfluoroalkyl group having 1 to 6 carbon atoms or an alkyl group having 1 to 6 carbon atoms, $L^{b1}$ represents a divalent saturated hydrocarbon group having 1 to 24 carbon atoms, a $—CH_2—$included in the divalent saturated hydrocarbon group may be replaced by —O—or —CO—, and a hydrogen atom included in the divalent saturated hydrocarbon group may be substituted with a fluorine atom or a hydroxy group, Y represents a methyl group which may have a substituent or an alicyclic hydrocarbon group having 3 to 24 carbon atoms which may have a substituent, and a $—CH_2—$included in the alicyclic hydrocarbon group may be replaced by —O—, —S—, $—SO_2—$or —CO—, and $Z^+$represents an organic cation.

16. A resist composition comprising the carboxylate according to claim 1 and a resin including a structural unit having an acid labile group.

17. A resist composition comprising a resin including the structural unit represented by formula (IP) according to claim 1 and a structural unit having an acid labile group.

18. A resist composition comprising the carboxylate according to claim 1 and a resin including the structural unit represented by formula (IP) according to claim 1.

19. A method for producing a resist pattern, which comprises:

(1) a step of applying the resist composition according to claim 13 on a substrate, (2) a step of drying the applied composition to form a composition layer, (3) a step of exposing the composition layer, (4) a step of heating the exposed composition layer, and (5) a step of developing the heated composition layer.

20. A carboxylate represented by formula (I) or a structural unit represented by formula (IP):

(I)

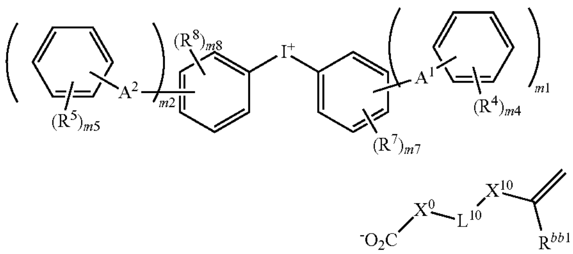

(IP)

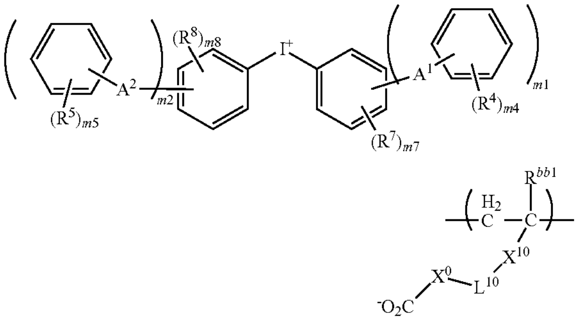

wherein, in formula (I) and formula (IP), $R^4$ represents a halogen atom, a hydroxy group or a haloalkyl group having 1 to 12 carbon atoms, $R^5$ and $R^7$ each independently represent a halogen atom, a hydroxy group, a haloalkyl group having 1 to 12 carbon atoms or a hydrocarbon group having 1 to 18 carbon atoms, each of the hydrocarbon group may have a substituent, and a $—CH_2—$included in each of the haloalkyl group and the hydrocarbon group may be replaced by —O—, —CO—, —S—or $—SO_2—$, $R^8$ represents a branched alkyl group having 3 or 4 carbon atoms, $A^1$ represents *—$X^{01}$-L-01-or *-$L^{01}$-$X^{01}$—, $X^{01}$ represents-O—or —S—, $L^{01}$ represents a single bond or a hydrocarbon group having 1 to 18 carbon atoms, the hydrocarbon group may have a substituent, and —$CH_2$—included in each of the hydrocarbon group may be replaced by —O—, —CO—, or —S—,

*** represents a bonding site to a benzene ring to which $I^+$ is bonded, $A^2$ represents a hydrocarbon group having 1 to 20 carbon atoms, each of the hydrocarbon group may have a substituent of a halogen or a cyano group, and —$CH_2$—included in each of the hydrocarbon group may be replaced by —O—, —CO—, or —S—, m1 represents an integer of 1 to 5, and when m1 is 2 or more, a plurality of groups in parentheses may be the same or different from each other, m2 represents 0, m4 represents an integer of 1 to 5, and when m4 is 2 or more, a plurality of $R^4$ may be the same or different from each other, m5 represents 0, m7 represents an integer of 0 to 4, and when m7 is 2 or more, a plurality of $R^7$ may be the same or different from each other, m8 represents 1, in which 1<m1+m7<5,0≤m2+m8≤5, $X^0$ represents a single bond or a hydrocarbon group having 1 to 72 carbon atoms which may have a substituent, and —$CH_2$—included in the hydrocarbon group may be replaced by —O—, —S—, —CO—or —$SO_2$—, $R^{bb1}$ represents a hydrogen atom, a halogen atom, or an alkyl group having 1 to 6 carbon atoms which may have a halogen atom, $X^{10}$ represents a single bond, *—O—**, *—CO—O—**, *—O—CO—O—** or *-Ax-Ph-Ay-**, Ph represents a phenylene group which may have a substituent, Ax represents a single bond, an ether bond, an ester bond or a carbonic acid ester bond, Ay represents a single bond, an ether bond, an ester bond or a carbonic acid ester bond,

* represents a bonding site to carbon atoms to which $R^{bb1}$ is bonded,

** represents a bonding site to $L^{10}$, and $L^{10}$ represents a single bond or a hydrocarbon group having 1 to 36 carbon atoms which may have a substituent, and a —$CH_2$—included in each of the hydrocarbon group may be replaced by —O—, —S—, —$SO_2$—or —CO—.

21. A carboxylate represented by formula (I) or a structural unit represented by formula (IP):

(I)

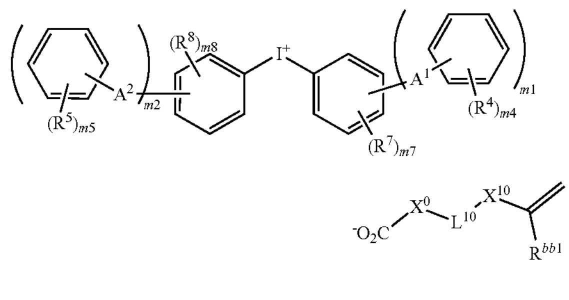

-continued (IP)

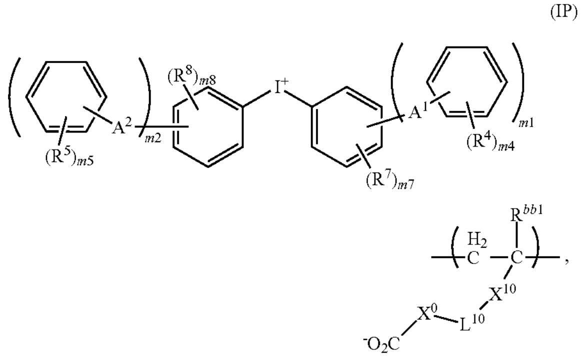

wherein, in formula (I) and formula (IP)

$R^4$, $R^5$, and $R^7$ and $R^8$ each independently represent a halogen atom, a hydroxy group, a haloalkyl group having 1 to 12 carbon atoms or a hydrocarbon group having 1 to 18 carbon atoms, each of the hydrocarbon group may have a substituent, and a —$CH_2$—included in each of the haloalkyl group and the hydrocarbon group may be replaced by —O—, —CO—, —S—or —$SO_2$—, $R^8$ represents an iodine atom, a fluorine atom, a hydroxy group, an alkyl group having 1 to 4 carbon atoms, a haloalkyl group having 1 to 4 carbon atoms or an alkoxy group having 1 to 3 carbon atoms, when m4 is 1 or more, one $R^4$ of one or more $R^4$s is an iodine atom, $A^1$ and $A^2$ each independently represent a hydrocarbon group having 1 to 20 carbon atoms, each of the hydrocarbon group may have a substituent, and —$CH_2$— included in each of the hydrocarbon group may be replaced by —O—, —CO—, or —S—, m1 represents an integer of 1 to 5, and when m1 is 2 or more, a plurality of groups in parentheses may be the same or different from each other, m2 represents an integer of 1 to 5, and when m2 is 2 or more, a plurality of groups in parentheses may be the same or different from each other, m4 represents an integer of 0 to 5, and when m4 is 2 or more, a plurality of $R^4$ may be the same or different from each other, m5 represents an integer of 0 to 5, and when m5 is 2 or more, a plurality of $R^5$ may be the same or different from each other, m7 represents an integer of 0 to 4, and when m7 is 2 or more, a plurality of $R^7$ may be the same or different from each other, m8 represents an integer of 0 to 5, and when m8 is 2 or more, a plurality of $R^8$ may be the same or different from each other, in which 1<m1+m7<5.0<m2+m8≤5, $X^0$ represents a single bond or a hydrocarbon group having 1 to 72 carbon atoms which may have a substituent, and —$CH_2$—included in the hydrocarbon group may be replaced by —O—, —S—, —CO—or —$SO_2$—, $R^{bb1}$ represents a hydrogen atom, a halogen atom, or an alkyl group having 1 to 6 carbon atoms which may have a halogen atom, $X^{10}$ represents a single bond, *—O—** *—CO—O—**, *—O—CO—O—** or *-Ax-Ph-Ay-**-, Ph represents a phenylene group which may have a substituent, Ax represents a single bond, an ether bond, an ester bond or a carbonic acid ester bond, Ay represents a single bond, an ether bond, an ester bond or a carbonic acid ester bond,

* represents a bonding site to carbon atoms to which $R^{bb1}$ is bonded,

** represents a bonding site to $L^{10}$, and $L^{10}$ represents a single bond or a hydrocarbon group having 1 to 36 carbon atoms which may have a substituent, and a —$CH_2$—included in each of the hydrocarbon group may be replaced by —O—, —S—, —$SO_2$—or —CO—.

22. The carboxylate according to claim 2, wherein $X^{01}$ or $X^{02}$ is —CO—or —S—.

23. The carboxylate according to claim 1, wherein:

m2 represents an integer of 1 to 5 and m5 is 1 or more, at least one $R^5$ of one or more $R^5$s is a hydroxy group.

* * * * *